United States Patent
Chen et al.

(10) Patent No.: US 9,908,890 B2
(45) Date of Patent: Mar. 6, 2018

(54) SELECTIVE INHIBITORS OF CONSTITUTIVE ANDROSTANE RECEPTOR

(71) Applicant: ST. JUDE CHILDREN'S RESEARCH HOSPITAL, Memphis, TN (US)

(72) Inventors: Taosheng Chen, Germantown, TN (US); Milu Cherian, Memphis, TN (US); Wenwei Lin, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 15/519,109

(22) PCT Filed: Oct. 16, 2015

(86) PCT No.: PCT/US2015/056032
§ 371 (c)(1),
(2) Date: Apr. 13, 2017

(87) PCT Pub. No.: WO2016/064682
PCT Pub. Date: Apr. 28, 2016

(65) Prior Publication Data
US 2017/0226115 A1    Aug. 10, 2017

Related U.S. Application Data

(60) Provisional application No. 62/066,227, filed on Oct. 20, 2014.

(51) Int. Cl.
| | | |
|---|---|---|
| *C07D 487/08* | (2006.01) | |
| *C07D 403/06* | (2006.01) | |
| *C07D 401/06* | (2006.01) | |
| *C07D 409/06* | (2006.01) | |
| *C07D 403/14* | (2006.01) | |
| *C07D 401/14* | (2006.01) | |
| *C07D 413/14* | (2006.01) | |
| *C07D 405/12* | (2006.01) | |
| *C07D 223/28* | (2006.01) | |
| *C07D 223/22* | (2006.01) | |

(52) U.S. Cl.
CPC ......... *C07D 487/08* (2013.01); *C07D 223/22* (2013.01); *C07D 223/28* (2013.01); *C07D 401/06* (2013.01); *C07D 401/14* (2013.01); *C07D 403/06* (2013.01); *C07D 403/14* (2013.01); *C07D 405/12* (2013.01); *C07D 409/06* (2013.01); *C07D 413/14* (2013.01)

(58) Field of Classification Search
None
See application file for complete search history.

(56) References Cited

U.S. PATENT DOCUMENTS

| 5,116,974 A | 5/1992 | Wunderlich et al. |
|---|---|---|
| 2004/0097408 A1* | 5/2004 | Leder ............... A61K 31/00 514/310 |
| 2007/0066570 A1 | 3/2007 | Solomon |
| 2009/0304615 A1 | 12/2009 | Orlow et al. |

OTHER PUBLICATIONS

Burkin et al., Immunochemical Properties of Conjugated Antigens from N-substituted Phenothiazines and Dibenzazepines with Antiarrhythmic Activity, 2008, Applied Biochemistry and Microbiology, vol. 44, No. 5, 541-544.*
Ansel et al., Pharmaceutical Dosage Forms and Drug Delivery Systems, Ed. 6, 196 & 1456-7 (1995).
Almarasson, Ö. et al., Crystal Engineering of the Composition of Pharmaceutical Phases. Do Pharmaceutical Co-Crystals Represent a New Path to Improved Medicines? Chem Commun (Camb). 2004; (17) 1889-96.
Auerbach, S.S. et al., Alternatively Spliced Isoforms of the Human Constitutive Androstane Receptor. Nucl Acids Res. 2003; 31(12):3194-207.
Auerbach, S.S. et al., Retinoid X Receptor-α-Dependent Transactivation by a Naturally Occurring Structural Variant of Human Constitutive Androstane Receptor (NR1I3). Mol Pharmacol. 2005; 68(5):1239-53.
Bae, Y. et al., Repression of CAR-Mediated Transactivation of CYP2B Genes by the Orphan Nuclear Receptor, short Heterodimer Partner (SHP). DNA Cell Biol. 2004; 23(2):81-91.
Baes, M. et al., A New Orphan Member of the Nuclear Hormone Receptor Superfamily that Interacts with a Subset of Retinoic Acid Response Elements. Mol Cell Biol. 1994; 14(3):1544-52.
Breuker, C. et al., Hepatic Expression of Thyroid Hormone-Responsive Spot 14 Protein is Regulated by Constitutive Androstane Receptor (NR1I3). Endocrinology. 2010; 151(4):1653-61.
Chen, T. et al., A Single Amino Acid Controls the Functional Switch of Human Constitutive Androstane Receptor (CAR) 1 to the Xenobiotic-Sensitive Splicing Variant CAR3. J Pharmacol Exp Ther. 2010; 332(1):106-15.
Cherian, M.T. et al., A Competitive Inhibitor that Reduces Recruitment of Androgen Receptor to Androgen-Responsive Genes. J Biol Chem. 2012; 287(28):23368-80.
Cherian, M.T. et al., CINPA1 is an Inhibitor of Constitutive Androstane Receptor that Does Not Activate Pregnane X Receptor. Mol Pharmacol. 2015; 87(5):878-89.
di Masi, A. et al., Nuclear Receptors CAR and PXR: Molecular, Functional, and Biomedical Aspects. Mol Aspects Med. 2009; 30(5):297-343.
Faucette, S.R. et al., Differential Regulation of Hepatic CYP2B6 and CYP3A4 Genes by Constitutive Androstane Receptor but Not Pregnane X Receptor. J Pharmacol Exp Ther. 2006; 317(3):1200-9.

(Continued)

*Primary Examiner* — Kristin Vajda
(74) *Attorney, Agent, or Firm* — Ballard Spahr LLP

(57) ABSTRACT

The compounds of the invention are antagonists of CAR, with specificity for CAR over other proteins including PXR. The disclosed compounds are useful in treating or controlling cell proliferative disorders, in particular oncological disorders, such as cancer. This abstract is intended as a scanning tool for purposes of searching in the particular art and is not intended to be limiting of the present invention.

20 Claims, 27 Drawing Sheets

(56) References Cited

OTHER PUBLICATIONS

Faucette, S.R. et al., Relative Activation of Human Pregnane X Receptor versus Constitutive Androstane Receptor Defines Distinct Classes of CYP2B6 and CYP3A4 Inducers. J Pharmacol Exp Ther. 2007; 320(1):72-80.
Fishman et al., Medicine. 2d Ed., J.B. Lippincott Co., Philadelphia (1985).
Forman, B.M. et al., Androstane Metabolites Bind to and Deactivate the Nuclear Receptor CAR-?. Nature. 1998; 395(6702):612-5.
Fritz, J. et al., RNA-Regulated Interaction of Transportin-1 and Exportin-5 with the Double-Stranded RNA-Binding Domain Regulates Nucleocytoplasmic Shuttling of ADAR1. Mol Cell Biol. 2009; 29(6):1487-97.
Honkakoski, P. et al., The Nuclear Orphan Receptor CAR-Retinoid X Receptor Heterodimer Activates the Phenobarbital-Responsive Enhancer Module of the CYP2B Gene. Mol Cell Biol. 1998; 18(10):5652-8.
Huang, W. et al., Meclizine is an Agonist Ligand for Mouse Constitutive Androstane Receptor (CAR) and an Inverse Agonist for Human CAR. Mol Endocrinol. 2004; 18(10):2402-8.
Huang, W. et al., Xenobiotic Stress Induces Hepatomegaly and Liver Tumors via the Nuclear Receptor Constitutive Androstane Receptor. Mol Endocrinol. 2005; 19(6):1646-53.
Jones, S.A. et al., The Pregnane X Repector: A Promiscuous Xenobiotic Receptor that has Diverged During Evolution. Mol Endocrinol. 2000; 14(1):27-39.
Jyrkkärinne, J. et al., Molecular Determinants of Steroid Inhibition for the Mouse Constitutive Androstane Receptor. J Med Chem. 2003; 46(22):4687-95.
Kachaylo, E.M. et al., Constitutive Androstane Receptor (CAR) is a Xenosensor and Target for Therapy. Biochemistry (Mosc). 2011; 76:1087-97.
Kozma, David, CRC Handbook of Optical resolutions via Diastereomeric Salt Formation, CRC Press (2001).
Küblbeck, J. et al., New in Vitro Tools to Study Human Constitutive Androstane Receptor (CAR) Biology: Discovery and Comparison of Human CAR Inverse Agonists. Mol Pharmaceut. 2011; 8(6):2424-33.
Lau, A.J. et al., Differential Effect of Meclizine on the Activity of Human Pregnane X Receptor and Constitutive Androstane Receptor. J Pharmacol Exp Ther. 2011; 336(3):816-26.
Li, G. et al., A Tea Catechin, Epigallocatechin-3-Gallate, is a Unique Modulator of the Farnesoid X Receptor. Toxicol Appl Pharmacol. 2012; 258(2):268-74.
Li, L. et al., The Peripheral Benzodiazepine Receptor Ligand 1-(2-Chlorophenyl-methylpropyl)-3-isoquinoline-carboxamide is a Novel Antagonist of Human Constitutive Androstane Receptor. Mol Pharmacol. 2008; 74(2):443-53.
Lin, W. et al., Cyclin-Dependent Kinase 2 negatively Regulates Human Pregnane X receptor-Mediated CYP3A4 Gene Expression in HepG2 Liver Carcinoma Cells. J Biol Chem. 2008; 283(45): 30650-7.
Ma, X. et al., The Pregnane X Receptor: From Bench to Bedside. Expert Opin Drug Metab Toxicol. 2008; 4(7):895-908.
Maglich, J.M. et al., Identification of a Novel Human Constitutive Androstane Receptor (CAR) Agonist and Its Use in the Identification of CAR Target Genes. J Biol Chem. 2003; 278(19):17277-83.
Min, G. et al., Glucocorticoid Receptor-interacting Protein 1 Mediates Ligand-independent Nuclear Translocation and Activation of Constitutive Androstane Receptor in Vivo. J Biol Chem. 2002; 277(29):26356-63.
Moore, L.B. et al., Orphan Nuclear Receptors Constitutive Androstane Receptor and Pregnane X receptor Share Xenobiotic and Steroid Ligands. J Biol Chem. 2000; 275(20):15122-7.
Moore, L.B. et al., Pregnane X Receptor (PXR), Constitutive Androstane Receptor (CAR), and Benzoate X Receptor (BXR) Define Three Pharmacologically Distinct Classes of Nuclear Receptors. Mol Endocrinol. 2002; 16(5):977-86.
Mutoh, S. et al., Phenobarbital Indirectly Activates the Constitutive Active Androstane Receptor (CAR) by Inhibition of Epidermal Growth Factor Receptor Signaling. Sci Signal. 2013; 6(274):ra31.
Remington: The Science and Practice of Pharmacy, 19th Ed., Gennaro, Ed., Mack Publishing Co., Easton, PA (1995).
Takwi, A.A. et al., miR-137 Regulates the Constitutive Androstane Receptor and Modulates Doxorubicin Sensitivity in Parental and Doxorubicin-Resistant Neuroblastoma Cells. Oncogene. 2014; 33(28):3717-29.
Timsit, Y.E. and Negishi, M., CAR and PXR: The Xenobiotic-Sensing Receptors. Steroids. 2007; 72(3):231-46.
Wang, H. et al., A Novel Distal Enhancer Module Regulated by Pregnane X Receptor/Constitutive Androstane Receptor is Essential for the Maximal Induction of CYP2B6 Gene Expression. J Biol Chem. 2003; 278(16):14146-52.
Wang, Y. et al., The Inhibition of Constitutive Androstane Receptor-Mediated Pathway Enhances the Effects of Anticancer Agents in Ovarian Cancer Cells. Biochem Pharm. 2014; 90(4):356-66.
Wang, Y.M. et al., Piperine Activates Human Pregnane X Receptor to Induce the Expression of Cytochrome P450 3A4 and Mutidrug Resistance Protein 1. Toxicol Appl Pharmacol. 2013; 272(1):96-107.
Wei, P. et al., Specific and Overlapping Functions of the Nuclear Hormone Receptors CAR and PXR in Xenobiotic Response. Pharmacogenomics J. 2002; 2(2):117-26.
Wu, B et al., 3D Structures and Ligand Specificities of Nuclear Xenobiotic Receptors CAR, PXR, and VDR. Drug Discov Today. 2013; 18(11-12):574-81.
Yamamoto, Y. et al., The Orphan Nuclear Receptor Constitutive Active/Androstane Receptor is Essential for Liver Tumor Promotion by Phenobarbital in Mice. Cancer Res. 2004; 64(20)7197-200.
Yu, D.D. et al., Development of Time Resolved Fluorescence Resonance Energy Transfer-Based Assay for FXR Antagonist Discovery. Bioorg Med Chem. 2013; 21(14):4266-78.
International Search Report and Written Opinion dated Jan. 7, 2016 by the International Searching Authority for International Application No. PCT/US2015/056032, which was filed on Oct. 16, 2015 and published as WO 2016/064682 on Apr. 28, 2016 (Inventor—Chen et al.; Applicant—St. Jude Children's Research Hospital;) (10 pages).
International Preliminary Report on Patentability dated Apr. 25, 2017 by the International Searching Authority for International Application No. PCT/US2015/056032, which was filed on Oct. 16, 2015 and published as WO 2016/064682 on Apr. 28, 2016 (Inventor—Chen et al.; Applicant—St. Jude Children's Research Hospital;) (8 pages).

\* cited by examiner

CINPA1

SEQUENCE LISTING

```
<160> NUMBER OF SEQ ID NOS: 14

<210> SEQ ID NO 1
<211> LENGTH: 26
<212> TYPE: DNA
<213> ORGANISM: Homo sapiens

<400> SEQUENCE: 1
gtaccgagct cggatccaac tagtaa                                         26

<210> SEQ ID NO 2
<211> LENGTH: 28
<212> TYPE: DNA
<213> ORGANISM: Homo sapiens

<400> SEQUENCE: 2
caggatccgc ggccgctcag ctgcagat                                       28

<210> SEQ ID NO 3
<211> LENGTH: 27
<212> TYPE: DNA
<213> ORGANISM: Homo sapiens

<400> SEQUENCE: 3
attcggatcc ataccatgga gagagct                                        27

<210> SEQ ID NO 4
<211> LENGTH: 27
<212> TYPE: DNA
<213> ORGANISM: Homo sapiens

<400> SEQUENCE: 4
ataagatctg gatccctagc tctgtga                                        27

<210> SEQ ID NO 5
<211> LENGTH: 20
<212> TYPE: DNA
<213> ORGANISM: Homo sapiens

<400> SEQUENCE: 5
aggcccttgg ttcaggaaag                                                20

<210> SEQ ID NO 6
<211> LENGTH: 20
<212> TYPE: DNA
<213> ORGANISM: Homo sapiens

<400> SEQUENCE: 6
```
ctgcctgtct catcctacgc                                            20

<210> SEQ ID NO 7
<211> LENGTH: 20
<212> TYPE: DNA
<213> ORGANISM: Homo sapiens

<400> SEQUENCE: 7
attgcacaac acagcaggag                                            20

<210> SEQ ID NO 8
<211> LENGTH: 20
<212> TYPE: DNA
<213> ORGANISM: Homo sapiens

<400> SEQUENCE: 8
caacccacac tttcctgacc                                            20

<210> SEQ ID NO 9
<211> LENGTH: 20
<212> TYPE: DNA
<213> ORGANISM: Homo sapiens

<400> SEQUENCE: 9
cagctggagg ggtcatcaaa                                            20

<210> SEQ ID NO 10
<211> LENGTH: 20
<212> TYPE: DNA
<213> ORGANISM: Homo sapiens

<400> SEQUENCE: 10
gctagccaga gacccttcac                                            20

<210> SEQ ID NO 11
<211> LENGTH: 22
<212> TYPE: DNA
<213> ORGANISM: Homo sapiens

<400> SEQUENCE: 11
aaggtcataa agcccagttt gt                                         22

<210> SEQ ID NO 12
<211> LENGTH: 21
<212> TYPE: DNA
<213> ORGANISM: Homo sapiens

<400> SEQUENCE: 12
cacctggggt caacacagga c                                          21

<210> SEQ ID NO 13
<211> LENGTH: 20
<212> TYPE: DNA
<213> ORGANISM: Homo sapiens

<400> SEQUENCE: 13
tactagcggt tttacgggcg                                            20

<210> SEQ ID NO 14
<211> LENGTH: 24
<212> TYPE: DNA
<213> ORGANISM: Homo sapiens

```
<400> SEQUENCE: 14
tcgaacagga ggagcagaga gcga                                              24
```

SELECTIVE INHIBITORS OF CONSTITUTIVE ANDROSTANE RECEPTOR

CROSS-REFERENCE TO RELATED APPLICATIONS

This Application is a 371 of International Application No. PCT/US2015/056032, filed on Oct. 16, 2015, which claims the benefit of U.S. Provisional Application No. 62/066,227, filed on Oct. 20, 2014, which is incorporated herein by reference in their entireties.

STATEMENT REGARDING FEDERALLY SPONSORED RESEARCH

This invention was made with U.S. Government support under grant number GM110034, awarded by the National Institute of Health (NIH). The U.S. government has certain rights in the invention.

REFERENCE TO A SEQUENCE LISTING SUBMITTED AS A TEXT FILE VIA EFS-WEB

The Sequence Listing submitted Oct. 16, 2015 as a text file named "19116_0027P1_SeqListing_ST25.txt," created on Oct. 14, 2015, and having a size of 2,397 bytes is hereby incorporated by reference pursuant to 37 C.F.R. § 1.52(e)(5).

BACKGROUND

Constitutive androstane receptor (CAR, MB67, NR1I3) (Baes, M., et al. (1994) Mol. Cell Biol. 14, 1544-1552) is a transcription factor that acts as a xenobiotic sensor, capable of regulating cellular function in response to xenobiotics and endobiotics (di Masi, A., De Marinis, E., Ascenzi, P., and Marino, M. (2009) Mol. Asp. Med. 30, 297-343; Ma, X., Idle, J. R., and Gonzalez, F. J. (2008) Exper. Opin. Drug Metab. Tox. 4, 895-908; and Timsit, Y. E., and Negishi, M. (2007) Steroids 72, 231-246). Activated CAR in tissues heterodimerizes with retinoid X receptor (RXR) and translocates to the nucleus. CAR shares a large portion of its metabolic functions with another member of the NR1 family, pregnane x receptor (PXR, NR1I2). PXR has structural features in the ligand binding domain (LBD) that allow it to successfully bind a diverse set of chemical motifs. CAR LBD is more compact and yet capable of binding varied structural entities (Wu, B., et al. (2013) Drug Discov. Today 18, 574-581). CAR and PXR bind similar response elements on chromatin and hence regulate an overlapping set of genes (Wei, P., et al. (2002) Pharmacogen. J. 2, 117-126). CAR remains a major player in xenobiotic metabolism by controlling the transactivation of many P450 enzymes and transporters, particularly CYP2B6 and multi-drug resistance 1 (MDR1). CAR is the molecular target of phenobarbital (PB)-induced hepatocellular carcinoma and activation of this receptor is an essential requirement for liver tumor development (Yamamoto, Y., et al. (2004) Cancer Res. 64, 7197-7200; and Huang, W., et al. (2005) Mol Endocrinol. 19, 1646-1653). CAR overexpression in neuroblastoma has been shown to drive doxorubicin resistance by increasing the levels of MDR1 expressed (Takwi, A. A., et al. (2013) Oncogene doi: 10.1038/onc.2013.330). CAR activation in ovarian cancer has been shown to decrease effectiveness of anticancer drugs (Wang, Y., et al. (2014) Biochem. Pharm. 90, 356-366), CAR activation was shown to cause hepatic lipogenesis and insulin insensitivity through upregulation of the thyroid hormone-responsive SPOT14 gene, which might promote fatty liver diseases and insulin resistance (Breuker, C., et al. (2010) Endocrinology 151, 1653-1661). CAR function in various diseases emphasizes the clinical and pharmacological importance of this receptor (e.g., see. Kachaylo, E. M., et al. (2011) Biokhimiia 76, 1087-1097).

There are multiple isoforms of CAR (Auerbach, S. S., et al. (2003) Nucl. Acids Res. 31, 3194-3207). Exogenously expressed hCAR1 spontaneously accumulates in the cell nuclei and tends to be constitutively active in the absence of agonists (Baes, M., et al. (1994) Mol. Cell Biol. 14, 1544-1552). CAR also exhibits high basal but low agonist-induced activation in immortalized cells (Faucette, S. R., et al. (2007) J. Pharm. Exper. Therap. 320, 72-80). The splice variant hCAR3 is inducible by agonists when overexpressed in cells (Auerbach, S. S., et al. (2003) Nucl. Acids Res. 31, 3194-3207; and Chen, T., et al. (2010) J. Pharm. Exper. Therap. 332, 106-115), but the agonist-inducible activity is not substantial without simultaneously overexpressing RXRα (Auerbach, S. S., et al. (2005) Mol. Pharm. 68, 1239-1253). In tissues expressing endogenous hCAR, the receptor is mostly cytoplasmic unless activated by direct binding to ligands such as 6-(4-chlorophenyl)imidazo[2,1-b][1,3]thiazole-5-carbaldehyde O-(3,4-dichlorobenzyl) oxime (CITCO) (Maglich, J. M., et al. (2003) J. Biol. Chem. 278, 17277-17283), or binding to indirect ligands such as phenobarbital (Honkakoski, P., et al. (1998) Mol. Cell Biol. 18, 5652-5658). Phenobarbital inhibits the EGF signaling pathway, ultimately resulting in activation of CAR via dephosphorylation at Thr(38) (Mutoh, S., et al. (2013) Sci. Signal 6, ra31). There are few known antagonistic modulators of hCAR, with PK11195 being the most potent of all reported inhibitors (Li, L., et al. (2008) Mol. Pharmacol. 74, 443-453). Clotrimazole, meclizine and androstanol are other moderate inverse agonists of CAR function in in vitro and cell-based transfection assays (Moore, L. B., et al. (2000) J. Biol. Chem. 275, 15122-15127; Huang, W., et al. (2004) Mol. Endocrinol. 18, 2402-2408; Moore, L. B., et al. (2002) Mol. Endocrinol. 16, 977-986). It has been observed that all of these CAR inhibitors are also moderate to potent activators of PXR function (Li, L., et al. (2008) Mol. Pharmacol. 74, 443-453; Moore, L. B., et al. (2002) Mol. Endocrinol. 16, 977-986; Lau, A. J., et al. (2011) J. Pharmacol. Exp. Ther. 336, 816-826; Jones, S. A., et al. (2000) Mol. Endocrinol. 14, 27-39).

In addition to a smaller, unique set of target genes, CAR and PXR co-regulate an overlapping set of metabolizing genes, although the strength of the response at each gene depends on the activation status of both the receptors (Wei, P., et al. (2002) Pharmacogenomics J. 2, 117-126). The CYP2B6 gene, although considered to be a predominantly CAR regulated gene, is also induced equally well by activated PXR (Faucette, S. R., et al. (2006) J. Pharmacol. Exp. Ther. 317, 1200-1209; Faucette, S. R, et al. (2007) J. Pharmacol. Exp. Ther. 320, 72-80). In tissues expressing both PXR and CAR proteins (i.e., the liver or colon) treatment with CAR inhibitors that activate PXR would result in a confused gene expression profile and interpretation of receptor function is confounded by this opposing dual activity of such CAR inhibitors.

Despite several known inhibitors of CAR, the identification of inhibitors that selectively inhibit CAR without activation of PXR has remained elusive. Thus, there remains a need for selective inhibitors of CAR that either simultaneously antagonize PXR, or at least, do not activate PXR. Identification of such selective inhibitors of CAR would be

SUMMARY

In accordance with the purpose(s) of the invention, as embodied and broadly described herein, the invention, in one aspect, relates to 1-(3-amino)-10,11-dihydro-5H-dibenzo[b,f]azepin-5-yl)alkan-1-ones useful as inhibitors of constitutive androstane receptor (CAR), methods of making same, pharmaceutical compositions comprising same, and methods of treating cancers associated with overexpression of CAR using same.

Disclosed are compounds having a structure represented by a formula:

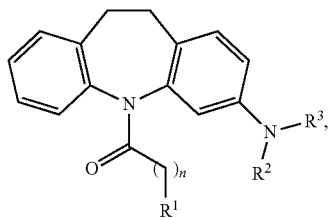

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl; or wherein $R^{11a}$, when present, is hydrogen and $R^{11b}$, when present, is —$C(CH_3)_2$ (C2-C8 alkyl); or wherein $R^{11a}$ and $R^{11b}$, when present, are optionally covalently bonded and, together with the nitrogen atom to which they are attached, comprise a 3- to 5-membered heterocycle; wherein $R^{11a}$ and $R^{11b}$, when present, are optionally covalently bonded and, together with the nitrogen atom to which they are attached, comprise a 6-membered heterocycle having a structure represented by a formula:

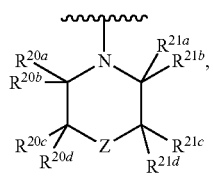

wherein Z, when present, is selected from C, NH, and $NCH_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —$(C=O)R^{13}$, —$(C=O)NR^{14a}R^{14b}$, —$(C=O)OR^{15}$, and $Ar^2$; wherein $R^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

Also disclosed are compounds having a structure represented by a formula:

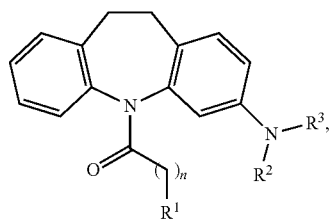

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl; or wherein $R^{11a}$, when present, is hydrogen and $R^{11b}$, when present, is —C(CH$_3$)$_2$(C2-C8 alkyl); or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

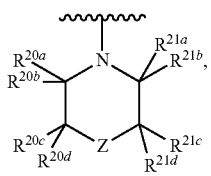

wherein Z, when present, is selected from C, NH, and NCH$_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —SO$_2$R$^{12}$, —(C=O)R$^{13}$, —(C=O)NR$^{14a}$R$^{14b}$, —(C=O)OR$^{15}$, and $Ar^2$; wherein $R^{12}$, when present, is selected from C1-C3 alkyl, C1-C3 monohaloalkyl, C1-C3 polyhaloalkyl, cyclopropyl, and —NR$^{22a}$R$^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and Cy$^2$, provided that $R^{15}$ is i-propyl only when n is 1, and provided that when n is 1 or 2 and each of $R^{11a}$ and $R^{11b}$ is ethyl then $R^{15}$ is not ethyl; wherein Cy$^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

Also disclosed are compounds having a structure represented by a formula:

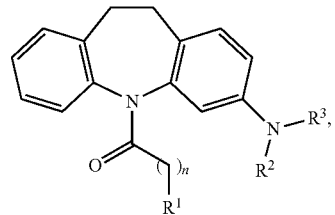

wherein n is an integer selected from 0, 1, 2, and 3; wherein $R^1$ is selected from —OR$^{10}$, —NR$^{11a}$R$^{11b}$, and $Ar^1$; wherein $R^{10}$, when present, is selected from hydrogen, C3-C8 alkyl, and Cy$^1$; wherein Cy$^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C2-C8 alkyl; or wherein $R^{11a}$, when present, is hydrogen and $R^{11b}$, when present, is —C(CH$_3$)$_2$(C2-C8 alkyl); or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

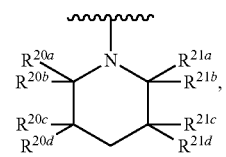

wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —(C=O)$R^{13}$, —(C=O)$NR^{14a}R^{14b}$, —(C=O)$OR^{15}$, and $Ar^2$; wherein $R^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 0, 1, or 2 and each of $R^{11a}$ and $R^{11b}$ is ethyl then $R^{15}$ is not methyl or ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

Also disclosed are compounds having a structure represented by a formula:

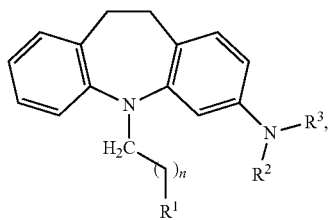

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl when n is 0, 1, or 3 and wherein each of $R^{11a}$ and $R^{11b}$, when present, is independently selected from C2-C8 alkyl when n is 2; or wherein $R^{11a}$, when present, is hydrogen and $R^{11b}$, when present, is —$C(CH_3)_2$(C2-C8 alkyl); or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

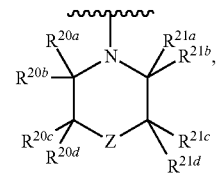

wherein Z, when present, is selected from C, NH, and $NCH_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —(C=O)$R^{13}$, —(C=O)$NR^{14a}R^{14b}$, —(C=O)$OR^{15}$, and $Ar^2$; wherein $R^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

Also disclosed are pharmaceutical compositions comprising an effective amount of at least one disclosed compound, at least one product of a disclosed method of making a compound, or a pharmaceutically acceptable salt thereof, and a pharmaceutically acceptable carrier.

Also disclosed are methods of treating a disorder of uncontrolled cellular proliferation associated with a CAR dysfunction in a subject, the method comprising the step of administering to the subject an effective amount of at least one disclosed compound.

Also disclosed are methods of treating a disorder of uncontrolled cellular proliferation in a subject, the method comprising administering to the subject an effective amount of at least one disclosed compound, at least one product of a disclosed method of making a compound, or a pharmaceutically acceptable salt thereof.

Also disclosed are methods of treating a disorder of uncontrolled cellular proliferation in a subject, the method comprising administering to the subject: (a) an effective amount of at least one disclosed compound, at least one product of a disclosed method of making a compound, or a pharmaceutically acceptable salt thereof; and (b) an effective amount of at least one chemotherapeutic agent, or a pharmaceutically acceptable salt thereof; thereby treating the disorder of uncontrolled cellular proliferation in the subject.

Also disclosed are methods of inhibiting CAR activity in a subject, the method comprising the step of administering to the subject an effective amount of at least one disclosed compound, at least one product of a disclosed method of making a compound, or a pharmaceutically acceptable salt thereof.

Also disclosed are methods of inhibiting growth of at least one cell, comprising the step of contacting the at least one cell with an effective amount of at least one disclosed compound, at least one product of a disclosed method of making a compound, or a pharmaceutically acceptable salt thereof.

Also disclosed are kits comprising at least one disclosed compound, at least one product of a disclosed method of making a compound, or a pharmaceutically acceptable salt thereof; and one or more of:

(a) at least one agent known to increase CAR activity;
(b) at least one agent known to decrease CAR activity;
(c) at least one agent known to treat a disorder of uncontrolled cellular proliferation;
(d) instructions for treating a disorder associated with CAR dysfunction; or
(e) instructions for treating a disorder of uncontrolled cellular proliferation.

BRIEF DESCRIPTION OF THE DRAWINGS

The accompanying figures, which are incorporated in and constitute a part of this specification, illustrate several aspects and together with the description serve to explain the principles of the invention.

FIG. 2A shows representative data for inhibition of CAR by CINPA1, clotrimazole (CLZ), or PK11195 (positive control). Activity in DMSO-treated samples was set as 0% inhibition; activity in samples treated with 9 µM PK11195 was set as 100% CAR inhibition. After a 24 h incubation, cells were treated with DMSO (negative control) or indicated concentrations of CINPA1, clotrimazole (CLZ), or PK11195 (positive control). Luciferase activity was measured 24 h after treatment by using SteadyLite™ reagent. Activity in DMSO-treated samples was set as 0% inhibition; activity in samples treated with 9 µM PK11195 was set as 100% CAR inhibition. GraphPad Prism was used to fit the data into a dose-response equation to derive $IC_{50}$ values. FIG. 2B shows representative data for inhibition of PXR by DMSO (negative control), CINPA1, clotrimazole (CLZ), PK11195, or rifampicin ("Rif;" positive control). The percentage of PXR activation was calculated by setting that of DMSO-treated cells (negative control) to 0%, and that of 5 µM rifampicin-treated cells (positive control) to 100%. HepG2 cells stably expressing hPXR and CYP3A4-luciferase reporter (PXR Clone 1) were treated with indicated compounds for 24 h. Luciferase activity was measured 24 h after treatment by using SteadyLite reagent. The percentage of PXR activation was calculated by setting that of DMSO-treated cells (negative control) to 0%, and that of 5 µM rifampicin-treated cells (positive control) to 100%. The highest concentration of CINPA1 tested (40 µM) is shown here, and minimal or no PXR activation was observed at lower concentrations (FIG. 10B).

FIG. 3A shows representative data for treatment of HepG2-PXR Clone 1 cells DMSO or 18 µM of CINPA1 in the presence or absence of 5 µM rifampicin for 24 h before assaying the cells for luciferase activity. FIG. 3B-FIG. 3I show representative data for treatment of GeneBLAzer® cells treated with DMSO (negative control), a predetermined concentration of the indicated nuclear receptor ("NR") antagonist (positive control; concentration as detailed in Examples), or 18 µM of CINPA1 in the presence or absence the indicated NR agonist (i.e., indicated below treatments). NR-mediated β-lactamase activity was measured as a FRET ratio after 24 h treatment. Data is presented as % Activity, determined by setting the maximum FRET signal obtained for each receptor (in the respective agonist+DMSO wells) to 100%. eGugg=e Guggulsterone, Feno=Fenofibrate, GW9=GW9662, 22HC=22 (S)-hydroxycholesterol, 9-cis RA=9-cis retinoic acid.

FIG. 4A shows representative data for the treatment of HepG2 cells transfected with hCAR1 and CYP2B6-luc plasmid in order to mimic conditions used in the luciferase screening assays. The transfected cells were treated with the indicated concentrations of the indicated compounds for 24 hr. Cells were treated with indicated compounds for 24 h, and viability was measured by using CellTiter-Glo® reagent. ("Rif" indicates rifampicin). FIG. 4B, FIG. 4C, and FIG. 4D show representative data for treatment of HepG2, LS174T, and HEK293T cells, respectively, with DMSO (control), CINPA1, clotrimazole (CLZ) or PK11195 at the indicated concentrations. Cell viability was measured 4 days post treatment by using CellTiter-Glo® reagent. Viability of cells treated with DMSO (negative control) was set to 100% in all assays.

FIG. 5A shows representative data for the effect of the indicated treatments on expression of CYP2B6 or CYP3A4 mRNA in HepG2 cells stably expressing hCAR1 (HepG2-hCAR1cells). Briefly, the cells were treated with DMSO (control), 1 µM CITCO, 1 µM CINPA1, or 1 µM PK11195 in triplicated wells for 24 h. RNA was extracted, cDNA synthesized, and gene expression analyzed by performing real-time PCR using Taqman probes for each gene. FIG. 5B shows representative data for the effect of the indicated treatments on expression of CYP2B6 or CYP3A4 mRNA in LS174T cells. LS174T cells were maintained in 10% charcoal-dextran-treated, FBS media for 4 days before the experiment. Cells were treated with DMSO, 5 µM CITCO, 1 µM CINPA1, or 5 µM PK11195 for 24 h. FIG. 5C shows representative data for the effect of the indicated treatments on expression of CYP2B6 mRNA in human primary hepatocytes from Donor 1 (HPH-Donor1 cells). FIG. 5D shows representative data for the effect of the indicated treatments on expression of CYP2B6 mRNA in human primary hepatocytes from Donor 2 (HPH-Donor2 cells). FIG. 5E shows representative data for the effect of the indicated treatments on expression of CYP2B6 mRNA in human primary hepatocytes from Donor 3 (HPH-Donor3 cells). Briefly, human primary hepatocytes (HPH) were maintained in William's E media with supplements for 4 days before treatment. Cells were treated in the presence or absence of 1 µM CITCO, and DMSO, 5 µM PK11195, or CINPA1 (5 µM treatment for Donor 1, 1 µM for Donor 2, and 0.3 µM for Donor 3) for 48 h. RNA extracted was used for cDNA synthesis and measured by performing quantitative real-time PCR assays with Taqman probes. In Panel C HPH-Donor 1, PK11195 alone was tested, but CITCO+PK11195 could not be tested due to limited hepatocyte availability. *, p<0.05 compared to DMSO-treated samples.

FIG. 6A shows representative data demonstrating the dose response inhibition of CAR binding to PGC-1α coactivator peptide. Briefly, CAR binding to PGC-1α coactivator peptide was determined by using the LanthaScreen® fluorescent coregulator peptide assay. Fluorescein-labeled PGC-1α peptide (125 nM) was complexed with GST-hCAR-LBD (5 nM) and Tb-anti-GST antibody (5 nM) as described in Experimental Procedures. Compounds (clotrimazole, PK11195 or CINPA1) at concentrations ranging from 70 µM to 3.5 nM (1-to-3 dilutions for 10 concentration levels) were used along with DMSO as a negative control, and clotrimazole (42 µM) was used as a positive control. % Inhibition was calculated for each treatment, and the data were normalized to the positive control (42 µM clotrimazole, 100% inhibition) and negative control (DMSO, 0% inhibition). FIG. 6B shows representative data for the level of CAR protein under different treatment conditions in human primary hepatocytes. Briefly, Human primary hepatocytes (Donor 3) were treated with DMSO, 1 µM CITCO, 5 µM CINPA1, or 10 µM PK11195 for 48 h. Lysates were prepared, and CAR expression was analyzed by Western blot using CAR monoclonal antibody (Clone N4111, R&D Systems). β-actin was used as a loading control. FIG. 6B shows representative immunofluorescence data obtained in U2OS cells following treatment with the indicated compounds. Briefly, U2OS cells were transfected to express FLAG-hCAR1. Cells were treated with 1 µM CITCO, 5 µM CINPA1 or 5 µM PK11195 for 2 h before fixing and staining with anti-FLAG-M2 antibody (Sigma). Secondary antibody labeled with Alexa Fluor® 555 dye was used to visualize FLAG-tagged hCAR1 (shown in the second column) using a NikonC 1Si microscope. Nuclei were stained with DAPI (shown in the first column). The third column shows the merged images for DAPI and FLAG-tagged hCAR1.

FIG. 7A shows representative data on the effect of the indicated treatments on the interaction of CAR with co-activators. Briefly, mammalian two-hybrid assays were set up in HEK293T cells transfected with expression plasmids encoding VP16AD-hCAR1 fusion protein, GAL4DBD-co-activator fusion proteins, and the reporter plasmid pG5luc. Cells were treated with DMSO (control), 5 µM CITCO, 5 µM CINPA1, 10 µM PK11195, or 1 µM CITCO+5 µM CINPA1 for 24 h prior to measuring luciferase activities. Fold interaction represents pG5luc reporter activity normalized to the Renilla luciferase internal control. Data presented are the mean±SD of at least three independent transfections. *, p<0.001 compared to DMSO treatment within the indicated co-activator set. FIG. 7B shows representative data on the effect of the indicated treatments on the interaction of CAR with co-repressors. Briefly, mammalian two-hybrid assays were set up in HEK293T cells transfected with expression plasmids encoding VP16AD-hCAR1 fusion protein, GAL4DBD-co-repressor fusion proteins, and the reporter plasmid pG51luc. Cells were treated with DMSO (control), 5 µM CITCO, 5 µM CINPA1, 10 µM PK11195, or 1 µM CITCO+5 µM CINPA1 for 24 h prior to measuring luciferase activities. Fold interaction represents pG5luc reporter activity normalized to the Renilla luciferase internal control. Data presented are the mean±SD of at least three independent transfections. *, p<0.001 compared to DMSO treatment within the indicated co-repressor set.

FIG. 8A shows PBREM and XREM (dNR3) in the CYP2B6 promoter region. FIG. 8B and FIG. 8C show the fold enrichment of CAR at CYP2B6-dNR3 and CYP2B6-PBREM sites, respectively, in the promoter region following the indicated treatment in human primary hepatocytes. Briefly, human primary hepatocytes from three separate donors (as indicated in FIG. 8B and FIG. 8C) were treated overnight with DMSO, 1 µM CITCO, 5 µM CINPA1, or 10 µM PK11195. Protein complexes were cross-linked and chromatin was immunoprecipitated by using anti-CAR antibody or control IgG. CAR occupancy at two separate CYP2B6 promoter regions (dNR3 and PBREM) was determined by performing quantitative RT-PCR assays. Fold-enrichment normalized to IgG control was plotted. Data represent the mean±SD of 3 experiments. *, p<0.01 comparing CITCO treatment to DMSO treatment.

FIG. 9A, FIG. 9B, and FIG. 9C show the fold enrichment of CAR at CYP2B6-dNR3, CYP3A4-XREM, and CYP2B6-dNR3 sites, respectively, in the promoter region following the indicated treatment in human primary hepatocytes or HepG2-hCAR1 cells, as indicated in the figures. Briefly, in FIG. 9A and FIG. 9B freshly plated human hepatocytes were treated for 45 min with DMSO, 0.1 µM CITCO, 1 µM CINPA1, or 0.1 µM CITCO+1 µM CINPA1, whereas in FIG. 9C HepG2-hCAR1 stable cells were treated for 4 h with DMSO, 1 µM CITCO, 5 µM CINPA1, or 1 µM CITCO+5 µM CINPA1. Protein complexes were cross-linked and chromatin was immunoprecipitated by using anti-CAR antibody, anti-RNA polymerase II (RPol) antibody, or control IgG. CAR or RPol occupancy at the CYP2B6-dNR3 region and CYP3A4-XREM region was determined by performing quantitative RT-PCR assays. Fold-enrichment was normalized to IgG control. Data represent the mean±SD of 3 experiments. *, $p<0.001$ and #, $p<0.01$ comparing CITCO to DMSO samples. **, $p<0.001$ and ##, $p<0.01$ comparing CITCO+CINPA1 to CITCO samples.

FIG. 10A shows representative data demonstrating that CINPA1 inhibits luciferase expression from a CYP3A4-luciferase construct. Briefly, HepG2 cells were transiently transfected with plasmids expressing hCAR1, CYP3A4-luc reporter and control plasmid pTK-RL. After 24 h incubation, cells were treated with DMSO (control), 1 µM CITCO, 5 µM PK11195, 1 µM or 5 µM CINPA1, or 5 µM rifampicin (Rif) for 24 hours. Dual luciferase activity was measured 24 h after treatment using Dual-Glo® luciferase reagent. *Renilla* luciferase was used to normalize firefly luciferase values and % Luciferase activity was calculated by setting DMSO to 100%. $p<0.001$, when comparing DMSO to all treatments except 5 µM rifampicin. FIG. 10B shows representative data demonstrating CINPA1 does not inhibit PXR activity at low concentrations. Briefly, HepG2-PXR Clone 1 cells were treated with CINPA1 in a dose-responsive format (40 µM to 2 nM, 1-to-2 dilutions for 10 concentrations) in the presence or absence of 5 µM rifampicin (Rif) for 24 h before luciferase assay using SteadyLite™. % PXR activity was calculated by setting DMSO (negative. control) treated cells to 0% and 5 µM rifampicin (positive. control) treated cells to 100%. GraphPad Prism was used to fit the data into a dose-response stimulation equation to derive $IC_{50}$ values. FIG. 10C shows representative data demonstrating that CINPA1 inhibits luciferase expression from a CYP2B6-luciferase construct. Briefly, U2OS cells were transiently transfected with plasmids expressing hCAR1, CYP2B6-luc reporter and control plasmid pTK-RL. After 24 h incubation, cells were treated with DMSO (negative control), 1 µM CITCO, 5 µM CINPA1, 1 µM CITCO+5 µM CINPA1 or 5 µM PK11195. Dual luciferase activity was measured 24 h after treatment. *Renilla* luciferase was used to normalize firefly luciferase values and % Luciferase activity was calculated by setting DMSO to 100%. *, $p<0.0001$ comparing CITCO+CINPA1 to CITCO treated cells.

FIG. 11A shows representative quantitative RT-PCR analysis of CAR mRNA expression in HepG2-hCAR1 Clone 17 cells when compared to parental HepG2 cells. 18S was used as the internal control and showed no change in threshold cycle (Ct) between the two cell lines. FIG. 11B shows representative Western Blot analysis using anti-FLAG antibody, showing FLAG-tagged CAR protein expression levels in the various selected clones. Clone 17 had very high expression levels of hCAR1 and was used in subsequent studies described herein.

FIG. 12A shows representative data obtained using HepG2-hCAR1 Clone17. Briefly, HepG2-hCAR1 Clone17 cells were plated and treated with DMSO (control), 0.1 µM CINPA1 or 1 µM PK11195 in triplicate wells for 24 h. FIG. 12B shows representative data obtained using LS174T cells. Briefly, LS174T were maintained in 10% charcoal-dextran treated-FBS media for 4 days prior to the experiment. Cells were treated with DMSO, 1 µM CINPA1 or 5 µM PK11195 for 24 h. For the data shown in both FIG. 12A and FIG. 12B, RNA extracted was used for cDNA synthesis and measured by quantitative real-time PCR with Taqman probes. MDR1 mRNA was normalized to the internal control 18S and DMSO treated samples were set to 1. *, $p<0.05$ when compared to DMSO samples.

Figure 1A:
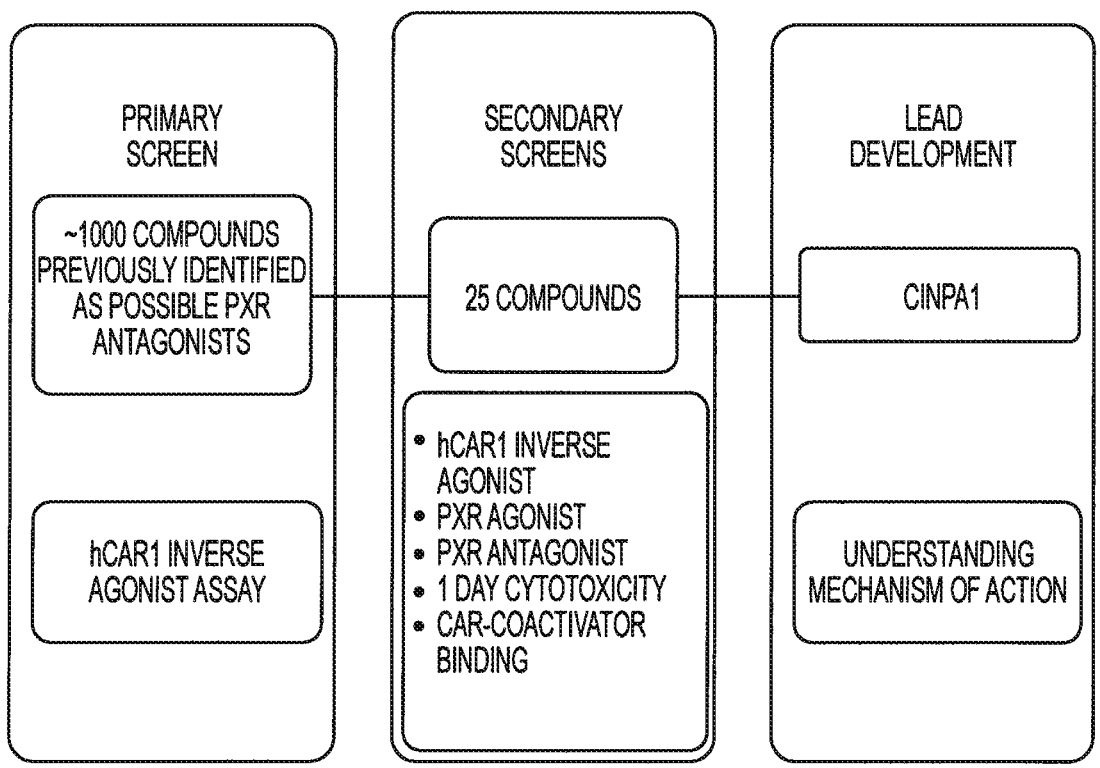
FIG. 1A shows a flowchart illustrating the screening strategy used to identify inhibitors of CAR activity.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are a disorder of cellular proliferation.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a disorder of cellular proliferation prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$—OA$^2$ or —OA$^1$—(OA$^2$)$_a$—OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A1$, —$OS(O)_2A1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH═CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)O^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)$C(O)O$—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\bullet$ (or the ring formed by taking two independent occurrences of $R^\bullet$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

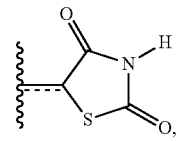

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

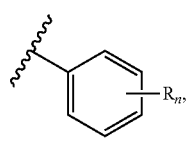

which is understood to be equivalent to a formula:

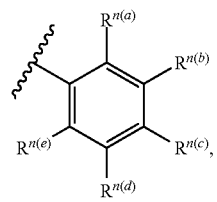

wherein n is typically an integer. That is, $R''$ is understood to represent five independent substituents, $R^{n(a)}$, $R^{n(b)}$, $R^{n(c)}$, $R^{n(d)}$, $R^{n(e)}$. In each such case, each of the five $R''$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

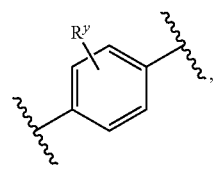

wherein $R^y$ represents, for example, 0-2 independent substituents selected from $A^1$, $A^2$, and $A^3$, which is understood to be equivalent to the groups of formulae:

wherein $R^y$ represents 0 independent substituents

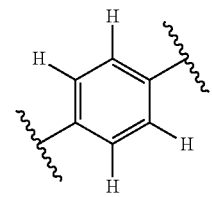

wherein $R^y$ represents 1 independent substituent

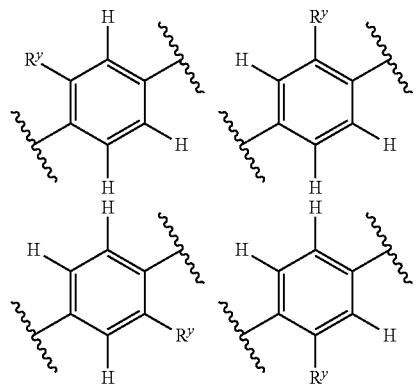

wherein $R^y$ represents 2 independent substituents

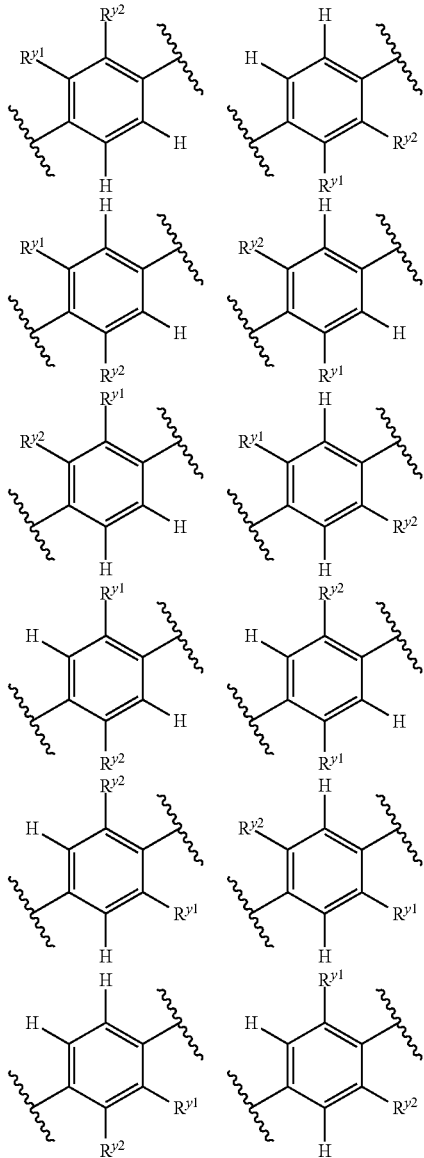

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

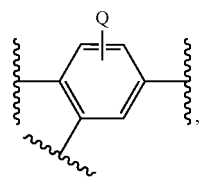

wherein, for example, Q comprises three substituents independently selected from hydrogen and A, which is understood to be equivalent to a formula:

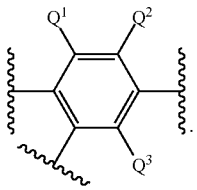

Again, by "independent substituents," it is meant that each Q substituent is independently defined as hydrogen or A, which is understood to be equivalent to the groups of formulae:

wherein Q comprises three substituents independently selected from H and A

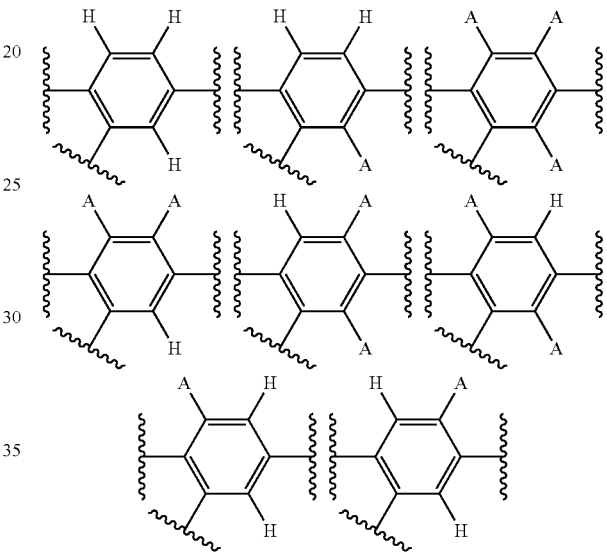

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating or controlling cell proliferative disorders, in particular oncological disorders, such as cancer. The compounds and pharmaceutical compositions containing the compounds can be useful in the treatment or control of solid tumors, such as breast, colon, lung and prostate tumors.

In one aspect, the disclosed compounds exhibit inhibition of CAR. In a further aspect, the disclosed compounds exhibit antagonism of CAR. In a still further aspect, the disclosed compounds are selective for CAR over pregnane x receptor (PXR).

In one aspect, the compounds of the invention are useful in the treatment cell proliferative disorders associated with CAR dysfunction and other diseases in which CARs are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds having a structure represented by a formula:

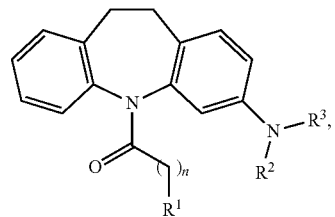

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl; or wherein $R^{11a}$, when present, is hydrogen and $R^{11b}$, when present, is —$C(CH_3)_2$ (C2-C8 alkyl); or wherein $R^{11a}$ and $R^{11b}$, when present, are optionally covalently bonded and, together with the nitrogen atom to which they are attached, comprise a 3- to 5-membered heterocycle; wherein $R^{11a}$ and $R^{11b}$, when present, are optionally covalently bonded and, together with the nitrogen atom to which they are attached, comprise a 6-membered heterocycle having a structure represented by a formula:

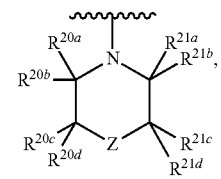

wherein Z, when present, is selected from C, NH, and $NCH_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —$(C=O)R^{13}$, —$(C=O)NR^{14a}R^{14b}$, —$(C=O)OR^{15}$, and $Ar^2$; wherein $R^{12}$, when present, is selected from C1-C3 alkyl, C1-C3 monohaloalkyl, C1-C3 polyhaloalkyl, cyclopropyl, and —NR$^{22a}$R$^{22b}$; wherein each of R$^{22a}$ and R$^{22b}$, when present, is independently selected from hydrogen, C1-C3 alkyl, C1-C3 monohaloalkyl, C1-C3 polyhaloalkyl, and cyclopropyl; or wherein R$^{22a}$ and R$^{22b}$, when present, are optionally covalently bonded and, together with the nitrogen atom to which they are attached, comprise a 3- to 6-membered heterocycle; wherein R$^{13}$, when present, is selected from C1-C3 alkyl, C1-C3 monohaloalkyl, C1-C3 polyhaloalkyl, and cyclopropyl; wherein each of R$^{14a}$ and R$^{14b}$, when present, is independently selected from hydrogen, C1-C3 alkyl, C1-C3 monohaloalkyl, C1-C3 polyhaloalkyl, and cyclopropyl; or wherein R$^{14a}$ and R$^{14b}$, when present, are optionally covalently bonded and, together with the nitrogen atom to which they are attached, comprise a 3- to 6-membered heterocycle; wherein R$^{15}$, when present, is selected from hydrogen, C1-C4 alkyl, C1-C4 monohaloalkyl, C1-C4 polyhaloalkyl, and Cy$^2$, provided that R$^{15}$ is i-propyl only when n is 1, and provided that when n is 1 or 2 and each of R$^{11a}$ and R$^{11b}$ is ethyl then R$^{15}$ is not ethyl; wherein Cy$^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein Ar$^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

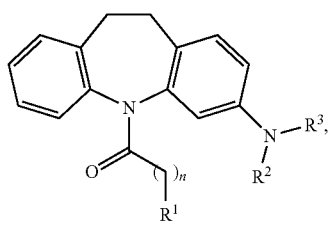

wherein n is an integer selected from 0, 1, 2, and 3; wherein R$^1$ is selected from —OR$^{10}$, —NR$^{11a}$R$^{11b}$, and Ar$^1$; wherein R$^{10}$, when present, is selected from hydrogen, C1-C8 alkyl, and Cy$^1$; wherein Cy$^1$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of R$^{11a}$ and R$^{11b}$, when present, is independently selected from hydrogen and C1-C8 alkyl; or wherein each of R$^{11a}$ and R$^{11b}$, when present, are optionally covalently bonded and, together with the nitrogen atom to which they are attached, comprise a 3- to 6-membered heterocycle; wherein Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, and C1-C4 polyhaloalkyl; and wherein two of the substituents are optionally covalently bonded, and together with the intermediate atoms, comprise an optionally substituted 5- to 6-membered fused ring group; wherein R$^2$ is selected from hydrogen and C1-C4 alkyl; wherein R$^3$ is selected from —SO$_2$R$^{12}$, —(C=O)R$^{13}$, —(C=O)NR$^{14a}$R$^{14b}$, —(C=O)OR$^{15}$, and Ar$^2$; wherein R$^{12}$, when present, is selected from C1-C3 alkyl, C1-C3 monohaloalkyl, C1-C3 polyhaloalkyl, cyclopropyl, and —NR$^{22a}$R$^{22b}$; wherein each of R$^{22a}$ and R$^{22b}$, when present, is independently selected from hydrogen, C1-C3 alkyl, C1-C3 monohaloalkyl, C1-C3 polyhaloalkyl, and cyclopropyl; or wherein R$^{22a}$ and R$^{22b}$, when present, are optionally covalently bonded and, together with the nitrogen atom to which they are attached, comprise a 3- to 6-membered heterocycle; wherein R$^{13}$, when present, is selected from C1-C3 alkyl, C1-C3 monohaloalkyl, C1-C3 polyhaloalkyl, and cyclopropyl; wherein each of R$^{14a}$ and R$^{14b}$, when present, is independently selected from hydrogen, C1-C3 alkyl, C1-C3 monohaloalkyl, C1-C3 polyhaloalkyl, and cyclopropyl; or wherein R$^{14a}$ and R$^{14b}$, when present, are optionally covalently bonded and, together with the nitrogen atom to which they are attached, comprise a 3- to 6-membered heterocycle; wherein R$^{15}$, when present, is selected from hydrogen, C1-C4 alkyl, C1-C4 monohaloalkyl, C1-C4 polyhaloalkyl, and Cy$^2$; wherein Cy$^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein Ar$^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, and C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

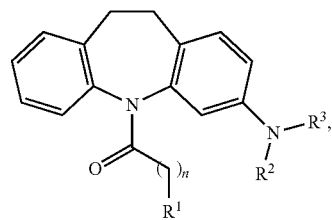

wherein n is an integer selected from 1, 2, and 3; wherein R$^1$ is selected from —OR$^{10}$, —NR$^{11a}$R$^{11b}$, and Ar$^1$; wherein R$^{10}$, when present, is selected from hydrogen, C1-C8 alkyl, and Cy$^1$; wherein Cy$^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of R$^{11a}$ and R$^{11b}$, when present, is independently selected from C1-C8 alkyl; or wherein R$^{11a}$, when present, is hydrogen and R$^{11b}$, when present, is —C(CH$_3$)$_2$(C2-C8 alkyl); or wherein each of R$^{11a}$ and R$^{11b}$, when present, are optionally covalently bonded and, together with the nitrogen atom to which they are attached, comprise a 3- to 5-membered heterocycle; or wherein each of R$^{11a}$ and R$^{11b}$, when present, are optionally covalently bonded and, together with the nitrogen atom to which they are attached, comprise a 6-membered heterocycle having a structure represented by a formula:

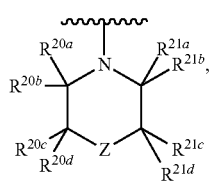

wherein Z, when present, is selected from C, NH, and NCH$_3$; wherein each of R$^{20a}$, R$^{20b}$, R$^{20c}$, and R$^{20d}$, when present, is independently selected from hydrogen and C1-C4 alkyl, provided that R$^{20a}$ and R$^{20b}$ are not simultaneously hydrogen; or wherein each of R$^{20a}$ and R$^{20c}$, when present, are hydrogen and R$^{20b}$ and R$^{20d}$, when present, are optionally covalently bonded and, together with the nitrogen atom to which they are attached, comprise a 5- to 6-membered heterocycle; wherein each of R$^{21a}$, R$^{21b}$, R$^{21c}$, and R$^{21d}$, when present, is independently selected from hydrogen and C1-C4 alkyl, provided that R$^{21a}$ and R$^{21b}$ are not simultaneously hydrogen; or wherein each of R$^{21a}$ and R$^{21c}$, when present, are hydrogen and R$^{21b}$ and R$^{21d}$, when present, are optionally covalently bonded and, together with the nitrogen atom to which they are attached, comprise a 5- to 6-membered heterocycle; wherein Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein R$^2$ is selected from hydrogen and C1-C4 alkyl; wherein R$^3$ is selected from —SO$_2$R$^{12}$, —(C=O)R$^{13}$, —(C=O)NR$^{14a}$R$^{14b}$, —(C=O)OR$^{15}$, and Ar$^2$; wherein R$^{12}$, when present, is selected from C1-C3 alkyl, C1-C3 monohaloalkyl, C1-C3 polyhaloalkyl, cyclopropyl, and —NR$^{22a}$R$^{22b}$; wherein each of R$^{22a}$ and R$^{22b}$, when present, is independently selected from hydrogen, C1-C3 alkyl, C1-C3 monohaloalkyl, C1-C3 polyhaloalkyl, and cyclopropyl; or wherein R$^{22a}$ and R$^{22b}$, when present, are optionally covalently bonded and, together with the nitrogen atom to which they are attached, comprise a 3- to 6-membered heterocycle; wherein R$^{13}$, when present, is selected from C1-C3 alkyl, C1-C3 monohaloalkyl, C1-C3 polyhaloalkyl, and cyclopropyl; wherein each of R$^{14a}$ and R$^{14b}$, when present, is independently selected from hydrogen, C1-C3 alkyl, C1-C3 monohaloalkyl, C1-C3 polyhaloalkyl, and cyclopropyl; or wherein R$^{14a}$ and R$^{14b}$, when present, are optionally covalently bonded and, together with the nitrogen atom to which they are attached, comprise a 3- to 6-membered heterocycle; wherein R$^{15}$, when present, is selected from hydrogen, C1-C4 alkyl, C1-C4 monohaloalkyl, C1-C4 polyhaloalkyl, and Cy$^2$, provided that R$^{15}$ is i-propyl only when n is 1, and provided that when n is 1 or 2 and each of R$^{11a}$ and R$^{11b}$ is ethyl then R$^{15}$ is not ethyl; wherein Cy$^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein Ar$^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

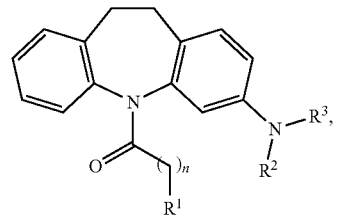

wherein n is an integer selected from 0, 1, 2, and 3; wherein R$^1$ is selected from —OR$^{10}$, —NR$^{11a}$R$^{11b}$, and Ar$^1$; wherein R$^{10}$, when present, is selected from hydrogen, C3-C8 alkyl, and Cy$^1$; wherein Cy$^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of R$^{11a}$ and R$^{11b}$, when present, is independently selected from C2-C8 alkyl; or wherein R$^{11a}$, when present, is hydrogen and R$^{11b}$, when present, is —C(CH$_3$)$_2$(C2-C8 alkyl); or wherein each of R$^{11a}$ and R$^{11b}$, when present, are optionally covalently bonded and, together with the nitrogen atom to which they are attached, comprise a 3- to 5-membered heterocycle; or wherein each of R$^{11a}$ and R$^{11b}$, when present, are optionally covalently bonded and, together with the nitrogen atom to which they are attached, comprise a 6-membered heterocycle having a structure represented by a formula:

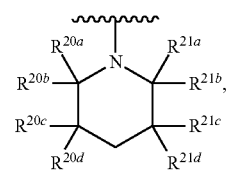

wherein each of R$^{20a}$, R$^{20b}$, R$^{20c}$, and R$^{20d}$, when present, is independently selected from hydrogen and C1-C4 alkyl, provided that R$^{20a}$ and R$^{20b}$ are not simultaneously hydrogen; or wherein each of R$^{20a}$ and R$^{20c}$, when present, are hydrogen and R$^{20b}$ and R$^{20d}$, when present, are optionally covalently bonded and, together with the nitrogen atom to which they are attached, comprise a 5- to 6-membered heterocycle; wherein each of R$^{21a}$, R$^{21b}$, R$^{21c}$, and R$^{21d}$, when present, is independently selected from hydrogen and C1-C4 alkyl, provided that R$^{21a}$ and R$^{21b}$ are not simultaneously hydrogen; or wherein each of R$^{21a}$ and R$^{21c}$, when present, are hydrogen and R$^{21b}$ and R$^{21d}$, when present, are optionally covalently bonded and, together with the nitrogen atom to which they are attached, comprise a 5- to 6-membered heterocycle; wherein Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein R$^2$ is selected from hydrogen and C1-C4 alkyl; wherein R$^3$ is selected from —SO$_2$R$^{12}$, —(C=O)R$^{13}$, —(C=O)NR$^{14a}$R$^{14b}$, —(C=O)OR$^{15}$, and Ar$^2$; wherein R$^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 0, 1, or 2 and each of $R^{11a}$ and $R^{11b}$ is ethyl then $R^{15}$ is not methyl or ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

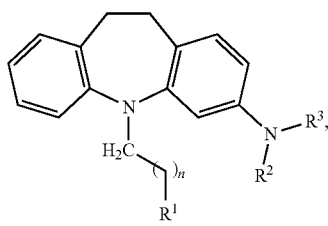

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl when n is 0, 1, or 3 and wherein each of $R^{11a}$ and $R^{11b}$, when present, is independently selected from C2-C8 alkyl when n is 2; or wherein $R^{11a}$, when present, is hydrogen and $R^{11b}$, when present, is —$C(CH_3)_2(C2-C8\ alkyl)$; or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

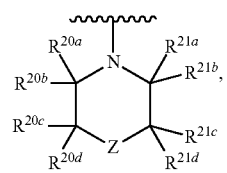

wherein Z, when present, is selected from C, NH, and $NCH_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —$(C=O)R^{13}$, —$(C=O)NR^{14a}R^{14b}$, —$(C=O)OR^{15}$, and $Ar^2$; wherein $R^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

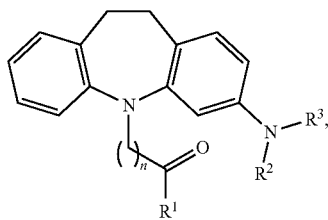

wherein n is an integer selected from 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C1-C8 alkyl; or wherein $R^{11a}$, when present, is hydrogen and $R^{11b}$, when present, is —$C(CH_3)_2$(C2-C8 alkyl); or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

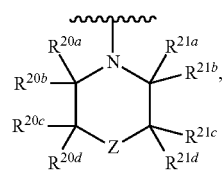

wherein Z, when present, is selected from C, NH, and $NCH_3$; wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle; wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle; wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; wherein $R^2$ is selected from hydrogen and C1-C4 alkyl; wherein $R^3$ is selected from —$SO_2R^{12}$, —$(C=O)R^{13}$, —$(C=O)NR^{14a}R^{14b}$, —$(C=O)OR^{15}$, and $Ar^2$; wherein $R^{12}$, when present, is selected from C1-C3 alkyl, C1-C3 monohaloalkyl, C1-C3 polyhaloalkyl, cyclopropyl, and —$NR^{22a}R^{22b}$; wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle; wherein $R^{13}$, when present, is selected from C1-C3 alkyl, C1-C3 monohaloalkyl, C1-C3 polyhaloalkyl, and cyclopropyl; wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle; wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl; wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, the invention relates to compounds having a structure represented by a formula:

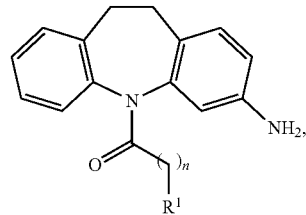

wherein n is an integer selected from 0, 1, 2, and 3; wherein $R^1$ is selected from —$OR^{10}$, —$NR^{11a}R^{11b}$, and $Ar^1$; wherein $R^{10}$, when present, is selected from hydrogen, C1-C8 alkyl, and $Cy^1$; wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; wherein each of $R^{11a}$ and $R^{11b}$, when present, is independently selected from C2-C8 alkyl; or wherein $R^{11a}$, when present, is hydrogen and $R^{11b}$, when present, is —$C(CH_3)_2$(C2-C8 alkyl); or wherein each of $R^{11a}$ and $R^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

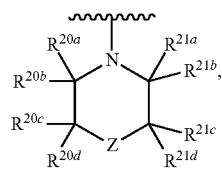

wherein Z, when present, is selected from C, NH, and NCH$_3$; wherein each of R$^{20a}$, R$^{20b}$, R$^{20c}$, and R$^{20d}$, when present, is independently selected from hydrogen and C1-C4 alkyl, provided that R$^{20a}$ and R$^{20b}$ are not simultaneously hydrogen; or wherein each of R$^{20a}$ and R$^{20c}$, when present, are hydrogen and R$^{20b}$ and R$^{20d}$, when present, are optionally covalently bonded and, together with the nitrogen atom to which they are attached, comprise a 5- to 6-membered heterocycle; wherein each of R$^{21a}$, R$^{21b}$, R$^{21c}$, and R$^{21d}$, when present, is independently selected from hydrogen and C1-C4 alkyl, provided that R$^{21a}$ and R$^{21b}$ are not simultaneously hydrogen; or wherein each of R$^{21a}$ and R$^{21c}$, when present, are hydrogen and R$^{21b}$ and R$^{21d}$, when present, are optionally covalently bonded and, together with the nitrogen atom to which they are attached, comprise a 5- to 6-membered heterocycle; wherein Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group; or a pharmaceutically acceptable salt thereof.

In one aspect, n is an integer selected from 0, 1, 2, and 3. In a still further aspect, n is an integer selected from 0, 1, and 2. In yet a further aspect, n is an integer selected from 0 and 1. In an even further aspect, n is an integer selected from 1 and 2. In a still further aspect, n is 3. In yet a further aspect, n is 2. In an even further aspect, n is 1. In a still further aspect, n is 0.

In one aspect, n is an integer selected from 1, 2, and 3. In a still further aspect, n is an integer selected from 1 and 2. In yet a further aspect, n is 3. In an even further aspect, n is 2. In a still further aspect, n is 1.

In a further aspect, the compound has a structure represented by a formula:

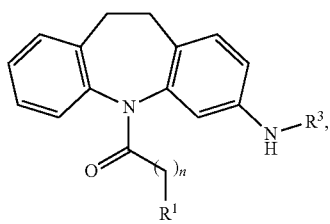

or a pharmaceutically acceptable salt thereof.

In a still further aspect, the compound has a structure represented by a formula selected from:

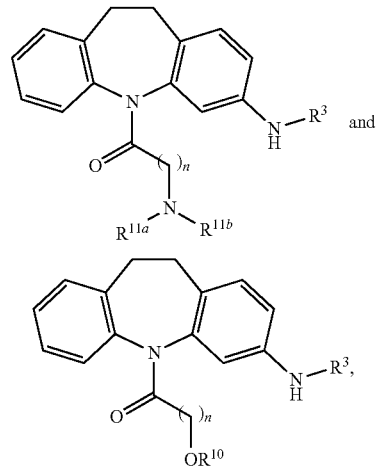

or a pharmaceutically acceptable salt thereof.

In yet a further aspect, the compound has a structure represented by a formula selected from:

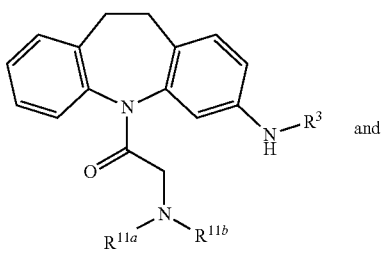

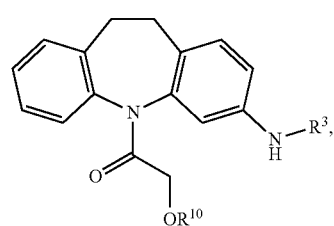

or a pharmaceutically acceptable salt thereof.

In an even further aspect, the compound has a structure represented by a formula:

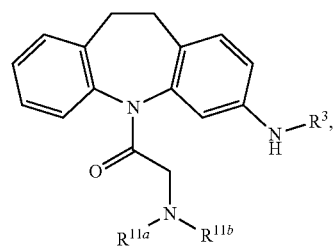

or a pharmaceutically acceptable salt thereof.

In a still further aspect, the compound has a structure represented by a formula:

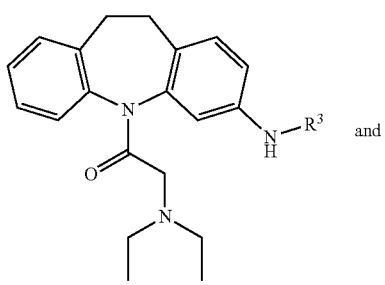 and

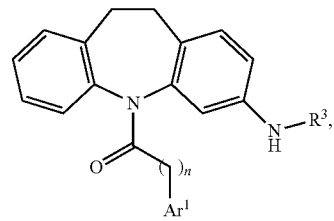

or a pharmaceutically acceptable salt thereof.

In a still further aspect, the compound has a structure represented by a formula:

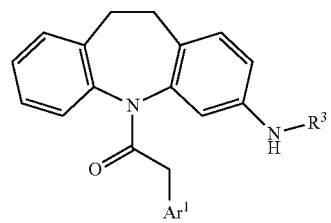

or a pharmaceutically acceptable salt thereof.

In yet a further aspect, the compound has a structure represented by a formula:

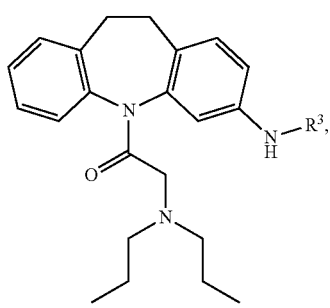

or a pharmaceutically acceptable salt thereof.

In a further aspect, the compound has a structure represented by a formula:

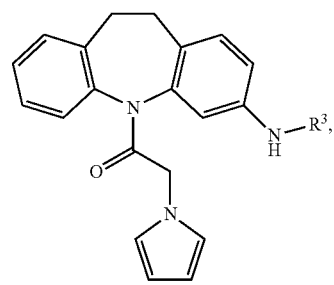

or a pharmaceutically acceptable salt thereof.

In a further aspect, the compound has a structure represented by a formula:

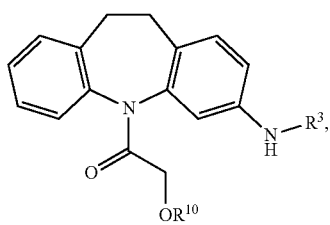

or a pharmaceutically acceptable salt thereof.

In a still further aspect, the compound has a structure represented by a formula:

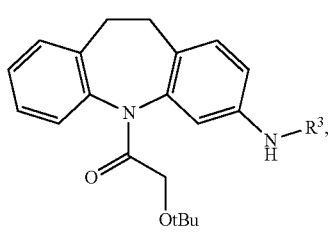

or a pharmaceutically acceptable salt thereof.

In a further aspect, the compound has a structure represented by a formula:

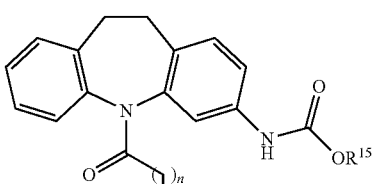

and

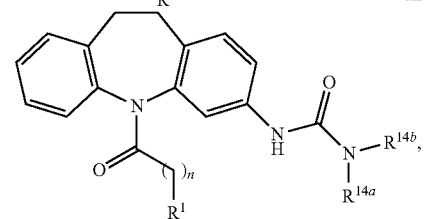

or a pharmaceutically acceptable salt thereof.

In a still further aspect, the compound has a structure represented by a formula:

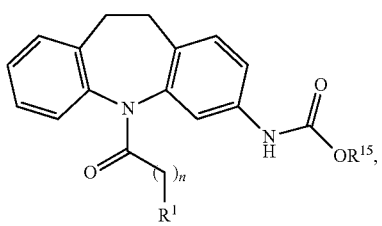

or a pharmaceutically acceptable salt thereof.

In yet a further aspect, the compound has a structure represented by a formula:

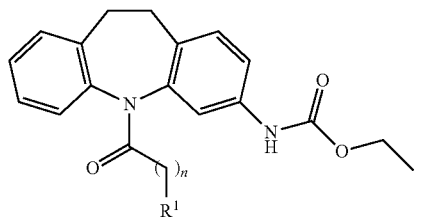

and

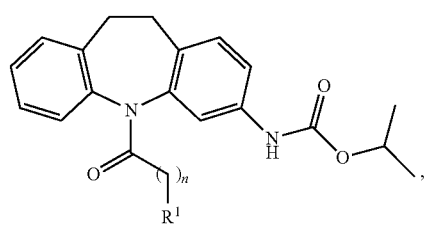

or a pharmaceutically acceptable salt thereof.

In a further aspect, the compound has a structure represented by a formula:

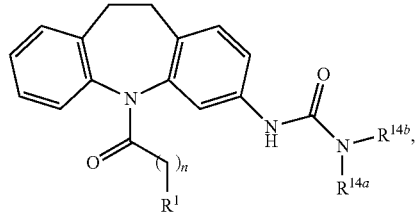

or a pharmaceutically acceptable salt thereof.

In a still further aspect, the compound has a structure represented by a formula:

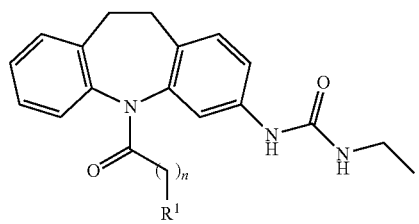

or

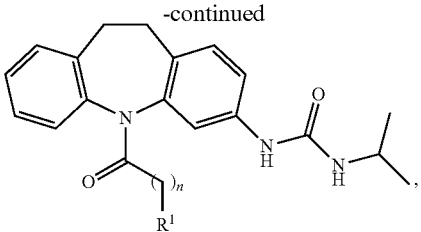

or a pharmaceutically acceptable salt thereof.

In yet a further aspect, the compound has a structure represented by a formula:

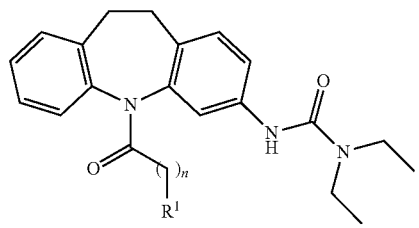

and

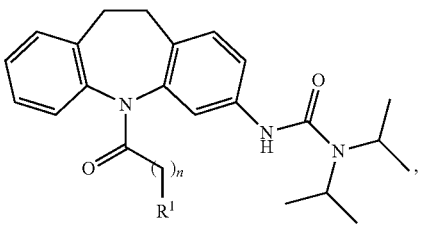

or a pharmaceutically acceptable salt thereof.

In a further aspect, the compound has a structure represented by a formula:

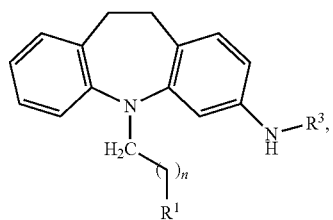

or a pharmaceutically acceptable salt thereof.

In a further aspect, the compound has a structure represented by a formula:

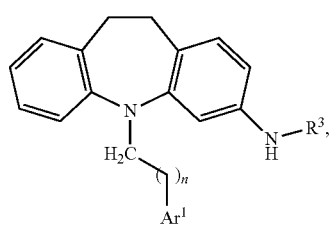

or a pharmaceutically acceptable salt thereof.

In a further aspect, the compound has a structure represented by a formula:

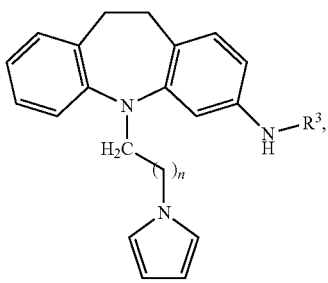

or a pharmaceutically acceptable salt thereof.

In a further aspect, the compound has a structure represented by a formula:

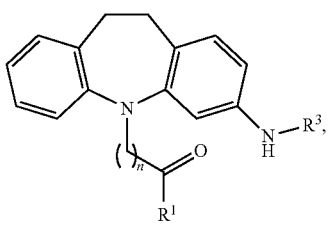

or a pharmaceutically acceptable salt thereof.

In a further aspect, the compound has a structure represented by a formula:

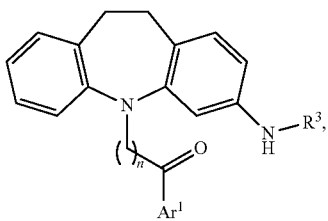

or a pharmaceutically acceptable salt thereof.

In a further aspect, the compound has a structure represented by a formula:

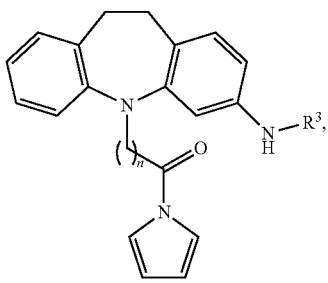

or a pharmaceutically acceptable salt thereof.

In a further aspect, the compound has a structure represented by a formula:

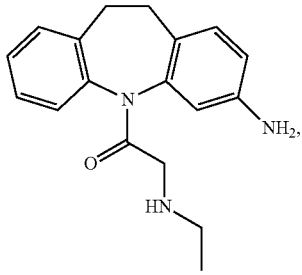 [SMILES: CCNCC(=O)N1c2ccccc2CCc2ccc(N)cc21]

or a pharmaceutically acceptable salt thereof.

a. Z Groups

In one aspect, Z, when present, is selected from C, NH, and $NCH_3$. In a further aspect, Z, when present, is selected from C and NH. In a still further aspect, Z, when present, is selected from C and $NCH_3$. In yet a further aspect, Z, when present, is selected from NH and $NCH_3$. In an even further aspect, Z, when present, is C. In a still further aspect, Z, when present, is NH. In yet a further aspect, Z, when present, is $CH_3$.

b. $R^1$ Groups

In one aspect, $R^1$ is selected from $-OR^{10}$, $-NR^{11a}R^{11b}$, and $Ar^1$. In a further aspect, $R^1$ is selected from $-OR^{10}$ and $-NR^{11a}R^{11b}$. In a still further aspect, $R^1$ is selected from $-OR^{10}$ and $Ar^1$. In yet a further aspect, $R^1$ is selected from $-NR^{11a}R^{11b}$ and $Ar^1$. In an even further aspect, $R^1$ is $-OR^{10}$. In a still further aspect, $R^1$ is $-NR^{11a}R^{11b}$. In yet a further aspect, $R^1$ is $Ar^1$.

In a further aspect, $R^1$ is selected from $-OH$, $-OCH_3$, $-OCH_2CH_3$, $-OCH_2CH_2CH_3$, $-OCH(CH_3)_2$, $-OCy^1$, $-N(CH_3)_2$, $-N(CH_2CH_3)_2$, $-N(CH_2CH_2CH_3)_2$, $-N(CH(CH_3)_2)_2$, $-N(CH_3)CH_2CH_3$, $-N(CH_3)CH_2CH_2CH_3$, $-N(CH_3)CH(CH_3)_2$, $-NHC(CH_3)_2CH_2CH_3$, $-NHC(CH_3)_2CH_2CH_2CH_3$, aziridinyl, azetidinyl, pyrrolidinyl, and $Ar^1$. In a still further aspect, $R^1$ is selected from $-OH$, $-OCH_3$, $-OCH_2CH_3$, $-OCy^1$, $-N(CH_3)_2$, $-N(CH_2CH_3)_2$, $-N(CH_3)CH_2CH_3$, $-NHC(CH_3)_2CH_2CH_3$, aziridinyl, azetidinyl, and $Ar^1$. In yet a further aspect, $R^1$ is selected from $-OH$, $-OCH_3$, $-OCy^1$, $-N(CH_3)_2$, aziridinyl, and $Ar^1$.

In a further aspect, $R^1$ is selected from $-OH$, $-OCH_3$, $-OCH_2CH_3$, $-OCH_2CH_2CH_3$, $-OCH(CH_3)_2$, $-OCy^1$, and $Ar^1$. In a still further aspect, $R^1$ is selected from $-OH$, $-OCH_3$, $-OCH_2CH_3$, $-OCy^1$, and $Ar^1$. In yet a further aspect, $R^1$ is selected from $-OH$, $-OCH_3$, $-OCy^1$, and $Ar^1$.

In a further aspect, $R^1$ is selected from $-OH$, $-OCH_3$, $-OCH_2CH_3$, $-OCH_2CH_2CH_3$, $-OCH(CH_3)_2$, and $-OCy^1$. In a still further aspect, $R^1$ is selected from $-OH$, $-OCH_3$, $-OCH_2CH_3$, and $-OCy^1$. In yet a further aspect, $R^1$ is selected from $-OH$, $-OCH_3$, and $-OCy^1$. In an even further aspect, $R^1$ is $-OCy^1$. In a still further aspect, $R^1$ is $-OCH_3$. In yet a further aspect, $R^1$ is $-OH$.

In a further aspect, $R^1$ is selected from $-N(CH_3)_2$, $-N(CH_2CH_3)_2$, $-N(CH_2CH_2CH_3)_2$, $-N(CH(CH_3)_2)_2$, $-N(CH_3)CH_2CH_3$, $-N(CH_3)CH_2CH_2CH_3$, $-N(CH_3)CH(CH_3)_2$, $-NHC(CH_3)_2CH_2CH_3$, $-NHC(CH_3)_2CH_2CH_2CH_3$, aziridinyl, azetidinyl, pyrrolidinyl, and $Ar^1$. In a still further aspect, $R^1$ is selected from $-N(CH_3)_2$, $-N(CH_2CH_3)_2$, $-N(CH_3)CH_2CH_3$, $-NHC(CH_3)_2CH_2CH_3$, aziridinyl, azetidinyl, and $Ar^1$. In yet a further aspect, $R^1$ is selected from $-N(CH_3)_2$, aziridinyl, and $Ar^1$. In an even further aspect, $R^1$ is selected from $-N(CH_3)_2$ and $Ar^1$.

In a further aspect, $R^1$ is selected from —N(CH$_3$)$_2$, —N(CH$_2$CH$_3$)$_2$, —N(CH$_2$CH$_2$CH$_3$)$_2$, —N(CH(CH$_3$)$_2$)$_2$, —N(CH$_3$)CH$_2$CH$_3$, —N(CH$_3$)CH$_2$CH$_2$CH$_3$, —N(CH$_3$)CH(CH$_3$)$_2$, —NHC(CH$_3$)$_2$CH$_2$CH$_3$, —NHC(CH$_3$)$_2$CH$_2$CH$_2$CH$_3$, aziridinyl, azetidinyl, and pyrrolidinyl. In a still further aspect, $R^1$ is selected from —N(CH$_3$)$_2$, —N(CH$_2$CH$_3$)$_2$, —N(CH$_3$)CH$_2$CH$_3$, —NHC(CH$_3$)$_2$CH$_2$CH$_3$, aziridinyl, and azetidinyl. In yet a further aspect, $R^1$ is selected from —N(CH$_3$)$_2$, and aziridinyl. In an even further aspect, $R^1$ is —N(CH$_3$)$_2$. In a still further aspect, $R^1$ is —N(CH$_2$CH$_3$)$_2$.

c. $R^2$ Groups

In one aspect, $R^2$ is selected from hydrogen and C1-C4 alkyl. In a further aspect, $R^2$ is C1-C4 alkyl. In a still further aspect, $R^2$ is ethyl. In yet a further aspect, $R^2$ is methyl. In an even further aspect, $R^2$ is hydrogen.

In a further aspect, $R^2$ is selected from hydrogen, methyl, ethyl, propyl, isopropyl, tert-butyl, sec-butyl, and isobutyl. In a still further aspect, $R^2$ is selected from hydrogen, methyl, ethyl, propyl, and isopropyl. In yet a further aspect, $R^2$ is selected from hydrogen, methyl, and ethyl. In an even further aspect, $R^2$ is selected from hydrogen and ethyl. In a still further aspect, $R^2$ is selected from hydrogen and methyl.

a. $R^3$ Groups

In one aspect, $R^3$ is selected from —SO$_2$R$^{12}$, —C(=O)R$^{13}$, —C(=O)NR$^{14a}$R$^{14b}$, —C(=O)OR$^{15}$, and Ar$^2$. In a further aspect, $R^3$ is selected from —C(=O)R$^{13}$, —C(=O)NR$^{14a}$R$^{14b}$, —C(=O)OR$^{15}$, and Ar$^2$. In a still further aspect, $R^3$ is selected from —C(=O)NR$^{14a}$R$^{14b}$, —C(=O)OR$^{15}$, and Ar$^2$. In yet a further aspect, $R^3$ is selected from —C(=O)OR$^{15}$ and Ar$^2$. In an even further aspect, $R^3$ is —SO$_2$R$^{12}$. In a still further aspect, $R^3$ is —C(=O)R$^{13}$. In yet a further aspect, $R^3$ is —C(=O)NR$^{14a}$R$^{14b}$. In an even further aspect, $R^3$ is —C(=O)OR$^{15}$. In a still further aspect, $R^3$ is Ar$^2$.

In a further aspect, $R^3$ is selected from —SO$_2$R$^{12}$, —C(=O)R$^{13}$, —C(=O)NR$^{14a}$R$^{14b}$, and —C(=O)OR$^{15}$. In a still further aspect, $R^3$ is selected from —C(=O)R$^{13}$, —C(=O)NR$^{14a}$R$^{14b}$, and —C(=O)OR$^{15}$. In yet a further aspect, $R^3$ is selected from —C(=O)NR$^{14a}$R$^{14b}$ and —C(=O)OR$^{15}$.

In a further aspect, $R^3$ is selected from —SO$_2$CH$_3$, —SO$_2$CH$_2$CH$_3$, —SO$_2$CH$_2$F, —SO$_2$CH$_2$Cl, —SO$_2$CH$_2$CH$_2$F, —SO$_2$CH$_2$CH$_2$Cl, —SO$_2$CHF$_2$, —SO$_2$CF$_3$, —SO$_2$CHCl$_2$, —SO$_2$CCl$_3$, —SO$_2$CH$_2$CHF$_2$, —SO$_2$CH$_2$CF$_3$, —SO$_2$CH$_2$CHCl$_2$, —SO$_2$CH$_2$CCl$_3$, —SO$_2$cyclopropyl, —SO$_2$NH$_2$, —SO$_2$NHCH$_3$, —SO$_2$N(CH$_3$)$_2$, —SO$_2$NHCH$_2$CH$_3$, —SO$_2$N(CH$_2$CH$_3$)$_2$, —C(=O)CH$_3$, —C(=O)CH$_2$CH$_3$, —C(=O)CH$_2$F, —C(=O)CH$_2$Cl, —C(=O)CH$_2$CH$_2$F, —C(=O)CH$_2$CH$_2$Cl, —C(=O)CHF$_2$, —C(=O)CF$_3$, —C(=O)CHCl$_2$, —C(=O)CCl$_3$, —C(=O)CH$_2$CHF$_2$, —C(=O)CH$_2$CF$_3$, —C(=O)CH$_2$CHCl$_2$, —C(=O)CH$_2$CCl$_3$, —C(=O)cyclopropyl, —C(=O)NH$_2$, —C(=O)NHCH$_3$, —C(=O)N(CH$_3$)$_2$, —C(=O)NHCH$_2$CH$_3$, —C(=O)N(CH$_2$CH$_3$)$_2$, —C(=O)OCH$_3$, —C(=O)OCH$_2$CH$_3$, —C(=O)OCH$_2$F, —C(=O)OCH$_2$Cl, —C(=O)OCH$_2$CH$_2$F, —C(=O)OCH$_2$CH$_2$Cl, —C(=O)OCHF$_2$, —C(=O)OCF$_3$, —C(=O)OCHCl$_2$, —C(=O)OCCl$_3$, —C(=O)OCH$_2$CHF$_2$, —C(=O)OCH$_2$CF$_3$, —C(=O)OCH$_2$CHCl$_2$, —C(=O)OCH$_2$CCl$_3$, —C(=O)OCy$^2$, and Ar$^2$. In a still further aspect, $R^3$ is selected from —SO$_2$CH$_3$, —SO$_2$CH$_2$F, —SO$_2$CH$_2$Cl, —SO$_2$CHF$_2$, —SO$_2$CF$_3$, —SO$_2$CHCl$_2$, —SO$_2$CCl$_3$, —SO$_2$cyclopropyl, —SO$_2$NH$_2$, —SO$_2$NHCH$_3$, —SO$_2$N(CH$_3$)$_2$, —C(=O)CH$_3$, —C(=O)CH$_2$F, —C(=O)CH$_2$Cl, —C(=O)CHF$_2$, —C(=O)CF$_3$, —C(=O)CHCl$_2$, —C(=O)NH$_2$, —C(=O)NHCH$_3$, —C(=O)N(CH$_3$)$_2$, —C(=O)OCH$_3$, —C(=O)OCH$_2$F, —C(=O)OCH$_2$Cl, —C(=O)OCHF$_2$, —C(=O)OCF$_3$, —C(=O)OCHCl$_2$, —C(=O)OCCl$_3$, —C(=O)OCy$^2$, and Ar$^2$.

In a further aspect, $R^3$ is selected from —SO$_2$CH$_3$, —SO$_2$CH$_2$CH$_3$, —SO$_2$CH$_2$F, —SO$_2$CH$_2$Cl, —SO$_2$CH$_2$CH$_2$F, —SO$_2$CH$_2$CH$_2$Cl, —SO$_2$CHF$_2$, —SO$_2$CF$_3$, —SO$_2$CHCl$_2$, —SO$_2$CCl$_3$, —SO$_2$CH$_2$CHF$_2$, —SO$_2$CH$_2$CF$_3$, —SO$_2$CH$_2$CHCl$_2$, —SO$_2$CH$_2$CCl$_3$, —SO$_2$cyclopropyl, —SO$_2$NH$_2$, —SO$_2$NHCH$_3$, —SO$_2$N(CH$_3$)$_2$, —SO$_2$NHCH$_2$CH$_3$, —SO$_2$N(CH$_2$CH$_3$)$_2$, —C(=O)CH$_3$, —C(=O)CH$_2$CH$_3$, —C(=O)CH$_2$F, —C(=O)CH$_2$Cl, —C(=O)CH$_2$CH$_2$F, —C(=O)CH$_2$CH$_2$Cl, —C(=O)CHF$_2$, —C(=O)CF$_3$, —C(=O)CHCl$_2$, —C(=O)CCl$_3$, —C(=O)CH$_2$CHF$_2$, —C(=O)CH$_2$CF$_3$, —C(=O)CH$_2$CHCl$_2$, —C(=O)CH$_2$CCl$_3$, —C(=O)cyclopropyl, —C(=O)NH$_2$, —C(=O)NHCH$_3$, —C(=O)N(CH$_3$)$_2$, —C(=O)NHCH$_2$CH$_3$, —C(=O)N(CH$_2$CH$_3$)$_2$, —C(=O)OCH$_3$, —C(=O)OCH$_2$F, —C(=O)OCH$_2$Cl, —C(=O)OCHF$_2$, —C(=O)OCF$_3$, —C(=O)OCHCl$_2$, —C(=O)OCCl$_3$, and —C(=O)OCy$^2$.

In a further aspect, $R^3$ is selected from —SO$_2$CH$_3$, —SO$_2$CH$_2$CH$_3$, —SO$_2$CH$_2$F, —SO$_2$CH$_2$Cl, —SO$_2$CH$_2$CH$_2$F, —SO$_2$CH$_2$CH$_2$Cl, —SO$_2$CHF$_2$, —SO$_2$CF$_3$, —SO$_2$CHCl$_2$, —SO$_2$CCl$_3$, —SO$_2$CH$_2$CHF$_2$, —SO$_2$CH$_2$CF$_3$, —SO$_2$CH$_2$CHCl$_2$, —SO$_2$CH$_2$CCl$_3$, —SO$_2$cyclopropyl, —SO$_2$NH$_2$, —SO$_2$NHCH$_3$, —SO$_2$N(CH$_3$)$_2$, —SO$_2$NHCH$_2$CH$_3$, and —SO$_2$N(CH$_2$CH$_3$)$_2$. In a still further aspect, $R^3$ is selected from —SO$_2$CH$_3$, —SO$_2$CH$_2$F, —SO$_2$CH$_2$Cl, —SO$_2$CHF$_2$, —SO$_2$CF$_3$, —SO$_2$CHCl$_2$, —SO$_2$CCl$_3$, —SO$_2$cyclopropyl, —SO$_2$NH$_2$, —SO$_2$NHCH$_3$, and —SO$_2$N(CH$_3$)$_2$. In yet a further aspect, $R^3$ is selected from —SO$_2$CH$_3$, —SO$_2$NH$_2$, —SO$_2$NHCH$_3$, and —SO$_2$N(CH$_3$)$_2$. In an even further aspect, $R^3$ is —SO$_2$CH$_3$. In a still further aspect, $R^3$ is —SO$_2$CH$_2$CH$_3$. In yet a further aspect, $R^3$ is —SO$_2$NH$_2$. In an even further aspect, $R^3$ is —SO$_2$NHCH$_3$. In a still further aspect, $R^3$ is —SO$_2$N(CH$_3$)$_2$.

In a further aspect, $R^3$ is selected from —C(=O)CH$_3$, —C(=O)CH$_2$CH$_3$, —C(=O)CH$_2$F, —C(=O)CH$_2$Cl, —C(=O)CH$_2$CH$_2$F, —C(=O)CH$_2$CH$_2$Cl, —C(=O)CHF$_2$, —C(=O)CF$_3$, —C(=O)CHCl$_2$, —C(=O)CCl$_3$, —C(=O)CH$_2$CHF$_2$, —C(=O)CH$_2$CF$_3$, —C(=O)CH$_2$CHCl$_2$, —C(=O)CH$_2$CCl$_3$, —C(=O)cyclopropyl, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$. In a still further aspect, $R^3$ is selected from —C(=O)CH$_3$, —C(=O)CH$_2$F, —C(=O)CH$_2$Cl, —C(=O)CHF$_2$, —C(=O)CF$_3$, —C(=O)CHCl$_2$, —C(=O)CCl$_3$, —C(=O)cyclopropyl, —C(=O)NH$_2$, —C(=O)NHCH$_3$, and —C(=O)N(CH$_3$)$_2$. In yet a further aspect, $R^3$ is selected from —C(=O)CH$_3$, —C(=O)NH$_2$, —C(=O)NHCH$_3$, and —C(=O)N(CH$_3$)$_2$. In an even further aspect, $R^3$ is —C(=O)CH$_3$. In a still further aspect, $R^3$ is —C(=O)

CH$_2$CH$_3$. In yet a further aspect, R$^3$ is —C(=O)NH$_2$. In an even further aspect, R$^3$ is —C(=O)NHCH$_3$. In a still further aspect, R$^3$ is —C(=O)N(CH$_3$)$_2$.

In a further aspect, R$^3$ is selected from —C(=O)OCH$_3$, —C(=O)OCH$_2$CH$_3$, —C(=O)OCH$_2$F, —C(=O)OCH$_2$Cl, —C(=O)OCH$_2$CH$_2$F, —C(=O)OCH$_2$CH$_2$Cl, —C(=O)OCHF$_2$, —C(=O)OCF$_3$, —C(=O)OCHCl$_2$, —C(=O)OCCl$_3$, —C(=O)OCH$_2$CHF$_2$, —C(=O)OCH$_2$CF$_3$, —C(=O)OCH$_2$CHCl$_2$, —C(=O)OCH$_2$CCl$_3$, and —C(=O)OCy$^2$. In a still further aspect, R$^3$ is selected from —C(=O)OCH$_3$, —C(=O)OCH$_2$F, —C(=O)OCH$_2$Cl, —C(=O)OCHF$_2$, —C(=O)OCF$_3$, —C(=O)OCHCl$_2$, —C(=O)OCCl$_3$, and —C(=O)OCy$^2$. In yet a further aspect, R$^3$ is selected from —C(=O)OCH$_3$ and —C(=O)OCy$^2$. In an even further aspect, R$^3$ is —C(=O)OCH$_3$. In a still further aspect, R$^3$ is —C(=O)OCH$_2$CH$_3$. In yet a further aspect, R$^3$ is —C(=O)OCy$^2$.

b. R$^{10}$ Groups

In one aspect, R$^{10}$, when present, is selected from hydrogen, C1-C8 alkyl, and Cy$^1$. In a still further aspect, R$^{10}$, when present, is selected from hydrogen, C1-C4 alkyl, and Cy$^1$.

In one aspect, R$^{10}$, when present, is selected from hydrogen, C3-C8 alkyl, and Cy$^1$. In a still further aspect, R$^{10}$, when present, is selected from hydrogen, C3-C5 alkyl, and Cy$^1$;

In a further aspect, R$^{10}$, when present, is selected from hydrogen and Cy$^1$. In a still further aspect, R$^{10}$, when present, is hydrogen. In yet a further aspect, R$^{10}$, when present, is Cy$^1$.

In a further aspect, R$^{10}$, when present, is selected from hydrogen and C1-C8 alkyl. In a still further aspect, R$^{10}$, when present, is selected from hydrogen and C1-C4 alkyl. In yet a further aspect, R$^{10}$, when present, is t-butyl. In an even further aspect, R$^{10}$, when present, is ethyl. In a still further aspect, R$^{10}$, when present, is methyl. In yet a further aspect, R$^{10}$, when present, is C1-C8 alkyl. In an even further aspect, R$^{10}$, when present, is C1-C4 alkyl. In a still further aspect, R$^{10}$, when present, is hydrogen.

In a further aspect, R$^{10}$, when present, is selected from hydrogen and C3-C8 alkyl. In a still further aspect, R$^{10}$, when present, is selected from hydrogen and C3-C5 alkyl. In yet a further aspect, R$^{10}$, when present, is C3-C8 alkyl. In an even further aspect, R$^{10}$, when present, is C3-C5 alkyl.

In a further aspect, R$^{10}$, when present, is selected from hydrogen, methyl, ethyl, propyl, isopropyl, tert-butyl, sec-butyl, and isobutyl. In a still further aspect, R$^{10}$, when present, is selected from hydrogen, methyl, ethyl, propyl, and isopropyl. In yet a further aspect, R$^{10}$, when present, is selected from hydrogen, methyl, and ethyl. In an even further aspect, R$^{10}$, when present, is selected from hydrogen and ethyl. In a still further aspect, R$^{10}$, when present, is selected from hydrogen and methyl.

In a further aspect, R$^{10}$, when present, is selected from hydrogen, propyl, isopropyl, tert-butyl, sec-butyl, and isobutyl. In a still further aspect, R$^{10}$, when present, is selected from hydrogen, propyl, and isopropyl. In yet a further aspect, R$^{10}$, when present, is selected from hydrogen and propyl. In an even further aspect, R$^{10}$, when present, is selected from hydrogen and isopropyl.

c. R$^{11a}$ and R$^{11b}$ Groups

In one aspect, each of R$^{11a}$ and R$^{11b}$, when present, is independently C1-C8 alkyl; or R$^{11a}$, when present, is hydrogen and R$^{11b}$, when present, is —C(CH$_3$)$_2$(C2-C8 alkyl); or each of R$^{11a}$ and R$^{11b}$, when present, are optionally covalently bonded to the nitrogen atom to which they are attached, comprise a 3- to 5-membered heterocycle; or each of R$^{11a}$ and R$^{11b}$, when present, are optionally covalently bonded and, together with the nitrogen atom to which they are attached, comprise a 6-membered heterocycle having a structure represented by a formula:

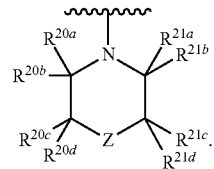

In one aspect, each of R$^{11a}$ and R$^{11b}$, when present, is independently selected from hydrogen and C1-C8 alkyl; or each of R$^{11a}$ and R$^{11b}$, when present, are optionally covalently bonded and, together with the nitrogen atom to which they are attached, comprise a 3- to 6-membered heterocycle.

In one aspect, each of R$^{11a}$ and R$^{11b}$, when present, is independently selected from C2-C8 alkyl; or wherein R$^{11a}$, when present, is hydrogen and R$^{11b}$, when present, is —C(CH$_3$)$_2$(C2-C8 alkyl); or wherein each of R$^{11a}$ and R$^{11b}$, when present, are optionally covalently bonded and, together with the nitrogen atom to which they are attached, comprise a 3- to 5-membered heterocycle; or wherein each of R$^{11a}$ and R$^{11b}$, when present, are optionally covalently bonded and, together with the nitrogen atom to which they are attached, comprise a 6-membered heterocycle having a structure represented by a formula:

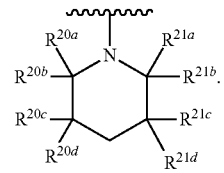

In one aspect, each of R$^{11a}$ and R$^{11b}$, when present, is independently selected from C1-C8 alkyl when n is 0, 1, or 3 and wherein each of R$^{11a}$ and R$^{11b}$, when present, is independently selected from C2-C8 alkyl when n is 2; or wherein R$^{11a}$, when present, is hydrogen and R$^{11b}$, when present, is —C(CH$_3$)$_2$(C2-C8 alkyl); or wherein each of R$^{11a}$ and R$^{11b}$, when present, are optionally covalently bonded and, together with the nitrogen atom to which they are attached, comprise a 3- to 5-membered heterocycle; or wherein each of R$^{11a}$ and R$^{11b}$, when present, are optionally covalently bonded and, together with the nitrogen atom to which they are attached, comprise a 6-membered heterocycle having a structure represented by a formula:

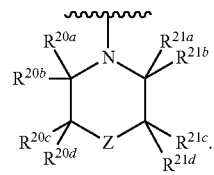

In a further aspect, R$^{11a}$, when present, is hydrogen and R$^{11b}$, when present, is —C(CH$_3$)$_2$(C2-C8 alkyl); or wherein each of R$^{11a}$ and R$^{11b}$, when present, are optionally covalently bonded and, together with the nitrogen atom to which they are attached, comprise a 3- to 5-membered heterocycle; or wherein each of $R^{11a}$ and $R^{11b}$, when present, are optionally covalently bonded and, together with the nitrogen atom to which they are attached, comprise a 6-membered heterocycle having a structure represented by a formula:

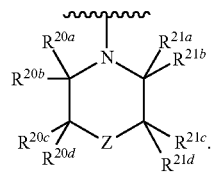

In a further aspect, each of $R^{11a}$ and $R^{11b}$, when present, is independently C1-C8 alkyl. In a still further aspect, each of $R^{11a}$ and $R^{11b}$, when present, is independently C1-C4 alkyl. In yet a further aspect, each of $R^{11a}$ and $R^{11b}$, when present, is independently selected from methyl, ethyl, propyl, and isopropyl. In an even further aspect, each of $R^{11a}$ and $R^{11b}$, when present, is independently selected from methyl and ethyl. In a still further aspect, each of $R^{11a}$ and $R^{11b}$, when present, is ethyl. In yet a further aspect, each of $R^{11a}$ and $R^{11b}$, when present, is methyl.

In a further aspect, each of $R^{11a}$ and $R^{11b}$, when present, is independently C2-C8 alkyl. In a still further aspect, each of $R^{11a}$ and $R^{11b}$, when present, is independently C2-C4 alkyl. In yet a further aspect, each of $R^{11a}$ and $R^{11b}$, when present, is independently selected from ethyl, propyl, and isopropyl. In an even further aspect, each of $R^{11a}$ and $R^{11b}$, when present, is propyl. In a still further aspect, each of $R^{11a}$ and $R^{11b}$, when present, is isopropyl.

In a further aspect, $R^{11a}$, when present, is hydrogen and $R^{11b}$, when present, is —C(CH$_3$)$_2$(C2-C8 alkyl). In a still further aspect, $R^{11a}$, when present, is hydrogen and $R^{11b}$, when present, is —C(CH$_3$)$_2$(C2-C4 alkyl). In yet a further aspect, $R^{11a}$, when present, is hydrogen and $R^{11b}$, when present, is selected from —C(CH$_3$)$_2$CH$_3$, —C(CH$_3$)$_2$CH$_2$CH$_3$, —C(CH$_3$)$_2$CH$_2$CH$_2$CH$_3$, and —C(CH$_3$)$_2$CH(CH$_3$)$_2$. In an even further aspect, $R^{11a}$, when present, is hydrogen and $R^{11b}$, when present, is selected from —C(CH$_3$)$_2$CH$_3$, —C(CH$_3$)$_2$CH$_2$CH$_3$. In a still further aspect, $R^{11a}$, when present, is hydrogen and $R^{11b}$, when present, is —C(CH$_3$)$_2$CH$_2$CH$_3$. In yet a further aspect, $R^{11a}$, when present, is hydrogen and $R^{11b}$, when present, is —C(CH$_3$)$_2$CH$_3$.

In a further aspect, each of $R^{11a}$ and $R^{11b}$, when present, are optionally covalently bonded and, together with the nitrogen atom to which they are attached, comprise a 3- to 5-membered heterocycle. In a still further aspect, each of $R^{11a}$ and $R^{11b}$, when present, are optionally covalently bonded and, together with the nitrogen atom to which they are attached, comprise a 3- to 5-membered heterocycle selected from aziridine, azetidine, and pyrrolidine. In yet a further aspect, each of $R^{11a}$ and $R^{11b}$, when present, are optionally covalently bonded and, together with the nitrogen atom to which they are attached, comprise a 3- to 5-membered cycle selected from aziridine and azetidine. In an even further aspect, each of $R^{11a}$ and $R^{11b}$, when present, are optionally covalently bonded and, together with the nitrogen atom to which they are attached, comprise an aziridine. In a still further aspect, each of $R^{11a}$ and $R^{11b}$, when present, are optionally covalently bonded and, together with the nitrogen atom to which they are attached, comprise an azetidine. In yet a further aspect, each of $R^{11a}$ and $R^{11b}$, when present, are optionally covalently bonded and, together with the nitrogen atom to which they are attached, comprise a pyrrolidine.

In a further aspect, each of $R^{11a}$ and $R^{11b}$, when present, are optionally covalently bonded and, together with the nitrogen atom to which they are attached, comprise a 3- to 5-membered heterocycle selected from:

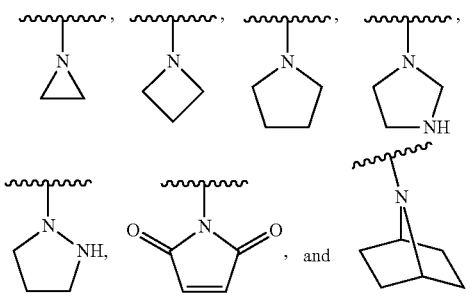

In a still further aspect, $R^{11a}$ and $R^{11b}$, when present, are optionally covalently bonded and, together with the nitrogen atom to which they are attached, comprise a 3- to 5-membered heterocycle selected from:

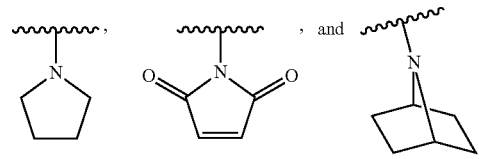 [SMILES: *N1CCCC1 ; *N1C(=O)C=CC1=O ; *N1C2CCC1CC2]

In a further aspect, each of $R^{11a}$ and $R^{11b}$, when present, are optionally covalently bonded and, together with the nitrogen atom to which they are attached, comprise a 6-membered heterocycle having a structure represented by a formula:

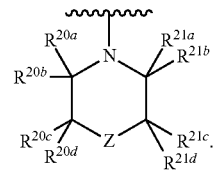

In a still further aspect, each of $R^{11a}$ and $R^{11b}$, when present, are optionally covalently bonded and, together with the nitrogen atom to which they are attached, comprise a 6-membered heterocycle having a structure represented by a formula:

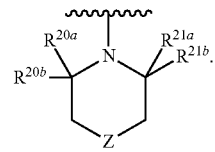

In yet a further aspect, each of $R^{11a}$ and $R^{11b}$, when present, are optionally covalently bonded and, together with the nitrogen atom to which they are attached, comprise a 6-membered heterocycle having a structure represented by a formula:

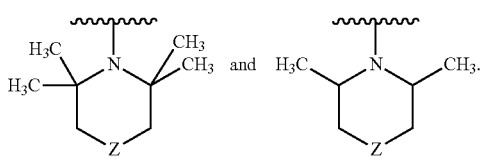

In an even further aspect, each of $R^{11a}$ and $R^{11b}$, when present, are optionally covalently bonded and, together with the nitrogen atom to which they are attached, comprise a 6-membered heterocycle having a structure represented by a formula:

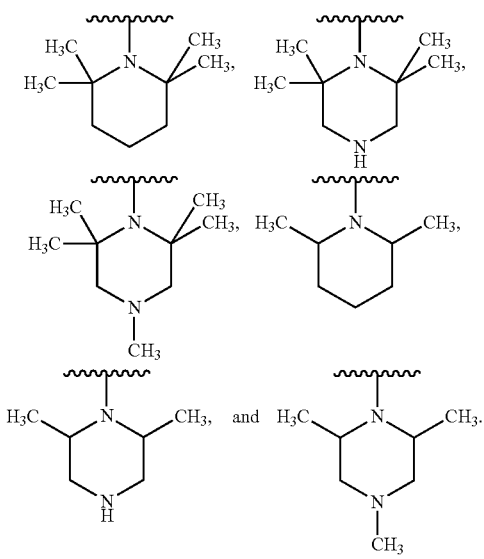

In a still further aspect, each of $R^{11a}$ and $R^{11b}$, when present, are optionally covalently bonded and, together with the nitrogen atom to which they are attached, comprise a 6-membered heterocycle having a structure represented by a formula:

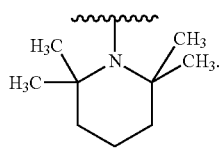

In a further aspect, each of $R^{11a}$ and $R^{11b}$, when present, are optionally covalently bonded and, together with the nitrogen atom to which they are attached, comprise a 6-membered heterocycle having a structure represented by a formula:

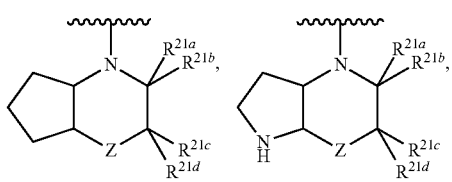

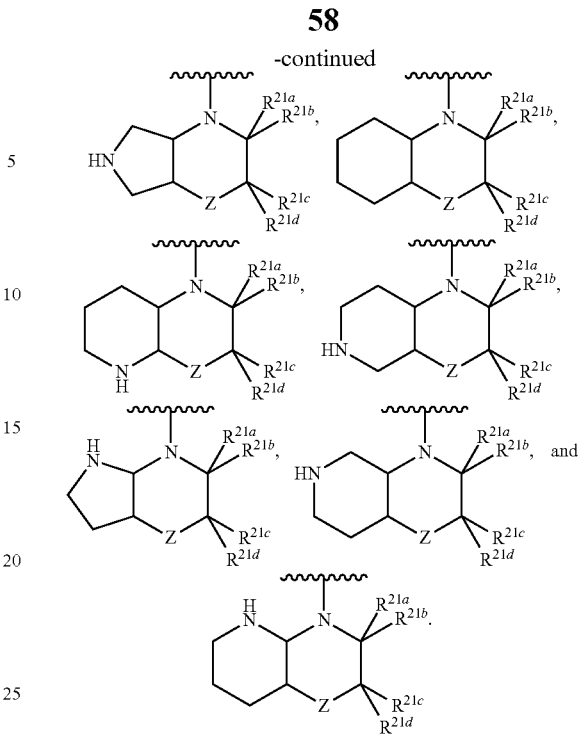

In a further aspect, each of $R^{11a}$ and $R^{11b}$, when present, is independently selected from hydrogen and C1-C8 alkyl. In a still further aspect, each of $R^{11a}$ and $R^{11b}$, when present, is independently selected from hydrogen and C1-C4 alkyl. In yet a further aspect, each of $R^{11a}$ and $R^{11b}$, when present, is hydrogen.

In a further aspect, each of $R^{11a}$ and $R^{11b}$, when present, is independently selected from hydrogen, methyl, ethyl, propyl, isopropyl, tert-butyl, sec-butyl, and isobutyl. In a still further aspect, each of $R^{11a}$ and $R^{11b}$, when present, is independently selected from hydrogen, methyl, ethyl, propyl, and isopropyl. In yet a further aspect, each of $R^{11a}$ and $R^{11b}$, when present, is independently selected from hydrogen, methyl, and ethyl. In an even further aspect, each of $R^{11a}$ and $R^{11b}$, when present, is independently selected from hydrogen and ethyl. In a still further aspect, each of $R^{11a}$ and $R^{11b}$, when present, is independently selected from hydrogen and methyl.

In a further aspect, each of $R^{11a}$ and $R^{11b}$, when present, are optionally covalently bonded and, together with the nitrogen atom to which they are attached, comprise a 3- to 6-membered heterocycle. In a still further aspect, each of $R^{11a}$ and $R^{11b}$, when present, are optionally covalently bonded and, together with the nitrogen atom to which they are attached, comprise a 3- to 6-membered heterocycle selected from aziridine, azetidine, pyrrolidine, piperidine, morpholine, and piperazine. In yet a further aspect, each of $R^{11a}$ and $R^{11b}$, when present, are optionally covalently bonded and, together with the nitrogen atom to which they are attached, comprise a 3- to 6-membered heterocycle selected from aziridine, azetidine, and pyrrolidine. In an even further aspect, each of $R^{11a}$ and $R^{11b}$, when present, are optionally covalently bonded and, together with the nitrogen atom to which they are attached, comprise a 3- to 6-membered heterocycle selected from aziridine and azetidine. In a still further aspect, each of $R^{11a}$ and $R^{11b}$, when present, are optionally covalently bonded and, together with the nitrogen atom to which they are attached, comprise an aziridine. In yet a further aspect, each of $R^{11a}$ and $R^{11b}$, when present, are optionally covalently bonded and, together with the nitrogen atom to which they are attached, comprise an azetidine. In an even further aspect, each of $R^{11a}$ and $R^{11b}$, when present, are optionally covalently bonded and, together with the nitrogen atom to which they are attached, comprise a pyrrolidine. In a still further aspect, each of $R^{11a}$ and $R^{11b}$, when present, are optionally covalently bonded and, together with the nitrogen atom to which they are attached, comprise a piperidine. In yet a further aspect, each of $R^{11a}$ and $R^{11b}$, when present, are optionally covalently bonded and, together with the nitrogen atom to which they are attached, comprise a morpholine. In an even further aspect, each of $R^{11a}$ and $R^{11b}$, when present, are optionally covalently bonded and, together with the nitrogen atom to which they are attached, comprise a piperazine.

d. $R^{12}$ Groups

In one aspect, $R^{12}$, when present, is selected from C1-C3 alkyl, C1-C3 monohaloalkyl, C1-C3 polyhaloalkyl, cyclopropyl, and —$NR^{22a}R^{22b}$. In a further aspect, $R^{12}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, cyclopropyl, and —$NR^{22a}R^{22b}$. In a still further aspect, $R^{12}$, when present, is selected from hydrogen, methyl, —$CH_2F$, —$CH_2Cl$, —$CHF_2$, —$CF_3$, —$CHCl_2$, —$CCl_3$, cyclopropyl, and —$NR^{22a}R^{22b}$. In yet a further aspect, $R^{12}$, when present, is selected from hydrogen, methyl, —$CH_2F$, —$CHF_2$, —$CF_3$, cyclopropyl, and —$NR^{22a}R^{22b}$. In an even further aspect, $R^{12}$, when present, is selected from hydrogen, methyl, —$CF_3$, cyclopropyl, and —$NR^{22a}R^{22b}$.

In a further aspect, $R^{12}$, when present, is selected from hydrogen, C1-C3 monohaloalkyl, C1-C3 polyhaloalkyl, cyclopropyl, and —$NR^{22a}R^{22b}$. In a still further aspect, $R^{12}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, cyclopropyl, and —$NR^{22a}R^{22b}$. In yet a further aspect, $R^{12}$, when present, is selected from hydrogen, —$CH_2F$, —$CH_2Cl$, —$CHF_2$, —$CF_3$, —$CHCl_2$, —$CCl_3$, cyclopropyl, and —$NR^{22a}R^{22b}$. In an even further aspect, $R^{12}$, when present, is selected from hydrogen, —$CH_2F$, —$CHF_2$, —$CF_3$, cyclopropyl, and —$NR^{22a}R^{22b}$. In a still further aspect, $R^{12}$, when present, is selected from hydrogen, —$CF_3$ cyclopropyl, and —$NR^{22a}R^{22b}$.

In a further aspect, $R^{12}$, when present, is selected from hydrogen, C1-C3 alkyl, cyclopropyl, and —$NR^{22a}R^{22b}$. In a still further aspect, $R^{12}$, when present, is selected from hydrogen, methyl, ethyl, cyclopropyl, and —$NR^{22a}R^{22b}$. In yet a further aspect, $R^{12}$, when present, is selected from hydrogen, methyl, cyclopropyl, and —$NR^{22a}R^{22b}$.

In a further aspect, $R^{12}$, when present, is selected from hydrogen, C1-C3 alkyl, C1-C3 monohaloalkyl, and C1-C3 polyhaloalkyl. In a still further aspect, $R^{12}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{12}$, when present, is selected from hydrogen, methyl, —$CH_2F$, —$CH_2Cl$, —$CHF_2$, —$CF_3$, —$CHCl_2$, and —$CCl_3$. In an even further aspect, $R^{12}$, when present, is selected from hydrogen, methyl, —$CH_2F$, —$CHF_2$, and —$CF_3$. In a still further aspect, $R^{12}$, when present, is selected from hydrogen, methyl, and —$CF_3$.

In a further aspect, $R^{12}$, when present, is selected from hydrogen, C1-C3 monohaloalkyl, and C1-C3 polyhaloalkyl. In a still further aspect, $R^{12}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{12}$, when present, is selected from hydrogen, —$CH_2F$, —$CH_2Cl$, —$CHF_2$, —$CF_3$, —$CHCl_2$, and —$CCl_3$. In an even further aspect, $R^{12}$, when present, is selected from hydrogen, —$CH_2F$, —$CHF_2$, and —$CF_3$. In a still further aspect, $R^{12}$, when present, is selected from hydrogen and —$CF_3$.

In a further aspect, $R^{12}$, when present, is selected from hydrogen and C1-C3 alkyl. In a still further aspect, $R^{12}$, when present, is selected from hydrogen, methyl, and ethyl. In yet a further aspect, $R^{12}$, when present, is selected from hydrogen and methyl. In an even further aspect, $R^{12}$, when present, is hydrogen.

e. $R^{13}$ Groups

In one aspect, $R^{13}$, when present, is selected from C1-C3 alkyl, C1-C3 monohaloalkyl, C1-C3 polyhaloalkyl, and cyclopropyl. In a further aspect, $R^{13}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a still further aspect, $R^{13}$, when present, is selected from methyl, —$CH_2F$, —$CH_2Cl$, —$CHF_2$, —$CF_3$, —$CHCl_2$, —$CCl_3$, and cyclopropyl. In yet a further aspect, $R^{13}$, when present, is selected from methyl, —$CH_2F$, —$CHF_2$, —$CF_3$, and cyclopropyl. In an even further aspect, $R^{13}$, when present, is selected from methyl, —$CF_3$, and cyclopropyl.

In a further aspect, $R^{13}$, when present, is selected from C1-C3 monohaloalkyl, C1-C3 polyhaloalkyl, and cyclopropyl. In a still further aspect, $R^{13}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{13}$, when present, is selected from —$CH_2F$, —$CH_2Cl$, —$CHF_2$, —$CF_3$, —$CHCl_2$, —$CCl_3$, and cyclopropyl. In an even further aspect, $R^{13}$, when present, is selected from —$CH_2F$, —$CHF_2$, —$CF_3$, and cyclopropyl. In a still further aspect, $R^{13}$, when present, is selected from —$CF_3$ and cyclopropyl.

In a further aspect, $R^{13}$, when present, is selected from C1-C3 alkyl, and cyclopropyl. In a still further aspect, $R^{13}$, when present, is selected from methyl, ethyl, and cyclopropyl. In yet a further aspect, $R^{13}$, when present, is selected from methyl and cyclopropyl.

In a further aspect, $R^{13}$, when present, is selected from C1-C3 alkyl, C1-C3 monohaloalkyl, and C1-C3 polyhaloalkyl. In a still further aspect, $R^{13}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{13}$, when present, is selected from methyl, —$CH_2F$, —$CH_2Cl$, —$CHF_2$, —$CF_3$, —$CHCl_2$, and —$CCl_3$. In an even further aspect, $R^{13}$, when present, is selected from methyl, —$CH_2F$, —$CHF_2$, and —$CF_3$. In a still further aspect, $R^{13}$, when present, is selected from methyl and —$CF_3$.

In a further aspect, $R^{13}$, when present, is selected from C1-C3 monohaloalkyl, and C1-C3 polyhaloalkyl. In a still further aspect, $R^{13}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{13}$, when present, is selected from —$CH_2F$, —$CH_2Cl$, —$CHF_2$, —$CF_3$, —$CHCl_2$, and —$CCl_3$. In an even further aspect, $R^{13}$, when present, is selected from —CH$_2$F, —CHF$_2$, and —CF$_3$. In a still further aspect, R$^{13}$, when present, is —CF$_3$.

In a further aspect, R$^{13}$, when present, is C1-C3 alkyl. In a still further aspect, R$^{13}$, when present, is selected from methyl and ethyl. In yet a further aspect, R$^{13}$, when present, is propyl. In an even further aspect, R$^{13}$, when present, is isopropyl. In a still further aspect, R$^{13}$, when present, is ethyl. In yet a further aspect, R$^{13}$, when present, is methyl.

f. R$^{14a}$ and R$^{14b}$ Groups

In one aspect, each of R$^{14a}$ and R$^{14b}$, when present, is independently selected from hydrogen, C1-C3 alkyl, C1-C3 monohaloalkyl, C1-C3 polyhaloalkyl, and cyclopropyl; or wherein each of R$^{14a}$ and R$^{14b}$, when present, are optionally covalently bonded and, together with the nitrogen atom to which they are attached, comprise a 3- to 6-membered heterocycle.

In a further aspect, each of R$^{14a}$ and R$^{14b}$, when present, is independently selected from hydrogen, C1-C3 alkyl, C1-C3 monohaloalkyl, C1-C3 polyhaloalkyl, and cyclopropyl. In a still further aspect, each of R$^{14a}$ and R$^{14b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{14a}$ and R$^{14b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{14a}$ and R$^{14b}$, when present, is independently selected from hydrogen, methyl, —CH$_2$F, —CHF$_2$, —CF$_3$, and cyclopropyl. In a still further aspect, each of R$^{14a}$ and R$^{14b}$, when present, is independently selected from hydrogen, methyl, —CF$_3$, and cyclopropyl.

In a further aspect, each of R$^{14a}$ and R$^{14b}$, when present, is independently selected from hydrogen, C1-C3 monohaloalkyl, C1-C3 polyhaloalkyl, and cyclopropyl. In a still further aspect, each of R$^{14a}$ and R$^{14b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{14a}$ and R$^{14b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{14a}$ and R$^{14b}$, when present, is independently selected from hydrogen, —CH$_2$F, —CHF$_2$, —CF$_3$, and cyclopropyl. In a still further aspect, each of R$^{14a}$ and R$^{14b}$, when present, is independently selected from hydrogen, —CF$_3$ and cyclopropyl.

In a further aspect, each of R$^{14a}$ and R$^{14b}$, when present, is independently selected from hydrogen, C1-C3 alkyl, and cyclopropyl. In a still further aspect, each of R$^{14a}$ and R$^{14b}$, when present, is independently selected from hydrogen, methyl, ethyl, and cyclopropyl. In yet a further aspect, each of R$^{14a}$ and R$^{14b}$, when present, is independently selected from hydrogen, methyl, and cyclopropyl.

In a further aspect, each of R$^{14a}$ and R$^{14b}$, when present, is independently selected from hydrogen, C1-C3 alkyl, C1-C3 monohaloalkyl, and C1-C3 polyhaloalkyl. In a still further aspect, each of R$^{14a}$ and R$^{14b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{14a}$ and R$^{14b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{14a}$ and R$^{14b}$, when present, is independently selected from hydrogen, methyl, —CH$_2$F, —CHF$_2$, and —CF$_3$. In a still further aspect, each of R$^{14a}$ and R$^{14b}$, when present, is independently selected from hydrogen, methyl, and —CF$_3$.

In a further aspect, each of R$^{14a}$ and R$^{14b}$, when present, is independently selected from hydrogen, C1-C3 monohaloalkyl, and C1-C3 polyhaloalkyl. In a still further aspect, each of R$^{14a}$ and R$^{14b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{14a}$ and R$^{14b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{14a}$ and R$^{14b}$, when present, is independently selected from hydrogen, —CH$_2$F, —CHF$_2$, and —CF$_3$. In a still further aspect, each of R$^{14a}$ and R$^{14b}$, when present, is independently selected from hydrogen and —CF$_3$.

In a further aspect, each of R$^{14a}$ and R$^{14b}$, when present, is independently selected from hydrogen and C1-C3 alkyl. In a still further aspect, each of R$^{14a}$ and R$^{14b}$, when present, is independently selected from hydrogen, methyl, and ethyl. In yet a further aspect, each of R$^{14a}$ and R$^{14b}$, when present, is independently selected from hydrogen and methyl. In an even further aspect, each of R$^{14a}$ and R$^{14b}$, when present, is hydrogen.

In a further aspect, each of R$^{14a}$ and R$^{14b}$, when present, is C1-C3 alkyl. In a still further aspect, each of R$^{14a}$ and R$^{14b}$, when present, is selected from ethyl and methyl. In yet a further aspect, each of R$^{14a}$ and R$^{14b}$, when present, is ethyl. In an even further aspect, each of R$^{14a}$ and R$^{14b}$, when present, is methyl.

In a further aspect, R$^{14a}$, when present, is hydrogen, and R$^{14b}$, when present is selected from C1-C3 alkyl, C1-C3 monohaloalkyl, C1-C3 polyhaloalkyl, and cyclopropyl. In a still further aspect, R$^{14a}$, when present, is hydrogen, and R$^{14b}$, when present is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{14a}$, when present, is hydrogen, and R$^{14b}$, when present is selected from methyl, —CH$_2$F, —CH$_2$Cl, —CHF$_2$, —CF$_3$, —CHCl$_2$, —CCl$_3$, and cyclopropyl. In an even further aspect, R$^{14a}$, when present, is hydrogen, and R$^{14b}$, when present is selected from methyl, —CH$_2$F, —CHF$_2$, —CF$_3$, and cyclopropyl. In a still further aspect, R$^{14a}$, when present, is hydrogen, and R$^{14b}$, when present is selected from methyl, —CF$_3$, and cyclopropyl.

In a further aspect, R$^{14a}$, when present, is hydrogen, and R$^{14b}$, when present is selected from C1-C3 monohaloalkyl, C1-C3 polyhaloalkyl, and cyclopropyl. In a still further aspect, R$^{14a}$, when present, is hydrogen, and R$^{14b}$, when present is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{14a}$, when present, is hydrogen, and R$^{14b}$, when present is selected from —CH$_2$F, —CH$_2$Cl, —CHF$_2$, —CF$_3$, —CHCl$_2$, —CCl$_3$, and cyclopropyl. In an even further aspect, R$^{14a}$, when present, is hydrogen, and R$^{14b}$, when present is selected from —CH$_2$F, —CHF$_2$, —CF$_3$, and cyclopropyl. In a still further aspect, R$^{14a}$, when present, is hydrogen, and R$^{14b}$, when present is selected from —CF$_3$ and cyclopropyl.

In a further aspect, R$^{14a}$, when present, is hydrogen, and R$^{14b}$, when present is selected from C1-C3 alkyl, and cyclopropyl. In a still further aspect, $R^{14a}$, when present, is hydrogen, and $R^{14b}$, when present is selected from methyl, ethyl, and cyclopropyl. In yet a further aspect, $R^{14a}$, when present, is hydrogen, and $R^{14b}$, when present is selected from methyl, and cyclopropyl.

In a further aspect, $R^{14a}$, when present, is hydrogen, and $R^{14b}$, when present is selected from C1-C3 alkyl, C1-C3 monohaloalkyl, and C1-C3 polyhaloalkyl. In a still further aspect, $R^{14a}$, when present, is hydrogen, and $R^{14b}$, when present is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{14a}$, when present, is hydrogen, and $R^{14b}$, when present is selected from methyl, —CH$_2$F, —CH$_2$Cl, —CHF$_2$, —CF$_3$, —CHCl$_2$, and —CCl$_3$. In an even further aspect, $R^{14a}$, when present, is hydrogen, and $R^{14b}$, when present is selected from methyl, —CH$_2$F, —CHF$_2$, and —CF$_3$. In a still further aspect, $R^{14a}$, when present, is hydrogen, and $R^{14b}$, when present is selected from methyl, and —CF$_3$.

In a further aspect, $R^{14a}$, when present, is hydrogen, and $R^{14b}$, when present is selected from C1-C3 monohaloalkyl, and C1-C3 polyhaloalkyl. In a still further aspect, $R^{14a}$, when present, is hydrogen, and $R^{14b}$, when present is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{14a}$, when present, is hydrogen, and $R^{14b}$, when present is selected from —CH$_2$F, —CH$_2$Cl, —CHF$_2$, —CF$_3$, —CHCl$_2$, and —CCl$_3$. In an even further aspect, $R^{14a}$, when present, is hydrogen, and $R^{14b}$, when present is selected from —CH$_2$F, —CHF$_2$, and —CF$_3$. In a still further aspect, $R^{14a}$, when present, is hydrogen, and $R^{14b}$, when present is —CF$_3$.

In a further aspect, $R^{14a}$, when present, is hydrogen, and $R^{14b}$, when present is C1-C3 alkyl. In a still further aspect, $R^{14a}$, when present, is hydrogen, and $R^{14b}$, when present is selected from ethyl and methyl. In yet a further aspect, $R^{14a}$, when present, is hydrogen, and $R^{14b}$, when present is ethyl. In an even further aspect, $R^{14a}$, when present, is hydrogen, and $R^{14b}$, when present is methyl.

In a further aspect, each of $R^{14a}$ and $R^{14b}$, when present, are optionally covalently bonded and, together with the nitrogen atom to which they are attached, comprise a 3- to 6-membered heterocycle. In a still further aspect, each of $R^{14a}$ and $R^{14b}$, when present, are optionally covalently bonded and, together with the nitrogen atom to which they are attached, comprise a 3- to 6-membered heterocycle selected from aziridine, azetidine, pyrrolidine, piperidine, morpholine, and piperazine. In yet a further aspect, each of $R^{14a}$ and $R^{14b}$, when present, are optionally covalently bonded and, together with the nitrogen atom to which they are attached, comprise a 3- to 6-membered heterocycle selected from aziridine, azetidine, and pyrrolidine. In an even further aspect, each of $R^{14a}$ and $R^{14b}$, when present, are optionally covalently bonded and, together with the nitrogen atom to which they are attached, comprise a 3- to 6-membered heterocycle selected from aziridine and azetidine. In a still further aspect, each of $R^{14a}$ and $R^{14b}$, when present, are optionally covalently bonded and, together with the nitrogen atom to which they are attached, comprise an aziridine. In yet a further aspect, each of $R^{14a}$ and $R^{14b}$, when present, are optionally covalently bonded and, together with the nitrogen atom to which they are attached, comprise an azetidine. In an even further aspect, each of $R^{14a}$ and $R^{14b}$, when present, are optionally covalently bonded and, together with the nitrogen atom to which they are attached, comprise a pyrrolidine. In a still further aspect, each of $R^{14a}$ and $R^{14b}$, when present, are optionally covalently bonded and, together with the nitrogen atom to which they are attached, comprise a piperidine. In yet a further aspect, each of $R^{14a}$ and $R^{14b}$, when present, are optionally covalently bonded and, together with the nitrogen atom to which they are attached, comprise a morpholine. In an even further aspect, each of $R^{14a}$ and $R^{14b}$, when present, are optionally covalently bonded and, together with the nitrogen atom to which they are attached, comprise a piperazine.

a. $R^{15}$ Groups

In one aspect, $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl.

In one aspect, $R^{15}$, when present, is selected from hydrogen, C1-C4 alkyl, C1-C4 monohaloalkyl, C1-C4 polyhaloalkyl, and $Cy^2$.

In one aspect, $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 0, 1, or 2 and each of $R^{11a}$ and $R^{11b}$ is ethyl then $R^{15}$ is not methyl or ethyl.

In a further aspect, $R^{15}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and $Cy^2$. In a still further aspect, $R^{15}$, when present, is selected from hydrogen, methyl, —CH$_2$F, —CH$_2$Cl, —CHF$_2$, —CF$_3$, —CHCl$_2$, —CCl$_3$, and $Cy^2$. In yet a further aspect, $R^{15}$, when present, is selected from hydrogen, methyl, —CH$_2$F, —CHF$_2$, —CF$_3$, and $Cy^2$. In an even further aspect, $R^{15}$, when present, is selected from hydrogen, methyl, —CF$_3$, and $Cy^2$.

In a further aspect, $R^{15}$, when present, is selected from hydrogen, C1-C4 monohaloalkyl, C1-C4 polyhaloalkyl, and $Cy^2$. In a still further aspect, $R^{15}$, when present, is selected from hydrogen, C1-C3 monohaloalkyl, C1-C3 polyhaloalkyl, and $Cy^2$. In yet a further aspect, $R^{15}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and $Cy^2$. In an even further aspect, $R^{15}$, when present, is selected from hydrogen, —CH$_2$F, —CH$_2$Cl, —CHF$_2$, —CF$_3$, —CHCl$_2$, —CCl$_3$, and $Cy^2$. In a still further aspect, $R^{15}$, when present, is selected from hydrogen, —CH$_2$F, —CHF$_2$, —CF$_3$, and $Cy^2$. In yet a further aspect, $R^{15}$, when present, is selected from hydrogen, —CF$_3$ and $Cy^2$.

In a further aspect, $R^{15}$, when present, is selected from hydrogen, C1-C4 alkyl, and $Cy^2$. In a still further aspect, $R^{15}$, when present, is selected from hydrogen, C1-C3 alkyl, and $Cy^2$. In yet a further aspect, $R^{15}$, when present, is selected from hydrogen, methyl, ethyl, and $Cy^2$. In an even further aspect, $R^{15}$, when present, is selected from hydrogen, methyl, and $Cy^2$.

In a further aspect, $R^{15}$, when present, is selected from hydrogen, C1-C4 alkyl, C1-C4 monohaloalkyl, and C1-C4 polyhaloalkyl. In a still further aspect, $R^{15}$, when present, is selected from hydrogen, C1-C3 alkyl, C1-C3 monohaloalkyl, and C1-C3 polyhaloalkyl. In yet a further aspect, $R^{15}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In an even further aspect, $R^{15}$, when present, is selected from hydrogen, methyl, —CH$_2$F, —CH$_2$Cl, —CHF$_2$, —CF$_3$, —CHCl$_2$, and —CCl$_3$.

In a still further aspect, $R^{15}$, when present, is selected from hydrogen, methyl, —CH$_2$F, —CHF$_2$, and —CF$_3$. In yet a further aspect, $R^{15}$, when present, is selected from hydrogen, methyl, and —CF$_3$.

In a further aspect, $R^{15}$, when present, is selected from hydrogen, C1-C4 monohaloalkyl, and C1-C4 polyhaloalkyl. In a still further aspect, $R^{15}$, when present, is selected from hydrogen, C1-C3 monohaloalkyl, and C1-C3 polyhaloalkyl. In yet a further aspect, $R^{15}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In an even further aspect, $R^{15}$, when present, is selected from hydrogen, —CH$_2$F, —CH$_2$Cl, —CHF$_2$, —CF$_3$, —CHCl$_2$, and —CCl$_3$. In a still further aspect, $R^{15}$, when present, is selected from hydrogen, —CH$_2$F, —CHF$_2$, and —CF$_3$. In yet a further aspect, $R^{15}$, when present, is selected from hydrogen and —CF$_3$.

In a further aspect, $R^{15}$, when present, is C1-C4 alkyl. In a still further aspect, $R^{15}$, when present, is selected from methyl, ethyl, n-propyl, and i-propyl. In yet a further aspect, $R^{15}$, when present, is selected from methyl and ethyl. In an even further aspect, $R^{15}$, when present, is selected from n-butyl, sec-butyl, i-butyl, and t-butyl. In a still further aspect, $R^{15}$, when present, is selected from n-propyl and i-propyl. In yet a further aspect, $R^{15}$, when present, is t-butyl. In an even further aspect, $R^{15}$, when present, is i-propyl. In a still further aspect, $R^{15}$, when present, is ethyl. In yet a further aspect, $R^{15}$, when present, is methyl.

In a further aspect, $R^{15}$, when present, is selected from hydrogen and C1-C3 alkyl. In a still further aspect, $R^{15}$, when present, is selected from hydrogen, methyl, and ethyl. In yet a further aspect, $R^{15}$, when present, is selected from hydrogen and methyl. In an even further aspect, $R^{15}$, when present, is hydrogen.

b. $R^{20A}$, $R^{20B}$, $R^{20C}$, and $R^{20D}$ Groups

In one aspect, each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or each of $R^{20a}$ and $R^{20c}$, when present, are hydrogen and $R^{20b}$ and $R^{20d}$, when present, are optionally covalently bonded and, together with the intermediate atoms, comprise a 5- to 6-membered cycle.

In a further aspect, each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen. In a still further aspect, each of $R^{20a}$, $R^{20b}$, $R^{20c}$, and $R^{20d}$, when present, is ethyl. In yet a further aspect, each of $R^{20a}$, $R^{20b}$, $R^{20c}$, and $R^{20d}$, when present, is methyl. In an even further aspect, each of $R^{20a}$, $R^{20b}$, $R^{20c}$, and $R^{20d}$, when present, is hydrogen.

In a further aspect, each of $R^{20a}$, $R^{20b}$, $R^{20c}$, and $R^{20d}$, when present, is independently selected from hydrogen, methyl, ethyl, propyl, isopropyl, tert-butyl, sec-butyl, and isobutyl, provided that $R^{20a}$ and $R^{20b}$ are not simultaneously hydrogen. In a still further aspect, each of $R^{20a}$, $R^{20b}$, $R^{20c}$, and $R^{20d}$, when present, is independently selected from hydrogen, methyl, ethyl, propyl, and isopropyl. In yet a further aspect, each of $R^{20a}$, $R^{20b}$, $R^{20c}$, and $R^{20d}$, when present, is independently selected from hydrogen, methyl, and ethyl. In an even further aspect, each of $R^{20a}$, $R^{20b}$, $R^{20c}$, and $R^{20d}$, when present, is independently selected from hydrogen and ethyl. In a still further aspect, each of $R^{20a}$, $R^{20b}$, $R^{20c}$, and $R^{20d}$, when present, is independently selected from hydrogen and methyl.

In a further aspect, each of $R^{20a}$ and $R^{20d}$, when present, are hydrogen and $R^{20b}$ and $R^{20d}$, when present, are optionally covalently bonded and, together with the intermediate atoms, comprise a 5- to 6-membered cycle. In a still further aspect, each of $R^{20a}$ and $R^{20c}$, when present, are hydrogen and $R^{20b}$ and $R^{20d}$, when present, are optionally covalently bonded and, together with the intermediate atoms, comprise a 5-membered cycle. In yet a further aspect, each of $R^{20a}$ and $R^{20c}$, when present, are hydrogen and $R^{20b}$ and $R^{20d}$, when present, are optionally covalently bonded and, together with the intermediate atoms, comprise a 6-membered cycle.

c. $R^{21A}$, $R^{21B}$, $R^{21C}$, and $R^{21D}$ Groups

In one aspect, each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or each of $R^{21a}$ and $R^{21c}$, when present, are hydrogen and $R^{21b}$ and $R^{21d}$, when present, are optionally covalently bonded and, together with the intermediate atoms, comprise a 5- to 6-membered cycle.

In a further aspect, each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen. In a still further aspect, each of $R^{21a}$, $R^{21b}$, $R^{21c}$, and $R^{21d}$, when present, is ethyl. In yet a further aspect, each of $R^{21a}$, $R^{21b}$, $R^{21c}$, and $R^{21d}$, when present, is methyl. In an even further aspect, each of $R^{21a}$, $R^{21b}$, $R^{21c}$, and $R^{21d}$, when present, is hydrogen.

In a further aspect, each of $R^{21a}$, $R^{21b}$, $R^{21c}$, and $R^{21d}$, when present, is independently selected from hydrogen, methyl, ethyl, propyl, isopropyl, tert-butyl, sec-butyl, and isobutyl, provided that $R^{21a}$ and $R^{21b}$ are not simultaneously hydrogen. In a still further aspect, each of each of $R^{21a}$, $R^{21b}$, $R^{21c}$, and $R^{21d}$, when present, is independently selected from hydrogen, methyl, ethyl, propyl, and isopropyl. In yet a further aspect, each of each of $R^{21a}$, $R^{21b}$, $R^{21c}$, and $R^{21d}$, when present, is independently selected from hydrogen, methyl, and ethyl. In an even further aspect, each of each of $R^{21a}$, $R^{21b}$, $R^{21c}$, and $R^{21d}$, when present, is independently selected from hydrogen and ethyl. In a still further aspect, each of each of $R^{21a}$, $R^{21b}$, $R^{21c}$, and $R^{21d}$, when present, is independently selected from hydrogen and methyl.

In a further aspect, each of $R^{21a}$ and $R^{21c}$, when present, are hydrogen and $R^{21b}$ and $R^{21d}$, when present, are optionally covalently bonded and, together with the intermediate atoms, comprise a 5- to 6-membered cycle. In a still further aspect, each of $R^{21a}$ and $R^{21c}$, when present, are hydrogen and $R^{21b}$ and $R^{21d}$, when present, are optionally covalently bonded and, together with the intermediate atoms, comprise a 5-membered cycle. In yet a further aspect, each of $R^{21a}$ and $R^{21c}$, when present, are hydrogen and $R^{21b}$ and $R^{21d}$, when present, are optionally covalently bonded and, together with the intermediate atoms, comprise a 6-membered cycle.

d. $R^{22a}$ and $R^{22b}$ Groups

In one aspect, each of $R^{22a}$ and $R^{22b}$, when present, is independently selected from hydrogen, C1-C3 alkyl, C1-C3 monohaloalkyl, C1-C3 polyhaloalkyl, and cyclopropyl; or each of $R^{22a}$ and $R^{22b}$, when present, are optionally covalently bonded and, together with the nitrogen atom to which they are attached, comprise a 3- to 6-membered heterocycle.

In a further aspect, each of $R^{22a}$ and $R^{22b}$, when present, is independently selected from hydrogen, C1-C3 alkyl, C1-C3 monohaloalkyl, C1-C3 polyhaloalkyl, and cyclopropyl. In a still further aspect, each of $R^{22a}$ and $R^{22b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{22a}$ and $R^{22b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{22a}$ and R$^{22b}$, when present, is independently selected from hydrogen, methyl, —CH$_2$F, —CHF$_2$, —CF$_3$, and cyclopropyl. In a still further aspect, each of R$^{22a}$ and R$^{22b}$, when present, is independently selected from hydrogen, methyl, —CF$_3$, and cyclopropyl.

In a further aspect, each of R$^{22a}$ and R$^{22b}$, when present, is independently selected from hydrogen, C1-C3 monohaloalkyl, C1-C3 polyhaloalkyl, and cyclopropyl. In a still further aspect, each of R$^{22a}$ and R$^{22b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{22a}$ and R$^{22b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{22a}$ and R$^{22b}$, when present, is independently selected from hydrogen, —CH$_2$F, —CHF$_2$, —CF$_3$, and cyclopropyl. In a still further aspect, each of R$^{22a}$ and R$^{22b}$, when present, is independently selected from hydrogen, —CF$_3$ and cyclopropyl.

In a further aspect, each of R$^{22a}$ and R$^{22b}$, when present, is independently selected from hydrogen, C1-C3 alkyl, and cyclopropyl. In a still further aspect, each of R$^{22a}$ and R$^{22b}$, when present, is independently selected from hydrogen, methyl, ethyl, and cyclopropyl. In yet a further aspect, each of R$^{22a}$ and R$^{22b}$, when present, is independently selected from hydrogen, methyl, and cyclopropyl.

In a further aspect, each of R$^{22a}$ and R$^{22b}$, when present, is independently selected from hydrogen, C1-C3 alkyl, C1-C3 monohaloalkyl, and C1-C3 polyhaloalkyl. In a still further aspect, each of R$^{22a}$ and R$^{22b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{22a}$ and R$^{22b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{22a}$ and R$^{22b}$, when present, is independently selected from hydrogen, methyl, —CH$_2$F, —CHF$_2$, and —CF$_3$. In a still further aspect, each of R$^{22a}$ and R$^{22b}$, when present, is independently selected from hydrogen, methyl, and —CF$_3$.

In a further aspect, each of R$^{22a}$ and R$^{22b}$, when present, is independently selected from hydrogen, C1-C3 monohaloalkyl, and C1-C3 polyhaloalkyl. In a still further aspect, each of R$^{22a}$ and R$^{22b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{22a}$ and R$^{22b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{22a}$ and R$^{22b}$, when present, is independently selected from hydrogen, —CH$_2$F, —CHF$_2$, and —CF$_3$. In a still further aspect, each of R$^{22a}$ and R$^{22b}$, when present, is independently selected from hydrogen and methyl. In an even further aspect, each of R$^{22a}$ and R$^{22b}$, when present, is hydrogen.

In a further aspect, R$^{22a}$, when present, is hydrogen and R$^{22b}$, when present, is selected from C1-C3 alkyl, C1-C3 monohaloalkyl, C1-C3 polyhaloalkyl, and cyclopropyl. In a still further aspect, R$^{22a}$, when present, is hydrogen and R$^{22b}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{22a}$, when present, is hydrogen and R$^{22b}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{22a}$, when present, is hydrogen and R$^{22b}$, when present, is selected from methyl, —CH$_2$F, —CHF$_2$, —CF$_3$, and cyclopropyl. In a still further aspect, R$^{22a}$, when present, is hydrogen and R$^{22b}$, when present, is selected from methyl, —CF$_3$, and cyclopropyl.

In a further aspect, R$^{22a}$, when present, is hydrogen and R$^{22b}$, when present, is selected from C1-C3 monohaloalkyl, C1-C3 polyhaloalkyl, and cyclopropyl. In a still further aspect, R$^{22a}$, when present, is hydrogen and R$^{22b}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{22a}$, when present, is hydrogen and R$^{22b}$, when present, is selected from —CH$_2$F, —CH$_2$Cl, —CHF$_2$, —CF$_3$, —CHCl$_2$, —CCl$_3$, and cyclopropyl. In an even further aspect, R$^{22a}$, when present, is hydrogen and R$^{22b}$, when present, is selected from hydrogen, —CH$_2$F, —CHF$_2$, —CF$_3$, and cyclopropyl. In a still further aspect, R$^{22a}$, when present, is hydrogen and R$^{22b}$, when present, is selected from —CF$_3$ and cyclopropyl.

In a further aspect, R$^{22a}$, when present, is hydrogen and R$^{22b}$, when present, is selected from C1-C3 alkyl, and cyclopropyl. In a still further aspect, R$^{22a}$, when present, is hydrogen and R$^{22b}$, when present, is selected from methyl, ethyl, and cyclopropyl. In yet a further aspect, R$^{22a}$, when present, is hydrogen and R$^{22b}$, when present, is selected from methyl, and cyclopropyl.

In a further aspect, R$^{22a}$, when present, is hydrogen and R$^{22b}$, when present, is selected from C1-C3 alkyl, C1-C3 monohaloalkyl, and C1-C3 polyhaloalkyl. In a still further aspect, R$^{22a}$, when present, is hydrogen and R$^{22b}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{22a}$, when present, is hydrogen and R$^{22b}$, when present, is selected from methyl, —CH$_2$F, —CH$_2$Cl, —CHF$_2$, —CF$_3$, —CHCl$_2$, and —CCl$_3$. In an even further aspect, R$^{22a}$, when present, is hydrogen and R$^{22b}$, when present, is selected from methyl, —CH$_2$F, —CHF$_2$, and —CF$_3$. In a still further aspect, R$^{22a}$, when present, is hydrogen and R$^{22b}$, when present, is selected from methyl, and —CF$_3$.

In a further aspect, R$^{22a}$, when present, is hydrogen and R$^{22b}$, when present, is selected from C1-C3 monohaloalkyl, and C1-C3 polyhaloalkyl. In a still further aspect, R$^{22a}$, when present, is hydrogen and R$^{22b}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{22a}$, when present, is hydrogen and R$^{22b}$, when present, is selected from —CH$_2$F, —CH$_2$Cl, —CHF$_2$, —CF$_3$, —CHCl$_2$, and —CCl$_3$. In an even further aspect, R$^{22a}$, when present, is hydrogen and R$^{22b}$, when present, is selected from —CH$_2$F, —CHF$_2$, and —CF$_3$. In a still further aspect, R$^{22a}$, when present, is hydrogen and R$^{22b}$, when present, is —CF$_3$.

In a further aspect, R$^{22a}$, when present, is hydrogen and R$^{22b}$, when present, is C1-C3 alkyl. In a still further aspect, R$^{22a}$, when present, is hydrogen and R$^{22b}$, when present, is selected from methyl and ethyl. In yet a further aspect, R$^{22a}$, when present, is hydrogen and R$^{22b}$, when present, is ethyl. In an even further aspect, R$^{22a}$, when present, is hydrogen and R$^{22b}$, when present, is methyl.

In a further aspect, each of R$^{22a}$ and R$^{22b}$, when present, are optionally covalently bonded and, together with the nitrogen atom to which they are attached, comprise a 3- to 6-membered heterocycle. In a still further aspect, each of R$^{22a}$ and R$^{22b}$, when present, are optionally covalently bonded and, together with the nitrogen atom to which they are attached, comprise a 3- to 6-membered heterocycle selected from aziridine, azetidine, pyrrolidine, piperidine, morpholine, and piperazine. In yet a further aspect, each of R$^{22a}$ and R$^{22b}$, when present, are optionally covalently bonded and, together with the nitrogen atom to which they are attached, comprise a 3- to 6-membered heterocycle selected from aziridine, azetidine, and pyrrolidine. In an even further aspect, each of R$^{22a}$ and R$^{22b}$, when present, are optionally covalently bonded and, together with the nitrogen atom to which they are attached, comprise a 3- to 6-membered heterocycle selected from aziridine and azetidine. In a still further aspect, each of R$^{22a}$ and R$^{22b}$, when present, are optionally covalently bonded and, together with the nitrogen atom to which they are attached, comprise an aziridine. In yet a further aspect, each of R$^{22a}$ and R$^{22b}$, when present, are optionally covalently bonded and, together with the nitrogen atom to which they are attached, comprise an azetidine. In an even further aspect, each of R$^{22a}$ and R$^{22b}$, when present, are optionally covalently bonded and, together with the nitrogen atom to which they are attached, comprise a pyrrolidine. In a still further aspect, each of R$^{22a}$ and R$^{22b}$, when present, are optionally covalently bonded and, together with the nitrogen atom to which they are attached, comprise a piperidine. In yet a further aspect, each of R$^{22a}$ and R$^{22b}$, when present, are optionally covalently bonded and, together with the nitrogen atom to which they are attached, comprise a morpholine. In an even further aspect, each of R$^{22a}$ and R$^{22b}$, when present, are optionally covalently bonded and, together with the nitrogen atom to which they are attached, comprise a piperazine.

e. Ar$^1$ Groups

In one aspect, Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group. In a further aspect, Ar$^1$, when present, is C2-C6 heteroaryl substituted with 0, 1, or 2 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group. In a still further aspect, Ar$^1$, when present, is C2-C6 heteroaryl substituted with 0 or 1 group selected from halogen, C1-C4 alkyl, C1-C4 alkoxyalkyl, C1-C4 hydroxyalkyl, C1-C4 monohaloalkyl, C1-C4 polyhaloalkyl. In yet a further aspect, Ar$^1$, when present, is C2-C6 heteroaryl monosubstituted with a group selected from halogen, C1-C4 alkyl, C1-C4 alkoxyalkyl, C1-C4 hydroxyalkyl, C1-C4 monohaloalkyl, C1-C4 polyhaloalkyl. In an even further aspect, Ar$^1$, when present, is unsubstituted C2-C6 heteroaryl.

In a further aspect, Ar$^1$, when present, is C2-C6 heteroaryl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is selected from pyrrolyl and imidazolyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is pyrrolyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is imidazolyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^1$, when present, is C2-C6 heteroaryl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is C2-C6 heteroaryl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is C2-C6 heteroaryl substituted with 0, 1, 2, or 3 substituents independently selected from —F, —Cl, methyl, —OCH$_3$, —CF$_3$, and —CCl$_3$.

In a further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, —OCH$_3$, —CF$_3$, and —CCl$_3$.

In a further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, —OCH$_3$, —CF$_3$, and —CCl$_3$.

In a further aspect, Ar$^1$, when present, is selected from pyrrolyl and imidazolyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is selected from pyrrolyl and imidazolyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is selected from pyrrolyl and imidazolyl and substituted with 0, 1, 2, or 3 substituents independently selected from —F, —Cl, methyl, —OCH$_3$, —CF$_3$, and —CCl$_3$.

In a further aspect, Ar$^1$, when present, is imidazolyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is imidazolyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is imidazolyl substituted with 0, 1, 2, or 3 substituents independently selected from —F, —Cl, methyl, —OCH$_3$, —CF$_3$, and —CCl$_3$.

In a further aspect, Ar$^1$, when present, is pyrrolyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is pyrrolyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is pyrrolyl substituted with 0, 1, 2, or 3 substituents independently selected from —F, —Cl, methyl, —OCH$_3$, —CF$_3$, and —CCl$_3$.

In a further aspect, Ar$^1$, when present, is C2-C6 heteroaryl substituted with 0, 1, or 2 groups independently selected from halogen, C1-C4 alkyl, C1-C4 alkoxy, C1-C4 monohaloalkyl, and C1-C4 polyhaloalkyl. In a still further aspect, Ar$^1$, when present, is C2-C6 heteroaryl substituted with 0 or 1 group selected from halogen, C1-C4 alkyl, C1-C4 alkoxy, C1-C4 monohaloalkyl, and C1-C4 polyhaloalkyl. In yet a further aspect, Ar$^1$, when present, is C2-C6 heteroaryl monosubstituted with a group selected from halogen, C1-C4 alkyl, C1-C4 alkoxy, C1-C4 monohaloalkyl, and C1-C4 polyhaloalkyl.

In a further aspect, Ar$^1$, when present, is C2-C6 heteroaryl substituted with 0, 1, or 2 groups independently selected from halogen, C1-C2 alkyl, C1-C2 alkoxy, C1-C2 monohaloalkyl, and C1-C2 polyhaloalkyl. In a still further aspect, Ar$^1$, when present, is C2-C6 heteroaryl substituted with 0 or 1 group selected from halogen, C1-C2 alkyl, C1-C2 alkoxy, C1-C2 monohaloalkyl, and C1-C2 polyhaloalkyl. In yet a further aspect, Ar$^1$, when present, is C2-C6 heteroaryl monosubstituted with a group selected from halogen, C1-C2 alkyl, C1-C2 alkoxy, C1-C2 monohaloalkyl, and C1-C2 polyhaloalkyl.

In a further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0 or 1 group selected from halogen, C1-C2 alkyl, C1-C2 alkoxy, C1-C2 monohaloalkyl, and C1-C2 polyhaloalkyl. In yet a further aspect, Ar$^1$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and monosubstituted with a group selected from halogen, C1-C2 alkyl, C1-C2 alkoxy, C1-C2 monohaloalkyl, and C1-C2 polyhaloalkyl.

In a further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, Ar$^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0 or 1 group selected from halogen, C1-C2 alkyl, C1-C2 alkoxy, C1-C2 monohaloalkyl, and C1-C2 polyhaloalkyl. In yet a further aspect, $Ar^1$, when present, is selected from imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and monosubstituted with a group selected from halogen, C1-C2 alkyl, C1-C2 alkoxy, C1-C2 monohaloalkyl, and C1-C2 polyhaloalkyl.

In a further aspect, $Ar^1$, when present, is selected from pyrrolyl and imidazolyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^1$, when present, is selected from pyrrolyl and imidazolyl and substituted with 0 or 1 group selected from halogen, C1-C2 alkyl, C1-C2 alkoxy, C1-C2 monohaloalkyl, and C1-C2 polyhaloalkyl. In yet a further aspect, $Ar^1$, when present, is selected from pyrrolyl and imidazolyl and monosubstituted with a group selected from halogen, C1-C2 alkyl, C1-C2 alkoxy, C1-C2 monohaloalkyl, and C1-C2 polyhaloalkyl.

In a further aspect, $Ar^1$, when present, is imidazolyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^1$, when present, is imidazolyl substituted with 0 or 1 group selected from halogen, C1-C2 alkyl, C1-C2 alkoxy, C1-C2 monohaloalkyl, and C1-C2 polyhaloalkyl. In yet a further aspect, $Ar^1$, when present, is imidazolyl monosubstituted with a group selected from halogen, C1-C2 alkyl, C1-C2 alkoxy, C1-C2 monohaloalkyl, and C1-C2 polyhaloalkyl.

In a further aspect, $Ar^1$, when present, is pyrrolyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^1$, when present, is pyrrolyl substituted with 0 or 1 group selected from halogen, C1-C2 alkyl, C1-C2 alkoxy, C1-C2 monohaloalkyl, and C1-C2 polyhaloalkyl. In yet a further aspect, $Ar^1$, when present, is pyrrolyl monosubstituted with a group selected from halogen, C1-C2 alkyl, C1-C2 alkoxy, C1-C2 monohaloalkyl, and C1-C2 polyhaloalkyl.

f. $Ar^2$ Groups

In one aspect, $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group. In a further aspect, $Ar^2$, when present, is C2-C6 heteroaryl substituted with 0, 1, or 2 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group.

In a still further aspect, $Ar^2$, when present, is C2-C6 heteroaryl substituted with 0 or 1 group selected from halogen, C1-C4 alkyl, C1-C4 alkoxyalkyl, C1-C4 hydroxyalkyl, C1-C4 monohaloalkyl, C1-C4 polyhaloalkyl. In yet a further aspect, $Ar^2$, when present, is C2-C6 heteroaryl monosubstituted with a group selected from halogen, C1-C4 alkyl, C1-C4 alkoxyalkyl, C1-C4 hydroxyalkyl, C1-C4 monohaloalkyl, C1-C4 polyhaloalkyl. In an even further aspect, $Ar^2$, when present, is unsubstituted C2-C6 heteroaryl.

In a further aspect, $Ar^2$, when present, is C2-C6 heteroaryl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Ar^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a still further aspect, $Ar^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$Cl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^2$, when present, is oxadiazolyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, Ar$^2$, when present, is C2-C6 heteroaryl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is C2-C6 heteroaryl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is C2-C6 heteroaryl substituted with 0, 1, 2, or 3 substituents independently selected from —F, —Cl, methyl, —OCH$_3$, —CF$_3$, and —CCl$_3$.

In a further aspect, Ar$^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, —OCH$_3$, —CF$_3$, and —CCl$_3$.

In a further aspect, Ar$^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, —OCH$_3$, —CF$_3$, and —CCl$_3$.

In a further aspect, Ar$^2$, when present, is oxadiazolyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Ar$^1$, when present, is oxadiazolyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Ar$^1$, when present, is oxadiazolyl substituted with 0, 1, 2, or 3 substituents independently selected from —F, —Cl, methyl, —OCH$_3$, —CF$_3$, and —CCl$_3$.

In a further aspect, Ar$^2$, when present, is C2-C6 heteroaryl substituted with 0, 1, or 2 groups independently selected from halogen, C1-C4 alkyl, C1-C4 alkoxy, C1-C4 monohaloalkyl, and C1-C4 polyhaloalkyl. In a still further aspect, $Ar^2$, when present, is C2-C6 heteroaryl substituted with 0 or 1 group selected from halogen, C1-C4 alkyl, C1-C4 alkoxy, C1-C4 monohaloalkyl, and C1-C4 polyhaloalkyl. In yet a further aspect, $Ar^2$, when present, is C2-C6 heteroaryl monosubstituted with a group selected from halogen, C1-C4 alkyl, C1-C4 alkoxy, C1-C4 monohaloalkyl, and C1-C4 polyhaloalkyl.

In a further aspect, $Ar^2$, when present, is C2-C6 heteroaryl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^2$, when present, is C2-C6 heteroaryl substituted with 0 or 1 group selected from halogen, C1-C2 alkyl, C1-C2 alkoxy, C1-C2 monohaloalkyl, and C1-C2 polyhaloalkyl. In yet a further aspect, $Ar^2$, when present, is C2-C6 heteroaryl monosubstituted with a group selected from halogen, C1-C2 alkyl, C1-C2 alkoxy, C1-C2 monohaloalkyl, and C1-C2 polyhaloalkyl.

In a further aspect, $Ar^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0 or 1 group selected from halogen, C1-C2 alkyl, C1-C2 alkoxy, C1-C2 monohaloalkyl, and C1-C2 polyhaloalkyl. In yet a further aspect, $Ar^2$, when present, is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and monosubstituted with a group selected from halogen, C1-C2 alkyl, C1-C2 alkoxy, C1-C2 monohaloalkyl, and C1-C2 polyhaloalkyl.

In a further aspect, $Ar^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0 or 1 group selected from halogen, C1-C2 alkyl, C1-C2 alkoxy, C1-C2 monohaloalkyl, and C1-C2 polyhaloalkyl. In yet a further aspect, $Ar^2$, when present, is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo[d]oxazolyl, benzo[d]thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and monosubstituted with a group selected from halogen, C1-C2 alkyl, C1-C2 alkoxy, C1-C2 monohaloalkyl, and C1-C2 polyhaloalkyl.

In a further aspect, $Ar^2$, when present, is oxadiazolyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Ar^2$, when present, is oxadiazolyl substituted with 0 or 1 group selected from halogen, C1-C2 alkyl, C1-C2 alkoxy, C1-C2 monohaloalkyl, and C1-C2 polyhaloalkyl. In yet a further aspect, $Ar^2$, when present, is oxadiazolyl monosubstituted with a group selected from halogen, C1-C2 alkyl, C1-C2 alkoxy, C1-C2 monohaloalkyl, and C1-C2 polyhaloalkyl.

In a further aspect, $Ar^2$, when present, is a structure:

g. $Cy^1$ Groups

In one aspect, $Cy^1$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl. In a further aspect, $Cy^1$, when present, is C3-C6 cycloalkyl substituted with 0, 1, or 2 groups independently selected from halogen, C1-C4 alkyl, C1-C4 alkoxyalkyl, C1-C4 hydroxyalkyl, C1-C4 monohaloalkyl, C1-C4 polyhaloalkyl. In a still further aspect, $Cy^1$, when present, is C3-C6 cycloalkyl substituted with 0 or 1 group selected from halogen, C1-C4 alkyl, C1-C4 alkoxyalkyl, C1-C4 hydroxyalkyl, C1-C4 monohaloalkyl, C1-C4 polyhaloalkyl. In yet a further aspect, $Cy^1$, when present, is C3-C6 cycloalkyl monosubstituted with a group selected from halogen, C1-C4 alkyl, C1-C4 alkoxyalkyl, C1-C4 hydroxyalkyl, C1-C4 monohaloalkyl, C1-C4 polyhaloalkyl. In an even further aspect, $Cy^1$, when present, is unsubstituted C3-C6 cycloalkyl.

In one aspect, $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl. In a further aspect, $Cy^1$, when present, is C3-C6 cycloalkyl or C2-C5 heterocycloalkyl and substituted with 0, 1, or 2 groups independently selected from halogen, C1-C4 alkyl, C1-C4 alkoxyalkyl, C1-C4 hydroxyalkyl, C1-C4 monohaloalkyl, C1-C4 polyhaloalkyl. In a still further aspect, $Cy^1$, when present, is C3-C6 cycloalkyl or C2-C5 heterocycloalkyl and substituted with 0 or 1 group selected from halogen, C1-C4 alkyl, C1-C4 alkoxyalkyl, C1-C4 hydroxyalkyl, C1-C4 monohaloalkyl, C1-C4 polyhaloalkyl. In yet a further aspect, $Cy^1$, when present, is C3-C6 cycloalkyl or C2-C5 heterocycloalkyl and monosubstituted with a group selected from halogen, C1-C4 alkyl, C1-C4 alkoxyalkyl, C1-C4 hydroxyalkyl, C1-C4 monohaloalkyl, C1-C4 polyhaloalkyl. In an even further aspect, $Cy^1$, when present, is C3-C6 cycloalkyl or C2-C5 heterocycloalkyl and unsubstituted.

In a further aspect, $Cy^1$, when present, is C3-C6 cycloalkyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is C2-C5 heterocycloalkyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is selected from cyclopropyl, cyclobutyl, cyclopentyl, and cyclohexyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is cyclopropyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is oxetane substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is tetrahydro-2H-pyran substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^1$, when present, is C3-C6 cycloalkyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is C3-C6 cycloalkyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is C3-C6 cycloalkyl substituted with 0, 1, 2, or 3 substituents independently selected from —F, —Cl, methyl, —OCH$_3$, —CF$_3$, and —CCl$_3$.

In a further aspect, Cy$^1$, when present, is C2-C5 heterocycloalkyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is C2-C5 heterocycloalkyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is C2-C5 heterocycloalkyl substituted with 0, 1, 2, or 3 substituents independently selected from —F, —Cl, methyl, —OCH$_3$, —CF$_3$, and —CCl$_3$.

In a further aspect, Cy$^1$, when present, is selected from cyclopropyl, cyclobutyl, cyclopentyl, and cyclohexyl and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is selected from cyclopropyl, cyclobutyl, cyclopentyl, and cyclohexyl and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is selected from cyclopropyl, cyclobutyl, cyclopentyl, and cyclohexyl and substituted with 0, 1, 2, or 3 substituents independently selected from —F, —Cl, methyl, —OCH$_3$, —CF$_3$, and —CCl$_3$.

In a further aspect, Cy$^1$, when present, is cyclopropyl substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is cyclopropyl substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is cyclopropyl substituted with 0, 1, 2, or 3 substituents independently selected from —F, —Cl, methyl, —OCH$_3$, —CF$_3$, and —CCl$_3$.

In a further aspect, Cy$^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0, 1, 2, or 3 substituents independently selected from —F, —Cl, methyl, —OCH$_3$, —CF$_3$, and —CCl$_3$.

In a further aspect, Cy$^1$, when present, is oxetane substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is oxetane substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is oxetane substituted with 0, 1, 2, or 3 substituents independently selected from —F, —Cl, methyl, —OCH$_3$, —CF$_3$, and —CCl$_3$.

In a further aspect, Cy$^1$, when present, is tetrahydro-2H-thiopyran substituted with 0, 1, 2, or 3 substituents independently selected from —F, —Cl, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, Cy$^1$, when present, is tetrahydro-2H-thiopyran substituted with 0, 1, 2, or 3 substituents independently selected from —F, —Cl, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, and —CCl$_3$. In yet a further aspect, Cy$^1$, when present, is tetrahydro-2H-thiopyran substituted with 0, 1, 2, or 3 substituents independently selected from —F, —Cl, methyl, —OCH$_3$, —CF$_3$, and —CCl$_3$.

In a further aspect, Cy$^1$, when present, is C3-C6 cycloalkyl substituted with 0, 1, or 2 groups independently selected from halogen, C1-C4 alkyl, C1-C4 alkoxy, C1-C4 monohaloalkyl, and C1-C4 polyhaloalkyl. In a still further aspect, Cy$^1$, when present, is C3-C6 cycloalkyl substituted with 0 or 1 group selected from halogen, C1-C4 alkyl, C1-C4 alkoxy, C1-C4 monohaloalkyl, and C1-C4 polyhaloalkyl. In yet a further aspect, Cy$^1$, when present, is C3-C6 cycloalkyl monosubstituted with a group selected from halogen, C1-C4 alkyl, C1-C4 alkoxy, C1-C4 monohaloalkyl, and C1-C4 polyhaloalkyl.

In a further aspect, Cy$^1$, when present, is C3-C6 cycloalkyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, Cy$^1$, when present, is C3-C6 cycloalkyl substituted with 0 or 1 group selected from halogen, C1-C2 alkyl, C1-C2 alkoxy, C1-C2 monohaloalkyl, and C1-C2 polyhaloalkyl. In yet a further aspect, Cy$^1$, when present, is C3-C6 cycloalkyl monosubstituted with a group selected from halogen, C1-C2 alkyl, C1-C2 alkoxy, C1-C2 monohaloalkyl, and C1-C2 polyhaloalkyl.

In a further aspect, Cy$^1$, when present, is C2-C5 heterocycloalkyl substituted with 0, 1, or 2 groups independently selected from halogen, C1-C4 alkyl, C1-C4 alkoxy, C1-C4 monohaloalkyl, and C1-C4 polyhaloalkyl. In a still further aspect, Cy$^1$, when present, is C2-C5 heterocycloalkyl substituted with 0 or 1 group selected from halogen, C1-C4 alkyl, C1-C4 alkoxy, C1-C4 monohaloalkyl, and C1-C4 polyhaloalkyl. In yet a further aspect, $Cy^1$, when present, is C2-C5 heterocycloalkyl monosubstituted with a group selected from halogen, C1-C4 alkyl, C1-C4 alkoxy, C1-C4 monohaloalkyl, and C1-C4 polyhaloalkyl.

In a further aspect, $Cy^1$, when present, is C2-C5 heterocycloalkyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is C2-C5 heterocycloalkyl substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is C2-C5 heterocycloalkyl monosubstituted with a group selected from halogen, C1-C2 alkyl, C1-C2 alkoxy, C1-C2 monohaloalkyl, and C1-C2 polyhaloalkyl.

In a further aspect, $Cy^1$, when present, is selected from cyclopropyl, cyclobutyl, cyclopentyl, and cyclohexyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is selected from cyclopropyl, cyclobutyl, cyclopentyl, and cyclohexyl and substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is selected from cyclopropyl, cyclobutyl, cyclopentyl, and cyclohexyl and monosubstituted with a group selected from halogen, C1-C2 alkyl, C1-C2 alkoxy, C1-C2 monohaloalkyl, and C1-C2 polyhaloalkyl.

In a further aspect, $Cy^1$, when present, is cyclopropyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is cyclopropyl substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is cyclopropyl monosubstituted with a group selected from halogen, C1-C2 alkyl, C1-C2 alkoxy, C1-C2 monohaloalkyl, and C1-C2 polyhaloalkyl.

In a further aspect, $Cy^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is selected from oxirane, oxetane, tetrahydrofuran, tetrahydro-2H-pyran, thiirane, thietane, tetrahydrothiophene, tetrahydro-2H-thiopyran, aziridine, azetidine, pyrrolidine, and piperidine and monosubstituted with a group selected from halogen, C1-C2 alkyl, C1-C2 alkoxy, C1-C2 monohaloalkyl, and C1-C2 polyhaloalkyl.

In a further aspect, $Cy^1$, when present, is oxetane substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is oxetane substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is oxetane monosubstituted with a group selected from halogen, C1-C2 alkyl, C1-C2 alkoxy, C1-C2 monohaloalkyl, and C1-C2 polyhaloalkyl.

In a further aspect, $Cy^1$, when present, is tetrahydro-2H-thiopyran substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^1$, when present, is tetrahydro-2H-thiopyran substituted with 0 or 1 group selected from halogen, C1-C2 alkyl, C1-C2 alkoxy, C1-C2 monohaloalkyl, and C1-C2 polyhaloalkyl. In yet a further aspect, $Cy^1$, when present, is tetrahydro-2H-thiopyran monosubstituted with a group selected from halogen, C1-C2 alkyl, C1-C2 alkoxy, C1-C2 monohaloalkyl, and C1-C2 polyhaloalkyl.

h. $Cy^2$ Groups

In one aspect, $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl. In a further aspect, $Cy^2$, when present, is C3-C6 cycloalkyl substituted with 0, 1, or 2 groups independently selected from halogen, C1-C4 alkyl, C1-C4 alkoxyalkyl, C1-C4 hydroxyalkyl, C1-C4 monohaloalkyl, C1-C4 polyhaloalkyl. In a still further aspect, $Cy^2$, when present, is C3-C6 cycloalkyl substituted with 0 or 1 group selected from halogen, C1-C4 alkyl, C1-C4 alkoxyalkyl, C1-C4 hydroxyalkyl, C1-C4 monohaloalkyl, C1-C4 polyhaloalkyl. In yet a further aspect, $Cy^2$, when present, is C3-C6 cycloalkyl monosubstituted with a group selected from halogen, C1-C4 alkyl, C1-C4 alkoxyalkyl, C1-C4 hydroxyalkyl, C1-C4 monohaloalkyl, C1-C4 polyhaloalkyl. In an even further aspect, $Cy^2$, when present, is unsubstituted C3-C6 cycloalkyl.

In a further aspect, $Cy^2$, when present, is C3-C6 cycloalkyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^2$, when present, is selected from cyclopropyl, cyclobutyl, cyclopentyl, and cyclohexyl and substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, $Cy^2$, when present, is cyclopropyl substituted with 0, 1, 2, or 3 substituents independently selected from —F, —Cl, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, and —(CH₂)₂CI₃.

In a further aspect, $Cy^2$, when present, is C3-C6 cycloalkyl substituted with 0, 1, 2, or 3 substituents independently selected from —F, —Cl, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, and —CH₂CCl₃. In a still further aspect, $Cy^2$, when present, is C3-C6 cycloalkyl substituted with 0, 1, 2, or 3 substituents independently selected from —F, —Cl, methyl, ethyl, —OCH₃, —OCH₂CH₃, —CH₂F, —CH₂Cl, —CHF₂, —CF₃, —CH₂Cl, —CHCl₂, and —CCl₃. In yet a further aspect, $Cy^2$, when present, is C3-C6 cycloalkyl substituted with 0, 1, 2, or 3 substituents independently selected from —F, —Cl, methyl, —OCH₃, —CF₃, and —CCl₃.

In a further aspect, $Cy^2$, when present, is selected from cyclopropyl, cyclobutyl, cyclopentyl, and cyclohexyl and substituted with 0, 1, 2, or 3 substituents independently selected from —F, —Cl, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, and —CH₂CCl₃. In a still further aspect, $Cy^2$, when present, is selected from cyclopropyl, cyclobutyl, cyclopentyl, and cyclohexyl and substituted with 0, 1, 2, or 3 substituents independently selected from —F, —Cl, methyl, ethyl, —OCH₃, —OCH₂CH₃, —CH₂F, —CH₂Cl, —CHF₂, —CF₃, —CH₂Cl, —CHCl₂, and —CCl₃. In yet a further aspect, $Cy^2$, when present, is selected from cyclopropyl, cyclobutyl, cyclopentyl, and cyclohexyl and substituted with 0, 1, 2, or 3 substituents independently selected from —F, —Cl, methyl, —OCH₃, —CF₃, and —CCl₃.

In a further aspect, $Cy^2$, when present, is cyclopropyl substituted with 0, 1, 2, or 3 substituents independently selected from —F, —Cl, methyl, ethyl, propyl, isopropyl, —OCH₃, —OCH₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, and —CH₂CCl₃. In a still further aspect, $Cy^2$, when present, is cyclopropyl substituted with 0, 1, 2, or 3 substituents independently selected from —F, —Cl, methyl, ethyl, —OCH₃, —OCH₂CH₃, —CH₂F, —CH₂Cl, —CHF₂, —CF₃, —CH₂Cl, —CHCl₂, and —CCl₃. In yet a further aspect, $Cy^2$, when present, is cyclopropyl substituted with 0, 1, 2, or 3 substituents independently selected from —F, —Cl, methyl, —OCH₃, —CF₃, and —CCl₃.

In a further aspect, $Cy^2$, when present, is C3-C6 cycloalkyl substituted with 0, 1, or 2 groups independently selected from halogen, C1-C4 alkyl, C1-C4 alkoxy, C1-C4 monohaloalkyl, and C1-C4 polyhaloalkyl. In a still further aspect, $Cy^2$, when present, is C3-C6 cycloalkyl substituted with 0 or 1 group selected from halogen, C1-C4 alkyl, C1-C4 alkoxy, C1-C4 monohaloalkyl, and C1-C4 polyhaloalkyl. In yet a further aspect, $Cy^2$, when present, is C3-C6 cycloalkyl monosubstituted with a group selected from halogen, C1-C4 alkyl, C1-C4 alkoxy, C1-C4 monohaloalkyl, and C1-C4 polyhaloalkyl.

In a further aspect, $Cy^2$, when present, is C3-C6 cycloalkyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^2$, when present, is C3-C6 cycloalkyl substituted with 0 or 1 group selected from halogen, C1-C2 alkyl, C1-C2 alkoxy, C1-C2 monohaloalkyl, and C1-C2 polyhaloalkyl. In yet a further aspect, $Cy^2$, when present, is C3-C6 cycloalkyl monosubstituted with a group selected from halogen, C1-C2 alkyl, C1-C2 alkoxy, C1-C2 monohaloalkyl, and C1-C2 polyhaloalkyl.

In a further aspect, $Cy^2$, when present, is selected from cyclopropyl, cyclobutyl, cyclopentyl, and cyclohexyl and substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^2$, when present, is selected from cyclopropyl, cyclobutyl, cyclopentyl, and cyclohexyl and substituted with 0 or 1 group selected from halogen, C1-C2 alkyl, C1-C2 alkoxy, C1-C2 monohaloalkyl, and C1-C2 polyhaloalkyl. In yet a further aspect, $Cy^2$, when present, is selected from cyclopropyl, cyclobutyl, cyclopentyl, and cyclohexyl and monosubstituted with a group selected from halogen, C1-C2 alkyl, C1-C2 alkoxy, C1-C2 monohaloalkyl, and C1-C2 polyhaloalkyl.

In a further aspect, $Cy^2$, when present, is cyclopropyl substituted with 0, 1, or 2 groups independently selected from halogen, C1-C2 alkyl, C1-C2 alkoxy, C1-C2 monohaloalkyl, and C1-C2 polyhaloalkyl. In a still further aspect, $Cy^2$, when present, is cyclopropyl substituted with 0 or 1 group selected from halogen, C1-C2 alkyl, C1-C2 alkoxy, C1-C2 monohaloalkyl, and C1-C2 polyhaloalkyl. In yet a further aspect, $Cy^2$, when present, is cyclopropyl monosubstituted with a group selected from halogen, C1-C2 alkyl, C1-C2 alkoxy, C1-C2 monohaloalkyl, and C1-C2 polyhaloalkyl.

2. Example Compounds

In one aspect, a compound can be present as one or more of the following structures:

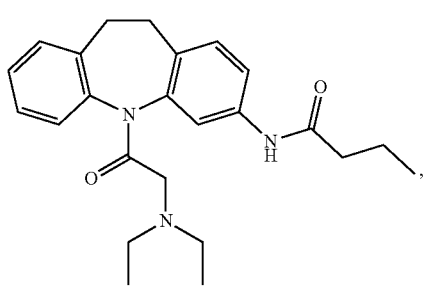

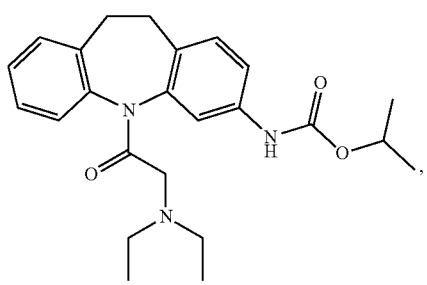

| 89 -continued | 90 -continued |
|---|---|
| 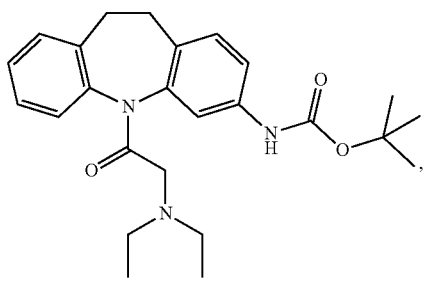 | 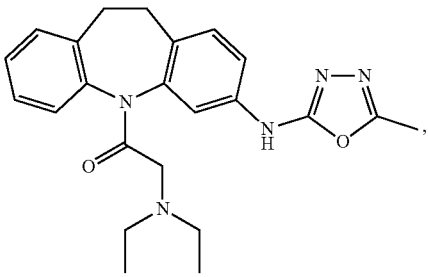 |
| 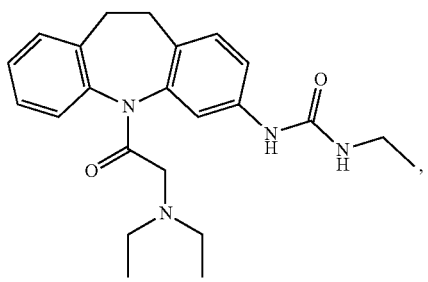 | 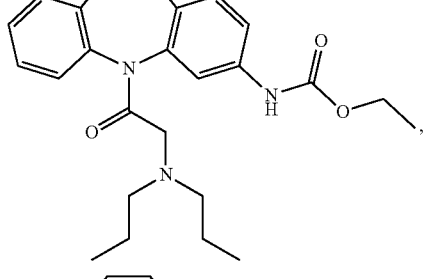 |
| 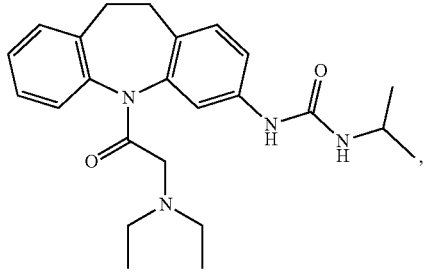 | 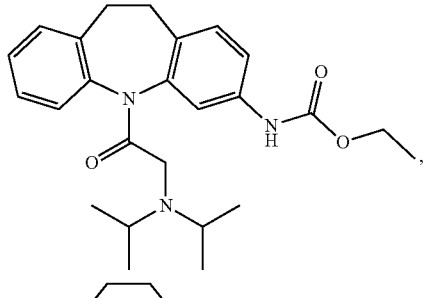 |
| 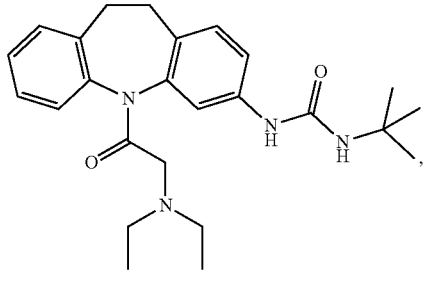 | 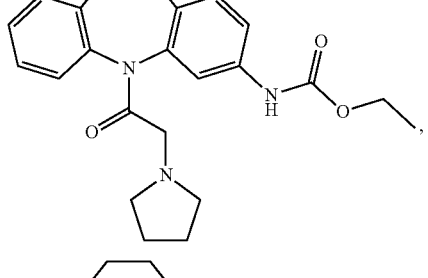 |
| 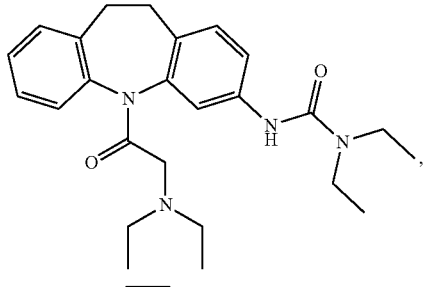 | 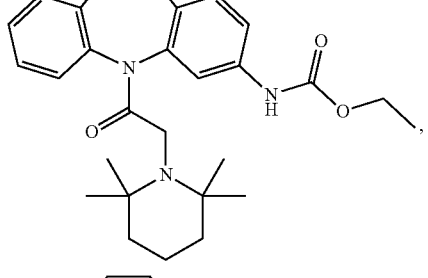 |
| 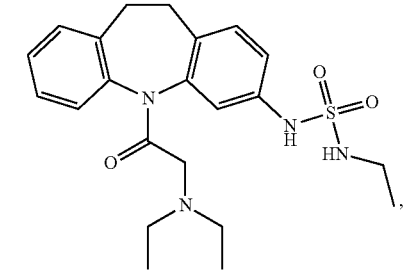 | 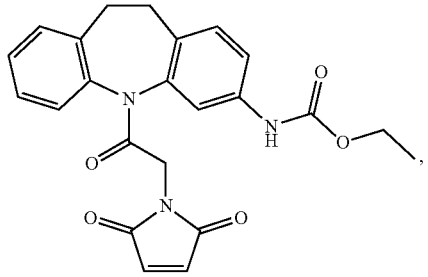 |

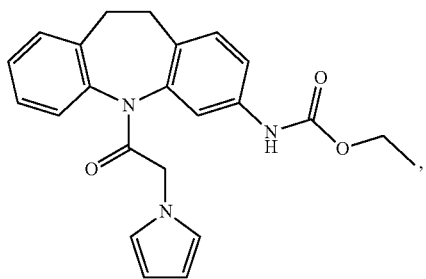
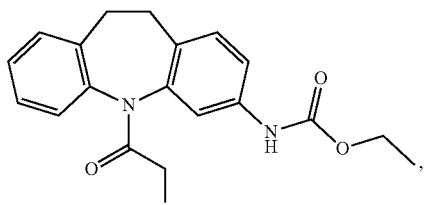
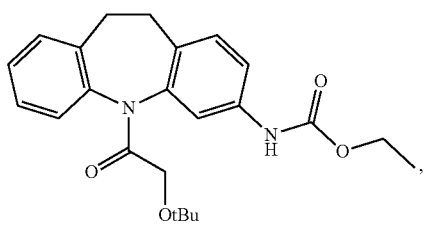
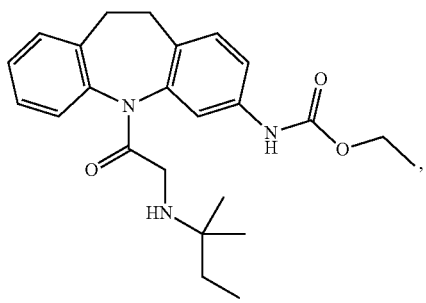
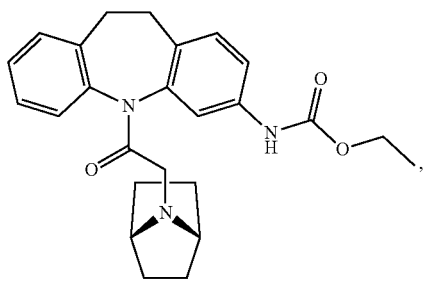
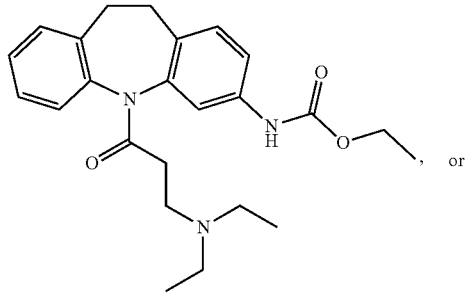, or
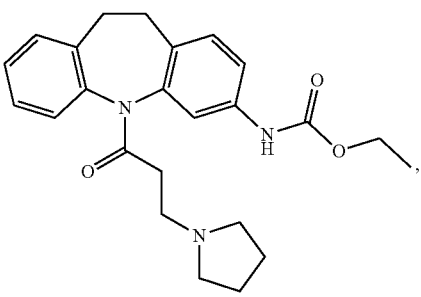
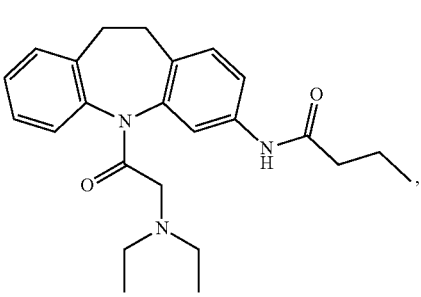
or a pharmaceutically acceptable salt thereof.
In a further aspect, a compound can be present as one or more of the following structures:
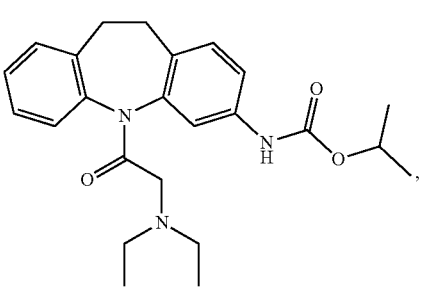
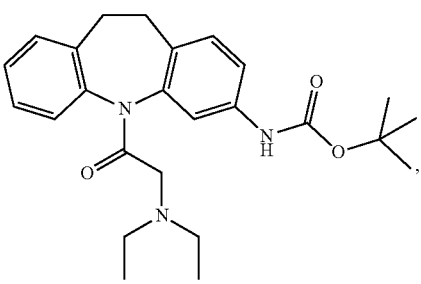
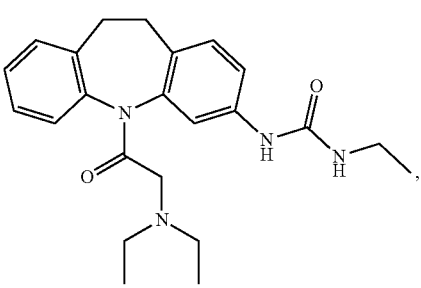

93
-continued

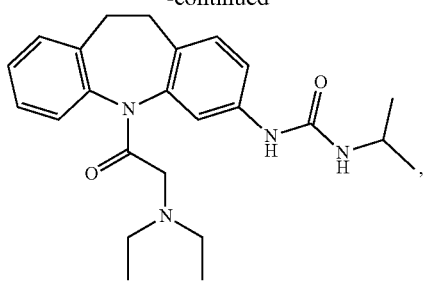

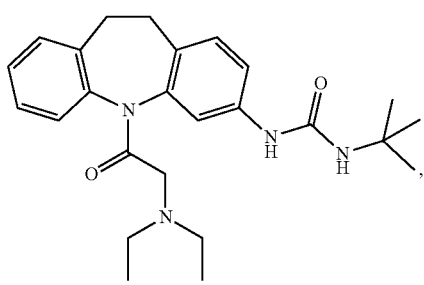

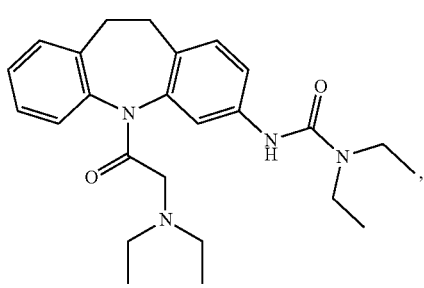

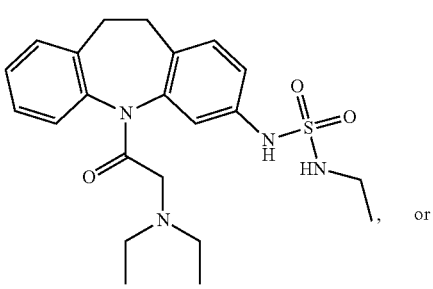, or

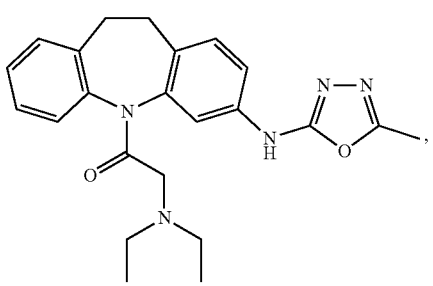

or a pharmaceutically acceptable sale thereof.

94

In a still further aspect, a compound can be present as:

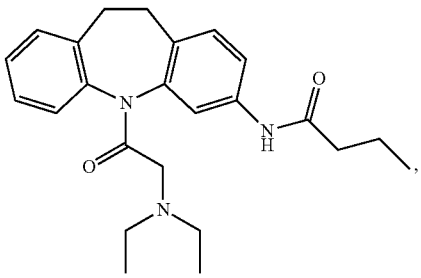 [SMILES: CCCC(=O)Nc1ccc2c(c1)N(C(=O)CN(CC)CC)c1ccccc1CC2]

or a pharmaceutically acceptable salt thereof.

In yet a further aspect, a compound can be present as one or more of the following structures:

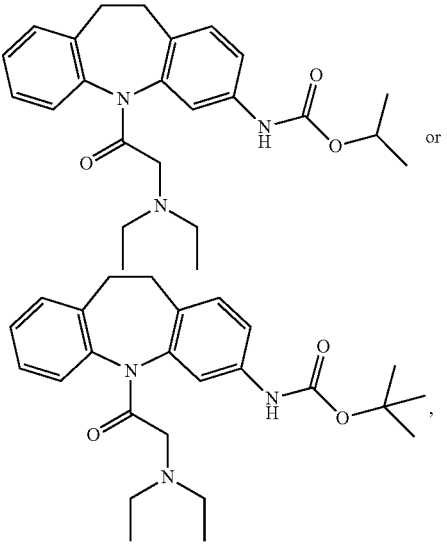

or a pharmaceutically acceptable salt thereof.

In an even further aspect, a compound can be present as one or more of the following structures:

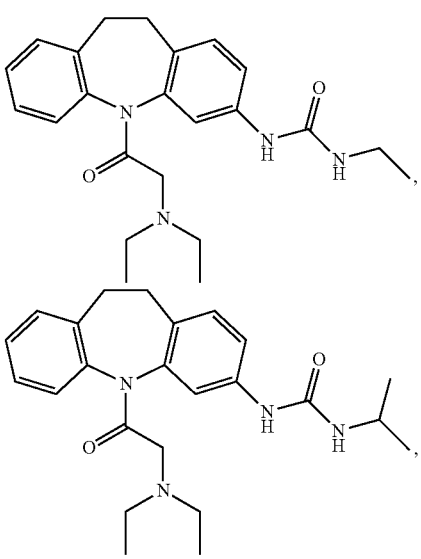

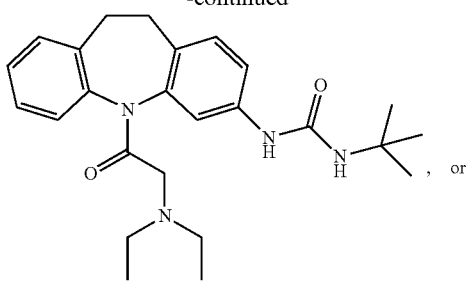
, or
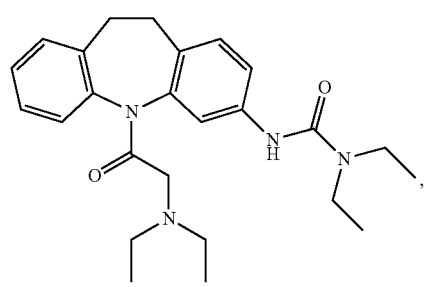
or a pharmaceutically acceptable salt thereof.
In a still further aspect, a compound can be present as:
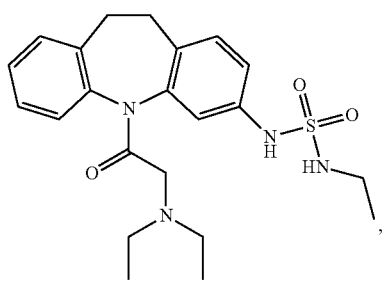 [SMILES: CCNS(=O)(=O)Nc1ccc2c(c1)N(C(=O)CN(CC)CC)c1ccccc1CC2]
or a pharmaceutically acceptable salt thereof.
In yet a further aspect, a compound can be present as:
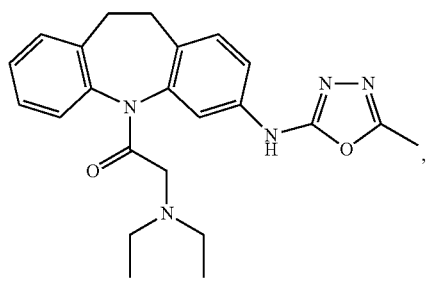 [SMILES: CCN(CC)CC(=O)N1c2ccccc2CCc2ccc(Nc3nnc(C)o3)cc21]
or a pharmaceutically acceptable salt thereof.
In a further aspect, a compound can be present as one or more of the following structures:
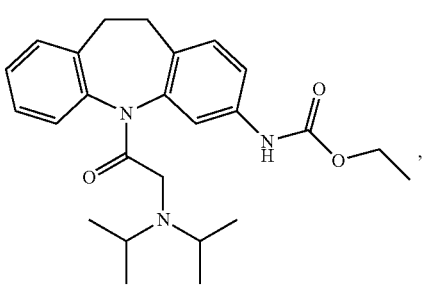
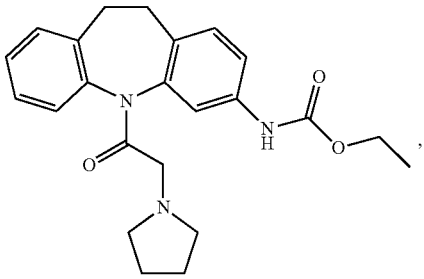
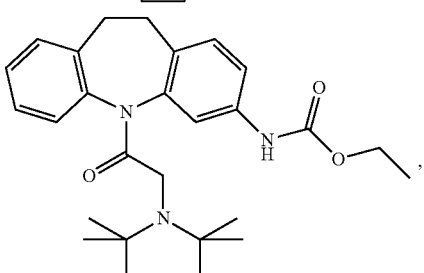
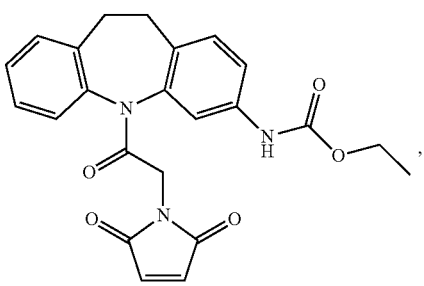
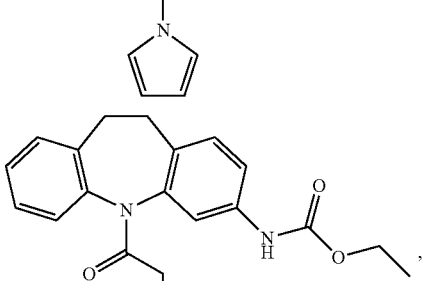

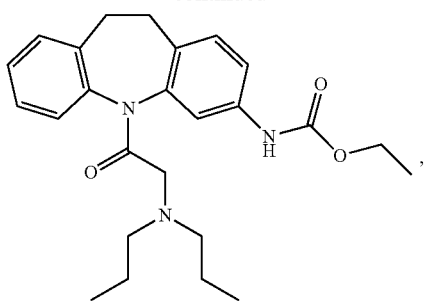
,
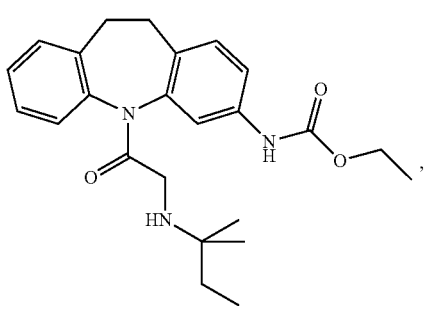
,
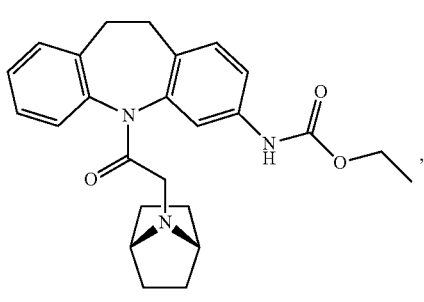
,
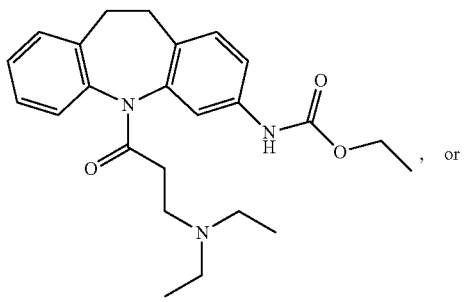
, or
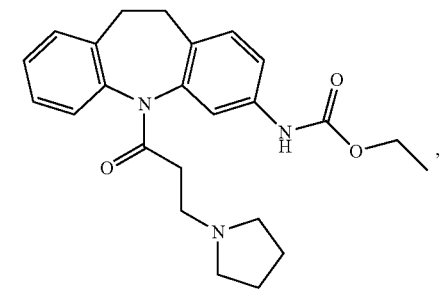 [SMILES: CCOC(=O)Nc1ccc2c(c1)N(C(=O)CCN1CCCC1)c1ccccc1CC2]
or a pharmaceutically acceptable salt thereof.
In a still further aspect, a compound can be present as one or more of the following structures:
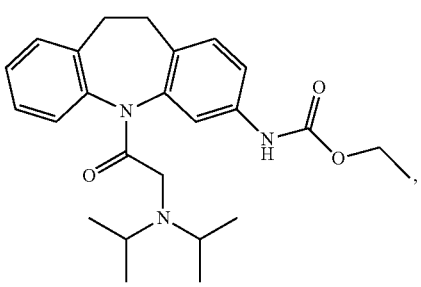
,
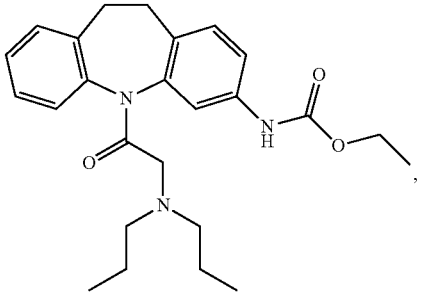
,
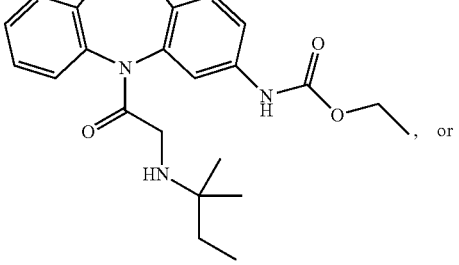
, or
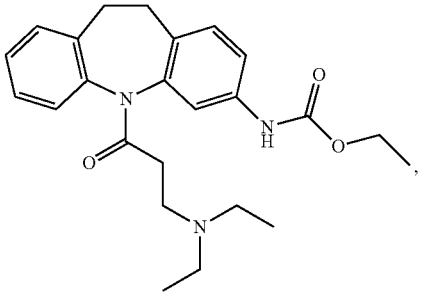
,
or a pharmaceutically acceptable salt thereof.
In yet a further aspect, a compound can be present as one or more of the following structures:
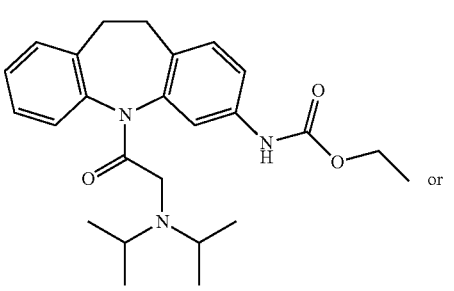
or -continued

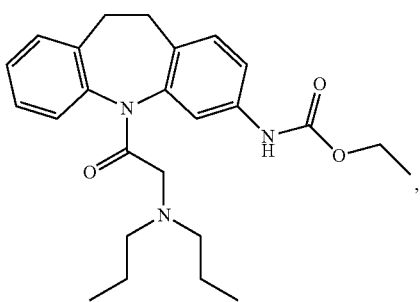

or a pharmaceutically acceptable salt thereof.

In an even further aspect, a compound can be present as:

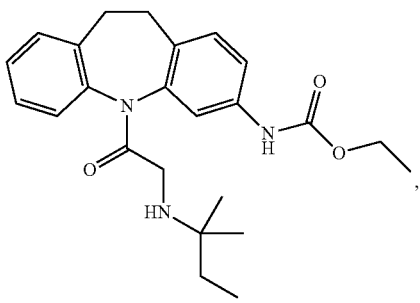 [SMILES: CCOC(=O)Nc1ccc2c(c1)N(C(=O)CNC(C)(C)CC)c1ccccc1CC2]

or a pharmaceutically acceptable thereof.

In a still further aspect, a compound can be present as:

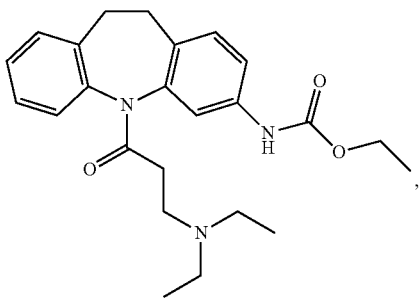 [SMILES: CCOC(=O)Nc1ccc2c(c1)N(C(=O)CCN(CC)CC)c1ccccc1CC2]

or a pharmaceutically acceptable salt thereof.

In a further aspect, a compound can be present as one or more of the following structures:

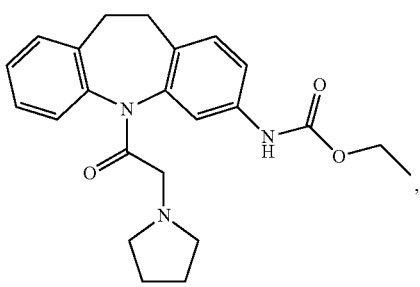

-continued

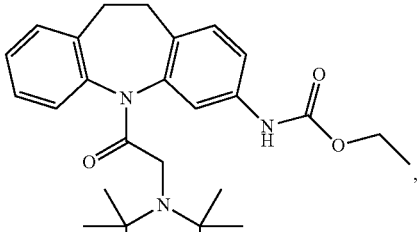

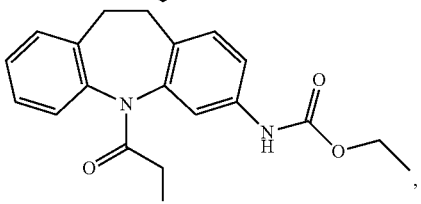

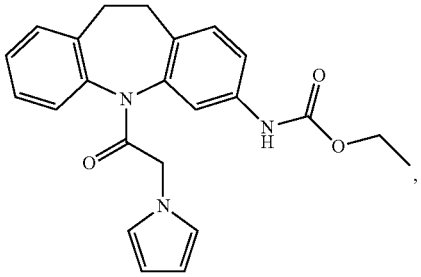

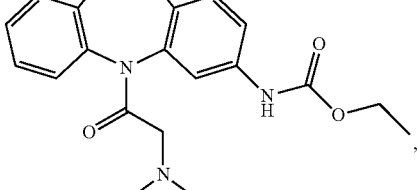

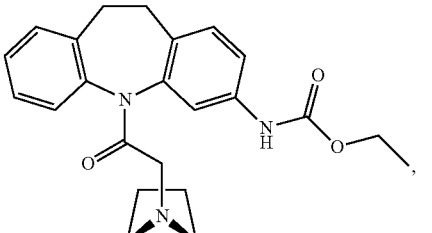, or

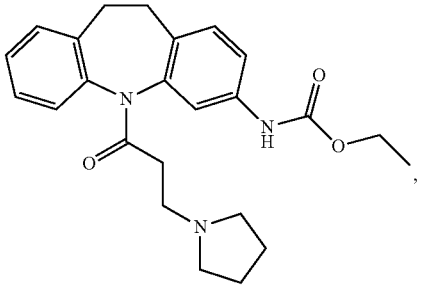

or a pharmaceutically acceptable salt thereof.

In a still further aspect, a compound can be present as one or more of the following structures:

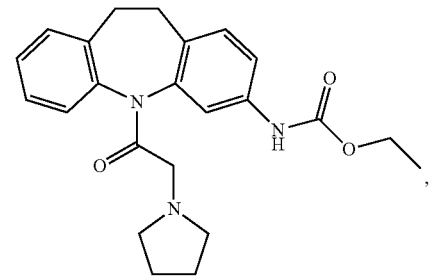

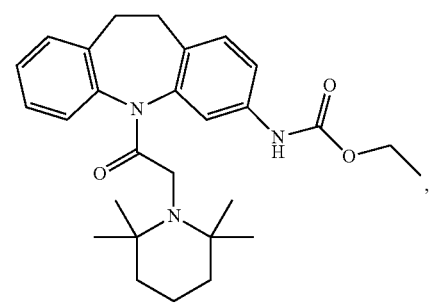

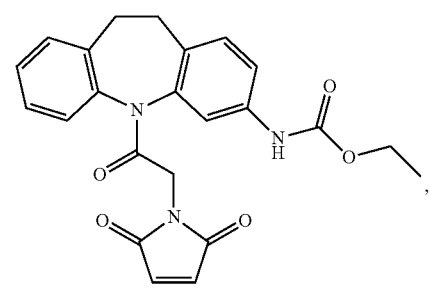

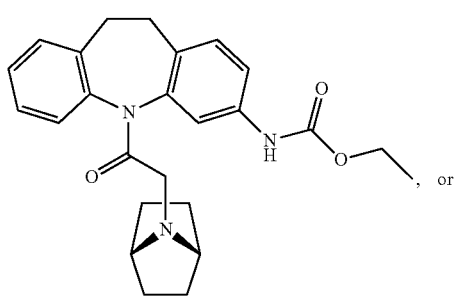

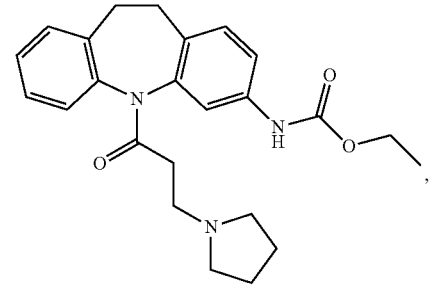 [SMILES: CCOC(=O)Nc1ccc2c(c1)N(C(=O)CCN1CCCC1)c1ccccc1CC2]

or a pharmaceutically acceptable salt thereof.

In yet a further aspect, a compound can be present as one or more of the following structures:

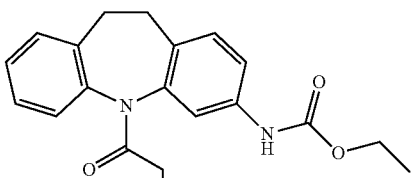

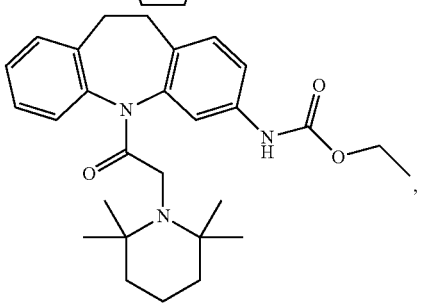

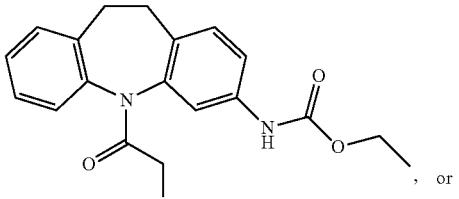

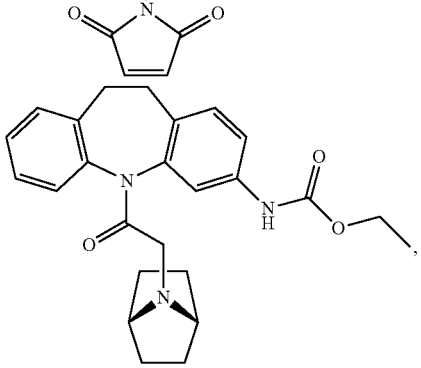

or a pharmaceutically acceptable salt thereof.

In an even further aspect, a compound can be present as one or more of the following structures:

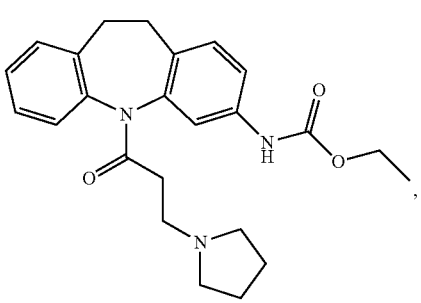 [SMILES: CCOC(=O)Nc1ccc2c(c1)N(C(=O)CCN1CCCC1)c1ccccc1CC2]

or a pharmaceutically acceptable derivative thereof.

In a further aspect, a compound can be present as one or more of the following structures:

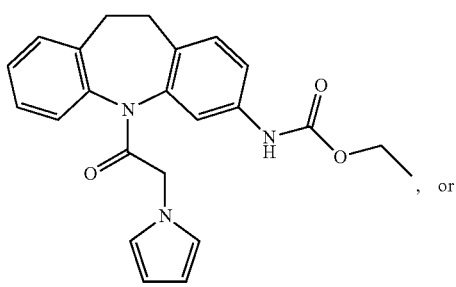
, or
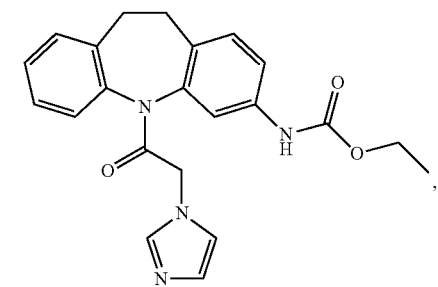
,
or a pharmaceutically acceptable salt thereof.
In a further aspect, a compound can be present as:
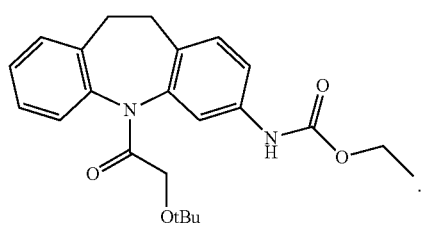 [SMILES: CCOC(=O)Nc1ccc2c(c1)N(C(=O)COC(C)(C)C)c1ccccc1CC2]
.
or a pharmaceutically acceptable salt thereof.
In a further aspect, a compound can be present as one or more of the following structures:
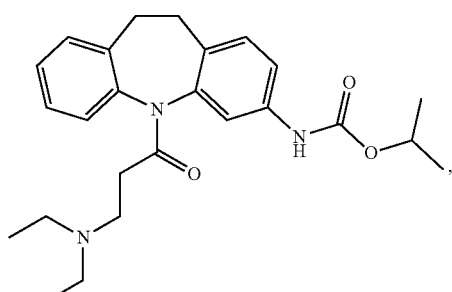
,
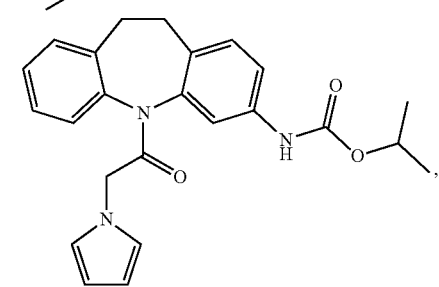
,
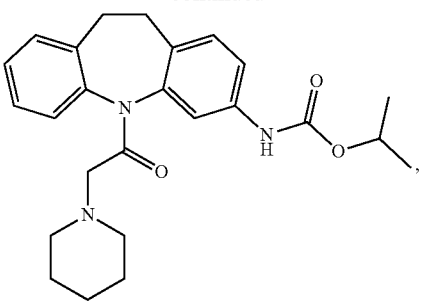
,
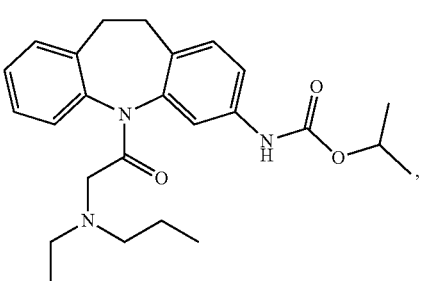
,
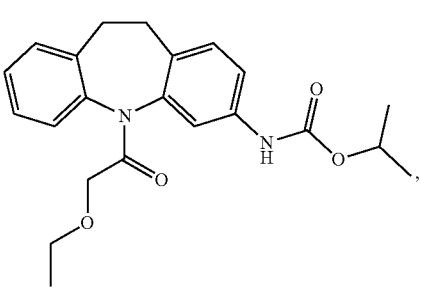
,
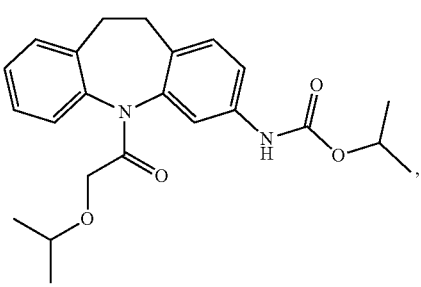
,
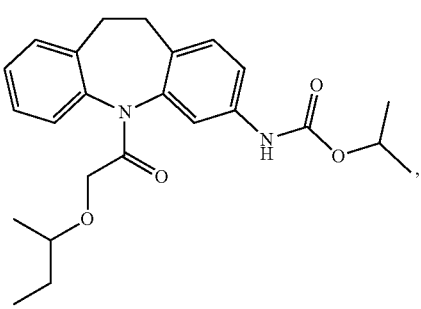
,

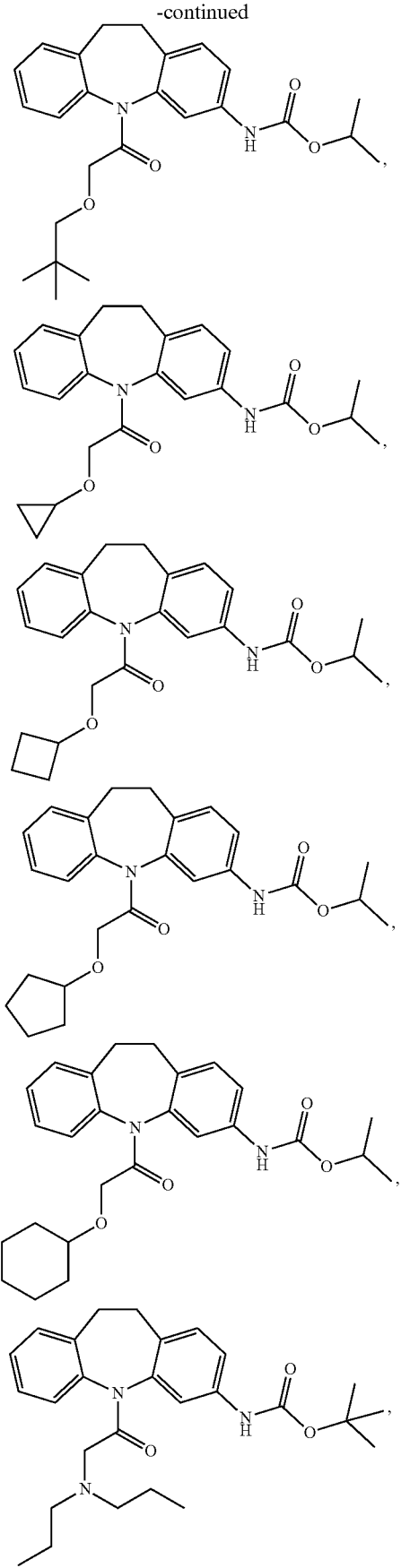
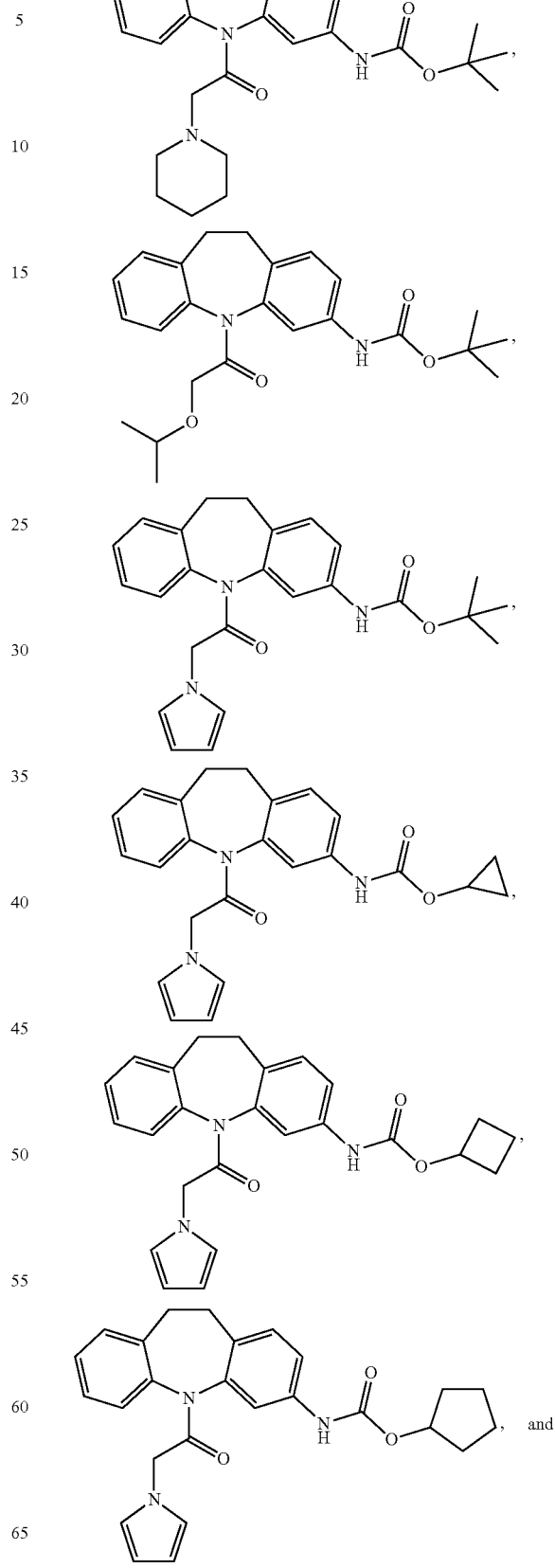

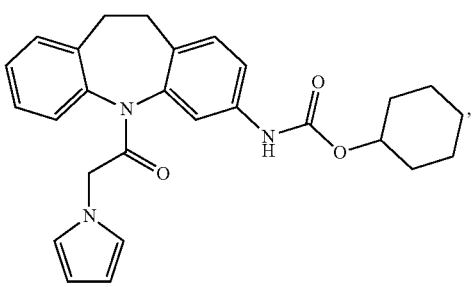
or a pharmaceutically acceptable salt thereof.
In a further aspect, a compound can be present as one or more of the following structures:
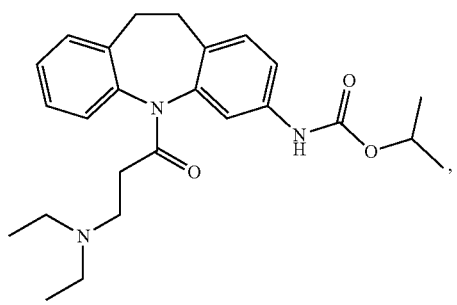
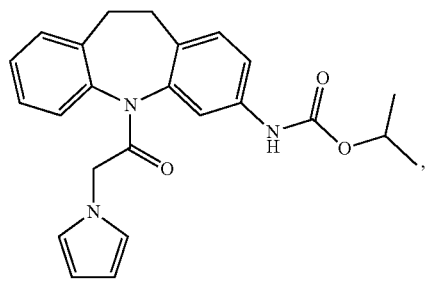
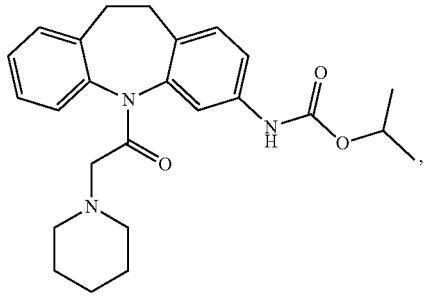
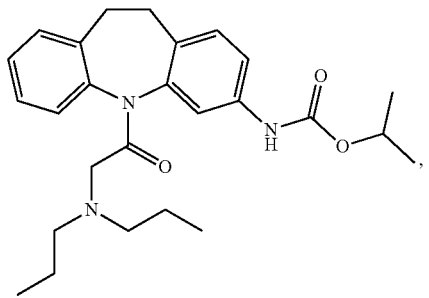
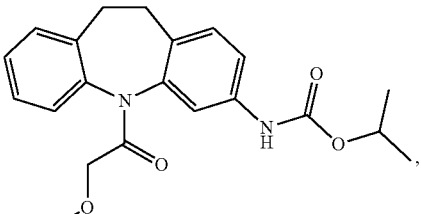
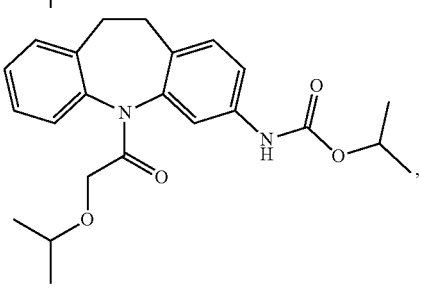
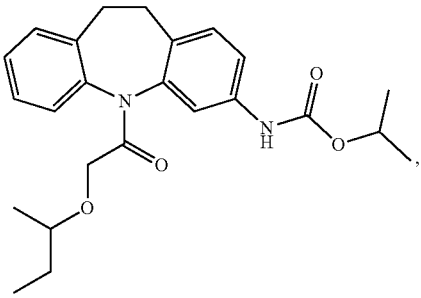
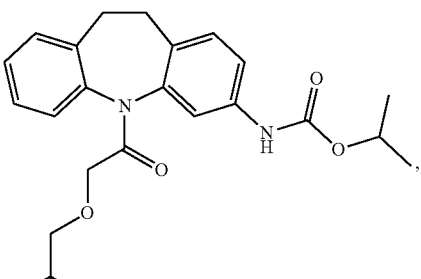
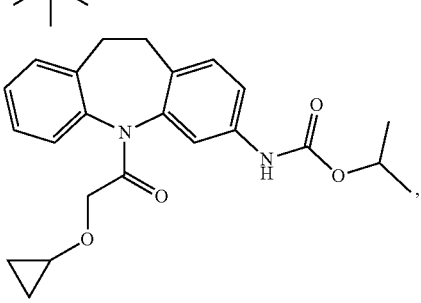
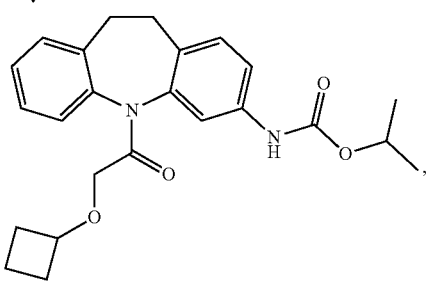

-continued

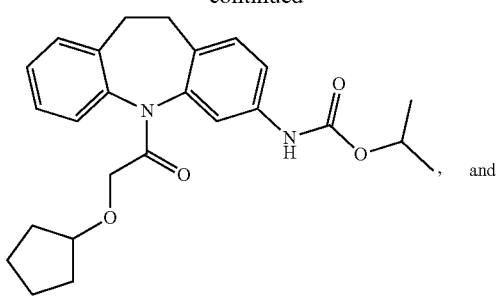

, and

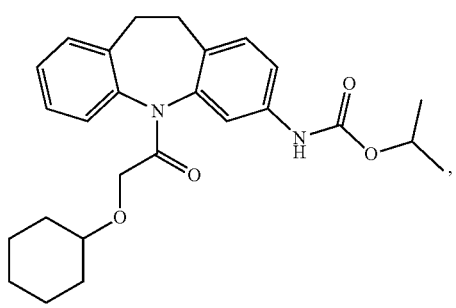

, or a pharmaceutically acceptable salt thereof.

In a further aspect, a compound can be present as one or more of the following structures:

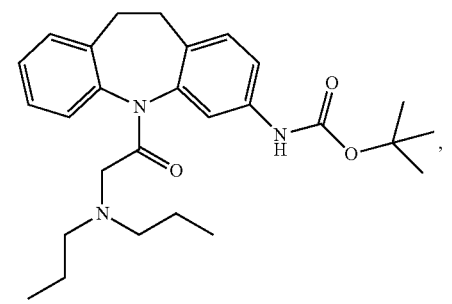

,

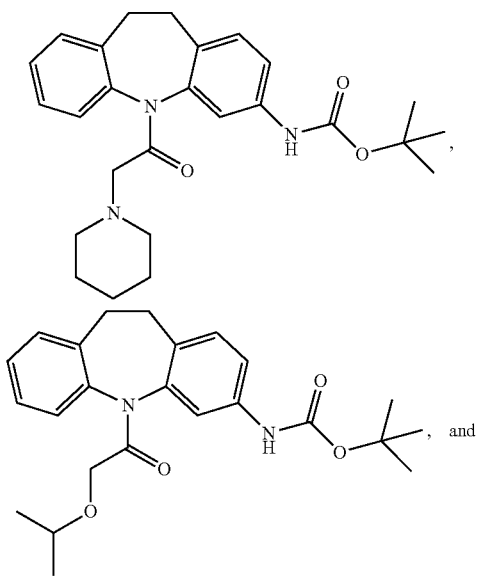

, and

-continued

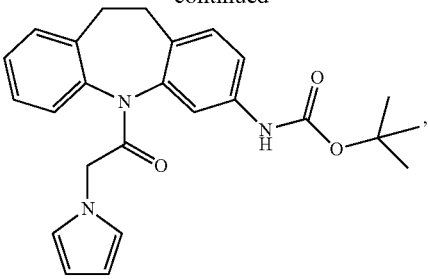

,

In a further aspect, a compound can be present as one or more of the following structures:

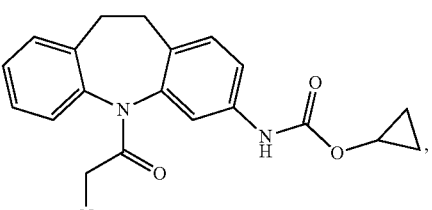

,

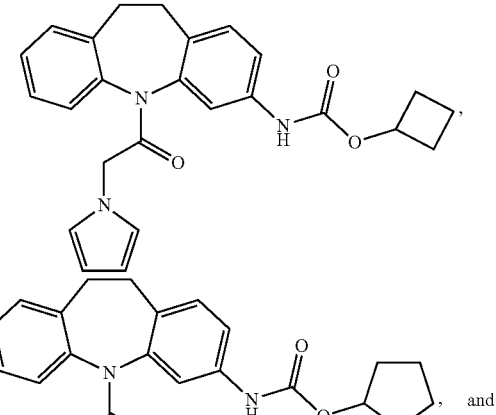

, and

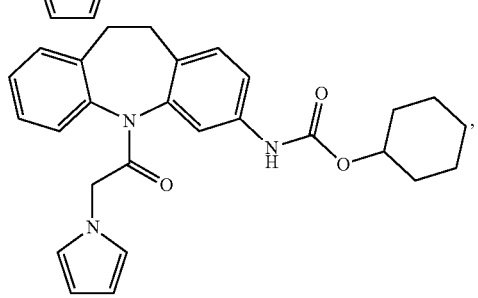

, or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as CAR antagonists, and such activity can be determined using the assay methods described herein.
In one aspect, a compound can be selected from:
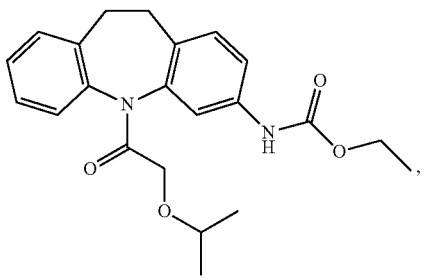,
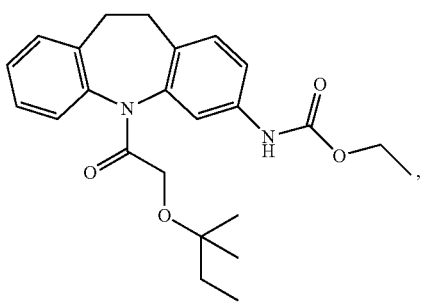,
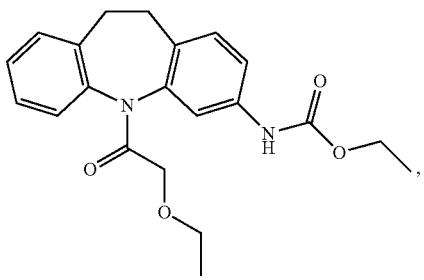,
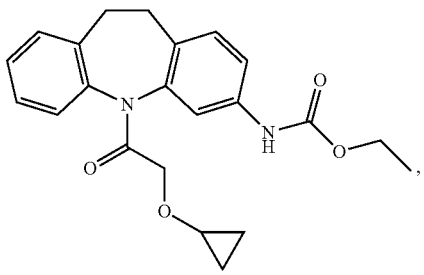,
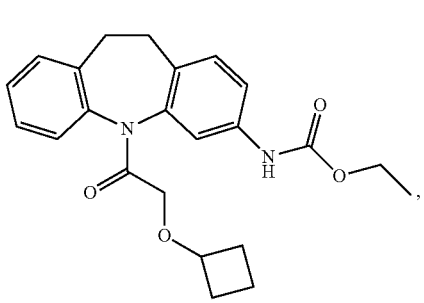,
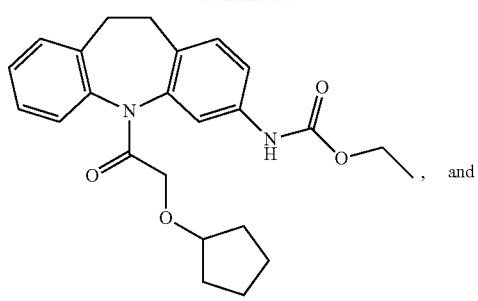, and
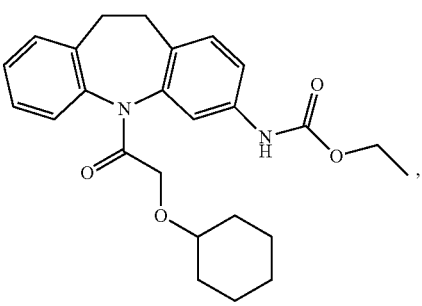,
or a pharmaceutically acceptable salt thereof.
In one aspect, a compound can be selected from:
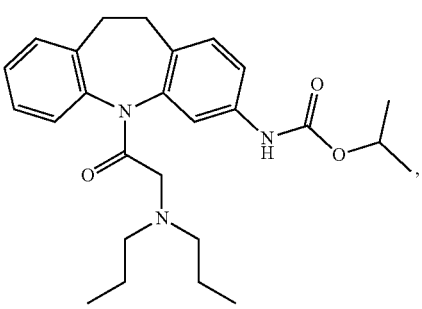,
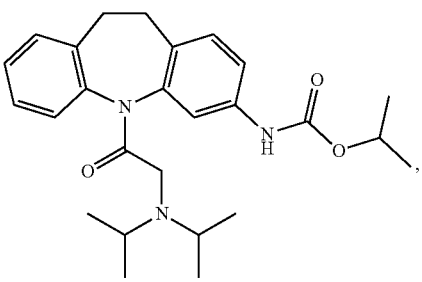,
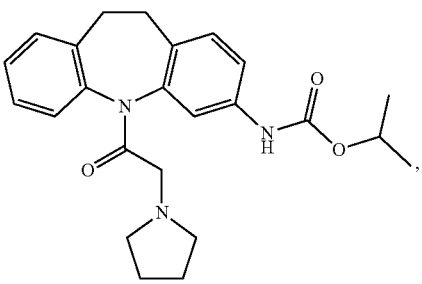, 113
-continued
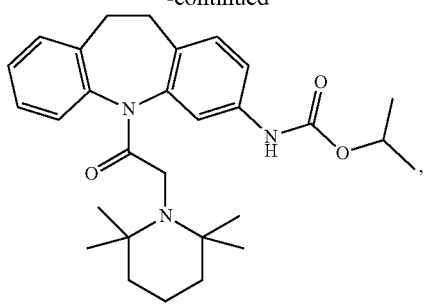,
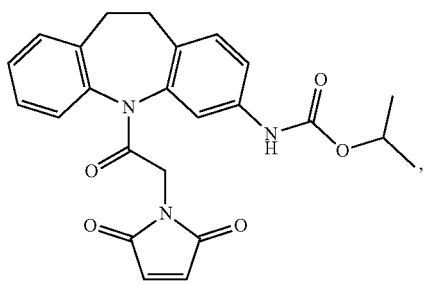,
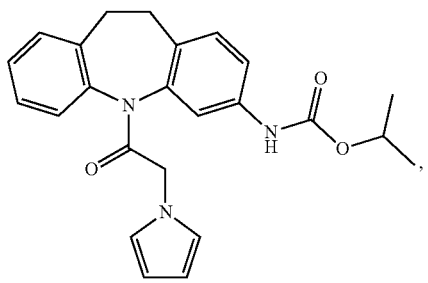,
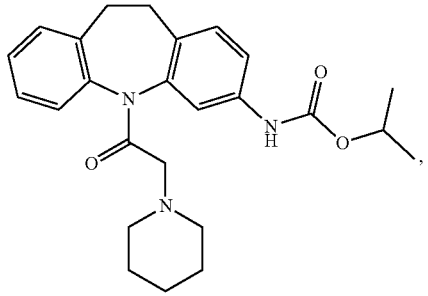,
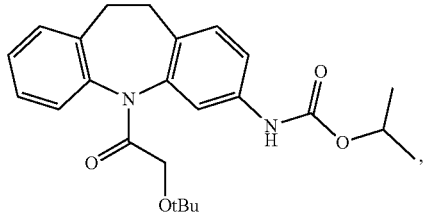,
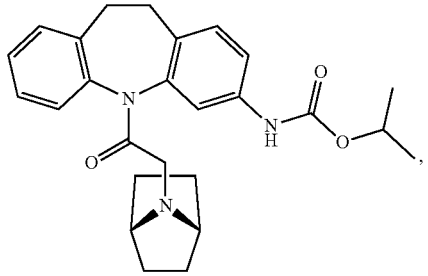,
114
-continued
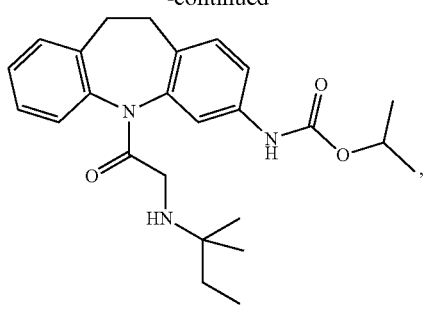,
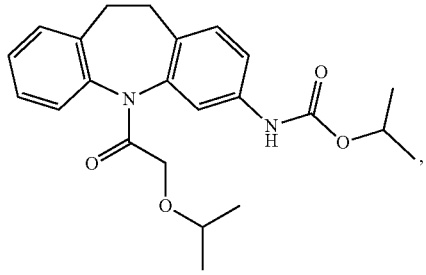,
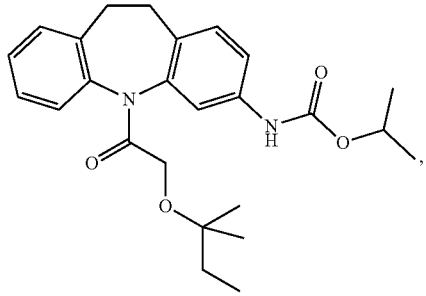,
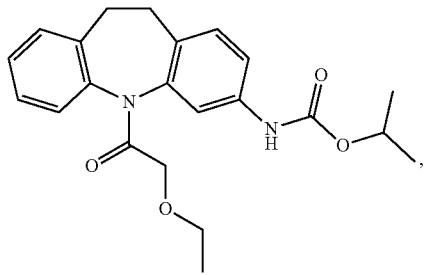,
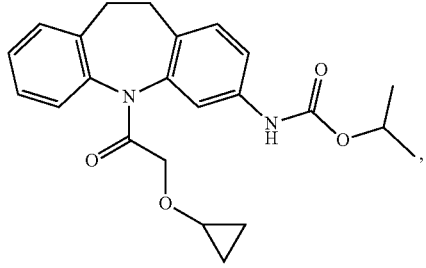,
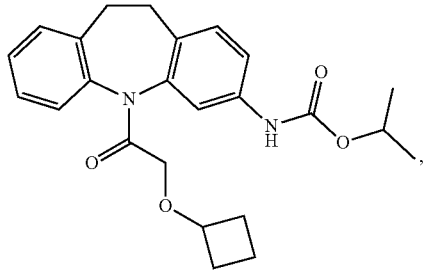,

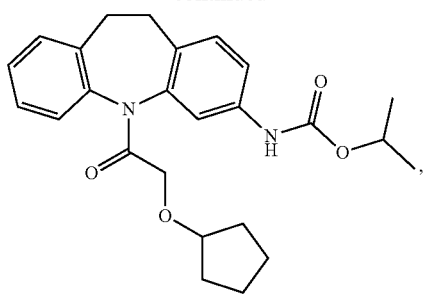
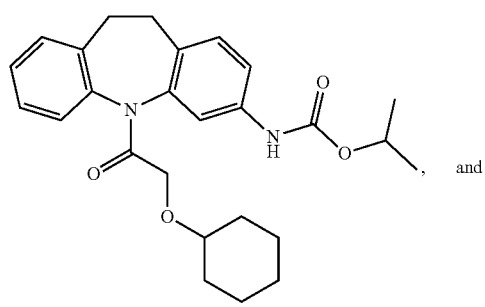, and
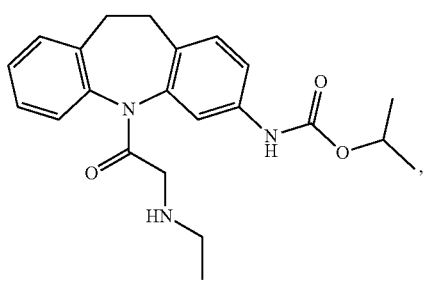
or a pharmaceutically acceptable salt thereof.
In one aspect, a compound can be selected from:
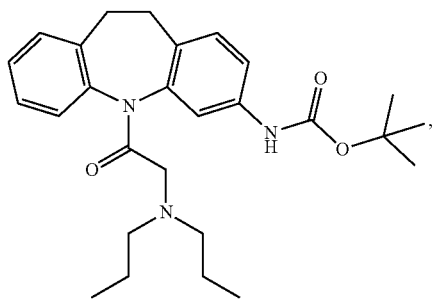
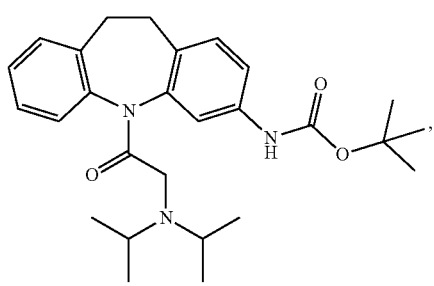
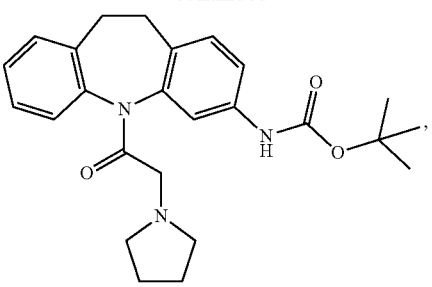
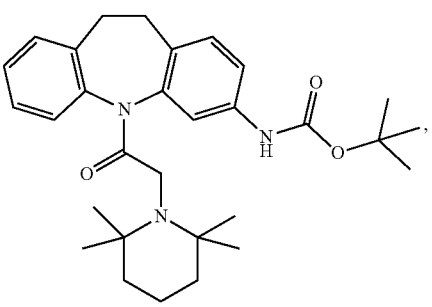
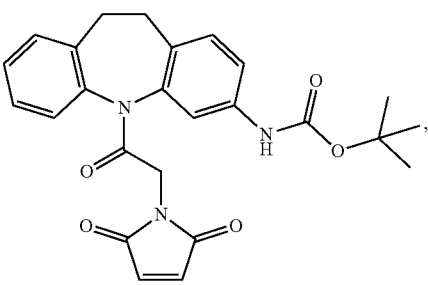
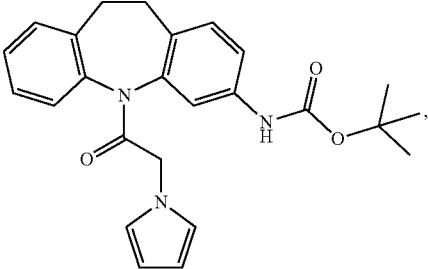
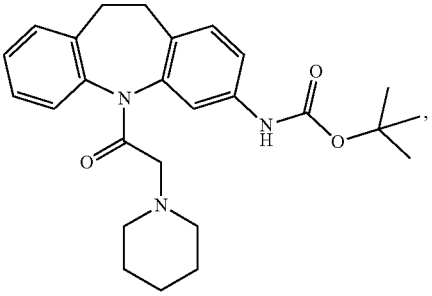
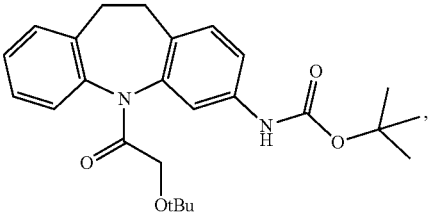

117
-continued
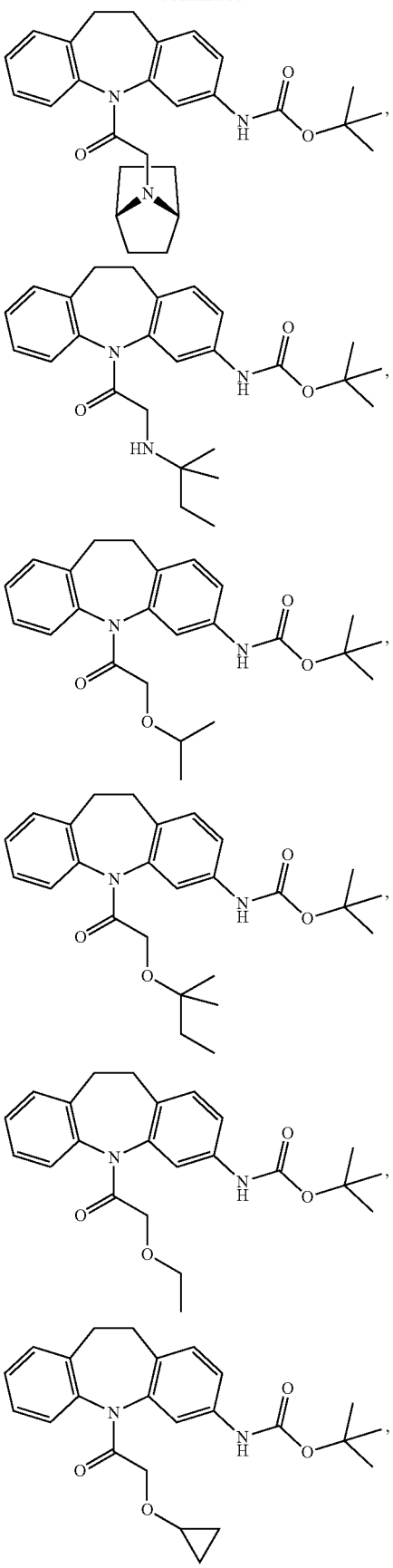
118
-continued
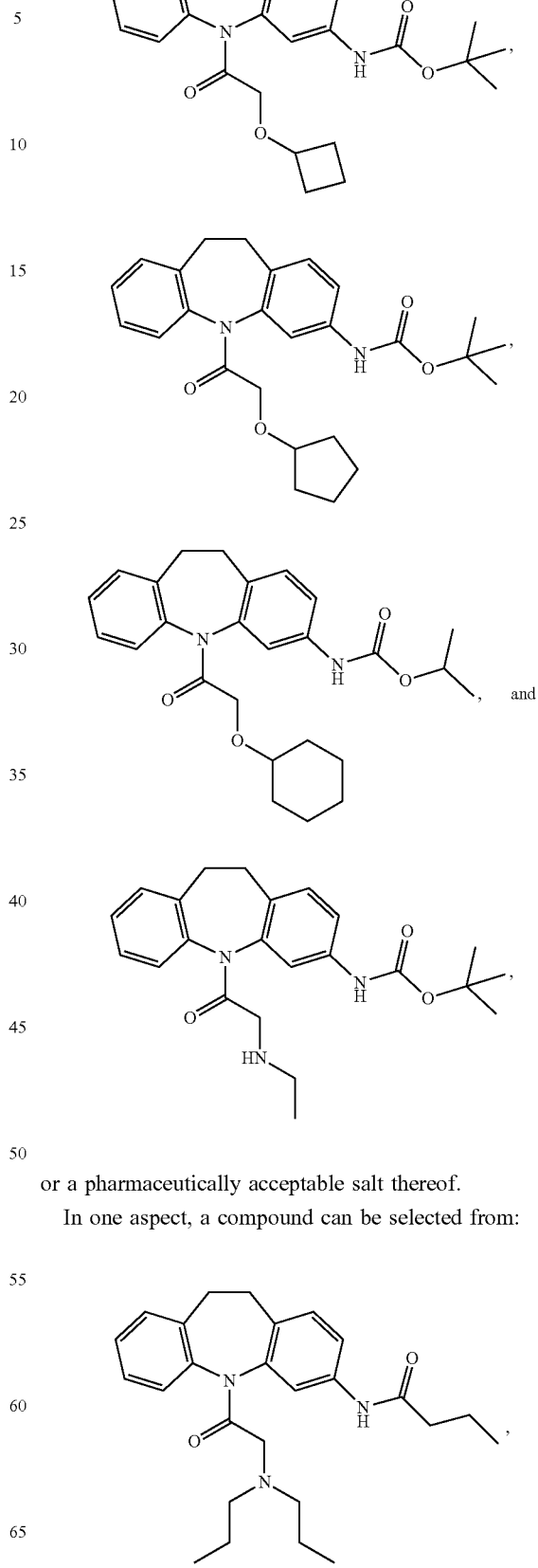
or a pharmaceutically acceptable salt thereof.
In one aspect, a compound can be selected from:
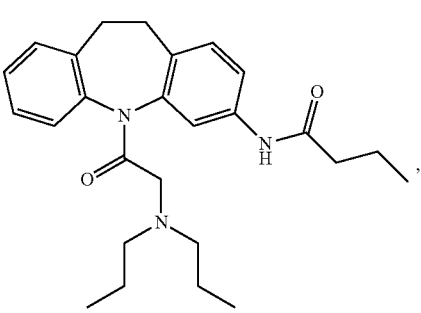

119
-continued
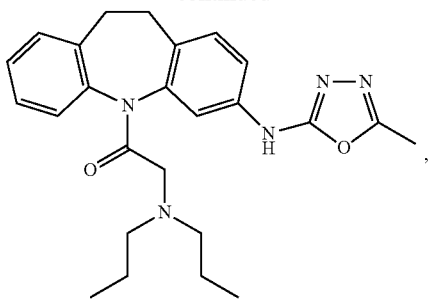
,
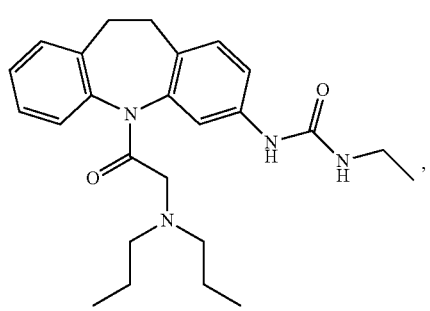 [SMILES: CCCN(CCC)CC(=O)N1c2ccccc2CCc2ccc(NS(=O)(=O)NCC)cc21]
,
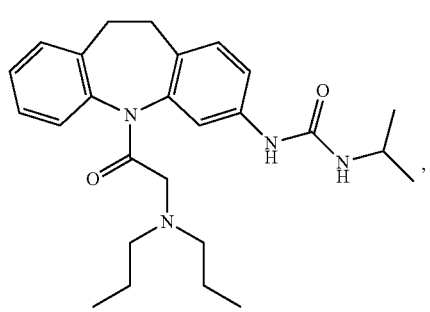
,
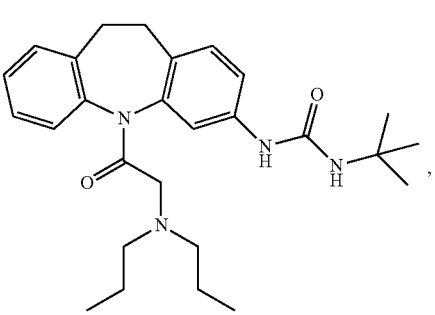
,
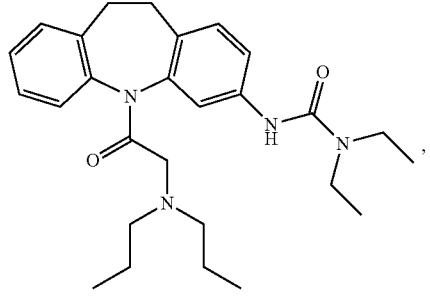
,
120
-continued
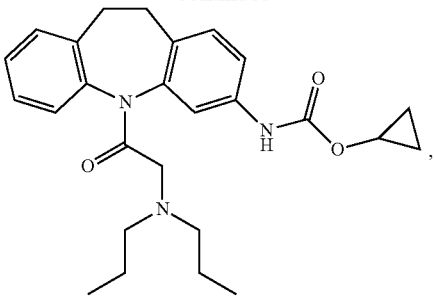
,
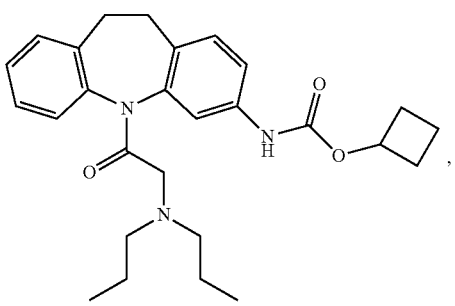
,
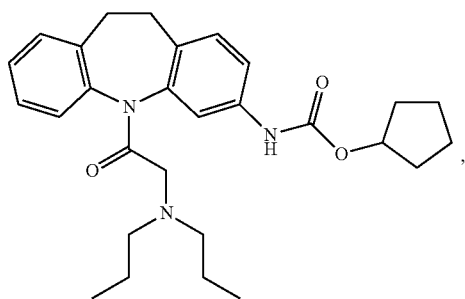
,
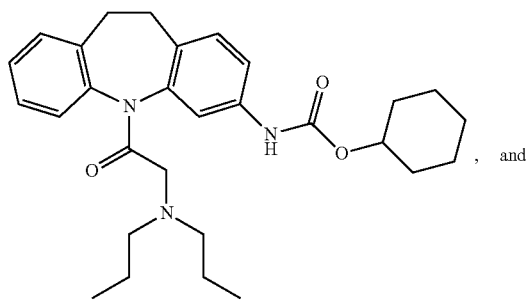
, and
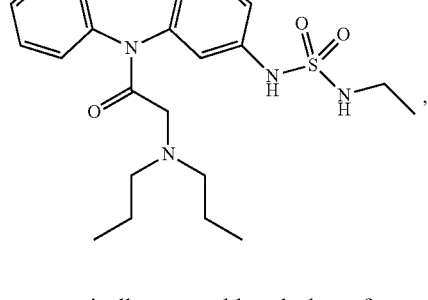
,
or a pharmaceutically acceptable salt thereof.

In one aspect, a compound can be selected from:
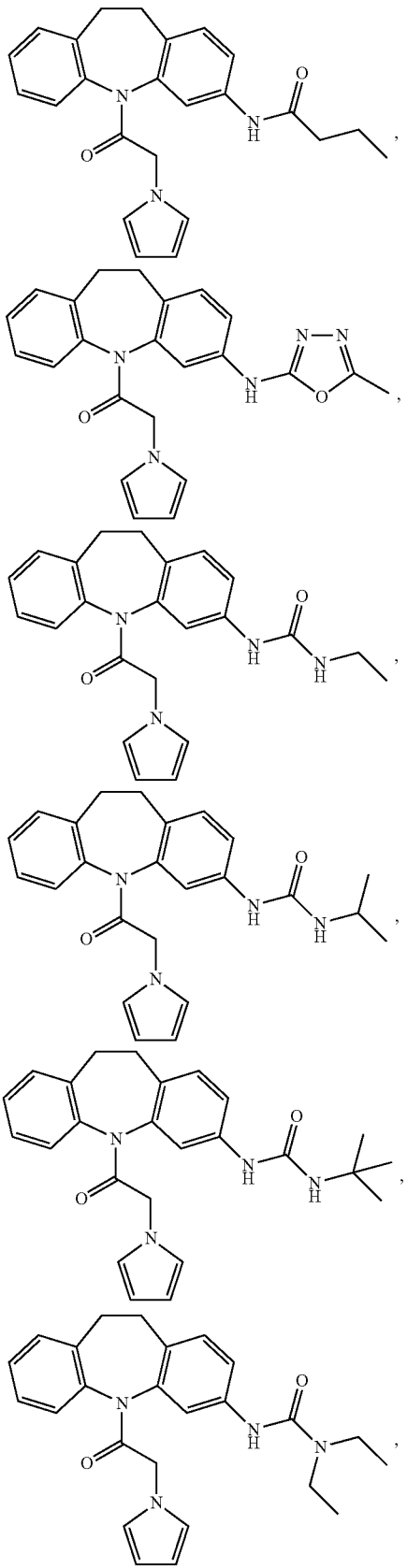
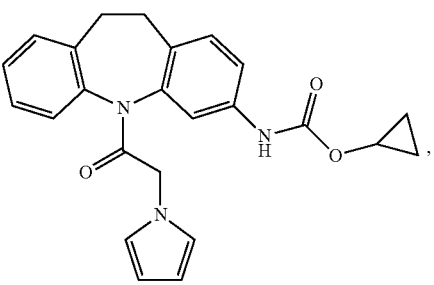
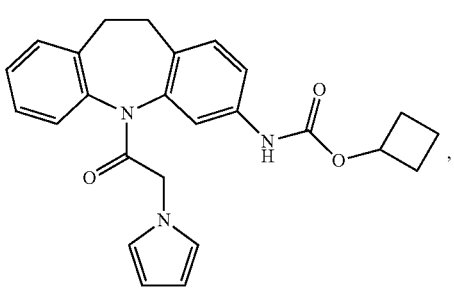
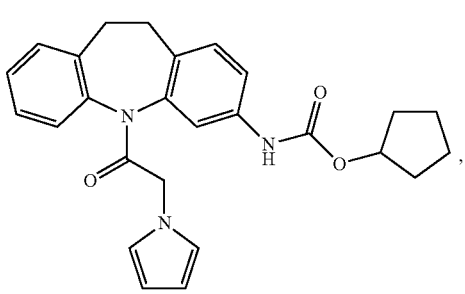
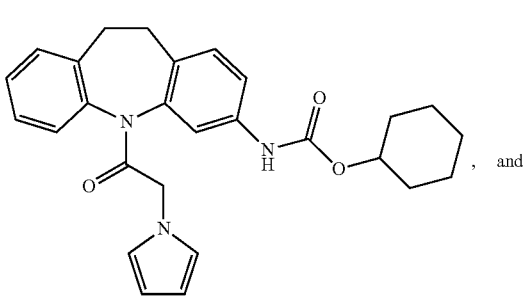, and
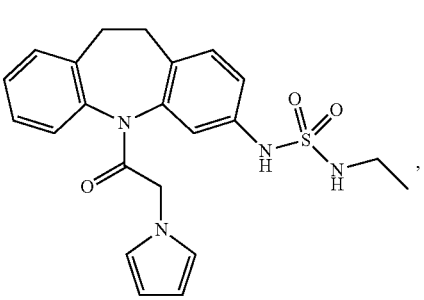
or a pharmaceutically acceptable salt thereof.

In one aspect, a compound can be selected from:
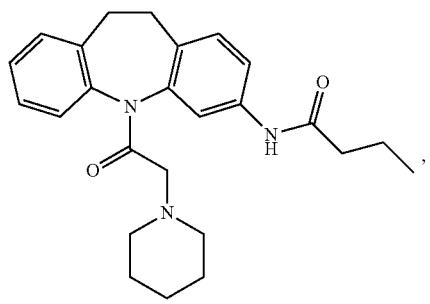
,
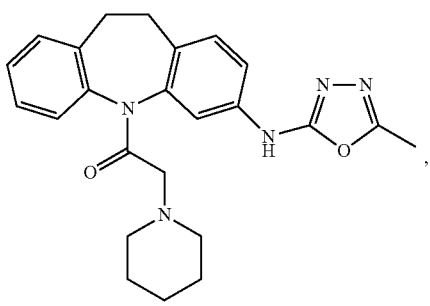
,
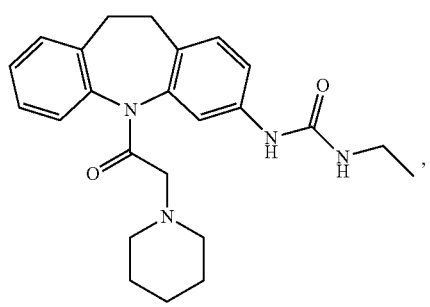
,
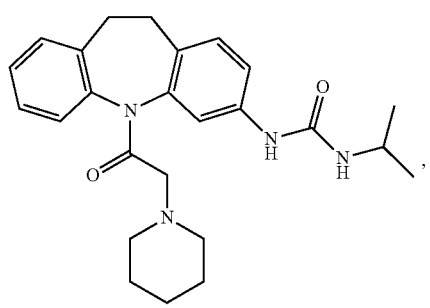
,
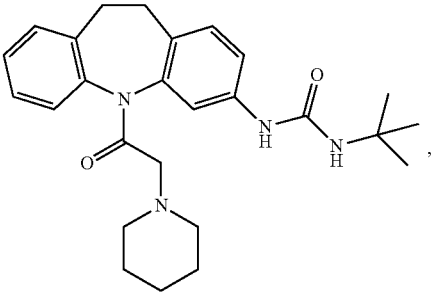
,
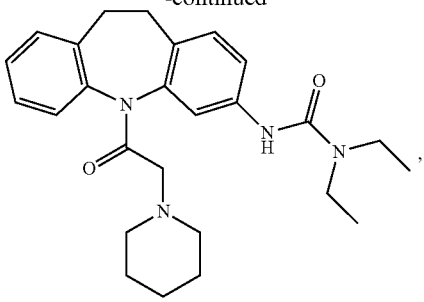
,
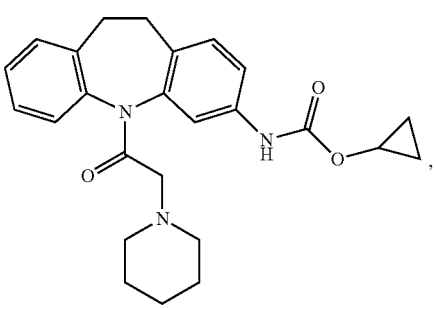
,
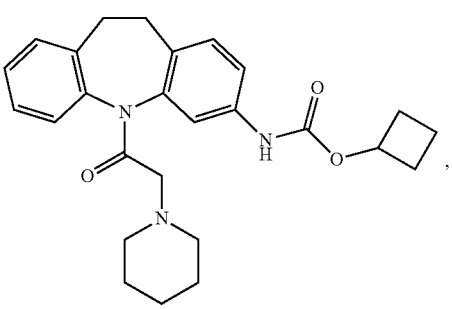
,
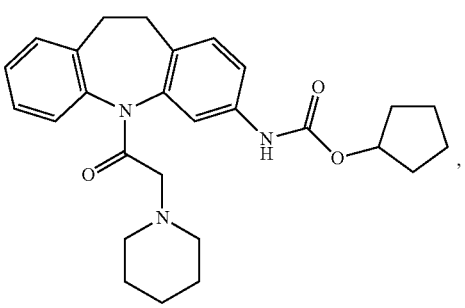
,
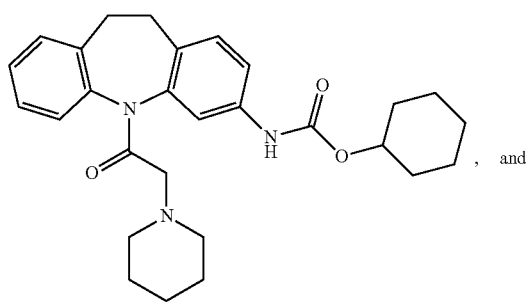
, and

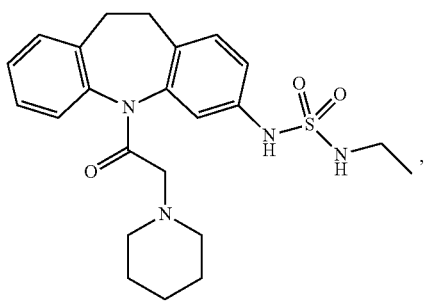 [SMILES: CCNS(=O)(=O)Nc1ccc2c(c1)N(C(=O)CN1CCCCC1)c1ccccc1CC2]
or a pharmaceutically acceptable salt thereof.
In one aspect, a compound can be selected from:
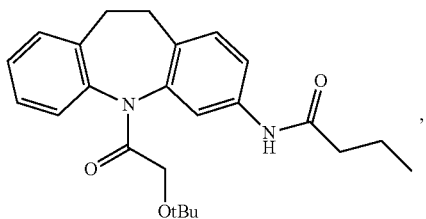
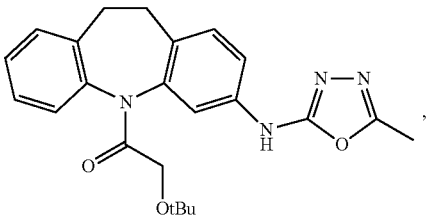
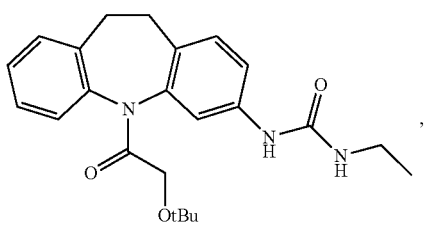
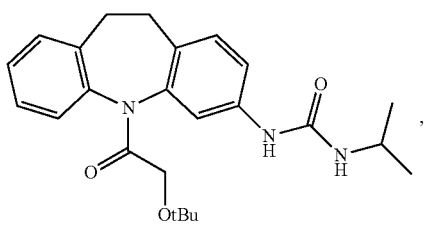
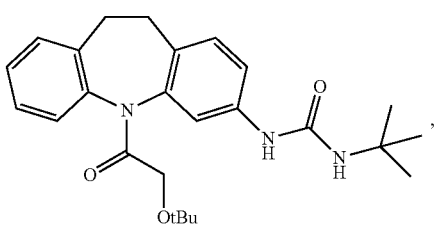
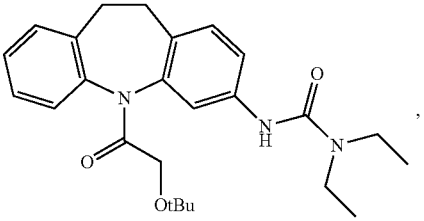
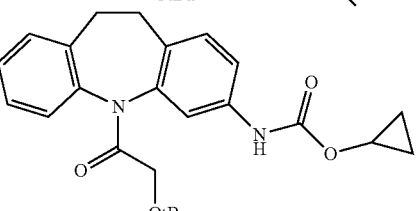
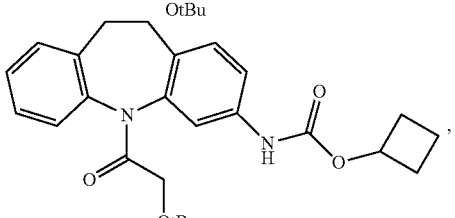
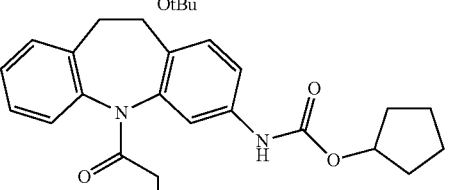
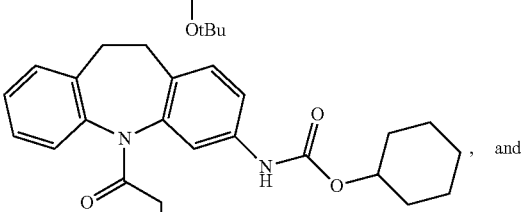
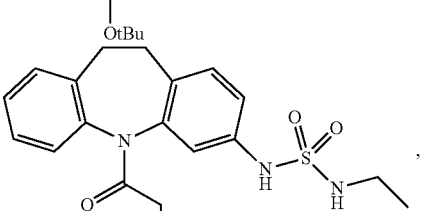
or a pharmaceutically acceptable salt thereof.
In one aspect, a compound can be selected from:
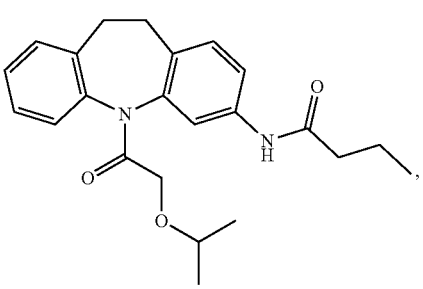

127
-continued
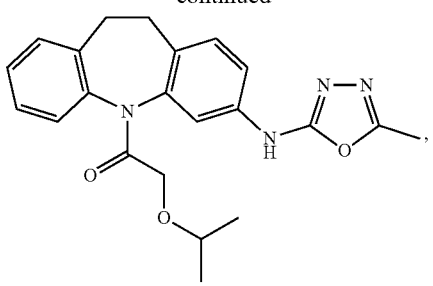
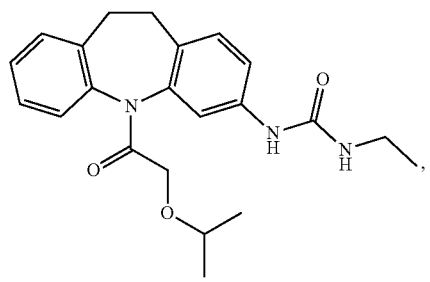
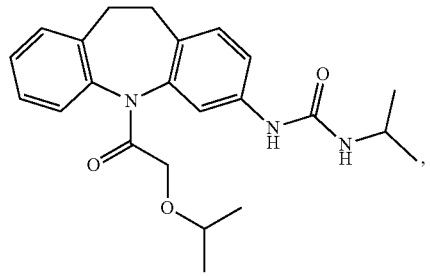
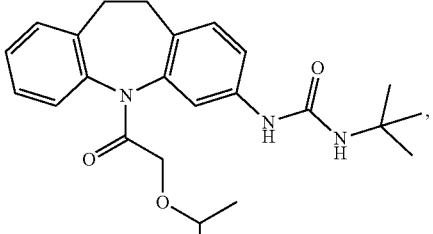
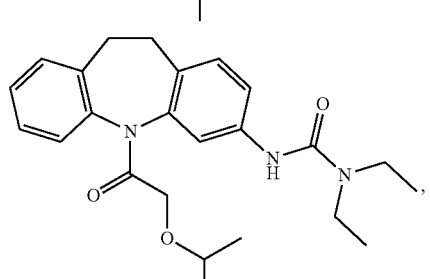
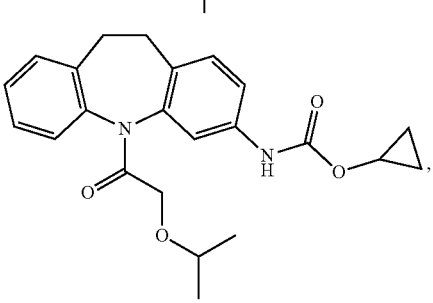
128
-continued
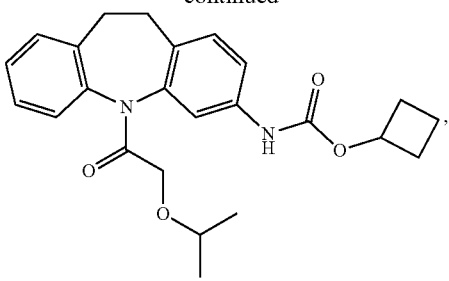
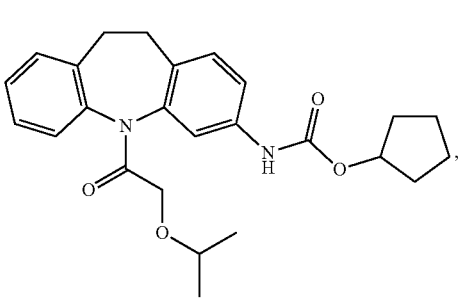
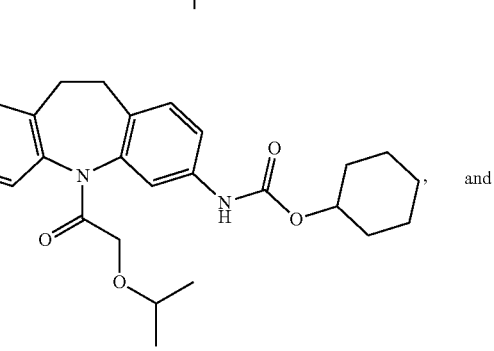, and
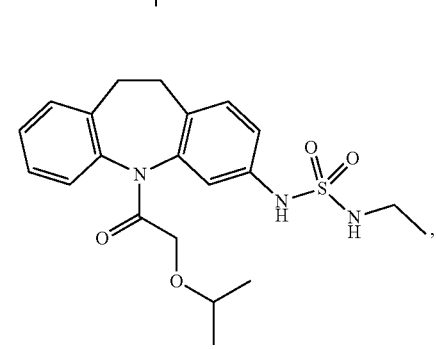
or a pharmaceutically acceptable salt thereof.
In one aspect, a compound can be selected from:
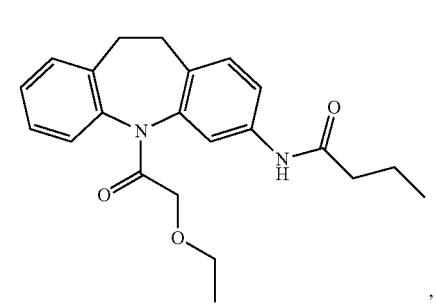

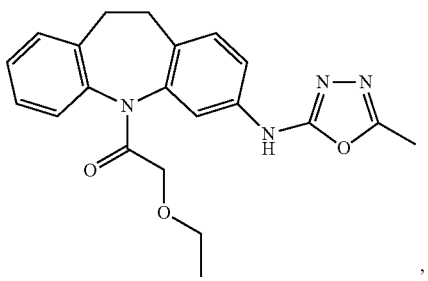
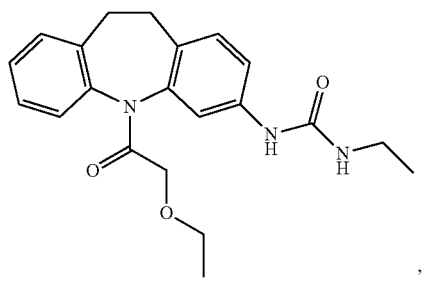
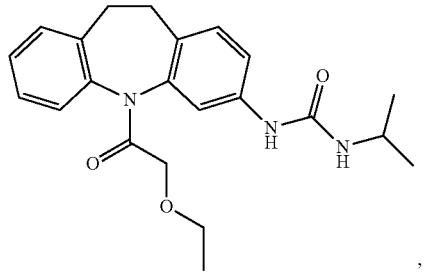
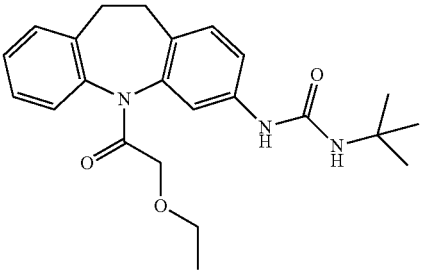
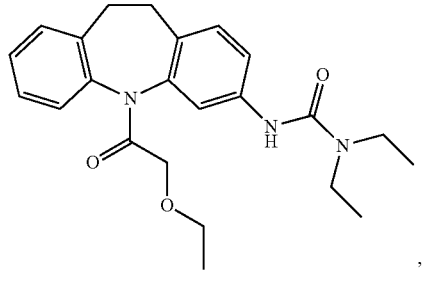
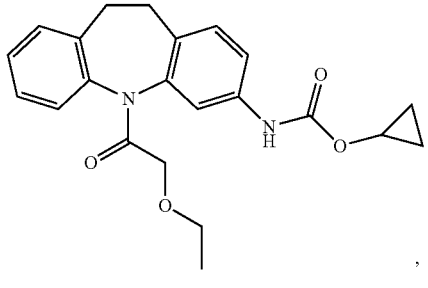
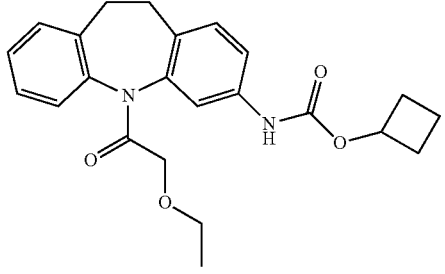
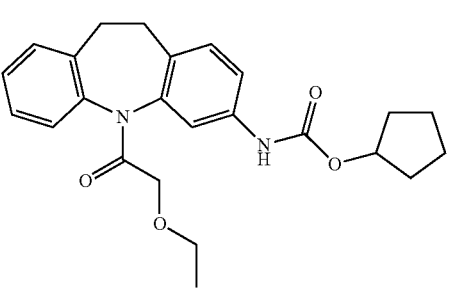
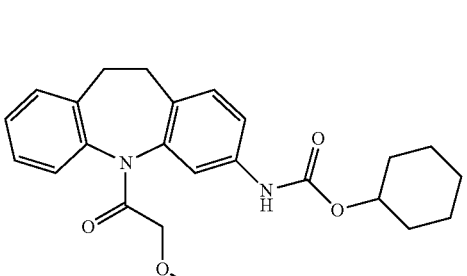
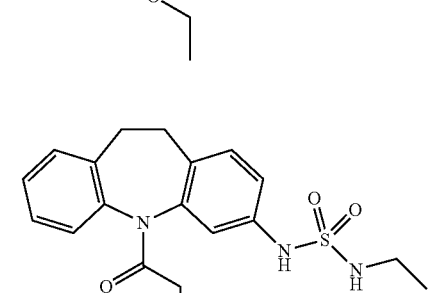
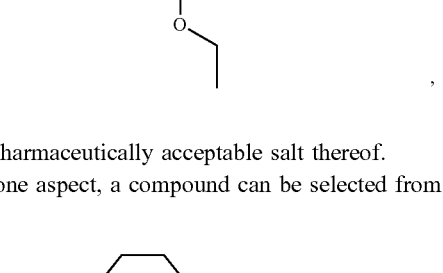
or a pharmaceutically acceptable salt thereof.
In one aspect, a compound can be selected from:
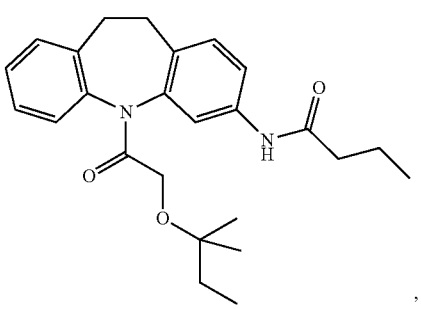

131
-continued
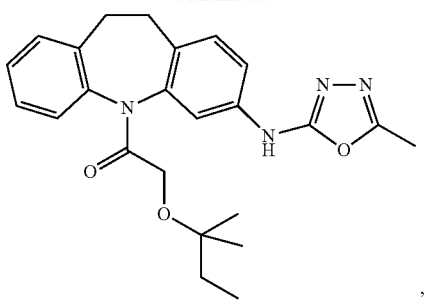
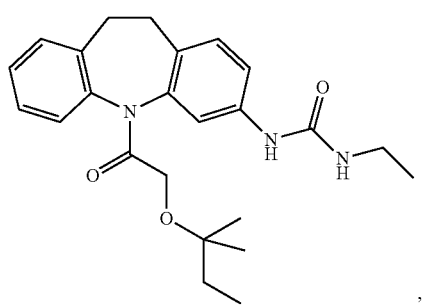
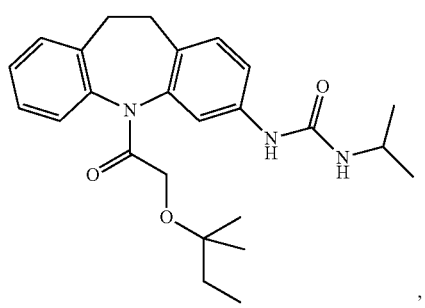
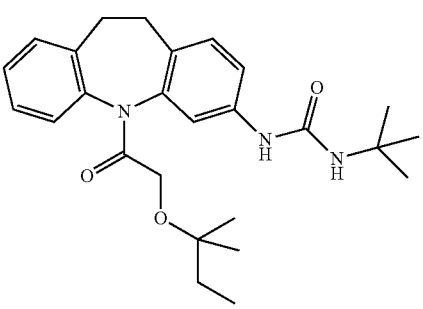
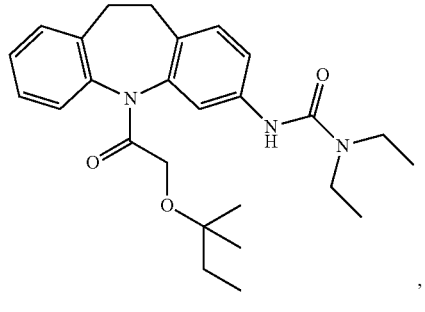
132
-continued
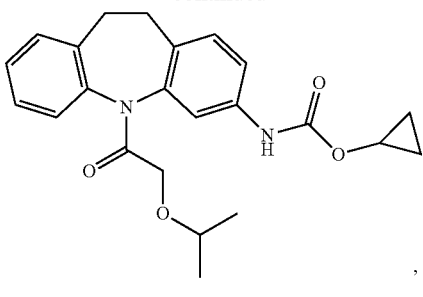
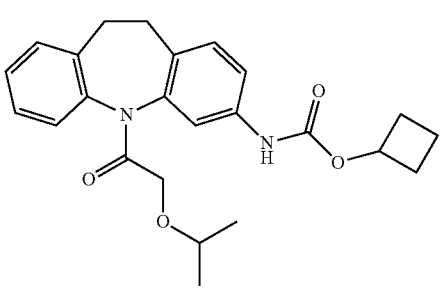
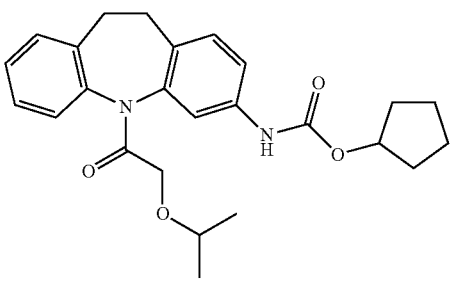
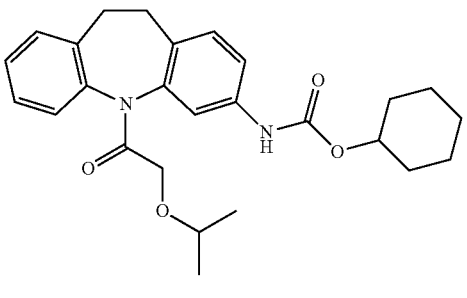
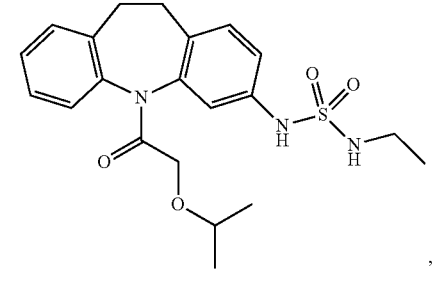
or a pharmaceutically acceptable salt thereof.

In one aspect, a compound can be selected from:

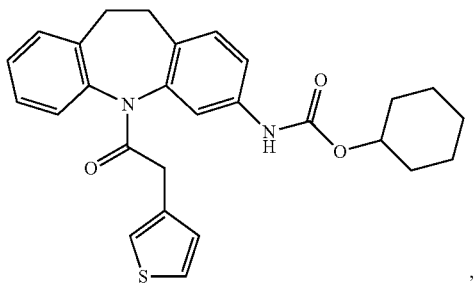

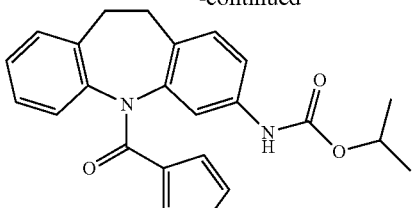

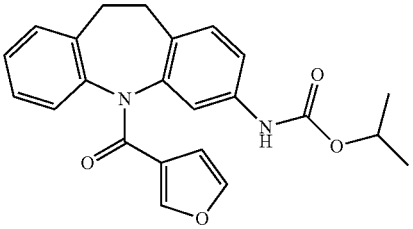

or a pharmaceutically acceptable salt thereof.

It is contemplated that one or more compounds can optionally be omitted from the disclosed invention.

It is understood that the disclosed compounds can be used in connection with the disclosed methods, compositions, kits, and uses.

It is understood that pharmaceutically acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, the invention relates to pharmaceutical compositions comprising an effective amount of at least one disclosed compound, at least one product of a disclosed method of making a compound, or a pharmaceutically acceptable salt thereof, and a pharmaceutically acceptable carrier. In a further aspect, the compound is a disclosed compound. In a still further aspect, the compound is a product of a disclosed method of making.

The compounds are active against CAR, and generally have $IC_{50}$ values against hCAR of less than about 80 nanomolar. $IC_{50}$ refers to the concentration of the compound that is required for 50% antagonism or inhibition of hCAR. $IC_{50}$ also refers to the concentration of a substance that is required for 50% antagonism or inhibition of CAR in vivo. The activity of the compounds, including $IC_{50}$, is determined according to the procedures discussed below in the Examples section. The compounds are selective for CAR over PXR.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of a cell proliferative disorder. In a still further aspect, the mammal has been diagnosed with a need for treatment of a cell proliferative disorder prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the composition further comprises at least one agent known to treat a cell proliferative disorder. In a still further aspect, at least one agent known to treat a cell proliferative disorder is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), iressa (gefinitib, Zd1839), XELODA® (capecitabine), Tarceva® (erlotinib), azacitidine (5-Azacytidine; 5-AzaC), temozolomide (Temodar®), gemcitabine (e.g., GEMZAR® (gemcitabine HCl)), and vasostatin.

In a further aspect, the composition further comprises at least one agent known to have a side effect of increasing the risk of a cell proliferative disorder.

It is understood that the disclosed compositions can be prepared from the disclosed compounds. It is also understood that the disclosed compositions can be employed in the disclosed methods of using.

D. Methods of Making the Compounds

In one aspect, the invention relates to methods of making compounds useful as inhibitors of CAR, which can be useful in the treatment of disorders of uncontrolled cellular proliferation and other diseases in which CAR is involved. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route 1

In one aspect, substituted (10,11-dihydro-5H-dibenzo[b,f]azepin-3-yl)carbamates can be prepared as shown below.

SCHEME 1A.

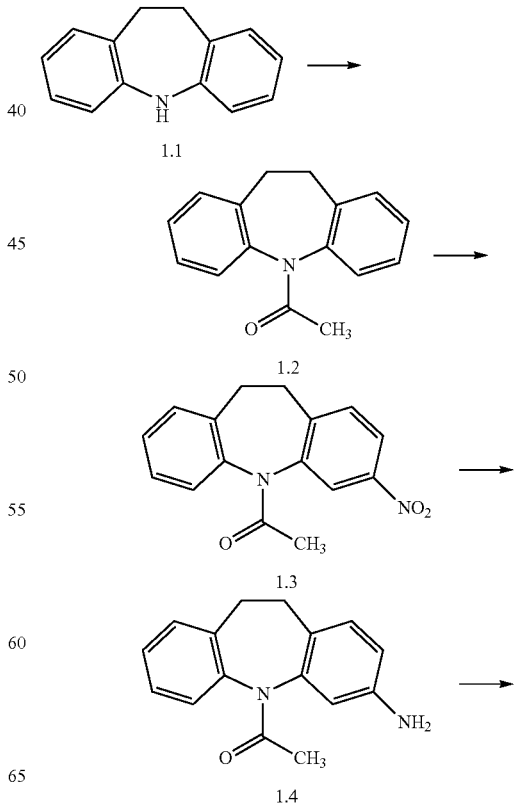

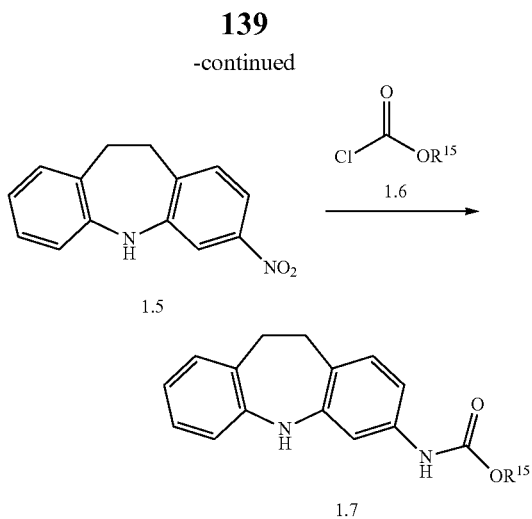

1.5

1.7

Compounds are represented in generic form, with substituents as noted in compound descriptions elsewhere herein. A more specific example is set forth below.

SCHEME 1B.

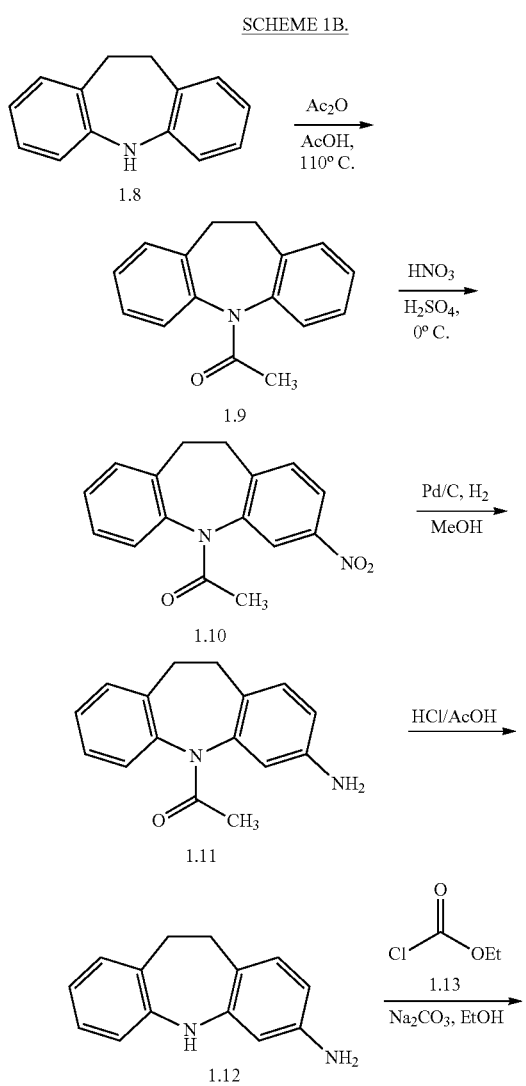

1.14

In one aspect, compounds of type 1.7, and similar compounds, can be prepared according to reaction Scheme 1B above. Thus, compounds of type 1.9 can be prepared by an acylation of an appropriate amine, e.g., 1.8 as shown above. Appropriate amines are commercially available or prepared by methods known to one skilled in the art. The acylation is carried out in the presence of an appropriate electrophile, e.g., acetic anhydride, and an appropriate acid, e.g., acetic acid, at an appropriate temperature, e.g., 110° C. Compounds of type 1.10 can be prepared by a nucleophilic aromatic substitution reaction of an appropriate aryl, e.g., 1.9 as shown above. The nucleophilic aromatic substitution reaction is carried out in the presence of an appropriate nucleophile, e.g., nitric acid in the presence of sulphuric acid, at an appropriate temperature, e.g., 0° C. Compounds of type 1.11 can be prepared by reduction of an appropriate nitrobenzene, e.g., 1.10 as shown above. The reduction is carried out in the presence of an appropriate reducing agent, e.g., hydrogen gas, in the presence of an appropriate catalyst, e.g., palladium on carbon, in an appropriate solvent, e.g., methanol. Compounds of type 1.12 can be prepared by reduction of an appropriate amide, e.g., 1.11 as shown above. The reduction is carried out in the presence of an appropriate acid, e.g., hydrochloric acid and acetic acid. Compounds of type 1.14 can be prepared by acylation of an appropriate amine, e.g., 1.12 as shown above. The acylation is carried out in the presence of an appropriate acid chloride, e.g., ethyl carbonochloridate (1.13) as shown above, and an appropriate base, e.g., sodium carbonate, in an appropriate solvent, e.g., ethanol. As can be appreciated by one skilled in the art, the above reaction provides an example of a generalized approach wherein compounds similar in structure to the specific reactants above (compounds similar to compounds of type 1.1, 1.2, 1.3, 1.4, 1.5, and 1.6), can be substituted in the reaction to provide substituted (10,11-dihydro-5H-dibenzo[b,f]azepin-3-yl)carbamates similar to Formula 1.7.

2. Route 2

In one aspect, substituted (10,11-dihydro-5H-dibenzo[b,f]azepin-3-yl)carbamates can be prepared as shown below.

SCHEME 2A.

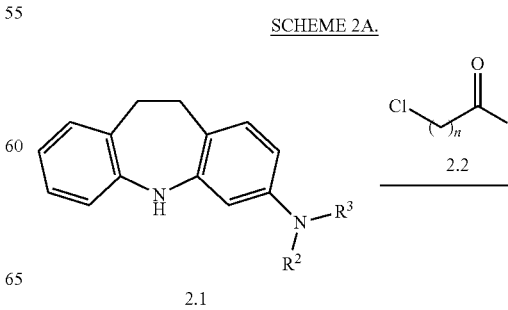

2.1

-continued

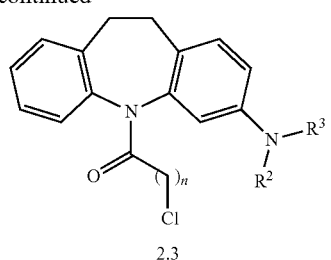

2.3

Compounds are represented in generic form, with substituents as noted in compound descriptions elsewhere herein. A more specific example is set forth below.

SCHEME 2B.

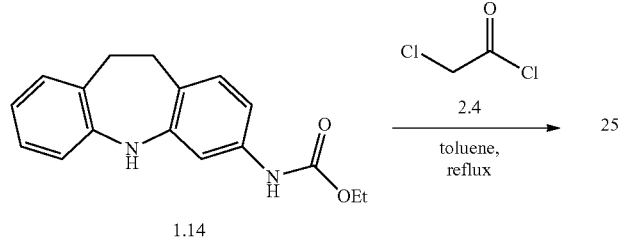

In one aspect, compounds of type 2.3, and similar compounds, can be prepared according to reaction Scheme 2B above. Thus, compounds of type 2.5 can be prepared by an acylation of an appropriate amine, e.g., 1.14 as shown above. The acylation is carried out in the presence of an appropriate electrophile, e.g., 2-chloroacetyl chloride (2.4), in an appropriate solvent, e.g., toluene. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted (10,11-dihydro-5H-dibenzo[b,f]azepin-3-yl)carbamates similar to Formula 2.3.

3. Route 3

In one aspect, substituted (10,11-dihydro-5H-dibenzo[b,f]azepin-3-yl)carbamates can be prepared as shown below.

SCHEME 3A.

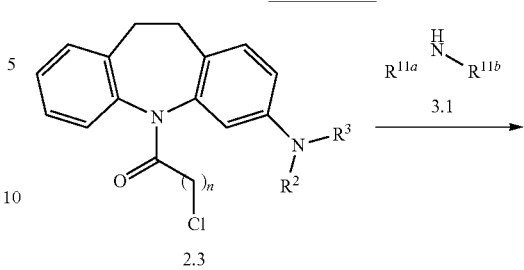

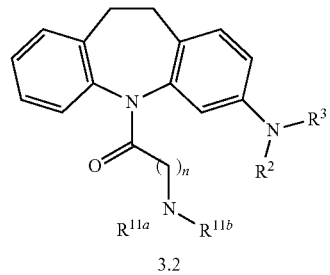

Compounds are represented in generic form, with substituents as noted in compound descriptions elsewhere herein. A more specific example is set forth below.

SCHEME 3B.

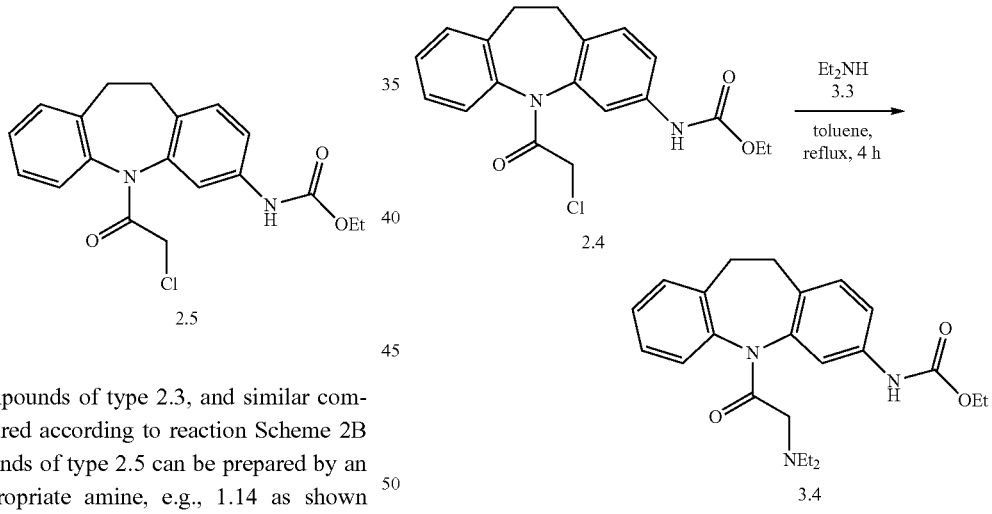

In one aspect, compounds of type 3.2, and similar compounds, can be prepared according to reaction Scheme 3B above. Thus, compounds of type 3.4 can be prepared by a substitution reaction of an appropriate halide, e.g., 2.4 as shown above. The substitution reaction is carried out in the presence of an appropriate nucleophile, e.g., diethylamine (3.3), in an appropriate solvent, e.g., toluene, for an appropriate period of time, e.g., 4 h. As can be appreciated by one skilled in the art, the above reaction provides an example of a generalized approach wherein compounds similar in structure to the specific reactants above (compounds similar to compounds of type 2.3 and 3.1), can be substituted in the reaction to provide substituted (10,11-dihydro-5H-dibenzo[b,f]azepin-3-yl)carbamates similar to Formula 3.2.

4. Route 4

In one aspect, substituted N-(5-(diethylglycyl)-10,11-dihydro-5H-dibenzo[b,f]azepin-3-yl)amides can be prepared as shown below.

SCHEME 4A.

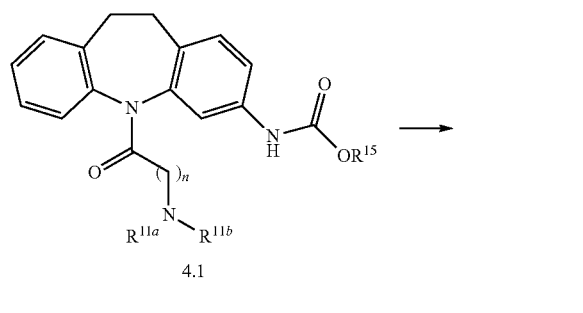
4.1

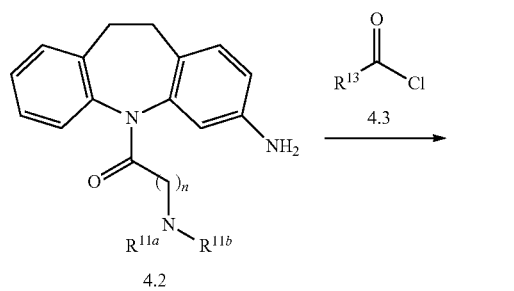
4.2

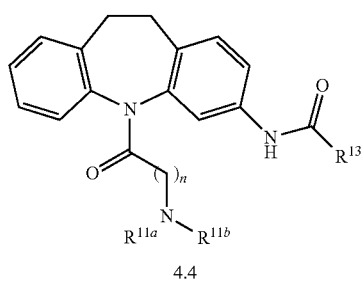
4.4

Compounds are represented in generic form, with substituents as noted in compound descriptions elsewhere herein. A more specific example is set forth below.

SCHEME 4B.

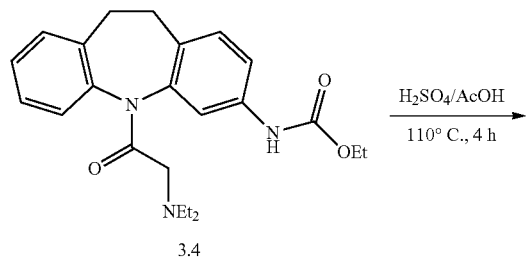
3.4

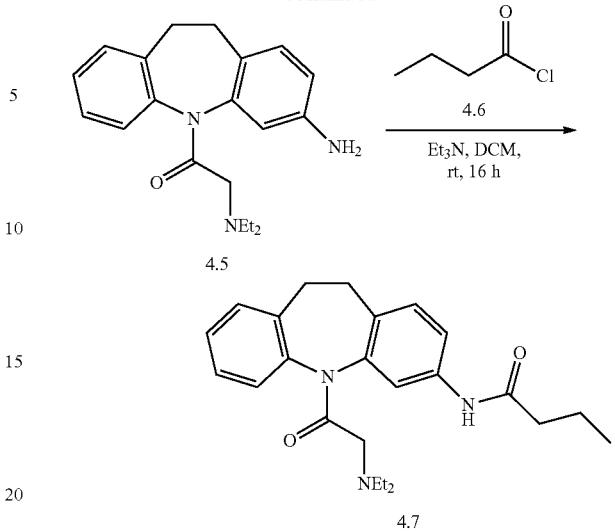

In one aspect, compounds of type 4.4, and similar compounds, can be prepared according to reaction Scheme 4B above. Thus, compounds of type 4.5 can be prepared by reduction of an appropriate amide, e.g., 3.2 as shown above. The reduction is carried out in the presence of an appropriate reducing agent, e.g., sulphuric acid, in an appropriate solvent, e.g., acetic acid, at an appropriate temperature, e.g., 110° C., for an appropriate period of time, e.g., 4 hours. Compounds of type 4.7 can be prepared by acylation of an appropriate amine, e.g., 4.5 as shown above. The acylation is carried out in the presence of an appropriate acid chloride, e.g., butyryl chloride (4.6), and an appropriate base, e.g., triethylamine, in an appropriate solvent, e.g., dichloromethane, for an appropriate period of time, e.g., 16 hours. As can be appreciated by one skilled in the art, the above reaction provides an example of a generalized approach wherein compounds similar in structure to the specific reactants above (compounds similar to compounds of type 4.1, 4.2, and 4.3), can be substituted in the reaction to provide substituted N-(5-(diethylglycyl)-10,11-dihydro-5H-dibenzo[b,f]azepin-3-yl)amides similar to Formula 4.4.

5. Route 5

In one aspect, substituted (5-(diethylglycyl)-10,11-dihydro-5H-dibenzo[b,f]azepin-3-yl)carbamates can be prepared as shown below.

SCHEME 5A.

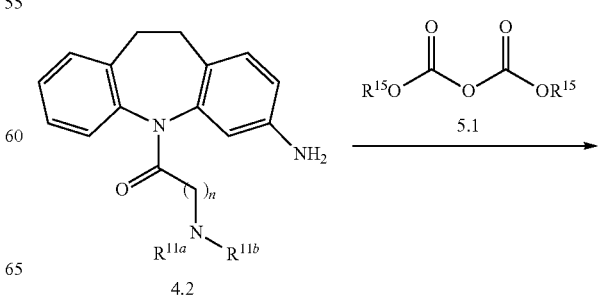
4.2

-continued

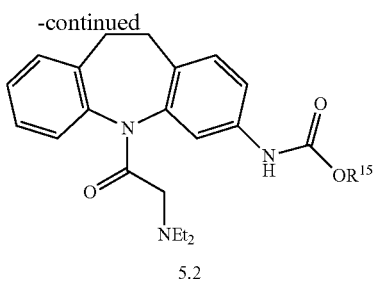

5.2

Compounds are represented in generic form, with substituents as noted in compound descriptions elsewhere herein. A more specific example is set forth below.

SCHEME 5B.

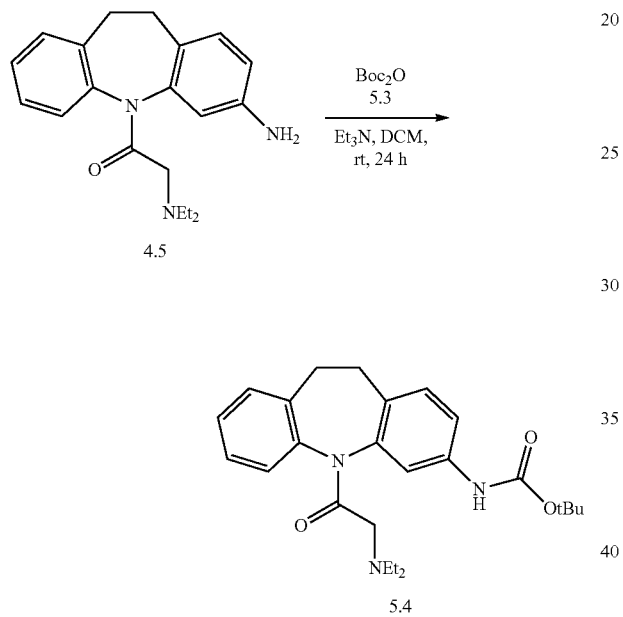

4.5

5.4

In one aspect, compounds of type 5.2, and similar compounds, can be prepared according to reaction Scheme 5B above. Thus, compounds of type 5.4 can be prepared by acylation of an appropriate amine, e.g., 4.5 as shown above. The acylation is carried out in the presence of an appropriate electrophile, e.g., di-tert-butyl dicarbonate (5.3), and an appropriate base, e.g., triethylamine, in an appropriate solvent, e.g., dichloromethane, for an appropriate period of time, e.g., 24 hours. As can be appreciated by one skilled in the art, the above reaction provides an example of a generalized approach wherein compounds similar in structure to the specific reactants above (compounds similar to compounds of type 4.2, and 5.1), can be substituted in the reaction to provide substituted (5-(diethylglycyl)-10,11-dihydro-5H-dibenzo[b,f]azepin-3-yl)carbamates similar to Formula 5.2.

6. Route 6

In one aspect, substituted 1-(5-(diethylglycyl)-10,11-dihydro-5H-dibenzo[b,f]azepin-3-yl)ureas can be prepared as shown below.

SCHEME 6A.

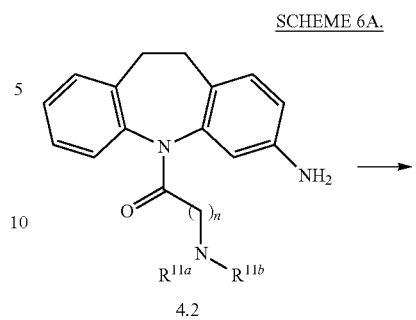

4.2

6.1

6.3

Compounds are represented in generic form, with substituents as noted in compound descriptions elsewhere herein. A more specific example is set forth below.

SCHEME 6B.

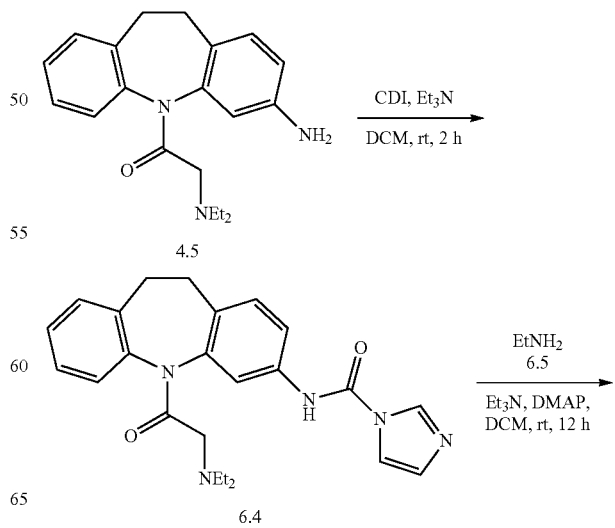

4.5

6.4

147

-continued

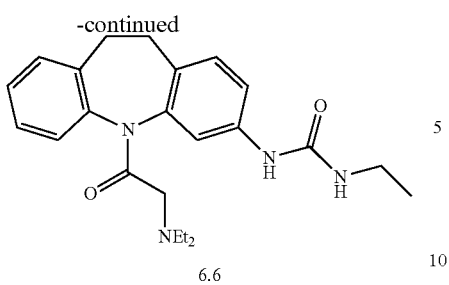

6.6

In one aspect, compounds of type 6.3, and similar compounds, can be prepared according to reaction Scheme 6B above. Thus, compounds of type 6.4 can be prepared by acylation of an appropriate amine, e.g., 4.5 as shown above. The acylation is carried out in the presence of an appropriate electrophile, e.g., carbonyldiimidazole, and an appropriate base, e.g., triethylamine, in an appropriate solvent, e.g., dichloromethane, for an appropriate period of time, e.g., 2 hours. Compounds of type 6.6 can be prepared by a displacement reaction of an appropriate amide, e.g., 6.4 as shown above. The displacement reaction is carried out in the presence of an appropriate amine, e.g., ethylamine (6.5), an appropriate activating agent, e.g., 4-dimethylaminopyridine, and an appropriate base, e.g., triethylamine, in an appropriate solvent, e.g., dichloromethane, for an appropriate period of time, e.g., 12 hours. As can be appreciated by one skilled in the art, the above reaction provides an example of a generalized approach wherein compounds similar in structure to the specific reactants above (compounds similar to compounds of type 4.2, 6.1, and 6.2), can be substituted in the reaction to provide substituted 1-(5-(diethylglycyl)-10,11-dihydro-5H-dibenzo[b,f]azepin-3-yl)ureas similar to Formula 6.3.

7. Route 7

In one aspect, substituted 1-(5-(diethylglycyl)-10,11-dihydro-5H-dibenzo[b,f]azepin-3-yl)sulfamides can be prepared as shown below.

SCHEME 7A.

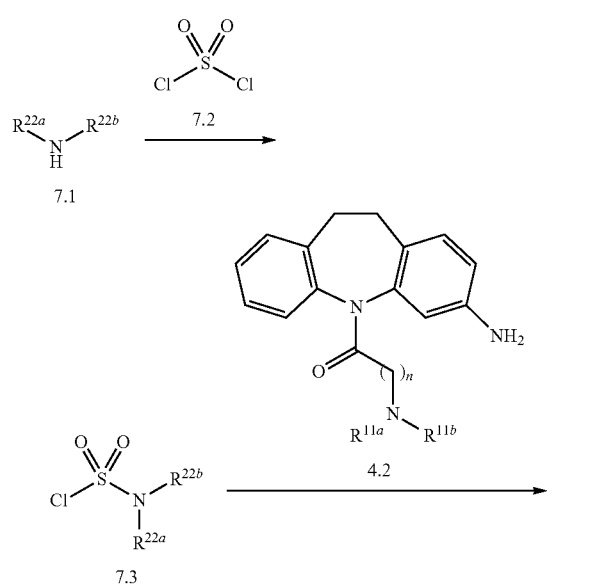

148

-continued

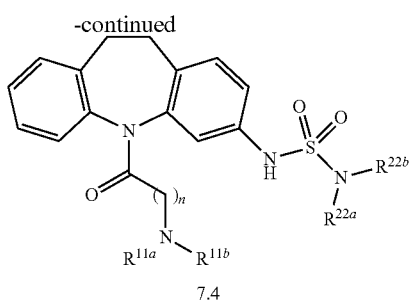

7.4

Compounds are represented in generic form, with substituents as noted in compound descriptions elsewhere herein. A more specific example is set forth below.

SCHEME 7B.

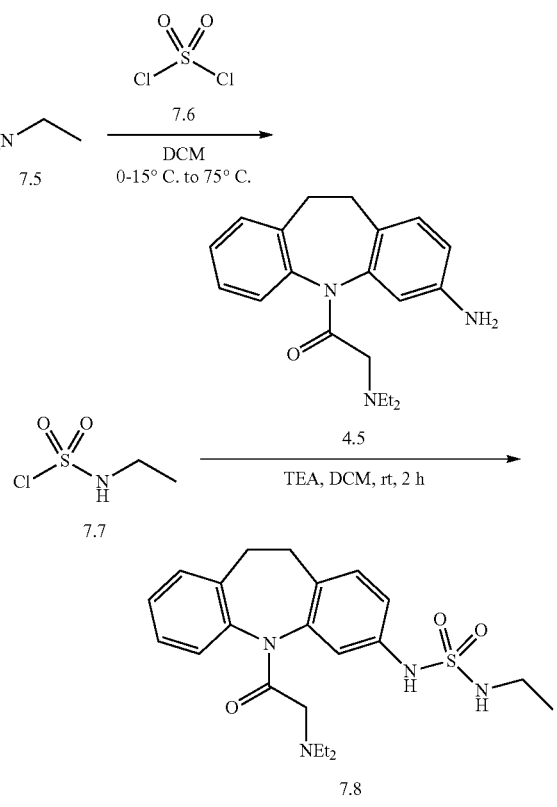

In one aspect, compounds of type 7.4, and similar compounds, can be prepared according to reaction Scheme 7B above. Thus, compounds of type 7.7 can be prepared by oxidation of an appropriate amine, e.g., 7.5 as shown above. The oxidation is carried out in the presence of an appropriate electrophile, e.g., sulfuryl dichloride (7.6), in an appropriate solvent, e.g., dichloromethane. Compounds of type 7.8 can be prepared by a substitution reaction of an appropriate sulfamoyl chloride, e.g., 7.7 as shown above. The substitution reaction is carried out in the presence of an appropriate amine, e.g., 1-(3-amino-10,11-dihydro-5H-dibenzo[b,f]azepin-5-yl)-2-(diethylamino)ethan-1-one (4.5), and an appropriate base, e.g., triethylamine, in an appropriate solvent, e.g., dichloromethane, for an appropriate period of time, e.g., 2 hours. As can be appreciated by one skilled in the art, the above reaction provides an example of a generalized approach wherein compounds similar in structure to the specific reactants above (compounds similar to compounds of type 7.1, 6.2, 7.3, and 4.2), can be substituted in the reaction to provide substituted 1-(5-(diethylglycyl)-10,11-dihydro-5H-dibenzo[b,f]azepin-3-yl)sulfamides similar to Formula 7.4.

8. Route 8

In one aspect, substituted 1-(3-amino-10,11-dihydro-5H-dibenzo[b,f]azepin-5-yl)-2-(diethylamino)ethan-1-ones can be prepared as shown below.

SCHEME 8A.

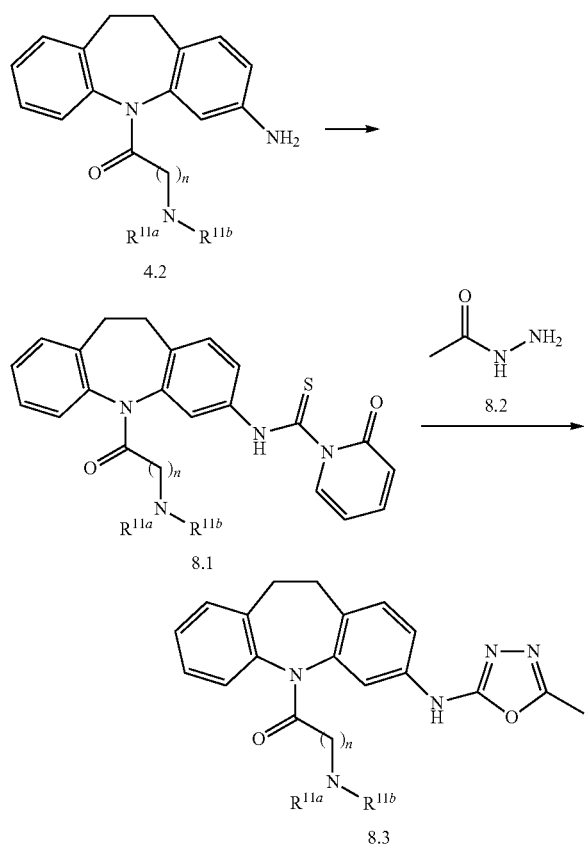

Compounds are represented in generic form, with substituents as noted in compound descriptions elsewhere herein. A more specific example is set forth below.

SCHEME 8B.

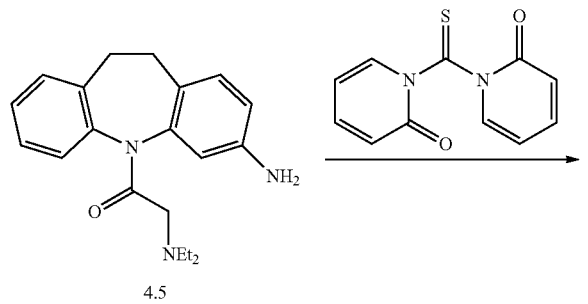

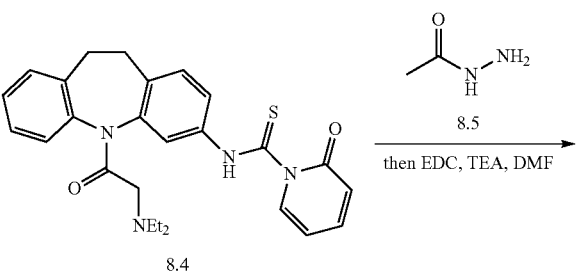

In one aspect, compounds of type 8.3, and similar compounds, can be prepared according to reaction Scheme 8B above. Thus, compounds of type 8.4 can be prepared by thioacylation of an appropriate amine, e.g., 1-(3-amino-10,11-dihydro-5H-dibenzo[b,f]azepin-5-yl)-2-(diethylamino) ethan-1-one (4.5) as shown above. The thioacylation is carried out in the presence of an appropriate electrophile, e.g., 1,1'-thiocarbonylbis(pyridin-2(1H)-one), in an appropriate solvent, e.g., dichloromethane, at an appropriate temperature, e.g., 0° C. Compounds of type 8.6 can be prepared by a cyclization reaction of an appropriate thiourea, e.g., 8.4 as shown above. The cyclization reaction is carried out in the presence of an appropriate amine, e.g., acetohydrazide (8.5), an appropriate activating agent, e.g., 1-ethyl-3-(3-dimethylaminopropyl)carbodiimide, and an appropriate base, e.g., triethylamine, in an appropriate solvent, e.g., dimethylformamide. As can be appreciated by one skilled in the art, the above reaction provides an example of a generalized approach wherein compounds similar in structure to the specific reactants above (compounds similar to compounds of type 4.2, 8.1, and 8.2), can be substituted in the reaction to provide substituted 1-(3-amino-10,11-dihydro-5H-dibenzo[b,f]azepin-5-yl)-2-(diethylamino)ethan-1-ones similar to Formula 8.3.

9. Route 9

In one aspect, substituted (10,11-dihydro-5H-dibenzo[b,f]azepin-3-yl)carbamates can be prepared as shown below.

SCHEME 9A.

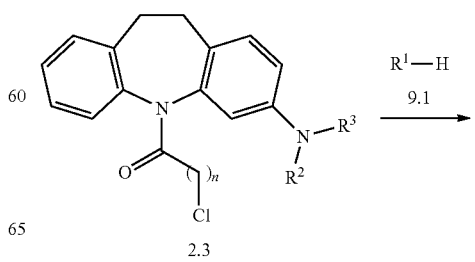

-continued

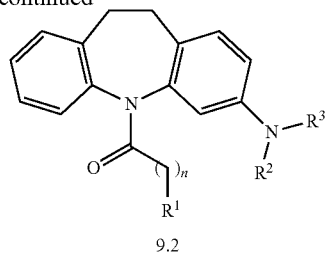

9.2

Compounds are represented in generic form, with substituents as noted in compound descriptions elsewhere herein. A more specific example is set forth below.

SCHEME 9B.

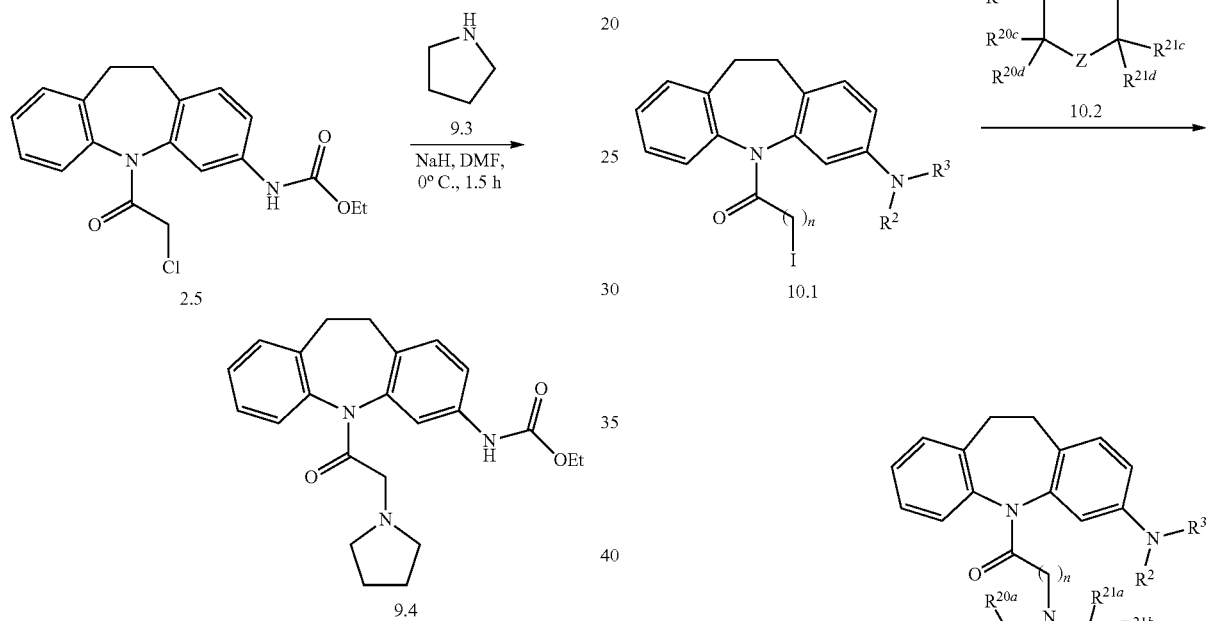

2.5

9.4

In one aspect, compounds of type 9.2, and similar compounds, can be prepared according to reaction Scheme 9B above. Thus, compounds of type 9.4 can be prepared by a displacement reaction of an appropriate halide, e.g., 2.5 as shown above. The displacement reaction is carried out in the presence of an appropriate nucleophile, e.g., pyrrolidine (9.3), in the presence of an appropriate base, e.g., sodium hydride, in an appropriate solvent, e.g., dimethylformamide, at an appropriate temperature, e.g., 0° C., for an appropriate period of time, e.g., 1.5 h. As can be appreciated by one skilled in the art, the above reaction provides an example of a generalized approach wherein compounds similar in structure to the specific reactants above (compounds similar to compounds of type 2.3 and 9.1), can be substituted in the reaction to provide substituted (10,11-dihydro-5H-dibenzo[b,f]azepin-3-yl)carbamates similar to Formula 9.2.

10. Route 10

In one aspect, substituted (10,11-dihydro-5H-dibenzo[b,f]azepin-3-yl)carbamates can be prepared as shown below.

SCHEME 10A.

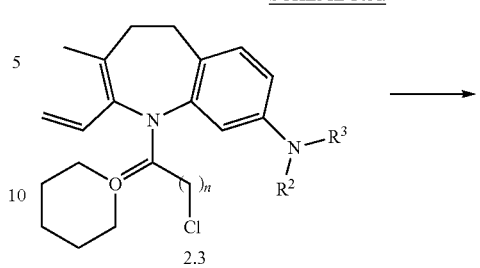

2.3

Compounds are represented in generic form, with substituents as noted in compound descriptions elsewhere herein. A more specific example is set forth below.

SCHEME 10B.

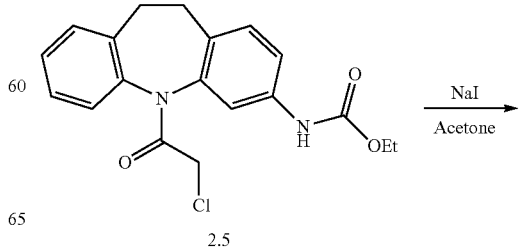

2.5

-continued

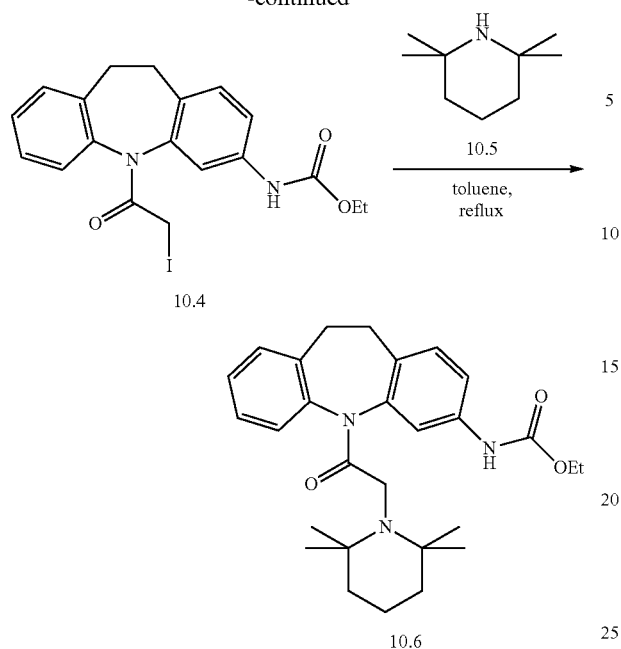

10.4

10.6

In one aspect, compounds of type 10.3, and similar compounds, can be prepared according to reaction Scheme 10B above. Thus, compounds of type 10.4 can be prepared by a substitution reaction of an appropriate halide, e.g., 2.5 as shown above. The substitution reaction is carried out in the presence of an appropriate nucleophile, e.g., sodium iodide, in an appropriate solvent, e.g., acetone. Compounds of type 10.6 can be prepared by a displacement reaction of an appropriate halide, e.g., 10.4 as shown above. The displacement reaction is carried out in the presence of an appropriate nucleophile, e.g., 2,2,6,6-tetramethylpiperidine (10.5), in an appropriate solvent, e.g., toluene. As can be appreciated by one skilled in the art, the above reaction provides an example of a generalized approach wherein compounds similar in structure to the specific reactants above (compounds similar to compounds of type 2.3, 10.1, and 10.2), can be substituted in the reaction to provide substituted (10,11-dihydro-5H-dibenzo[b,f]azepin-3-yl)carbamates similar to Formula 10.3.

11. Route 11

In one aspect, substituted (10,11-dihydro-5H-dibenzo[b,f]azepin-3-yl)carbamates can be prepared as shown below.

SCHEME 11A.

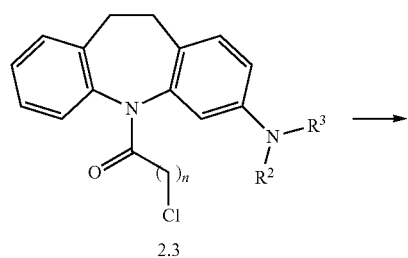

2.3

-continued

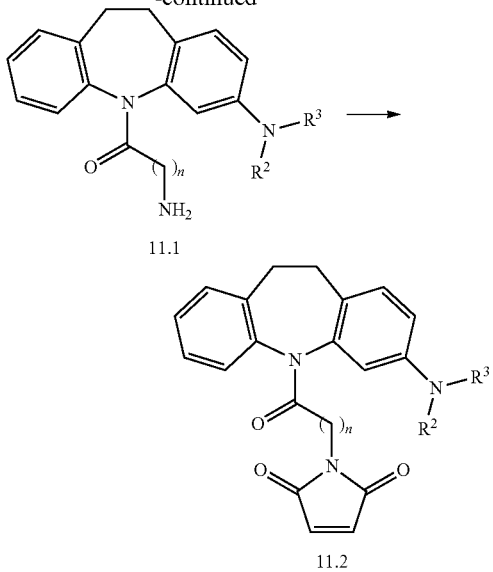

11.1

11.2

Compounds are represented in generic form, with substituents as noted in compound descriptions elsewhere herein. A more specific example is set forth below.

SCHEME 11B.

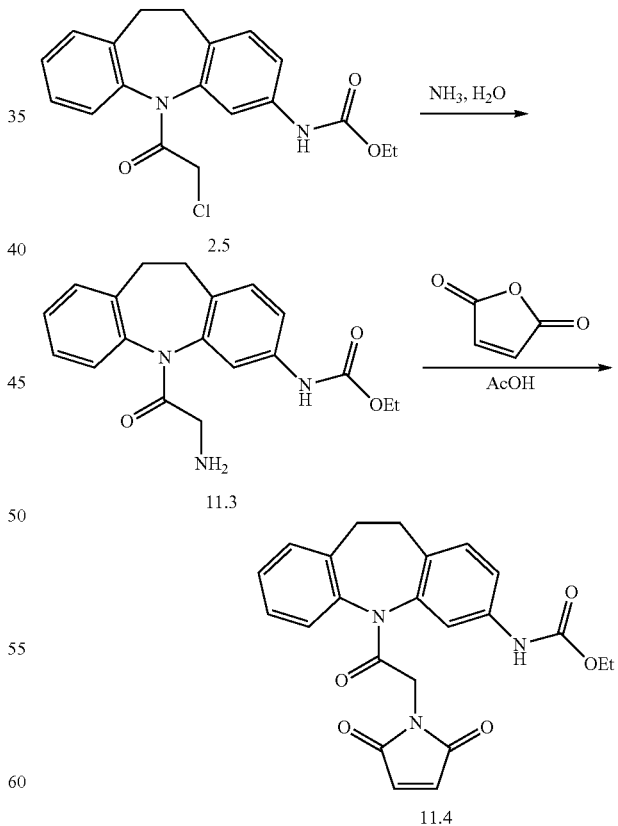

In one aspect, compounds of type 11.2, and similar compounds, can be prepared according to reaction Scheme 11B above. Thus, compounds of type 12.3 can be prepared by a substitution reaction of an appropriate halide, e.g., 2.5 as shown above. The substitution reaction is carried out in the presence of an appropriate nucleophile, e.g., aqueous ammonia. Compounds of type 11.4 can be prepared by a substitution reaction of an appropriate amine, e.g., 11.3 as shown above. The substitution reaction is carried out in the presence of an appropriate electrophile, e.g., furan-2,5-dione, in an appropriate solvent, e.g., acetic acid. As can be appreciated by one skilled in the art, the above reaction provides an example of a generalized approach wherein compounds similar in structure to the specific reactants above (compounds similar to compounds of type 2.3 and 11.1), can be substituted in the reaction to provide substituted (10,11-dihydro-5H-dibenzo[b,f]azepin-3-yl)carbamates similar to Formula 11.2.

12. Route 12

In one aspect, substituted (10,11-dihydro-5H-dibenzo[b,f]azepin-3-yl)carbamates can be prepared as shown below.

SCHEME 12A.

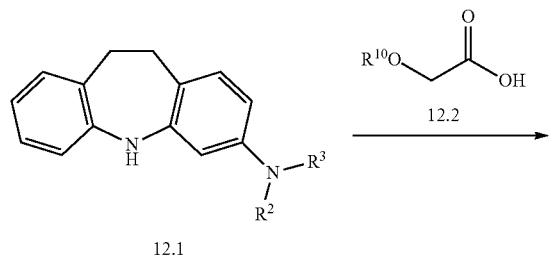

12.1

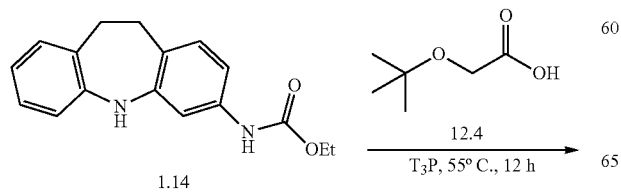

12.3

Compounds are represented in generic form, with substituents as noted in compound descriptions elsewhere herein. A more specific example is set forth below.

SCHEME 12B.

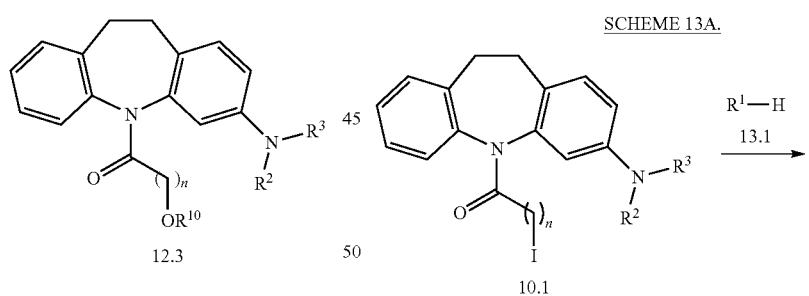

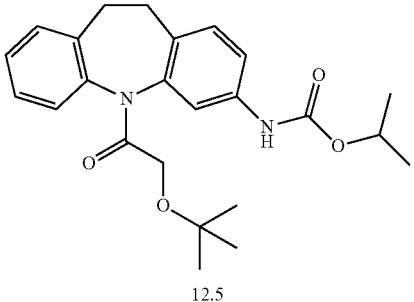

12.5

In one aspect, compounds of type 12.3, and similar compounds, can be prepared according to reaction Scheme 12B above. Thus, compounds of type 12.5 can be prepared by a coupling reaction of an appropriate amine, e.g., 1.14 as shown above. The coupling reaction is carried out in the presence of an appropriate carboxylic acid, e.g., 2-(tert-butoxy)acetic acid (13.4), and an appropriate coupling agent, e.g., propylphosphonic anhydride, at an appropriate temperature, e.g., 55° C., for a sufficient period of time, e.g., 12 h. As can be appreciated by one skilled in the art, the above reaction provides an example of a generalized approach wherein compounds similar in structure to the specific reactants above (compounds similar to compounds of type 12.1 and 12.2), can be substituted in the reaction to provide substituted (10,11-dihydro-5H-dibenzo[b,f]azepin-3-yl)carbamates similar to Formula 12.3.

13. Route 13

In one aspect, substituted (10,11-dihydro-5H-dibenzo[b,f]azepin-3-yl)carbamates can be prepared as shown below.

SCHEME 13A.

10.1

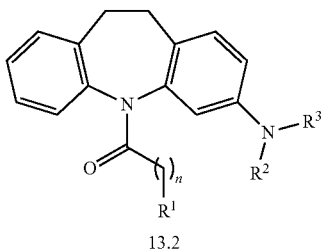

13.2

Compounds are represented in generic form, with substituents as noted in compound descriptions elsewhere herein. A more specific example is set forth below.

SCHEME 13B.

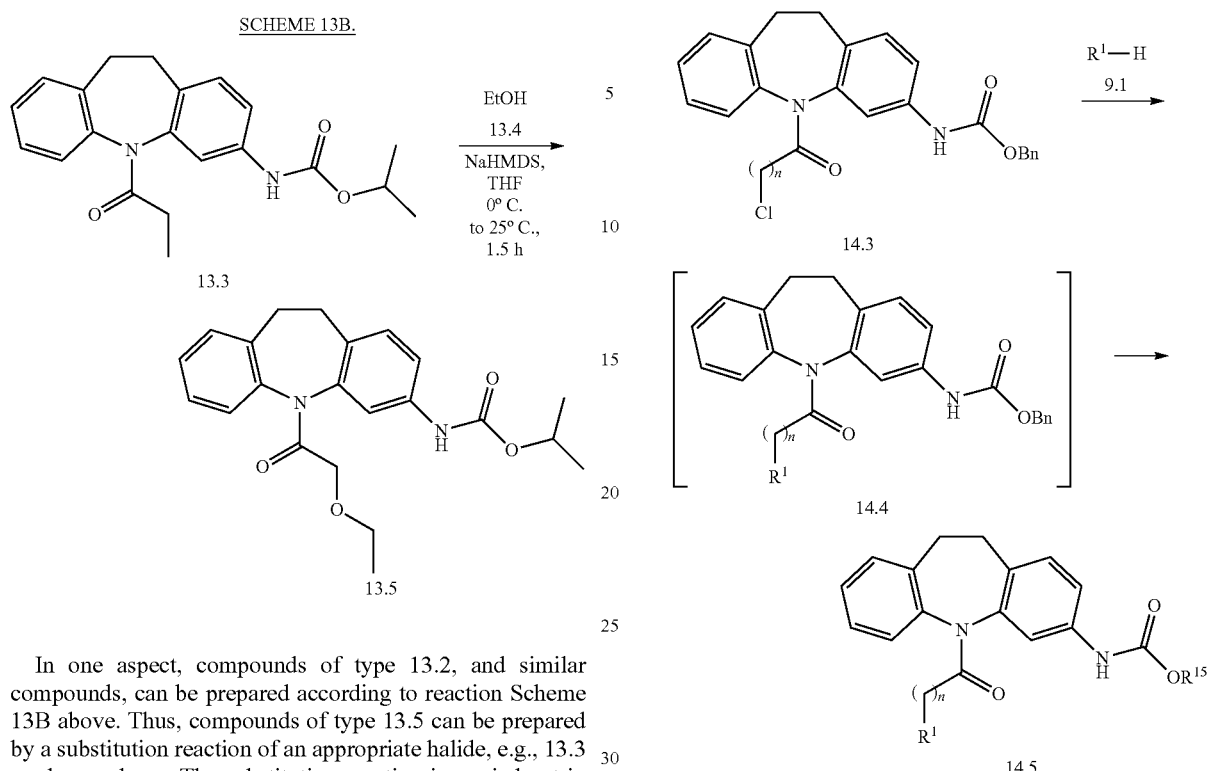

In one aspect, compounds of type 13.2, and similar compounds, can be prepared according to reaction Scheme 13B above. Thus, compounds of type 13.5 can be prepared by a substitution reaction of an appropriate halide, e.g., 13.3 as shown above. The substitution reaction is carried out in the presence of an appropriate nucleophile, e.g., ethanol (13.4), and an appropriate base, e.g., sodium bis(trimethylsilyl)amide, in an appropriate solvent, e.g., tetrahydrofuran, at an appropriate temperature range, e.g., from 0° C. to 25° C., for an appropriate period of time, e.g., 1.5 h. As can be appreciated by one skilled in the art, the above reaction provides an example of a generalized approach wherein compounds similar in structure to the specific reactants above (compounds similar to compounds of type 10.1 and 13.1), can be substituted in the reaction to provide substituted (10,11-dihydro-5H-dibenzo[b,f]azepin-3-yl)carbamates similar to Formula 13.2.

14. Route 14

In one aspect, substituted (10,11-dihydro-5H-dibenzo[b,f]azepin-3-yl)carbamates can be prepared as shown below.

SCHEME 14A.

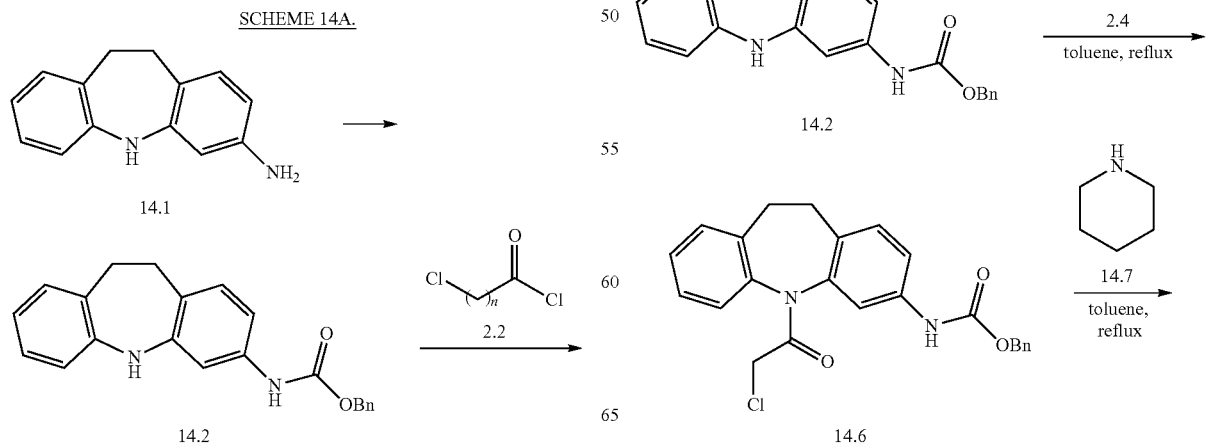

Compounds are represented in generic form, with substituents as noted in compound descriptions elsewhere herein. A more specific example is set forth below.

SCHEME 14B.

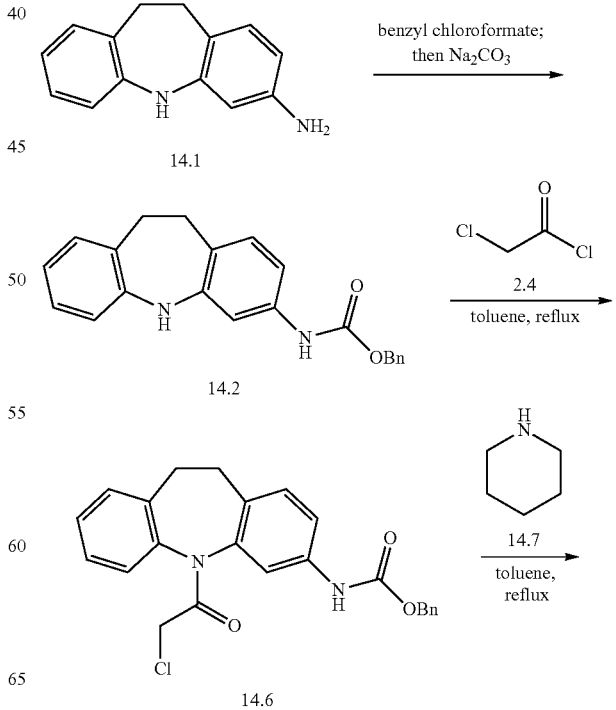

159
-continued

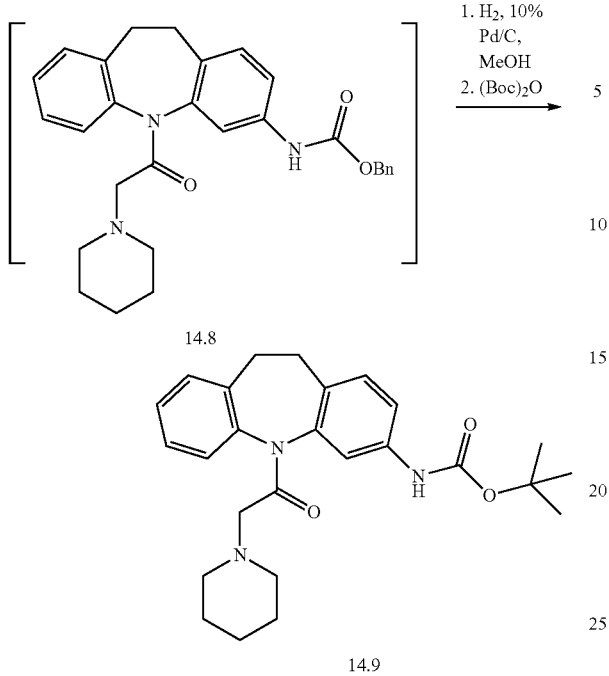

In one aspect, compounds of type 14.5, and similar compounds, can be prepared according to reaction Scheme 14B above. Thus, compounds of type 14.2 can be prepared by an acylation of an appropriate amine, e.g., 14.1 as shown above. Appropriate amines are commercially available or prepared by methods known to one skilled in the art. The acylation is carried out in the presence of an appropriate electrophile, e.g., benzyl chloroformate, followed by the addition of an appropriate base, e.g., sodium carbonate. Compounds of type 14.6 can be prepared by an acylation of an appropriate amine, e.g., 14.2 as shown above. The acylation is carried out in the presence of an appropriate electrophile, e.g., 2-chloroacetyl chloride (2.4), in an appropriate solvent, e.g., toluene. Compounds of type 14.8 can be prepared by a substitution reaction of an appropriate halide, e.g., 14.6 as shown above. The substitution reaction is carried out in the presence of an appropriate nucleophile, e.g., piperidine (14.7), in an appropriate solvent, e.g., toluene. Compounds of type 1.12 can be prepared by reduction of an appropriate amide, e.g., 1.11 as shown above. The reduction is carried out in the presence of an appropriate acid, e.g., hydrochloric acid and acetic acid. Compounds of type 14.9 can be prepared by deprotection of an appropriate benzyl carbamate, e.g., 14.8 as shown above, followed by alkylation of the resulting alcohol. The deprotection is carried out in the presence of an appropriate hydride source, e.g., hydrogen gas as shown above, and an appropriate catalyst, e.g., 10% palladium on carbon, in an appropriate solvent, e.g., methanol. The alkylation is carried out in the presence of an appropriate electrophile, e.g., di-tert-butyl dicarbonate. As can be appreciated by one skilled in the art, the above reaction provides an example of a generalized approach wherein compounds similar in structure to the specific reactants above (compounds similar to compounds of type 2.2, 9.1, 14.1, 14.2, 14.3, and 14.4), can be substituted in the reaction to provide substituted (10,11-dihydro-5H-dibenzo[b,f]azepin-3-yl)carbamates similar to Formula 14.5.

160

15. Route 15

In one aspect, substituted (10,11-dihydro-5H-dibenzo[b,f]azepin-3-yl)carbamates can be prepared as shown below.

SCHEME 15A.

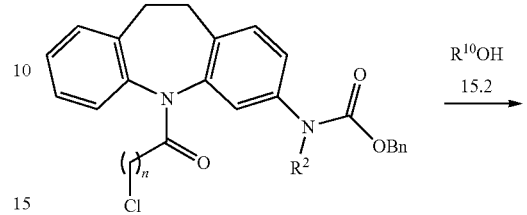

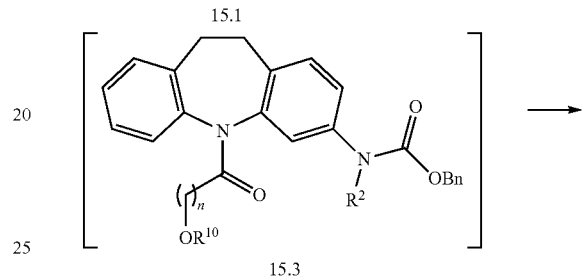

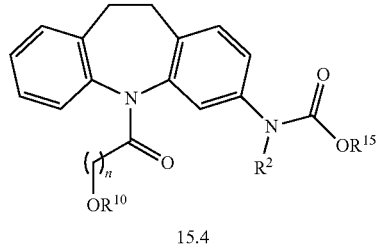

Compounds are represented in generic form, with substituents as noted in compound descriptions elsewhere herein. A more specific example is set forth below.

SCHEME 15B.

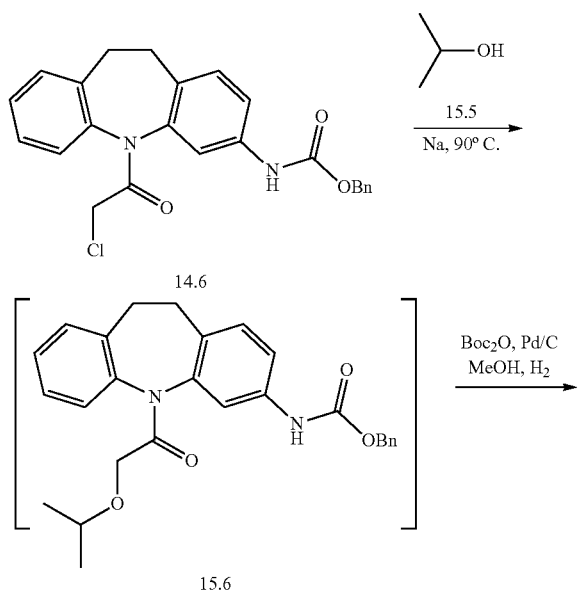

-continued

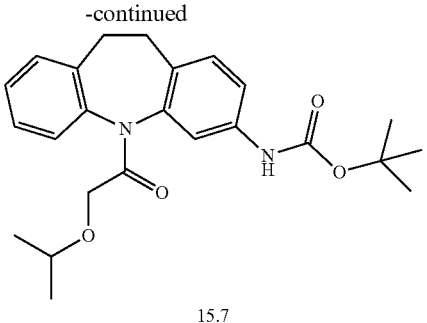

15.7

In one aspect, compounds of type 15.3, and similar compounds, can be prepared according to reaction Scheme 15B above. Thus, compounds of type 15.6 can be prepared by a substitution reaction of an appropriate halide, e.g., 14.6 as shown above. The substitution reaction is carried out in the presence of an appropriate nucleophile, e.g., isopropyl alcohol (15.5), and an appropriate metal, e.g., sodium, at an appropriate temperature, e.g., 90° C. Compounds of type 15.7 can be prepared by deprotection and alkylation of an appropriate benzyl carbamate, e.g., 15.6 as shown above. The deprotection/alkylation is carried out in the presence of an appropriate hydride source, e.g., hydrogen gas as shown above, and an appropriate catalyst, e.g., palladium on carbon, in an appropriate solvent, e.g., methanol, and an appropriate electrophile, e.g., di-tert-butyl dicarbonate. As can be appreciated by one skilled in the art, the above reaction provides an example of a generalized approach wherein compounds similar in structure to the specific reactants above (compounds similar to compounds of type 15.1, 15.2, and 15.3), can be substituted in the reaction to provide substituted (10,11-dihydro-5H-dibenzo[b,f]azepin-3-yl)carbamates similar to Formula 15.4.

16. Route 16

In one aspect, substituted (10,11-dihydro-5H-dibenzo[b,f]azepin-3-yl)carbamates can be prepared as shown below.

SCHEME 16A.

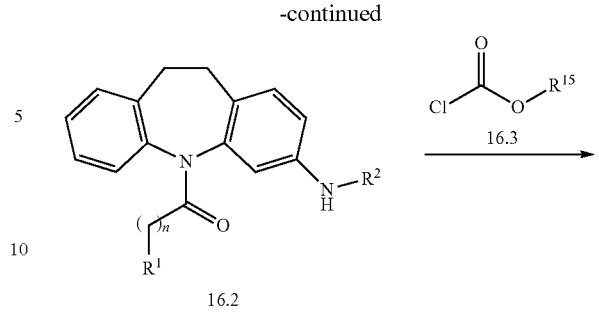

Compounds are represented in generic form, with substituents as noted in compound descriptions elsewhere herein. A more specific example is set forth below.

SCHEME 16B.

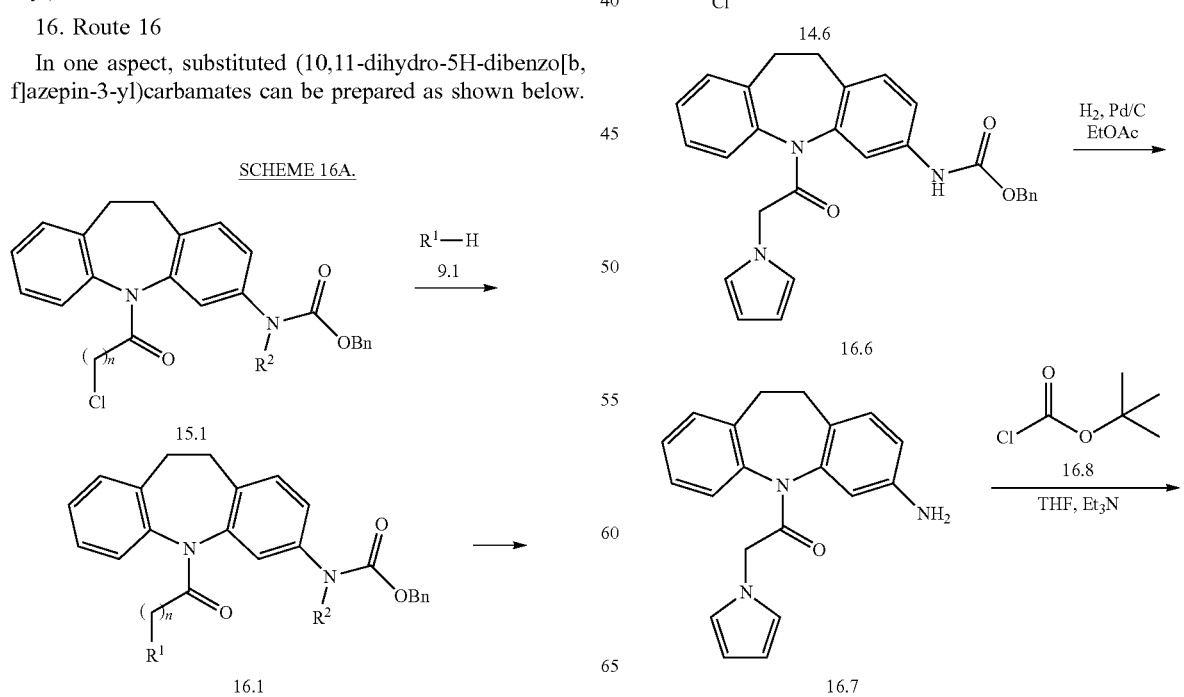

-continued

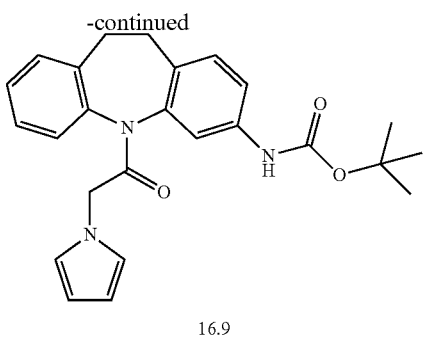

16.9

In one aspect, compounds of type 16.4, and similar compounds, can be prepare according to reaction Scheme 16B above. Thus, compounds of type 16.6 can be prepared by displacement of an appropriate halide, e.g., 14.6 as shown above. The displacement reaction is carried out in the presence of an appropriate nucleophile, e.g., 1H-pyrrole (16.5) and an appropriate base, e.g., sodium hydride, in an appropriate solvent, e.g., dimethylformamide. Compounds of type 16.7 can be prepared by reduction of an appropriate amine, e.g., 16.6 as shown above. The reduction is carried out in the presence of an appropriate reducing agent, e.g., hydrogen gas, and an appropriate catalyst, e.g., palladium on carbon, in an appropriate solvent, e.g., ethyl acetate. Compounds of type 16.9 can be prepared by an acylation of an appropriate amine, e.g., 16.7 as shown above. The acylation is carried out in the presence of an appropriate electrophile, e.g., tert-butyl carbonochloridate (16.8) and an appropriate base, e.g., triethylamine, in an appropriate solvent, e.g., tetrahydrofuran. As can be appreciated by one skilled in the art, the above reaction provides an example of a generalized approach wherein compounds similar in structure to the specific reactants above (compounds similar to compounds of type 9.1, 15.1, 16.1, 16.2, and 16.3), can be substituted in the reaction to provide substituted (10,11-dihydro-5H-dibenzo[b,f]azepin-3-yl)carbamates similar to Formula 16.4.

E. Methods of Inhibiting Car Activity in a Subject

In one aspect, the invention relates to a method of inhibiting CAR activity in a subject, the method comprising the step of administering to the subject an effective amount of at least one disclosed compound, at least one product of a disclosed method of making a compound, or a pharmaceutically acceptable salt thereof; thereby inhibiting CAR activity in a subject. In a further aspect, the compound is a disclosed compound. In a still further aspect, the compound is a product of a disclosed method of making.

In a further aspect, the compound exhibits inhibition of CAR with an $IC_{50}$ of less than about $6.0 \times 10^{-5}$ M. In a still further aspect, the compound exhibits inhibition of CAR with an $IC_{50}$ of less than about $4.0 \times 10^{-5}$ M. In yet a further aspect, the compound exhibits inhibition of CAR with an $IC_{50}$ of less than about $2.0 \times 10^{-5}$ M. In an even further aspect, the compound exhibits inhibition of CAR with an $IC_{50}$ of less than about $4.0 \times 10^{-6}$ M. In a still further aspect, the compound exhibits inhibition of CAR with an $IC_{50}$ of less than about $2.0 \times 10^{-6}$ M. In yet a further aspect, the compound exhibits inhibition of CAR with an $IC_{50}$ of less than about $4.0 \times 10^{-7}$ M. In an even further aspect, the compound exhibits inhibition of CAR with an $IC_{50}$ of less than about $2.0 \times 10^{-7}$ M. In a still further aspect, the compound exhibits inhibition of CAR with an $IC_{50}$ of less than about $4.0 \times 10^{-8}$ M. In yet a further aspect, the compound exhibits inhibition of CAR with an $IC_{50}$ of less than about $2.0 \times 10^{-8}$ M. In an even further aspect, the compound exhibits inhibition of CAR with an $IC_{50}$ of less than about $4.0 \times 10^{-9}$ M. In a still further aspect, the compound exhibits inhibition of CAR with an $IC_{50}$ of less than about $2.0 \times 10^{-9}$ M.

In a further aspect, the subject is a mammal. In a still further aspect, the mammal is a human.

In a further aspect, the effective amount is a therapeutically effective amount. In a still further aspect, the effective amount is a prophylactically effective amount.

In a further aspect, the subject has been diagnosed with a need of treatment of a disorder of uncontrolled cellular proliferation prior to the administering step. In a still further aspect, the method further comprises the step of identifying the subject as having a need of treatment of a disorder of uncontrolled cellular proliferation.

In a further aspect, the disorder of uncontrolled cellular proliferation is a cancer. In a still further aspect, the cancer is a hematological cancer. In yet a further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In yet a further aspect, the lymphoma is Hodgkin's lymphoma. In an even further aspect, the lymphoma is non-Hodgkin's lymphoma.

In a further aspect, the cancer is a solid tumor.

In a further aspect, the cancer is selected from a cancer of the brain, genitourinary tract, gastrointestinal tract, colon, rectum, breast, kidney, lymphatic system, stomach, lung, pancreas, and skin. In a still further aspect, the cancer is selected from prostate cancer, glioblastoma multiforme, endometrial cancer, breast cancer, and colon cancer. In yet a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the method further comprises co-administering the at least one compound with an effective amount of at least one chemotherapeutic agent. In a still further aspect, the at least one chemotherapeutic agent is a platinum-based agent. In yet a further aspect, the platinum-based agent is selected from carboplatin, cisplatin, transplatin, nedaplatin, oxaliplatin, picoplatin, satraplatin, transplatin, and triplatin. In an even further aspect, the at least one chemotherapeutic agent is an antibiotic agent. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is doxorubicin.

In a further aspect, co-administration is administration in a simultaneous manner. In a still further aspect, co-administration is administration in a sequential manner.

In a further aspect, the subject has been previously treated with a first dosage of the at least one chemotherapeutic agent. In a still further aspect, the subject has demonstrated a resistance to the at least one chemotherapeutic agent. In yet a further aspect, the at least one chemotherapeutic agent is administered at a second dosage, wherein the second dosage is lower than the first dosage.

F. Methods of Inhibiting Car Activity in at Least One Cell

In one aspect, the invention relates to a method of inhibiting CAR activity in at least one cell, comprising the step of contacting the at least one cell with an effective amount of at least one disclosed compound; or a pharmaceutically acceptable salt thereof; thereby inhibiting CAR activity in at least one cell. In a further aspect, the compound is a disclosed compound. In a still further aspect, the compound is a product of a disclosed method of making.

In a further aspect, the compound exhibits inhibition of CAR with an $IC_{50}$ of less than about $6.0 \times 10^{-5}$ M. In a still further aspect, the compound exhibits inhibition of CAR with an $IC_{50}$ of less than about $4.0 \times 10^{-5}$ M. In yet a further aspect, the compound exhibits inhibition of CAR with an $IC_{50}$ of less than about $2.0 \times 10^{-5}$ M. In an even further aspect, the compound exhibits inhibition of CAR with an $IC_{50}$ of less than about $4.0 \times 10^{-6}$ M. In a still further aspect, the compound exhibits inhibition of CAR with an $IC_{50}$ of less than about $2.0 \times 10^{-6}$ M. In yet a further aspect, the compound exhibits inhibition of CAR with an $IC_{50}$ of less than about $4.0 \times 10^{-7}$ M. In an even further aspect, the compound exhibits inhibition of CAR with an $IC_{50}$ of less than about $2.0 \times 10^{-7}$ M. In a still further aspect, the compound exhibits inhibition of CAR with an $IC_{50}$ of less than about $4.0 \times 10^{-8}$ M. In yet a further aspect, the compound exhibits inhibition of CAR with an $IC_{50}$ of less than about $2.0 \times 10^{-8}$ M. In an even further aspect, the compound exhibits inhibition of CAR with an $IC_{50}$ of less than about $4.0 \times 10^{-9}$ M. In a still further aspect, the compound exhibits inhibition of CAR with an $IC_{50}$ of less than about $2.0 \times 10^{-9}$ M.

In a further aspect, the cell is mammalian. In a still further aspect, the cell is human.

In a further aspect, the cell has been isolated from a mammal prior to the contacting step. In a still further aspect, contacting is via administration.

G. Methods of Inhibiting Growth of at Least One Cell

In one aspect, the invention relates to a method of inhibiting growth of at least one cell, comprising the step of contacting the at least one cell with an effective amount of at least one disclosed compound, at least one product of a disclosed method of making a compound, or a pharmaceutically acceptable salt thereof; thereby inhibiting growth of at least one cell. In a further aspect, the compound is a disclosed compound. In a still further aspect, the compound is a product of a disclosed method of making.

In a further aspect, the compound exhibits inhibition of CAR with an $IC_{50}$ of less than about $6.0 \times 10^{-5}$ M. In a still further aspect, the compound exhibits inhibition of CAR with an $IC_{50}$ of less than about $4.0 \times 10^{-5}$ M. In yet a further aspect, the compound exhibits inhibition of CAR with an $IC_{50}$ of less than about $2.0 \times 10^{-5}$ M. In an even further aspect, the compound exhibits inhibition of CAR with an $IC_{50}$ of less than about $4.0 \times 10^{-6}$ M. In a still further aspect, the compound exhibits inhibition of CAR with an $IC_{50}$ of less than about $2.0 \times 10^{-6}$ M. In yet a further aspect, the compound exhibits inhibition of CAR with an $IC_{50}$ of less than about $4.0 \times 10^{-7}$ M. In an even further aspect, the compound exhibits inhibition of CAR with an $IC_{50}$ of less than about $2.0 \times 10^{-7}$ M. In a still further aspect, the compound exhibits inhibition of CAR with an $IC_{50}$ of less than about $4.0 \times 10^{-8}$ M. In yet a further aspect, the compound exhibits inhibition of CAR with an $IC_{50}$ of less than about $2.0 \times 10^{-8}$ M. In an even further aspect, the compound exhibits inhibition of CAR with an $IC_{50}$ of less than about $4.0 \times 10^{-9}$ M. In a still further aspect, the compound exhibits inhibition of CAR with an $IC_{50}$ of less than about $2.0 \times 10^{-9}$ M.

In a further aspect, the cell is mammalian. In a still further aspect, the cell is human.

In a further aspect, the cell has been isolated from a mammal prior to the contacting step. In a still further aspect, contacting is via administration.

H. Methods of Using the Compounds

The compounds and pharmaceutical compositions of the invention are useful in treating or controlling cell proliferative disorders, in particular oncological disorders, such as cancer. The compounds and pharmaceutical compositions containing the compounds can be useful in the treatment or control of solid tumors, such as breast, colon, lung and prostate tumors, through the inhibition of CAR.

Examples of cell proliferative disorders for which the compounds and compositions can be useful in treating, include, but are not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. For a review of such disorders, see Fishman et al., 1985, *Medicine*, 2$^{nd}$ Ed., J.B. Lippincott Co., Philadelphia.

To treat or control the cell proliferative disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cell proliferative disorder, such as cancer.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition, such as cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or preventing a cell proliferative disorder, such as cancer. Thus, provided is a method comprising administering a therapeutically effective amount of a composition comprising a disclosed compound to a subject. In one aspect, the method can be a method for treating a disorder of uncontrolled cellular proliferation. In yet another aspect, the method can be a method for treating a cancer. In a still further aspect, the method can be a method for inhibiting CAR activity.

a. Treating a Disorder of Uncontrolled Cellular Proliferation in a Subject

In one aspect, the invention relates to a method of treating a disorder of uncontrolled cellular proliferation in a subject, the method comprising administering to the subject: (a) an effective amount of at least one disclosed compound, or a pharmaceutically acceptable salt thereof; and (b) an effective amount of at least one chemotherapeutic agent, or a pharmaceutically acceptable salt thereof; thereby treating the disorder of uncontrolled cellular proliferation in the subject. In a further aspect, the compound is a disclosed compound. In a still further aspect, the compound is a product of a disclosed method of making.

Examples of cell proliferative disorders include, but are not limited to, from leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the disorder of uncontrolled cellular proliferation is associated with a CAR dysfunction.

In a further aspect, the compound exhibits a decrease in CAR activity.

In a further aspect, the compound exhibits inhibition of CAR with an IC$_{50}$ of less than about 6.0×10$^{-5}$ M. In a still further aspect, the compound exhibits inhibition of CAR with an IC$_{50}$ of less than about 4.0×10$^{-5}$ M. In yet a further aspect, the compound exhibits inhibition of CAR with an IC$_{50}$ of less than about 2.0×10$^{-5}$ M. In an even further aspect, the compound exhibits inhibition of CAR with an IC$_{50}$ of less than about 4.0×10$^{-6}$ M. In a still further aspect, the compound exhibits inhibition of CAR with an IC$_{50}$ of less than about 2.0×10$^{-6}$ M. In yet a further aspect, the compound exhibits inhibition of CAR with an IC$_{50}$ of less than about 4.0×10$^{-7}$ M. In an even further aspect, the compound exhibits inhibition of CAR with an IC$_{50}$ of less than about 2.0×10$^{-7}$ M. In a still further aspect, the compound exhibits inhibition of CAR with an IC$_{50}$ of less than about 4.0×10$^{-8}$ M. In yet a further aspect, the compound exhibits inhibition of CAR with an IC$_{50}$ of less than about 2.0×10$^{-8}$ M. In an even further aspect, the compound exhibits inhibition of CAR with an IC$_{50}$ of less than about 4.0×10$^{-9}$ M. In a still further aspect, the compound exhibits inhibition of CAR with an IC$_{50}$ of less than about 2.0×10$^{-9}$ M.

In a further aspect, the subject is a mammal. In a still further aspect, the mammal is a human.

In a further aspect, the subject has been diagnosed with a need of treatment of the disorder of uncontrolled cellular proliferation prior to the administering step. In a still further aspect, the method further comprises the step of identifying the subject as having a need of treatment of the disorder of uncontrolled cellular proliferation.

In a further aspect, the effective amount is a therapeutically effective amount. In a still further aspect, the effective amount is a prophylactically effective amount.

In a further aspect, the disorder of uncontrolled cellular proliferation is a cancer. In a still further aspect, the cancer is a hematological cancer. In yet a further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In yet a further aspect, the lymphoma is Hodgkin's lymphoma. In an even further aspect, the lymphoma is non-Hodgkin's lymphoma.

In a further aspect, the cancer is a solid tumor.

In a further aspect, the cancer is selected from a cancer of the brain, genitourinary tract, gastrointestinal tract, colon, rectum, breast, kidney, lymphatic system, stomach, lung, pancreas, and skin. In a still further aspect, the cancer is selected from prostate cancer, glioblastoma multiforme, endometrial cancer, breast cancer, and colon cancer. In yet a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is treatment-resistant. In a still further aspect, the cancer is resistant to treatment with the at least one chemotherapeutic agent. In yet a further aspect, the at least one chemotherapeutic agent is a platinum-based agent. In an even further aspect, the platinum-based agent is selected from carboplatin, cisplatin, transplatin, nedaplatin, oxaliplatin, picoplatin, satraplatin, transplatin, and triplatin. In a still further aspect, the at least one chemotherapeutic agent is an antibiotic agent. In yet a further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In an even further aspect, the antibiotic agent is doxorubicin.

In a further aspect, the at least one compound and the at least one chemotherapeutic agent are administered simultaneously. In a still further aspect, the at least one compound and the at least one chemotherapeutic agent are administered sequentially.

In a further aspect, the at least one compound and the at least one chemotherapeutic agent are co-formulated. In a still further aspect, the at least one compound and the at least one chemotherapeutic agent are co-packaged.

In a further aspect, the subject has been previously treated with a first dosage of the at least one chemotherapeutic agent. In a still further aspect, the subject has demonstrated a resistance to the at least one chemotherapeutic agent. In yet a further aspect, the at least one chemotherapeutic agent is administered at a second dosage, wherein the second dosage is lower than the first dosage.

In a further aspect, the method further comprises the step of administering a therapeutically effective amount of at least one agent known to treat a cell proliferative disorder. In a still further aspect, the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), iressa (gefinitib, Zd1839), XELODA® (capecitabine), Tarceva® (erlotinib), azacitidine (5-Azacytidine; 5-AzaC), temozolomide (Temodar®), gemcitabine (e.g., GEMZAR® (gemcitabine HCl)), and vasostatin.

b. Treating a Disorder of Uncontrolled Cellular Proliferation Associated with a CAR Dysfunction in a Subject In one aspect, the invention relates to a method of treating a disorder of uncontrolled cellular proliferation associated with a CAR dysfunction in a subject, the method comprising the step of administering to the subject an effective amount of at least one disclosed compound; or a pharmaceutically acceptable salt thereof; thereby treating the disorder of uncontrolled cellular proliferation associated with CAR dysfunction in the subject. In a further aspect, the compound is a disclosed compound. In a still further aspect, the compound is a product of a disclosed method of making.

Examples of cell proliferative disorders include, but are not limited to, from leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the compound exhibits inhibition of CAR with an $IC_{50}$ of less than about $6.0 \times 10^{-5}$ M. In a still further aspect, the compound exhibits inhibition of CAR with an $IC_{50}$ of less than about $4.0 \times 10^{-5}$ M. In yet a further aspect, the compound exhibits inhibition of CAR with an $IC_{50}$ of less than about $2.0 \times 10^{-5}$ M. In an even further aspect, the compound exhibits inhibition of CAR with an $IC_{50}$ of less than about $4.0 \times 10^{-6}$ M. In a still further aspect, the compound exhibits inhibition of CAR with an $IC_{50}$ of less than about $2.0 \times 10^{-6}$ M. In yet a further aspect, the compound exhibits inhibition of CAR with an $IC_{50}$ of less than about $4.0 \times 10^{-7}$ M. In an even further aspect, the compound exhibits inhibition of CAR with an $IC_{50}$ of less than about $2.0 \times 10^{-7}$ M. In a still further aspect, the compound exhibits inhibition of CAR with an $IC_{50}$ of less than about $4.0 \times 10^{-8}$ M. In yet a further aspect, the compound exhibits inhibition of CAR with an $IC_{50}$ of less than about $2.0 \times 10^{-8}$ M. In an even further aspect, the compound exhibits inhibition of CAR with an $IC_{50}$ of less than about $4.0 \times 10^{-9}$ M. In a still further aspect, the compound exhibits inhibition of CAR with an $IC_{50}$ of less than about $2.0 \times 10^{-9}$ M.

In a further aspect, the subject is a mammal. In a still further aspect, the mammal is a human.

In a further aspect, the subject has been diagnosed with a need of treatment of the disorder of uncontrolled cellular proliferation prior to the administering step. In a still further aspect, the method further comprises the step of identifying the subject as having a need of treatment of the disorder of uncontrolled cellular proliferation.

In a further aspect, the effective amount is a therapeutically effective amount. In a still further aspect, the effective amount is a prophylactically effective amount.

In a further aspect, the disorder of uncontrolled cellular proliferation is a cancer. In a still further aspect, the cancer is a hematological cancer. In yet a further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In yet a further aspect, the lymphoma is Hodgkin's lymphoma. In an even further aspect, the lymphoma is non-Hodgkin's lymphoma.

In a further aspect, the cancer is a solid tumor.

In a further aspect, the cancer is selected from a cancer of the brain, genitourinary tract, gastrointestinal tract, colon, rectum, breast, kidney, lymphatic system, stomach, lung, pancreas, and skin. In a still further aspect, the cancer is selected from prostate cancer, glioblastoma multiforme, endometrial cancer, breast cancer, and colon cancer. In yet a further aspect, the cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the CAR dysfunction is associated with a treatment-resistant cancer. In a still further aspect, the treatment-resistant cancer is a hematological cancer. In yet a further aspect, the hematological cancer is selected from a leukemia, lymphoma, chronic myeloproliferative disorder, myelodysplastic syndrome, myeloproliferative neoplasm, plasma cell neoplasm (myeloma), solid tumor, sarcoma, and carcinoma.

In a further aspect, the treatment-resistant cancer is leukemia. In a still further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia.

In a further aspect, the treatment-resistant cancer is a lymphoma. In a still further aspect, the lymphoma is selected from AIDS-Related lymphoma, cutaneous T-Cell lymphoma, Hodgkin lymphoma, non-Hodgkin lymphoma, primary central nervous system lymphoma, mycosis fungoides and the Sézary Syndrome, heavy chain disease, and Waldenström macroglobulinemia. In yet a further aspect, the lymphoma is Hodgkin's lymphoma. In an even further aspect, the lymphoma is non-Hodgkin's lymphoma.

In a further aspect, the treatment-resistant cancer is a solid tumor. In a still further aspect, the treatment-resistant cancer is selected from a cancer of the brain, genitourinary tract, gastrointestinal tract, colon, rectum, breast, kidney, lymphatic system, stomach, lung, pancreas, and skin. In yet a further aspect, the treatment-resistant cancer is selected from prostate cancer, glioblastoma multiforme, endometrial cancer, breast cancer, and colon cancer. In an even further aspect, the treatment-resistant cancer is selected from synovioma, mesothelioma, Ewing's tumor, pancreatic cancer, breast cancer, ovarian cancer, prostate cancer, hepatoma, Wilms' tumor, cervical cancer, testicular cancer, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In a further aspect, the treatment-resistant cancer is a sarcoma. In a still further aspect, the sarcoma is selected from fibrosarcoma, myxosarcoma, liposarcoma, chondrosarcoma, osteogenic sarcoma, chordoma, angiosarcoma, endotheliosarcoma, lymphangiosarcoma, leiomyosarcoma, rhabdomyosarcoma, and lymphangioendotheliosarcoma.

In a further aspect, the treatment-resistant cancer is a carcinoma. In a still further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the CAR dysfunction is associated with resistance to treatment with at least on chemotherapeutic agent. In a still further aspect, the at least one chemotherapeutic agent is a platinum-based agent. In yet a further aspect, the platinum-based agent is selected from carboplatin, cisplatin, transplatin, nedaplatin, oxaliplatin, picoplatin, satraplatin, transplatin, and triplatin. In an even further aspect, the at least one chemotherapeutic agent is an antibiotic agent. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is doxorubicin.

In a further aspect, the method further comprises co-administering the at least one compound with an effective amount of at least one chemotherapeutic agent. In a still further aspect, the at least one chemotherapeutic agent is a platinum-based agent. In yet a further aspect, the platinum-based agent is selected from carboplatin, cisplatin, transplatin, nedaplatin, oxaliplatin, picoplatin, satraplatin, transplatin, and triplatin. In an even further aspect, the at least one chemotherapeutic agent is an antibiotic agent. In a still further aspect, the antibiotic agent is selected from one or more of daunorubicin, doxorubicin, epirubicin, idarubicin, actinomycin-D, bleomycin, and mitomycin-C, or a pharmaceutically acceptable salt thereof. In yet a further aspect, the antibiotic agent is doxorubicin.

In a further aspect, co-administration is administration in a simultaneous manner. In a still further aspect, co-administration is administration in a sequential manner.

In a further aspect, the subject has been previously treated with a first dosage of the at least one chemotherapeutic agent. In a still further aspect, the subject has demonstrated a resistance to the at least one chemotherapeutic agent. In yet a further aspect, the at least one chemotherapeutic agent is administered at a second dosage, wherein the second dosage is lower than the first dosage.

2. Use of Compounds

In one aspect, the invention relates to the use of a disclosed compound or a product of a disclosed method. In a further aspect, a use relates to the manufacture of a medicament for the treatment of a disorder of uncontrolled cellular proliferation in a mammal. In a further aspect, a use relates to treatment of a disorder of uncontrolled cellular proliferation in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for CAR antagonism. In one aspect, the use is characterized in that the mammal is a human. In one aspect, the use is characterized in that the disorder is a cell proliferative disorder associated with CAR dysfunction. In one aspect, the cell proliferative disorder associated with CAR dysfunction is treated by antagonism of CAR activity in a mammal.

In a further aspect, the use relates to the manufacture of a medicament for the treatment of a disorder associated with CAR dysfunction in a mammal. In a further aspect, the medicament is used in the treatment of a cell proliferative disorder associated with CAR dysfunction in a mammal.

In a further aspect, the use relates to antagonism of CAR activity in a mammal. In a further aspect, the use relates to modulating CAR activity in a mammal. In a still further aspect, the use relates to modulating CAR activity in a cell. In yet a further aspect, the mammal is a human.

In one aspect, the use is associated with the treatment of a cell proliferative disorder associated with CAR dysfunction. In a further aspect, the use is associated with a cell proliferative disorder selected from leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with CAR dysfunction in a mammal. In a further aspect, the disorder is a cell proliferative disorder.

3. Manufacture of a Medicament

In one aspect, the invention relates to a method for the manufacture of a medicament for treating a disease of uncontrolled cellular proliferation in a mammal, the method comprising combining a therapeutically effective amount of a disclosed compound or product of a disclosed method with a pharmaceutically acceptable carrier or diluent.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent. 4. KITS In one aspect, the invention relates to a kits comprising at least one disclosed compound, at least one product of a disclosed method of making a compound; or a pharmaceutically acceptable salt thereof; and one or more of:
   (a) at least one agent known to increase CAR activity;
   (b) at least one agent known to decrease CAR activity;
   (c) at least one agent known to treat a disorder of uncontrolled cellular proliferation;
   (d) instructions for treating a disorder associated with CAR dysfunction; or
   (e) instructions for treating a disorder of uncontrolled cellular proliferation.

In a further aspect, the compound is a disclosed compound. In a still further aspect, the compound is a product of a disclosed method of making.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In a further aspect, the at least one compound at the at least one agent known to increase CAR activity are co-packaged. In a still further aspect, the at least one compound at the at least one agent known to increase CAR activity are co-formulated.

In a further aspect, the at least one compound and the at least one agent known to decrease CAR activity are co-packaged. In a still further aspect, the at least one compound and the at least one agent known to decrease CAR activity are co-formulated.

In a further aspect, the at least one compound and the at least one agent known to treat a disorder of uncontrolled cellular proliferation are co-packaged. In a still further aspect, the at least one compound and the at least one agent known to treat a disorder of uncontrolled cellular proliferation are co-formulated.

In a further aspect, the kit further comprises a plurality of dosage forms, the plurality comprising one or more doses; wherein each dose comprises an effective amount of the at least one compound and the at least one agent known to treat a disorder of uncontrolled cellular proliferation. In a still further aspect, the effective amount is a therapeutically effective amount. In yet a further aspect, the effective amount is a prophylactically effective amount.

In a further aspect, each dose of the at least one compound and the at least one agent known to treat a disorder of cellular proliferation are co-formulated. In a still further aspect, each dose of the at least one compound and the at least one agent known to treat a disorder of cellular proliferation are co-packaged.

In a further aspect, the dosage forms are formulated for oral and/or intravenous administration. In a still further aspect, the dosage forms are formulated for oral administration. In yet a further aspect, the dosage forms are formulated for intravenous administration. In an even further aspect, the dosage form for the at least one compound is formulated for oral administration and the dosage form for the at least one agent known to treat a disorder of cellular proliferation is formulated for intravenous administration. In a still further aspect, the dosage form for the at least one compound is formulated for intravenous administration and the dosage form for the at least one agent known to treat a disorder of cellular proliferation is formulated for oral administration.

It is understood that the disclosed kits can be prepared from the disclosed compounds, products, and pharmaceutical compositions. It is also understood that the disclosed kits can be employed in connection with the disclosed methods of using.

I. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. General Experimental Methods a. Materials

HEK293T, HepG2, LS174T, and U2OS cells were obtained from American Type Culture Collection (Manassas, Va., USA). GeneBLAzer® Validated Assays for Nuclear Receptors, Tb-anti-GST antibody, GST-hCAR-LBD, Fluorescein-PGC-1α (Peroxisome proliferator-activated receptor gamma coactivator 1-alpha) coactivator peptide, TR-FRET coregulator buffer G, and 1 M DTT were obtained from Life Technologies (Carlsbad, Calif.) or Invitrogen (Carlsbad, Calif.). Charcoal dextran-treated fetal bovine serum (FBS) was obtained from HyClone (Logan, Utah). Anti-mouse IRDye secondary antibody was purchased from LI-COR Biosciences (Lincoln, Nebr., USA). Anti-CAR antibody (Clone N4111) was purchased from R&D Systems (Minneapolis, Minn.), and anti-RNA polymerase II, from EMD Millipore (USA). PK11195, rifampicin, clotrimazole, anti-Flag M2 antibody, and protease inhibitor cocktail were obtained from Sigma-Aldrich (St. Louis, Mo.). Dimethyl sulfoxide (DMSO) was purchased from Fisher Scientific (Pittsburgh, Pa., USA). Black 384-well low-volume assay plates were purchased from Corning (Tewksbury, Mass.). Allyl isothiocyanate and chemicals 81, 82, 84, 87, and 89 were purchased from ChemDiv (San Diego, Calif.). Chemicals 1, 80, 83, 85, and 86 were purchased from ChemBridge (San Diego, Calif.).w32

CITCO was obtained from Tocris Bioscience (Bristol, UK). CITCO is 6-(4-chlorophenyl)imidazo [2,1-b][1,3]thiazole-5-carbaldehyde O-(3,4-dichlorobenzyl) oxime, and the compound has the structure given by the formula:

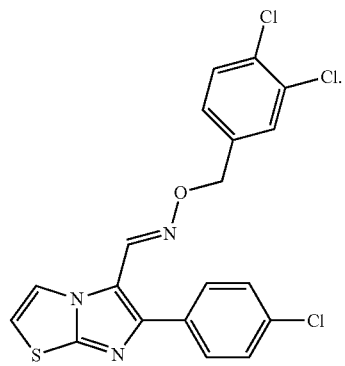 [SMILES: Clc1ccc(-c2nc3sccn3c2/C=N/OCc2ccc(Cl)c(Cl)c2)cc1]

CINPA1 was obtained from ChemDiv (San Diego, Calif.). CINPA1 is ethyl (5-(diethylglycyl)-10,11-dihydro-5H-dibenzo[b,f]azepin-3-yl)carbamate, and the compound has the structure given by the formula:

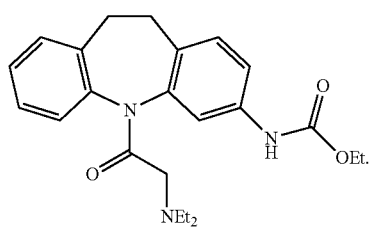

b. Cell Culture, Plasmids, and Transfection

A humidified incubator at 37° C. with 5% $CO_2$ was used to maintain all cell lines. HEK293T, HepG2, HepG2-PXR Clone 1 (Li, G., et al. (2012) Tox. Appl. Pharm. 258, 268-274; and Lin, W., et al. (2008) J. Biol. Chem. 283, 30650-30657), and LS174T cells were maintained in EMEM medium supplemented with 10% FBS and PenStrep (100 µg/mL; Life Technologies). GeneBLAzer cell lines were maintained according to manufacturer's instructions.

A clone of HepG2 cells stably over-expressing FLAG-hCAR1 (HepG2-hCAR1) was generated by antibiotic selection with G418 (Life Technologies), using a limited dilution method. HepG2-hCAR1 and HepG2-PXR Clone 1 cells were maintained in media containing G418 (500 µg/mL).

U2OS (human osteosarcoma derived) cells were maintained in Dulbecco's modified Eagle's medium containing 10% FBS, 1 mM sodium pyruvate, 100 U/ml penicillin, and 100 µg/ml streptomycin.

Primary human hepatocytes were obtained through the Liver Tissue Cell Distribution System (Donors 1-6, corresponding to case #13-001, 13-003, 13-005, 13-006, 14-005 and 14-008, respectively; Pittsburgh, Pa., USA) or from Triangle Research Labs (Donor 7, case # HUM4043; TRL, NC, USA) as detailed in Table 1 below, and maintained in Williams E medium containing Primary Hepatocyte Maintenance Supplement (Life Technologies).

TABLE 1

| Human primary hepatocytes | Source | Case Number |
|---|---|---|
| HPH 1 | University of Pittsburgh | 13-001 |
| HPH 2 | University of Pittsburgh | 13-003 |
| HPH 3 | University of Pittsburgh | 13-005 |
| HPH 4 | University of Pittsburgh | 13-006 |
| HPH 5 | University of Pittsburgh | 14-005 |
| HPH 6 | University of Pittsburgh | 14-008 |
| HPH 7 | Triangle Research Labs | HUM4043 |

The CAR expression vector (Flag-hCAR1 in pcDNA3.1 vector) and CYP3A4-luciferase reporter (CYP3A4-luc; in pGL3 vector) were previously described (Li, G., et al. (2012) Tox. Appl. Pharm. 258, 268-274). A luciferase reporter gene under the control of the CYP2B6 promoter region (phenobarbital-responsive enhancer module/xenobiotic responsive enhancer module, or PBREM/XREM), CYP2B6-luc, was as previously described (Wang, H., et al. (2003) J. Biol. Chem. 278, 14146-14152). The pK-Renilla luciferase plasmid was purchased from Promega (Madison, Wis., USA). Plasmids used for mammalian two-hybrid assays, pG5-Luc and pACT (a GAL4-luciferase reporter construct), were obtained from Promega (CheckMate). The pBIND-SRC-1 (621-765) plasmid was previously described (Wang, Y. M., et al. (2013) Toxicol. Appl. Pharm. 272, 96-107). The pBIND-mNCoR (1958-2401) and pBIND-SMRTα (2004-2517) plasmids were constructed as previously described (Wang, Y. M., et al. (2013) Toxicol. Appl. Pharm. 272, 96-107).

The pACT-hCAR1 plasmid was prepared by PCR amplification of hCAR1 by using oligonucleotides 5'-GTAC-CGAGCTCGGATCCAACTAGTAA-3' (SEQ ID NO.:1) and 5'-CAGGATCCGCGGCCGCTCAGCTGCAGAT-3' (SEQ ID NO.:2), digested using BamHI (Promega) and NotI (Promega), and ligating the resulting fragment into BamHI and NotI-cleaved pACT vector plasmid at a 1:7 molar ratio.

The pBIND-TIF2 plasmid was similarly prepared by PCR amplification of TIF2 using oligonucleotides 5'-ATTCG-GATCCATACCATGGAGAGAGCT-3' (SEQ ID NO.:3) and 5'-ATAAGATCTGGATCCCTAGCTCTGTGA-3' (SEQ ID NO.:4), digested using BamHI (Promega), and ligating the resulting fragment into BamHI-cleaved pBIND vector plasmid at a 1:10 molar ratio. All transfections were performed by using Fugene6 or Fugene HD (Promega) according to the manufacturer's recommendations.

c. Gene Expression Assays (i) Luciferase Assay

HepG2 cells grown in flasks were transfected with Flag-hCAR1 and CYP2B6-luciferase reporter at a 1:3 ratio with Fugene HD (Promega) and incubated for 24 h. Cells were trypsinized and plated in 384-well plates (CulturPlate-384, PerkinElmer) at 5000 cells/well for the primary or secondary screening assays. Cells were treated with chemicals transferred by using a pintool 24 h prior to measuring reporter luciferase activity with SteadyLite firefly luciferase reagent and an EnVision plate reader (PerkinElmer). The percentage of CAR inhibition was calculated by setting 50 µM PK11195 (positive control) to 100% inhibition and DMSO (negative control) to 0%. Unless otherwise noted, total DMSO (vehicle) concentration in all assays was maintained at or below 0.56%. Compounds were screened in a dose-responsive format (56 µM to 2.8 nM, 1-to-3 dilutions for 10 concentrations). PXR activity was measured in HepG2 cells stably transfected with hPXR and CYP3A4-luciferase reporter (previously described as PXR Clonel cells, see Li, G., et al. (2012) $Tox.\ Appl.\ Pharm.$ 258, 268-274; and Lin, W., et al. (2008) $J.\ Biol.\ Chem.$ 283, 30650-30657). Briefly, cells were treated with clotrimazole, PK11195 or CINPA1 at the indicated concentrations with or without 5 µM of hPXR agonist rifampicin in phenol red-free DMEM supplemented with 5% charcoal/dextran-treated FBS and incubated for 24 h before SteadyLite™ luciferase assays. The luminescence signal was detected by using an Envision plate reader (PerkinElmer) and used to calculate the percentage of PXR activation.

(ii) Geneblazer® Assay

GeneBLAzer® cells individually expressing the ligand-binding domains of either FXR, GR, LXRα, LXRβ, PPARγ, RXRα, RXRβ, or VDR fused to the GAL4-DNA binding domain (GAL4-DBD) were obtained from Life Technologies (Li, G., et al. (2012) $Tox.\ Appl.\ Pharm.$ 258, 268-274; and Yu, D. D., et al. (2013) $Bioorg.\ Med.\ Chem$ 21, 4266-4278). Upon activation with the respective agonist, β-lactamase is expressed under the transcriptional control of an Upstream Activator Sequence (UAS), and a FRET-based substrate (CCF2-AM) is used to measure the enzyme activity of β-lactamase. The following agonists were used at an excitatory concentration that resulted in at least 75% receptor activation ($EC_{75}$): 375 nM GW4064 for FXR; 3 nM dexamethasone for GR; 50 nM TO901317 for LXRα; 32 nM TO901317 for LXRβ; 52 nM rosglitazone for PPARγ; 267 nM 9-cis retinoic acid (9-cisRA) for RXRα and β; and 0.2 nM 1α, 25-dihydroxyvitamin D3 for VDR. Control antagonists for each receptor were used as suggested by the manufacturer: 25 µM e guggulsterone for FXR, 100 nM RU-486 for GR, 50 µM fenofibrate for LXRα/β, 10 µM GW9662 for PPARγ, 10 µM HX531 for RXRα/β, and 10 µM 22(S)-hydroxycholesterol for VDR.

(iii) Quantitative Real-Time PCR

Cell lines or human hepatocytes were treated with chemicals for 24-48 hours before RNA was extracted and purified by using the Maxwell 16LEV simplyRNA tissue kit (Promega). Then, cDNA was prepared from 2 µg of RNA, and diluted cDNA was used to perform quantitative RT-PCR assays by using TaqMan probes (ABI; 7500 Thermocycler) with 18S as the internal standard.

d. Mammalian Two-Hybrid Assay

The pACT-hCAR1, pBIND-coregulator peptide and pG5-luc were cotransfected into HEK293T cells. $Renilla$ luciferase is constitutively expressed from the pBIND plasmids. The Dual-Glo Luciferase Assay (Promega) was used to measure pG5-luc luciferase activity. The relative luciferase activity was determined by normalizing firefly luciferase activity with $Renilla$ luciferase activity.

e. TR-FRET Coactivator Recruitment Assay

The effect of putative CAR ligands on the recruitment or repression of PGC-1α binding to hCAR was evaluated by using a LanthaScreen TR-FRET assay according to the manufacturer's instructions. Briefly, GST-hCAR-LBD (5 nM) and a mixture of Tb-anti-GST antibody/Fl-PGC-1α peptide (5 nM/125 nM) was added to each well containing titrations of test compounds or DMSO solvent control. The final chemical concentrations were 70 µM to 3.5 nM (1-to-3 dilutions for 10 concentration levels). DMSO and clotrimazole (42 µM) were used as negative (0% inhibition) and positive (100% inhibition) controls, respectively. The final DMSO concentration was 0.7% in all assay wells. Assay plates were then briefly centrifuged and incubated at room temperature for 1 h, and TR-FRET emissions at 490 and 520 nm were measured following a 340-nm excitation. Emission signals collected on a PHERAStar plate reader (BMG Labtech, Durham, N.C.) were used to calculate the 520:490 TR-FRET ratio and normalized to positive and negative controls to derive individual % Inhibition values. The % Inhibition values were then plotted for individual chemicals. When applicable, the graphic software GraphPad Prism 5.04 (GraphPad Software, La Jolla, Calif., USA) was used to fit the data into a one-site competitive-binding equation to derive $IC_{50}$ values.

Alternatively, in black 384-well low-volume assay plates, titrations of chemicals (final concentrations in assay: clotrimazole, 1-to-3 dilutions from 42 µM to 0.71 nM for 11 concentration levels; other compounds, 1-to-3 dilutions from 70 µM to 1.18 nM for 11 concentration levels; DMSO, 0.7%) were mixed with fluorescein-PGC1α coactivator peptide (125 nM), GST-hCAR-LBD (5 nM), and Tb-anti-GST antibody (5 nM) in TR-FRET coregulator buffer G supplemented with 5 mM DTT at 20 µl per well. In addition, DMSO (final concentration: 0.7%) and clotrimazole (final concentration: 42 µM with 0.7% DMSO) were included in each plate and served as negative control (0% Inhibition) and positive control (100% Inhibition), respectively. The assay plates were then briefly spun down and incubated for 1 hour at room temperature (25° C.). The TR-FRET signals for individual wells were collected by using a PHERAstar FS plate reader (BMG Labtech; Durham, N.C., USA) with a 340-nm excitation filter, 100-µs delay time, and 200-µs integration time to measure the fluorescence emission ratio (10,000×520 nm/490 nm). The data were then normalized to positive control (42 µM clotrimazole, 100% inhibition) and negative control (DMSO, 0% inhibition) values by using Equation 1 to derive the % Inhibition for individual chemicals at respective concentrations.

$$\%\ \text{inhibition} = 100\% - 100\% \times \frac{(signal_{Chemical} - Signal_{42\ uM\ clotrimazole})}{(Signal_{DMSO} - Signal_{42\ uM\ clotrimazole})} \quad (1)$$

Where applicable, the data were fit into a sigmoidal dose-response equation to derive $IC_{50}$ values by using the graphic software GraphPad Prism 5.04 (GraphPad Software, La Jolla, Calif., USA).

f. Immunofluorescence

U2OS cells were transiently transfected to express FLAG-hCAR1. After 24 h, cells were treated with DMSO (control), 1 μM CITCO, 5 μM CINPA1, 1 μM CITCO+5 μM CINPA1 or 5 μM PK11195. Cells were fixed by using a 4% paraformaldehyde solution (Sigma), permeabilized by using 0.5% Triton X-100 in PBS, and incubated with FLAG-antibody overnight at 4° C. Cells were washed three times with PBS following each step. Secondary antibody labeled with Alexa Fluor® 555 dye was used to visualize FLAG-tagged hCAR1 (red) using a NikonC 1Si microscope. Nuclei were stained with DAPI (blue).

g. Chromatin Immunoprecipitation

ChIP was performed as described previously (Cherian, M. T., et al. (2012) *J. Biol. Chem.* 287, 23368-23380). Briefly, human hepatocytes in 6-well plates were maintained for 3-4 days in Williams E medium containing Primary Hepatocyte Maintenance Supplement (Life Technologies), with daily media changes. Nine wells were used for each treatment group. Hepatocytes in FIG. 8 were treated overnight with DMSO, 1 μM CITCO, 5 μM CINPA1, or 5 μM PK11195. The HepG2-hCAR1 stable cells in FIG. 9 were treated with DMSO, 1 μM CITCO, 5 μM CINPA1, or 1 μM CITCO+5 μM CINPA1 for 3 h. In FIG. 9, the hepatocytes from donor 7 were treated with DMSO, 0.1 μM CITCO, 1 μM CINPA1, or 0.1 μM CITCO+1 μM CINPA1 for 45 min. Proteins were cross-linked with 1% formaldehyde for 10 min. Cell extracts were digested for 10 min with 50 units of micrococcal nuclease (New England Biolabs) at 37° C. and further sonicated to yield sheared DNA fragments having an average length of 200-1000 base pairs. The sonicated samples were pelleted by centrifugation, and the supernatant was diluted 3- to 5-fold with ChIP dilution buffer (0.01% SDS, 1.1% Triton X-100, 1.2 mM EDTA, 16.7 mM Tris-HCl, pH 8.1, 167 mM NaCl, and protease inhibitor cocktail). Then, 100 L of diluted supernatant was reserved as input (10%) for each treatment. The samples were pre-cleared with protein G-Sepharose 4 Fast Flow (GE Healthcare) in ChIP dilution buffer (1:1) pre-blocked with sheared herring sperm DNA (200 ag/mL) and BSA (500 ag/mL; Roche). The samples were then divided, and the remaining proteins were incubated with either anti-CAR (Clone N4111, R&D Systems), anti-RNA polymerase II (clone CTD4H8, Millipore), or control mouse IgG overnight at 4° C. The antibody-protein-DNA complex was precipitated by incubating the samples with Protein G-Sepharose beads for 2 h at 4° C. The protein-DNA complex was washed and eluted from the beads with elution buffer (1% SDS, 0.1 μM NaHCO3). Cross-links were reversed, and DNA was eluted from the protein-DNA complexes by adding 200 mM NaCl and incubating overnight at 65° C. Protein was digested by incubation with proteinase K at 45° C. for 2 h. DNA was recovered and purified. Quantitative RT-PCR assays were performed to determine the change in CAR occupancy at various sites of CAR binding. The double-negative controls were a nonspecific antibody (normal mouse IgG) and primers coding for intergenic regions that do not bind CAR. Thermal cycling conditions were 95° C. for 10 min followed by 40-45 cycles of 25 s at 95° C., 30 s at 60° C., and 30 s at 72° C. The primers used are shown below in Table 2.

TABLE 2

| Primer | Sequence | SEQ. ID NO. |
|---|---|---|
| CYP2B6-PBREM forward | 5'-AGG CCC TTG GTT CAG GAA AG-3' | 5 |

TABLE 2-continued

| Primer | Sequence | SEQ. ID NO. |
|---|---|---|
| CYP2B6-PBREM reverse | 5'-CTG CCT GTC TCA TCC TAC GC-3' | 6 |
| CYP2B6-XREM (dNR3) forward | 5'-ATT GCA CAA CAC AGC AGG AG-3' | 7 |
| CYP2B6-XREM reverse | 5'-CAA CCC ACA CTT TCC TGA CC-3' | 8 |
| CAR-free region forward | 5'-CAG CTG GAG GGG TCA TCA AA-3' | 9 |
| CAR-free region reverse primer | 5'-GCT AGC AGA GAC CCC TTC AC-3'; | 10 |
| CYP3A4-XREM forward | 5'-AAG GTC ATA AAG CCC AGT TTG T-3' | 11 |
| CYP3A4-XREM reverse | 5'-CAC CTG GGG TCA ACA CAG GAC-3' | 12 |
| GAPDH promoter (ChIP positive control with RPol) forward | 5'-TAC TAG CGG TTT TAC GGG CG-3' | 13 |
| GAPDH promoter (ChIP positive control with RPol) reverse | 5'-TCG AAC AGG AGG AGC AGA GAG CGA-3' | 14 | h. CoAct Binding Inverse Agonist Assay

The effect of putative CAR ligands on the recruitment or repression of PGC-1α binding to hCAR was evaluated by using a LanthaScreen TR-FRET assay according to the manufacturer's instructions. Briefly, GST-hCAR-LBD (5 nM) and a mixture of Tb-anti-GST antibody/Fl-PGC-1α peptide (5 nM/125 nM) was added to each well containing titrations of test compounds or DMSO solvent control. The final chemical concentrations were 70 μM to 3.5 nM (1-to-3 dilutions for 10 concentration levels). DMSO and clotrimazole (42 μM) were used as negative (0% inhibition) and positive (100% inhibition) controls, respectively. The final DMSO concentration was 0.7% in all assay wells. Assay plates were then briefly centrifuged and incubated at room temperature for 1 h, and TR-FRET emissions at 490 and 520 nm were measured following a 340-nm excitation. Emission signals collected on a PHERAStar plate reader (BMG Labtech, Durham, N.C.) were used to calculate the 520:490 TR-FRET ratio and normalized to positive and negative controls to derive individual % Inhibition values. The % Inhibition values were then plotted for individual chemicals. When applicable, the graphic software GraphPad Prism 5.04 (GraphPad Software, La Jolla, Calif., USA) was used to fit the data into a one-site competitive-binding equation to derive IC50 values.

2. General Chemistry Procedures

The reactions, purities, or identities of final compounds were monitored or determined by thin layer chromatography (TLC) or on a Waters Acquity UPLC MS system with a C18 column in a 2 min gradient ($H_2O$+0.1% formic acid→Acetonitrile+0.1% formic acid) and detectors of PDA (215-400 nm), ELSD, and Acquity SQD ESI Positive MS. The purifications of reaction products were performed on a Dionex APS 3000 dual purification/analytical LC/PDA/MS system with a C18 column in a 15 min gradient ($H_2O$ with 0.05% $NH_3.H_2O$→Acetonitrile) and ESI Positive MS. All $^1$H NMR spectra were recorded on a Bruker AVANCE III (400 MHz). The chemical shift values are expressed in ppm (parts per million) relative to tetramethylsilane as the internal standard. Coupling constants (J) are reported in hertz (Hz).

a. Preparation of CINPA1 (Compound 1)

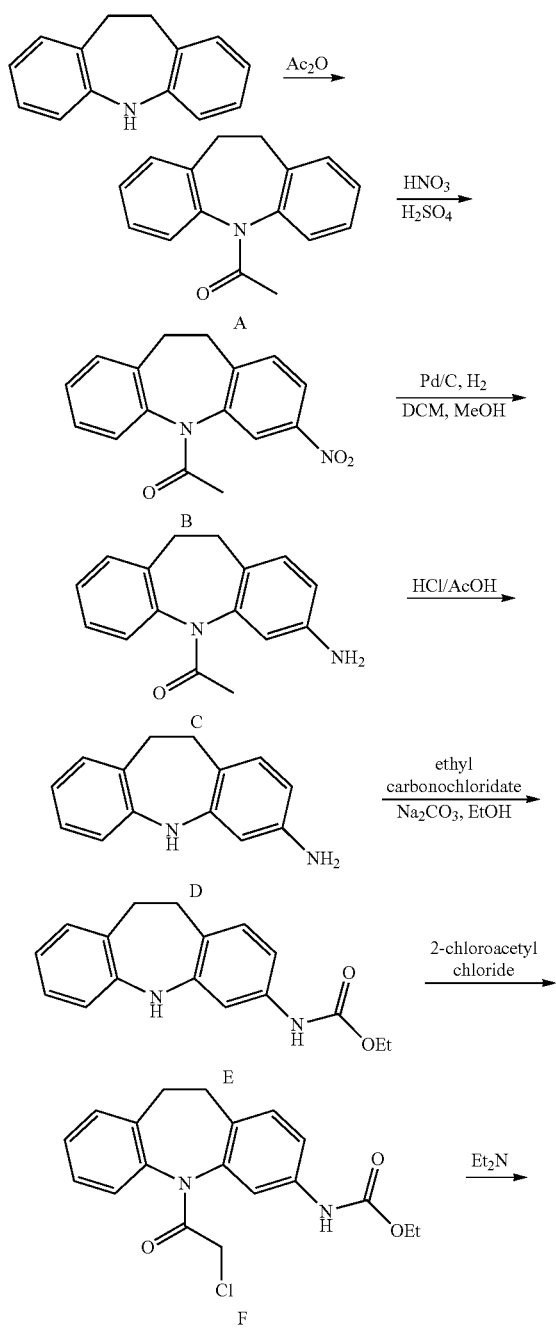

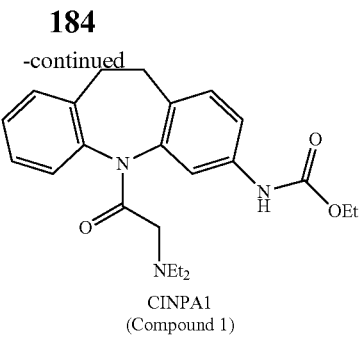

CINPA1
(Compound 1)

(i) Synthesis of 1-(10,11-dihydro-5H-dibenzo[b,f] azepin-5-yl)ethan-1-one (Compound A)

A mixture of compound 10,11-dihydro-5H-dibenzo[b,f] azepine (22.5 g, 0.11 mol) and $Ac_2O$ (26 g, 0.26 mol) in AcOH (32 g, 0.55 mol) in a three-necked flask was heated at 110° C. for 2 h. TLC showed no starting material at this time; the reaction was quenched by water, washed with aq. $Na_2CO_3$ and extracted with ethyl acetate. The ethyl acetate layers were concentrated under vacuum to give the crude product. The crude product then was purified by silica gel chromatography (Petroleum ether/ethyl acetate=10/1) to give compound 2 (23 g, 84%) as a white solid. LCMS: MS+1=238.2.

(ii) Synthesis of 1-(3-nitro-10,11-dihydro-5H-dibenzo[b,f]azepin-5-yl)ethan-1-one (Compound B)

Compound A (23 g, 0.097 mol) in $H_2SO_4$ (150 mL) was added dropwise with a solution of $HNO_3$ (3.67 g, 0.058 mol) in $H_2SO_4$ (50 mL) with stirring at 0° C. for 30 min. TLC showed starting material: product=1:1. The reaction mixture was poured into ice water and extracted with ethyl acetate. The ethyl acetate layer was concentrated under vacuum to give the crude product and the crude product was purified by silica gel chromatography (Petroleum ether/ethyl acetate=8/1) to compound B (7.8 g, 46%) as a white solid. LCMS: MS+1=283.0.

(iii) Synthesis of 1-(3-amino-10,11-dihydro-5H-dibenzo[b,f]azepin-5-yl)ethan-1-one (Compound C)

A mixture of compound B (7.8 g, 0.028 mol) and Pd/C (3.9 g) in MeOH (150 mL) was stirred at room temperature under $H_2$ for 2 h. LCMS showed the reaction was completed. The reaction solution was filtered and concentrated under vacuum to give the crude product. The crude product was triturated with ethyl acetate to give compound C (5.2 g, 77%) as a white solid. LCMS: MS+1=253.1

(iv) Synthesis of 10,11-dihydro-5H-dibenzo[b,f]azepin-3-amine (Compound D)

Compound C (5.2 g, 0.021 mol) in a solution of HCl (100 mL, 12 mol/L) and AcOH (100 mL) in a 250 mL flask was stirred at reflux for overnight. TLC showed the reaction was completed. The reaction solution was concentrated under reduced pressure and basified with $Na_2CO_3$ aqueous solution and extracted with ethyl acetate. The ethyl acetate phase was concentrated under vacuum to give the crude product. The crude product was purified by silica gel chromatography (Petroleum ether/ethyl acetate=5/1) to give compound D (2.2 g, 63%) as a brown solid. LCMS: MS+1=211.1

(v) Synthesis of ethyl (10,11-dihydro-5H-dibenzo[b,f]azepin-3-yl)carbamate (Compound E)

Compound D (2.2 g, 0.01 mol) in EtOH (20 mL) at a temperature of 5 to 7° C. was added ethyl carbonochloridate (8.94 g, 0.08 mol) in two portions followed by the addition of a solution of Na$_2$CO$_3$ (0.67 g) in 4 mL water. The resultant mixture was stirred for 2 h. TLC showed the reaction was completed. The reaction solution was poured into water and filtered to give compound E (2.6 g, 90%). LCMS: MS+1=283.1. $^1$H NMR (400 MHz, DMSO-d$_6$) ppm 1.24 (t, J=7.03 Hz, 3 H) 2.85-2.94 (m, 4 H) 4.10 (q, J=7.03 Hz, 2 H) 6.58-6.70 (m, 2 H) 6.85 (d, J=8.28 Hz, 1 H) 6.94-7.03 (m, 3 H) 7.21 (s, 1 H) 8.29 (s, 1 H) 9.40 (s, 1 H).

(vi) Synthesis of ethyl (5-(2-chloroacetyl)-10,11-dihydro-5H-dibenzo[b,f]azepin-3-yl)carbamate (Compound F)

A mixture of compound E (2.2 g, 7.8 mmol) and 2-chloroacetyl chloride (1.3 g, 11.5 mmol) in anhydrous toluene (20 mL) was stirred at reflux for 1 h, at which point the TLC showed the reaction was completed. The mixture was concentrated under vacuum to give compound F (2.8 g, 100%) as a gray solid. LCMS: MS+1=359.1. $^1$H NMR (400 MHz, DMSO-d$_6$) ppm 1.24 (t, J=7.03 Hz, 3 H) 2.65-2.86 (m, 2 H) 3.13-3.31 (m, 2 H) 4.07-4.22 (m, 3 H) 4.24-4.35 (m, 1 H) 7.12 (d, J=7.78 Hz, 1 H) 7.19-7.37 (m, 5 H) 7.48-7.67 (m, 1 H) 9.67 (d, J=14.56 Hz, 1 H).

(vii) Synthesis of ethyl (5-(diethylglycyl)-10,11-dihydro-5H-dibenzo[b,f]azepin-3-yl)carbamate (Compound 1)

Compound F (2.8 g, 7.8 mmol) and Et$_2$NH (1.02 g, 13 mmol) in anhydrous toluene (20 mL) was stirred at reflux for 4 h. TLC showed the reaction was incomplete (starting material: product=3:7). The reaction mixture was adjusted to pH 3 with aqueous HCl (1 mol/L) and washed with ethyl acetate. The aqueous phase was basified to pH 10 with Na$_2$CO$_3$ and extracted with ethyl acetate. The ethyl acetate layer was dries by anhydrous Na$_2$SO$_4$ and concentrated to give the crude product. The crude product was purified by preparative HPLC to give 1 (2.0 g, 72%) as a white solid. LCMS: MS+1=396.2. $^1$H NMR (400 MHz, DMSO-d6) δ (ppm) 0.80 (t, J=6.40 Hz, 6 H) 1.24 (t, J=7.15 Hz, 3 H) 2.45 (br. s., 4 H) 2.66-2.84 (m, 2 H) 3.11-3.31 (m, 4 H) 4.11 (q, J=7.03 Hz, 2 H) 7.08-7.31 (m, 5 H) 7.39-7.56 (m, 2 H) 9.61 (d, J=15.81 Hz, 1 H).

b. Synthesis of Compounds 2 and 3

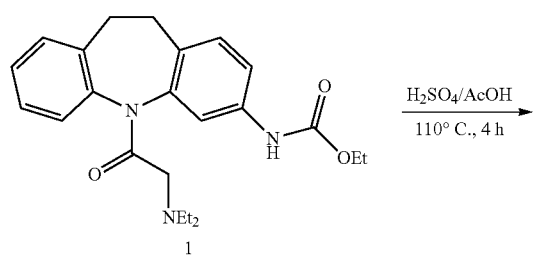

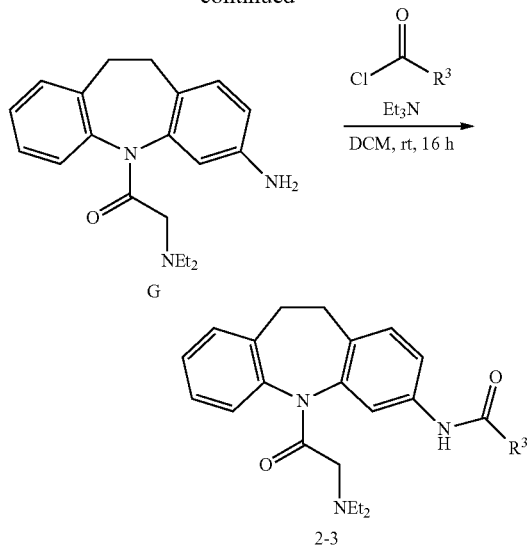

(i) Preparation of 1-(3-amino-10,11-dihydro-5H-dibenzo[b,f]azepin-5-yl)-2-(diethylamino)ethan-1-one (Compound G)

Compound 1 (2.5 g, 6.32 mmol) in H$_2$SO$_4$/AcOH (40 mL) was stirred at 120° C. for 4 h. LCMS showed starting material consumed. The mixture was basified to pH 7 with Na$_2$CO$_3$ aqueous solution and extracted with ethyl acetate (50 mL×3). The organic layer was dried by anhydrous Na$_2$SO$_4$ and concentrated to give compound G (2.0 g, 97.8%) as a light yellow oil. LCMS: MS+1=324.2. $^1$H NMR (400 MHz, DMSO-d$_6$) ppm 7.17-7.36 (m, 4 H), 6.76-6.99 (m, 1 H), 6.36-6.59 (m, 2 H), 4.92-5.15 (m, 2 H), 3.02-3.22 (m, 4 H), 2.51-2.81 (m, 4 H), 2.44 (br. s., 2 H), 0.75-0.87 (m, 6 H).

(ii) Preparation of N-(5-(diethylglycyl)-10,11-dihydro-5H-dibenzo[b,f]azepin-3-yl)butyramide (2)

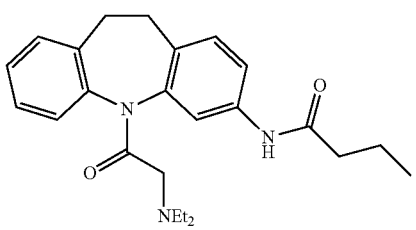

A mixture of G (180.00 mg, 556.53 μmol), butyryl chloride (118.60 mg, 1.11 mmol) and Et$_3$N (140.79 mg, 1.39 mmol) in dichloromethane (3 mL) was stirred at 10-35° C. for 16 h. LCMS showed all starting material consumed. The mixture was concentrated to give a residue. The residue was purified by preparative HPLC to give 2 (95.2 mg, 242 μmol, 43.4%). LCMS: MS+1=394.2. $^1$H NMR (300 MHz, DMSO-d$_6$) (ppm) 9.55 (br. s., 1H), 8.15 (s, 1H), 7.61 (d, J=1.88 Hz, 1H), 7.40 (dd, J=2.07, 8.29 Hz, 1H), 7.18-7.36 (m, 4H), 7.14 (d, J=8.29 Hz, 1H), 3.21 (d, J=1.13 Hz, 4H), 2.72-2.84 (m, 2H), 2.52-2.59 (m, 4H), 2.28 (t, J=7.25 Hz, 2H), 1.58-1.70 (m, 2H), 0.94 (t, J=7.44 Hz, 3H), 0.81-0.89 (m, 6H).

(iii) Preparation of N-(5-(diethylglycyl)-10,11-dihydro-5H-dibenzo[b,f]azepin-3-yl)isobutyramide (3)

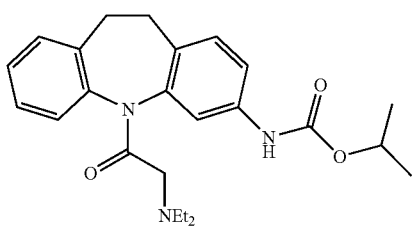

A mixture of G (180.00 mg, 556.53 μmol), isopropyl chloroformate (118.60 mg, 1.11 mmol) and Et₃N (140.79 mg, 1.39 mmol) in dichloromethane (3 mL) was stirred at 10-35° C. for 16 h. LCMS showed all starting material consumed. The mixture was concentrated to give a residue. The residue was purified by preparative HPLC to give 3 (61.1 mg, 149 mol, 26.8%). LCMS: MS+1=410.1. ¹H NMR (300 MHz, DMSO-d₆) (ppm) 9.16 (br. s., 1H), 8.15 (br. s., 1H), 7.49 (s, 1H), 7.17-7.35 (m, 5H), 7.12 (d, J=8.48 Hz, 1H), 4.91 (td, J=6.22, 12.43 Hz, 1H), 3.18-3.27 (m, 4H), 2.71-2.80 (m, 2H), 2.51-2.58 (m, 4H), 1.27 (dd, J=1.41, 6.31 Hz, 6H), 0.85 (t, J=7.16 Hz, 6H).

c. Synthesis of N-(5-(diethylglycyl)-10,11-dihydro-5H-dibenzo[b,f]azepin-3-yl)pivalamide (4)

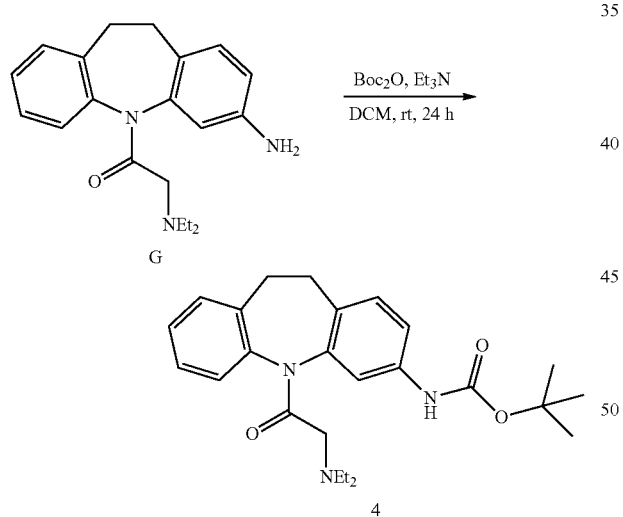

A mixture of G (100.00 mg, 309.19 μmol), Boc₂O (134.96 mg, 618.37 μmol) and Et₃N (78.22 mg, 772.96 μmol) in dichloromethane (2 mL) was stirred at 20-25° C. for 24 hr. LCMS showed all starting material consumed. The mixture was concentrated to give a residue. The residue was purified by preparative HPLC to give 4 (50.00 mg, 118.05 μmol, 38.18%) as a white solid. LCMS: MS+1=424.2. ¹H NMR (300 MHz, DMSO-d₆) (ppm) 8.95 (br. s., 1H), 8.16 (br. s., 1H), 7.49 (d, J=1.70 Hz, 1H), 7.16-7.36 (m, 5H), 7.11 (d, J=8.48 Hz, 1H), 3.20 (s, 4H), 2.71-2.84 (m, 2H), 2.51-2.58 (m, 4H), 1.49 (s, 9H), 0.86 (t, J=7.06 Hz, 6H).

d. Synthesis of Compounds 5-8

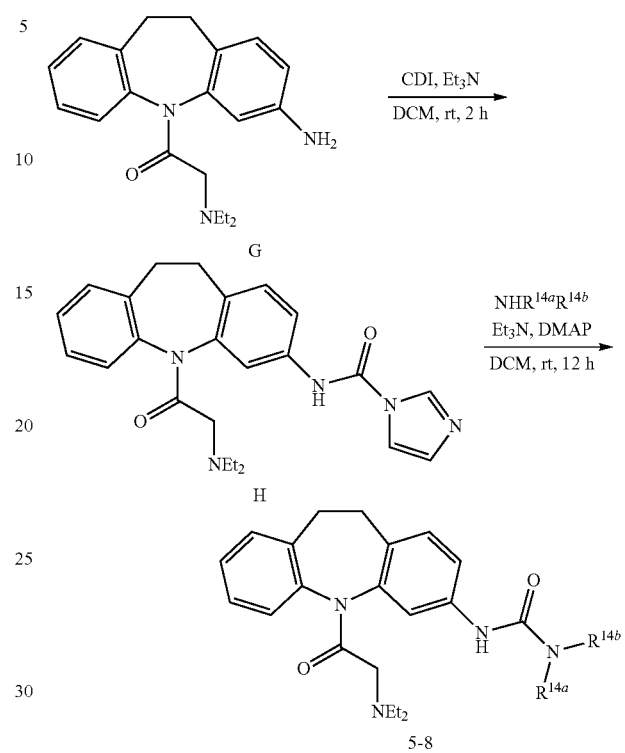

(i) Preparation of N-(5-(diethylglycyl)-10,11-dihydro-5H-dibenzo[b,f]azepin-3-yl)-1h-imidazole-1-carboxamide (Compound H)

A mixture of G (500.00 mg, 1.55 mmol), CDI (250.6 mg, 1.55 mmol) and Et₃N (312.86 mg, 3.09 mmol) in dichloromethane (5 mL) was stirred at 20-25° C. for 2 h. LCMS showed all starting material consumed. The mixture was used directly for next step without further purification.

(ii) Preparation of 1-(5-(diethylglycyl)-10,11-dihydro-5H-dibenzo[b,f]azepin-3-yl)-3-ethylurea (5)

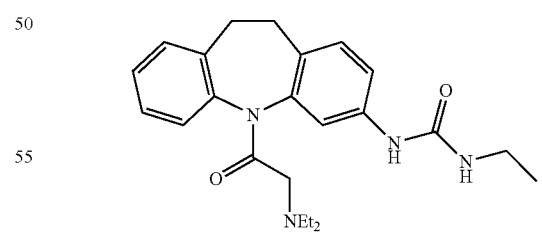

A mixture of ethylamine (574.84 μmol), H (120.00 mg, 287.42 μmol), DMAP (17.56 mg, 143.71 μmol) and Et₃N (29.08 mg, 287.42 μmol) in dichloromethane (2 mL) was stirred at 20-25° C. for 12 hr. LCMS showed all starting material consumed. The mixture was concentrated to give a residue. The residue was purified by preparative HPLC to give 5 (82.3 mg, 208 μmol, 72.6%) as a white solid. LCMS: MS+1=395.1. ¹H NMR (400 MHz, DMSO-d₆) δ (ppm) 8.22

(br. s., 1H), 8.14 (s, 1H), 7.44 (br. s., 1H), 7.13-7.36 (m, 5H), 7.06 (d, J=8.41 Hz, 1H), 5.95 (br. s., 1H), 3.07-3.18 (m, 6H), 2.69-2.80 (m, 2H), 2.50-2.58 (m, 4H), 0.99-1.14 (m, 3H), 0.77-0.88 (m, 6H).

(iii) Preparation of 1-(5-(diethylglycyl)-10,11-di-hydro-5H-dibenzo[b,f]azepin-3-yl)-3-isopropylurea
(6)

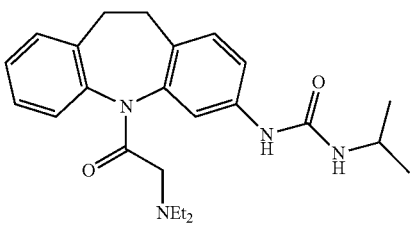

A mixture of iso-propylamine (574.84 μmol), H (120.00 mg, 287.42 μmol), DMAP (17.56 mg, 143.71 μmol) and Et₃N (29.08 mg, 287.42 μmol) in dichloromethane (2 mL) was stirred at 20-25° C. for 12 hr. LCMS showed all starting material consumed. The mixture was concentrated to give a residue. The residue was purified by preparative HPLC to give 6 (52.7 mg, 128 μmol, 44.9%) as a white solid. LCMS: MS+1=409.1. ¹H NMR (300 MHz, DMSO-d₆) δ (ppm) 8.07 (s, 1H), 7.44 (d, J=1.88 Hz, 1H), 7.12-7.35 (m, 5H), 7.03-7.09 (m, 1H), 5.77 (d, J=7.35 Hz, 1H), 3.78 (qd, J=6.59, 13.59 Hz, 1H), 3.16-3.34 (m, 4H), 2.69-2.82 (m, 2H), 2.51-2.56 (m, 4H), 1.04-1.19 (m, 6H), 0.86 (t, J=7.06 Hz, 6H).

(iv) Preparation of 1-(tert-butyl)-3-(5-(diethylgly-cyl)-10,11-dihydro-5H-dibenzo[b,f]azepin-3-yl)urea
(7)

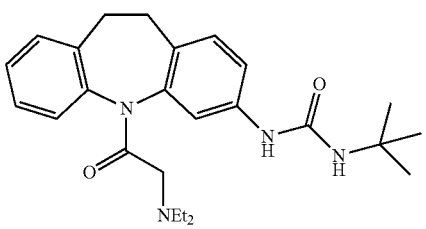

A mixture of tert-butylamine (574.84 μmol), H (120.00 mg, 287.42 μmol), DMAP (17.56 mg, 143.71 μmol) and Et₃N (29.08 mg, 287.42 μmol) in dichloromethane (2 mL) was stirred at 20-25° C. for 12 hr. LCMS showed all starting material consumed. The mixture was concentrated to give a residue. The residue was purified by preparative HPLC to give 7(71.7 mg, 170 μmol, 59.2%) as a white solid. LCMS: MS+1=423.2. ¹H NMR (400 MHz, DMSO-d₆) δ (ppm) 8.17 (s, 1H), 7.98 (br. s., 1H), 7.49 (s, 1H), 7.17-7.39 (m, 5H), 7.09 (d, J=8.16 Hz, 1H), 3.25-3.42 (m, 8H), 2.68-2.82 (m, 2H), 2.52-2.57 (m, 4H), 0.99-1.31 (m, 6H), 0.75-0.93 (m, 6H).

(v) Preparation of 3-(5-(diethylglycyl)-10,11-di-hydro-5H-dibenzo[b,f]azepin-3-yl)-1,1-diethylurea
(8)

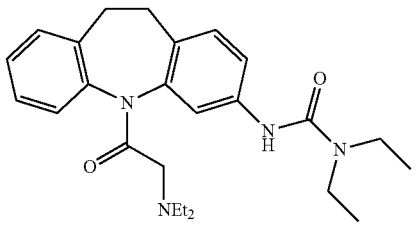

A mixture of diethylamine (574.84 μmol), H (120.00 mg, 287.42 μmol), DMAP (17.56 mg, 143.71 μmol) and Et₃N (29.08 mg, 287.42 μmol) in dichloromethane (2 mL) was stirred at 20-25° C. for 12 hr. LCMS showed all starting material consumed. The mixture was concentrated to give a residue. The residue was purified by preparative HPLC to give 8 (102.7 mg, 243 μmol, 84.8%) as a white solid. LCMS: MS+1=423.2. ¹H NMR (400 MHz, DMSO-d₆) δ (ppm) 8.05-8.23 (m, 2H), 7.44 (br. s., 1H), 7.32 (br. s., 1H), 7.16-7.27 (m, 3H), 7.00-7.12 (m, 2H), 5.81 (br. s., 1H), 3.26-3.37 (m, 4H), 2.67-2.80 (m, 2H), 2.51-2.56 (m, 4H), 1.29 (s, 9H), 0.77-0.90 (m, 6H).

e. Synthesis of Compound 9

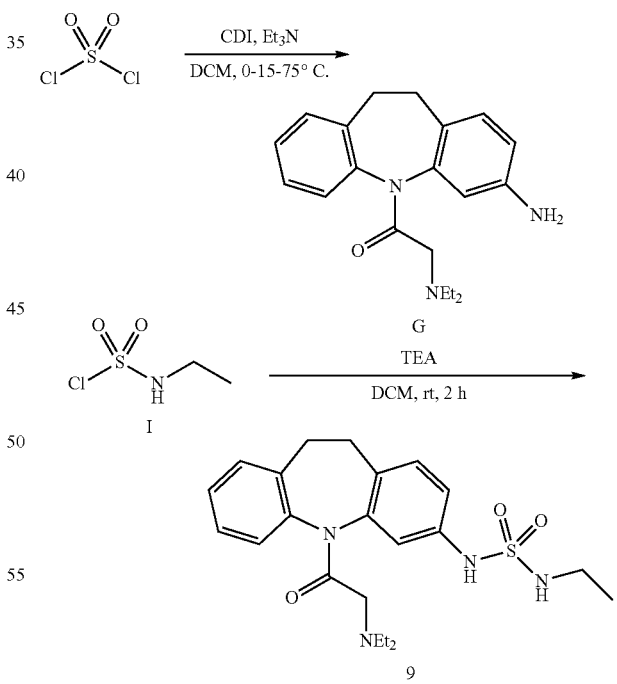

(i) Preparation of Ethylsulfamoyl Chloride
(Compound I)

Ethanamine (10.00 g, 221.83 mmol) in dichloromethane (30 mL) was added dropwise to a suspension of sulfuryl chloride (100.00 g, 740.91 mmol) at 0-10° C. After addition, the mixture was heated to 75° C. for 15 hr, and then cooled to 20° C. The mixture was concentrated to dryness to give compound I (50 g, crude) which was freshly used directly for the next step.

(ii) Preparation of 2-(diethylamino)-1-{14-[(ethyl-sulfamoyl)amino]tricyclo[9.4.0.0³·⁸]pentadeca-1(11), 3,5,7,12,14-hexaen-2-yl}ethan-1-one (9)

To a mixture of compound G (200.00 mg, 618.37µmol) in dichloromethane (6 mL) was added compound I (532.7 mg, 3.71 mmol), followed by dropwise addition of Et₃N (18.77 mg, 185.52 µmol). The mixture was stirred at 15-25° C. for 1 hr; at this time LCMS showed all starting material consumed. The mixture was concentrated to dryness, purified by preparative HPLC to give LTC-108 (76.6 mg, 178 µmol, 28.8%) as a light yellow solid. LCMS: MS+1=431.1. ¹H NMR (400 MHz, DMSO-d₆) δ (ppm) 9.62 (br. s., 1H), 6.94-7.57 (m, 8H), 3.03-3.28 (m, 4H), 2.64-2.93 (m, 4H), 2.44 (br. s., 4H), 0.96 (t, J=7.22 Hz, 3H), 0.79 (br. s., 6H).

f. Synthesis of 2-(diethylamino)-1-(3-((5-methyl-1, 3,4-oxadiazol-2-yl)amino)-10,11-dihydro-5H-dibenzo[b,f]azepin-5-yl)ethan-1-one (10)

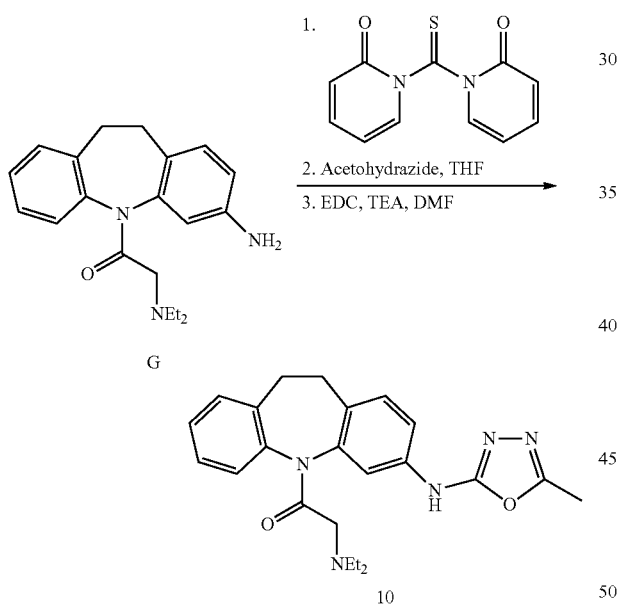

To a solution of compound G (320 mg, 989.39 µmol) in dichloromethane (1 mL) at 0° C. was added 1-(2-oxopyridine-1-carbothioyl)pyridin-2-one (344.70 mg, 1.48 mmol) in dichloromethane (0.5 mL) dropwise. The mixture was stirred at 20° C. for 16 hours. The mixture was concentrated and purified with silica gel chromatography (dichloromethane: MeOH=30:1). Acetohydrazide (146.59 mg, 1.98 mmol) in THF (1 mL) was added. The mixture was stirred at 20° C. for 16 hours and then concentrated; EDC (307.19 mg, 1.98 mmol), TEA (200.23 mg, 1.98 mmol) and DMF (1 mL) were added. The mixture was stirred at 20° C. for 16 hours. The residue was further purified by preparative HPLC to give 10 (39.8 mg, 98 µmol, 9.9%) as a yellow solid. LCMS: MS+1=406.3. ¹H NMR (400 MHz, DMSO-d₆) δ (ppm) 10.28 (br. s., 1H), 9.68 (br. s., 1H), 7.80-7.20 (m, 7H), 4.32 (br. s., 1H), 3.94-3.47 (m, 2H), 3.26 (br. s., 5H), 2.92-2.75 (m, 2H), 2.40 (s, 3H), 1.24 (br. s., 6H).

g. Synthesis of Compounds 11, 12, 20, 21, and 24

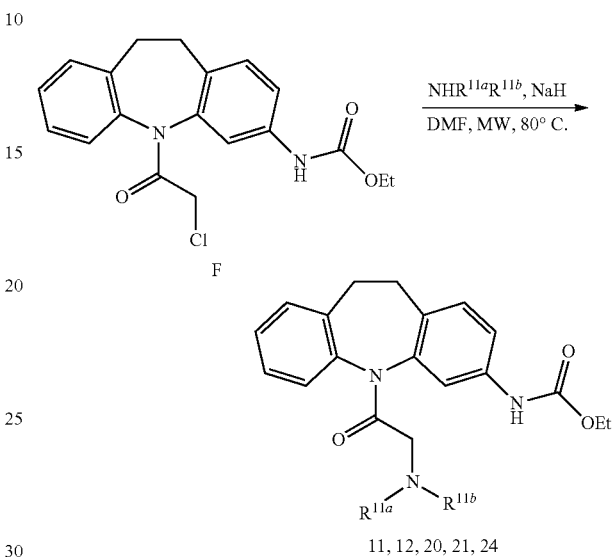

(i) Preparation of ethyl (5-(dipropylglycyl)-10,11-dihydro-5H-dibenzo[b,f]azepin-3-yl)carbamate (11)

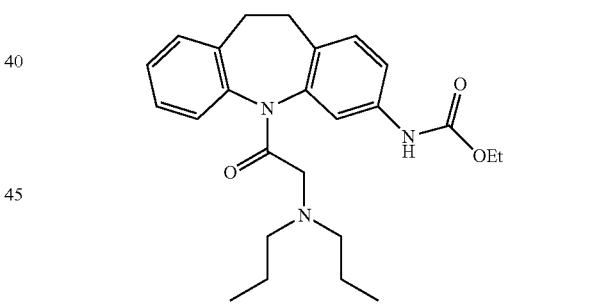

Dipropylamine (668.86 µmol) in DMF (2 mL) was added to Compound F (200 mg, 550 µmol) in DMF (1 mL). The reaction vessel was sealed and heated in the microwave to 80° C. for 0.5 h. LCMS showed all DP. The mixture was extracted with ethyl acetate (20 mL×2) and washed with brine (10 mL×2). The organic layer was dried with anhydrous Na₂SO₄ and concentrated to give a residue. The residue was purified by preparative HPLC to give 11 (115.9 mg, 274 µmol, 49.8%). LCMS: MS+1=424.2. ¹H NMR (400 MHz, DMSO-d₆) δ (ppm) 9.33 (br. s., 1 H), 8.15 (s, 1 H), 7.48 (s, 1 H), 7.18-7.33 (m, 5 H), 7.14 (d, J=8.28 Hz, 1 H), 4.14 (q, J=7.15 Hz, 2 H), 3.22 (br. s., 2 H), 2.73-2.80 (m, 2 H), 2.46 (t, J=7.28 Hz, 4 H), 1.21-1.36 (m, 7 H), 0.73-0.85 (m, 6 H).

193

(ii) Preparation of ethyl (5-(diisopropylglycyl)-10,11-dihydro-5H-dibenzo[b,f]azepin-3-yl)carbamate (12)

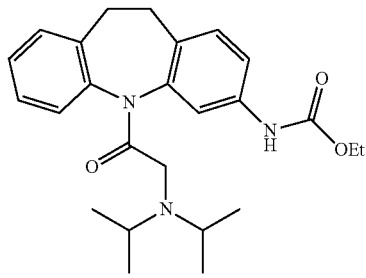 [SMILES: CCOC(=O)Nc1ccc2c(c1)N(C(=O)CN(C(C)C)C(C)C)c1ccccc1CC2]

Diisopropylamine (668.86 μmol) in DMF (2 mL) was added to Compound F (200 mg, 550 μmol) in DMF (1 mL). The reaction vessel was sealed and heated in the microwave to 80° C. for 0.5 h. LCMS showed all DP. The mixture was extracted with ethyl acetate (20 mL×2) and washed with brine (10 mL×2). The organic layer was dried with anhydrous $Na_2SO_4$ and concentrated to give a residue. The residue was purified by preparative HPLC to give 12 (45.2 mg, 106 μmol, 19.4%). LCMS: MS+1=424.2. $^1$H NMR (400 MHz, DMSO-$d_6$) δ (ppm) 9.31 (br. s., 1H), 8.14 (s, 1H), 7.46-7.53 (m, 1H), 7.17-7.35 (m, 5H), 7.13 (d, J=8.41 Hz, 1H), 4.13 (q, J=7.11 Hz, 2H), 3.21-3.28 (m, 4H), 2.99-3.04 (m, 2H), 2.72-2.80 (m, 2H), 1.25 (t, J=7.03 Hz, 3H), 0.82-1.03 (m, 12H).

(iii) Preparation of ethyl (5-(2-((1s,4s)-7-azabicyclo[2.2.1]heptan-7-yl)acetyl)-10,11-dihydro-5H-dibenzo[b,f]azepin-3-yl)carbamate (20)

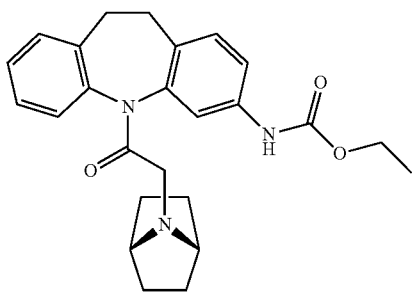 [SMILES: CCOC(=O)Nc1ccc2c(c1)N(C(=O)CN1[C@H]3CC[C@@H]1CC3)c1ccccc1CC2]

7-Azabicyclo[2.2.1]heptane (668.86 μmol) in DMF (2 mL) was added to Compound F (200 mg, 550 μmol) in DMF (1 mL). The reaction vessel was sealed and heated in the microwave to 80° C. for 0.5 h. LCMS showed all DP. The mixture was extracted with ethyl acetate (20 mL×2) and washed with brine (10 mL×2). The organic layer was dried with anhydrous $Na_2SO_4$ and concentrated to give a residue. The residue was purified by preparative HPLC to give 20 (75.7 mg, 180 μmol, 32.8%). LCMS: MS+1=420.1. $^1$H NMR (400 MHz, DMSO-$d_6$) δ (ppm) 9.32 (br. s., 1H), 8.18 (br. s., 1H), 7.49 (s, 1H), 7.17-7.37 (m, 5H), 7.12 (d, J=8.28 Hz, 1H), 4.06-4.18 (m, 2H), 3.20-3.29 (m, 2H), 3.02-3.15 (m, 4H), 2.65-2.83 (m, 2H), 1.44-1.62 (m, 4H), 1.13-1.30 (m, 7H)

194

(iv) Preparation of ethyl (5-(tert-pentylglycyl)-10,11-dihydro-5H-dibenzo[b,f]azepin-3-yl)carbamate (21)

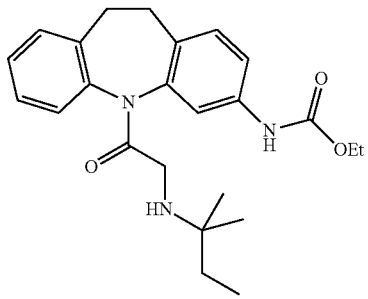 [SMILES: CCOC(=O)Nc1ccc2c(c1)N(C(=O)CNC(C)(C)CC)c1ccccc1CC2]

Tert-Amylamine (668.86 μmol) in DMF (2 mL) was added to 7 (200 mg, 550 μmol) in DMF (1 mL). The reaction vessel was sealed and heated in the microwave to 80° C. for 0.5 h. LCMS showed all DP. The mixture was extracted with ethyl acetate (20 mL×2) and washed with brine (10 mL×2). The organic layer was dried with anhydrous $Na_2SO_4$ and concentrated to give a residue. The residue was purified by preparative HPLC to give 21 (96.3 mg, 235 μmol, 42.8%). LCMS: MS+1=410.1. $^1$H NMR (400 MHz, DMSO-$d_6$) δ (ppm) 9.35 (br. s., 1H), 8.18 (s, 1H), 7.50 (s, 1H), 7.22-7.34 (m, 5H), 7.15 (d, J=8.28 Hz, 1H), 4.10-4.16 (m, 2H), 3.18-3.27 (m, 4H), 2.71-2.81 (m, 2H), 1.20-1.27 (m, 5H), 0.95 (s, 1H), 0.86 (s, 6H), 0.73-0.80 (m, 3H).

(V) Preparation of ethyl (5-(ethylglycyl)-10,11-dihydro-5H-dibenzo[b,f]azepin-3-yl)carbamate (24)

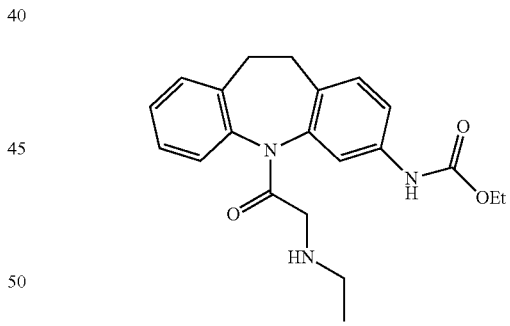

Ethylamine (668.86 mole) in DMF (2 mL) was added to Compound F (200 mg, 550 μmol) in DMF (1 mL). The reaction vessel was sealed and heated in the microwave to 80° C. for 0.5 h. LCMS showed all DP. The mixture was extracted with ethyl acetate (20 mL×2) and washed with brine (10 mL×2). The organic layer was dried with anhydrous $Na_2SO_4$ and concentrated to give a residue. The residue was purified by preparative HPLC to give 24 (104.5 mg, 284 μmol, 51.7%). LCMS: MS+1=368.1. $^1$H NMR (400 MHz, DMSO-$d_6$) δ 9.29 (br. s., 1H), 8.17 (br. s., 1H), 7.48 (s, 1H), 7.18-7.35 (m, 5H), 7.15 (d, J=8.48 Hz, 1H), 4.14 (q, J=6.97 Hz, 2H), 3.20-3.21 (m, 2H), 2.78 (d, J=9.42 Hz, 2H), 2.51-2.59 (m, 4H), 2.09 (s, 1H), 1.25 (t, J=7.06 Hz, 3H), 0.96 (t, J=7.06 Hz, 3H).

h. Synthesis of Compounds 13 and 16-18

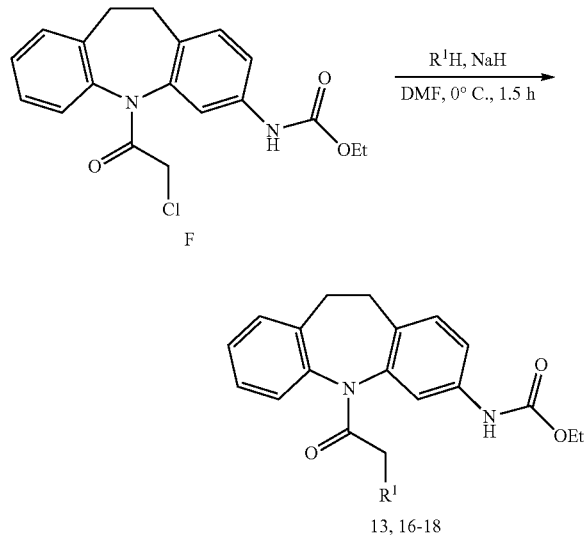

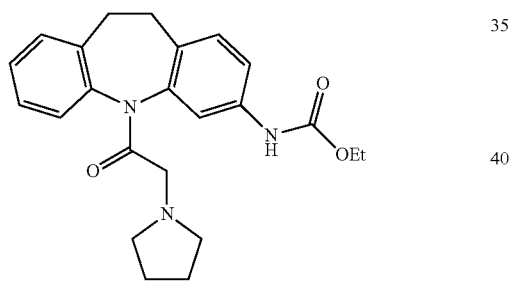

(i) Preparation of ethyl (5-(2-(pyrrolidin-1-yl)acetyl)-10,11-dihydro-5H-dibenzo[b,f]azepin-3-yl) carbamate (13)

NaH (33.44 mg, 1.39 mmol) was added to a solution of pyrrolidine (696.73 μmol) in DMF (2 mL) at 0° C. The mixture was stirred at 0° C. for 0.5 h. Then compound F (250.00 mg, 696.73 μmol) in DMF (1 mL) was added dropwise. The mixture was stirred at 0° C. for 1 h. LCMS showed starting material consumed. The reaction was quenched with NH$_4$Cl aqueous solution and extracted with ethyl acetate (20 mL×3) and washed with brine (20 mL×2). The organic layer was dried with anhydrous Na$_2$SO$_4$ and concentrated to give a residue. The residue was dissolved in MeOH (3 mL) and purified by preparative HPLC to give 13 (42.7 mg, 108 μmol, 15.5%). LCMS: MS+1=394.2. $^1$H NMR (400 MHz, DMSO-d$_6$) δ (ppm) 9.29 (s, 1H), 8.18 (br. s., 1H), 7.49 (d, J=2.13 Hz, 1H), 7.20-7.34 (m, 5H), 7.14 (d, J=8.28 Hz, 1H), 4.14 (q, J=7.03 Hz, 2H), 3.24-3.32 (m, 4H), 2.71-2.81 (m, 2H), 2.46-2.50 (m, 4H), 1.60-1.69 (m, 4H), 1.22-1.31 (m, 3H).

(ii) Preparation of ethyl (5-(2-(1H-pyrrol-1-yl)acetyl)-10,11-dihydro-5H-dibenzo[b,f]azepin-3-yl) carbamate (16)

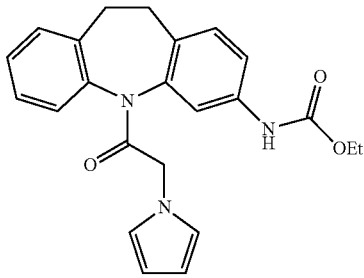 [SMILES: CCOC(=O)Nc1ccc2c(c1)N(C(=O)Cn1cccc1)c1ccccc1CC2]

NaH (33.44 mg, 1.39 mmol) was added to a solution of pyrrole (696.73 μmol) in DMF (2 mL) at 0° C. The mixture was stirred at 0° C. for 0.5 h. Then compound F (250.00 mg, 696.73 μmol) in DMF (1 mL) was added dropwise. The mixture was stirred at 0° C. for 1 h. LCMS showed starting material consumed. The reaction was quenched with NH$_4$Cl aqueous solution and extracted with ethyl acetate (20 mL×3) and washed with brine (20 mL×2). The organic layer was dried with anhydrous Na$_2$SO$_4$ and concentrated to give a residue. The residue was dissolved in MeOH (3 mL) and purified by preparative HPLC to give 16 (81.4 mg, 209 μmol, 30.0%). LCMS: MS+1=390.2. $^1$H NMR (400 MHz, CHCl$_3$) δ (ppm) 7.53 (br. s., 1H), 7.27-7.43 (m, 3H), 6.99-7.22 (m, 3H), 6.62 (d, J=14.43 Hz, 1H), 6.47 (d, J=9.79 Hz, 2H), 6.11 (t, J=1.94 Hz, 2H), 4.47-4.72 (m, 2H), 4.16-4.29 (m, 2H), 3.16 (br. s., 2H), 2.73 (d, J=9.41 Hz, 2H), 1.27-1.37 (m, 3H).

(iii) Preparation of ethyl (5-(2-(1H-imidazol-1-yl)acetyl)-10,11-dihydro-5H-dibenzo[b,f]azepin-3-yl) carbamate (17)

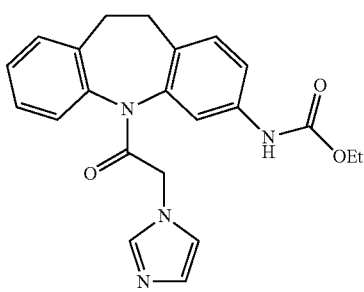 [SMILES: CCOC(=O)Nc1ccc2c(c1)N(C(=O)Cn1ccnc1)c1ccccc1CC2]

NaH (33.44 mg, 1.39 mmol) was added to a solution of imidazole (696.73 μmol) in DMF (2 mL) at 0° C. The mixture was stirred at 0° C. for 0.5 h. Then compound F (250.00 mg, 696.73 μmol) in DMF (1 mL) was added dropwise. The mixture was stirred at 0° C. for 1 h. LCMS showed starting material consumed. The reaction was quenched with NH$_4$Cl aqueous solution and extracted with ethyl acetate (20 mL×3) and washed with brine (20 mL×2). The organic layer was dried with anhydrous Na$_2$SO$_4$ and concentrated to give a residue. The residue was dissolved in MeOH (3 mL) and purified by preparative HPLC to give 17 (91.5 mg, 234 μmol, 33.7%). LCMS: MS+1=391.2. $^1$H NMR (300 MHz, DMSO-d$_6$) δ (ppm) 9.27 (br. s., 1H), 7.59

(s, 1H), 7.45 (s, 2H), 7.25-7.33 (m, 4H), 7.18 (d, J=8.29 Hz, 1H), 7.03 (s, 1H), 6.85 (s, 1H), 4.79 (d, J=9.80 Hz, 2H), 4.15 (q, J=6.97 Hz, 2H), 3.20-3.31 (m, 2H), 2.72-2.81 (m, 2H), 1.26 (t, J=7.06 Hz, 3H).

(iv) Preparation of ethyl (5-(2-(piperidin-1-yl)acetyl)-10,11-dihydro-5H-dibenzo[b,f]azepin-3-yl)carbamate (18)

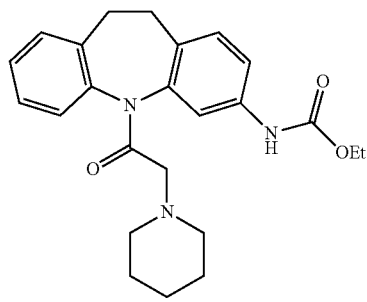 [SMILES: CCOC(=O)Nc1ccc2c(c1)N(C(=O)CN1CCCCC1)c1ccccc1CC2]

NaH (33.44 mg, 1.39 mmol) was added to a solution of piperidine (696.73 μmol) in DMF (2 mL) at 0° C. The mixture was stirred at 0° C. for 0.5 h. Then compound F (250.00 mg, 696.73 μmol) in DMF (1 mL) was added dropwise. The mixture was stirred at 0° C. for 1 h. LCMS showed starting material consumed. The reaction was quenched with NH₄Cl aqueous solution and extracted with ethyl acetate (20 mL×3) and washed with brine (20 mL×2). The organic layer was dried with anhydrous Na₂SO₄ and concentrated to give a residue. The residue was dissolved in MeOH (3 mL) and purified by preparative HPLC to give 18 (85.4 mg, 209 μmol, 30.1%). LCMS: MS+1=408.1. $^1$H NMR (300 MHz, DMSO-d₆) δ (ppm) 9.22 (br. s., 1H), 8.16 (s, 1H), 7.48 (d, J=2.07 Hz, 1H), 7.17-7.36 (m, 5H), 7.13 (d, J=8.48 Hz, 1H), 4.14 (q, J=7.10 Hz, 2H), 3.28 (br. s., 2H), 2.72-2.84 (m, 4H), 2.26-2.33 (m, 4H), 1.31-1.49 (m, 6H), 1.26 (t, J=7.06 Hz, 3H).

i. Synthesis of Compound 14

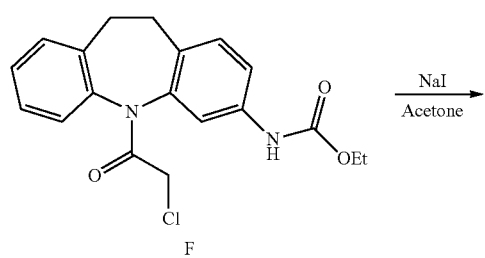

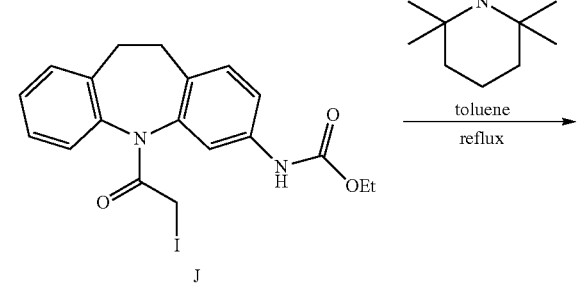

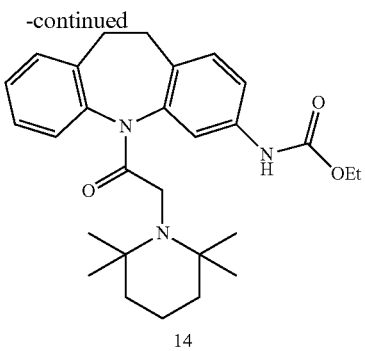

(i) Preparation of ethyl (5-(2-iodoacetyl)-10,11-dihydro-5H-dibenzo[b,f]azepin-3-yl)carbamate (Compound J)

Compound F (300.00 mg, 836.07 μmol) in acetone (5 mL) was added NaI (375.96 mg, 2.51 mmol) in one portion at 25° C. under N₂. The mixture was stirred at 25° C. for 10 hours. TLC showed the reaction was completed. The mixture was filtered and the filtrate was concentrated under vacuum to afford Compound J (325.00 mg, 721.79 μmol) as a yellow solid.

(ii) Preparation of ethyl (5-(2-(2,2,6,6-tetramethyl-piperidin-1-yl)acetyl)-10,11-dihydro-5H-dibenzo[b,f]azepin-3-yl)carbamate (14)

A mixture of Compound J (150.00 mg, 333.13 μmol) and 2,2,6,6-tetramethylpiperidine 2.00 g, 14.16 mmol) in toluene (10 mL) was heated to 120° C. and stirred for 16 hours. LCMS showed the reaction was completed. The mixture was cooled to 25° C. and concentrated in reduced pressure at 50° C. The residue was purified by preparative HPLC to afford 14 (10.00 mg, 12.94 μmol, 6.48%) as a yellow solid. LCMS: MS+1=464.2. $^1$H NMR (400 MHz, CDCl₃) δ (ppm) 1.12-1.51 (m, 15 H), 1.68 (d, J=5.77 Hz, 2 H), 2.78-2.93 (m, 3 H), 3.07-3.33 (m, 4 H), 3.56 (d, J=17.82 Hz, 1 H), 4.19 (ddt, J=10.54, 7.03, 3.64, 3.64 Hz, 3 H), 5.05 (d, J=17.82 Hz, 1 H), 7.16-7.32 (m, 5 H), 7.36-7.49 (m, 1 H), 8.00 (d, J=7.78 Hz, 1 H), 8.17 (br. s., 1 H), 9.27-9.52 (m, 1 H).

j. Synthesis of Compound 15

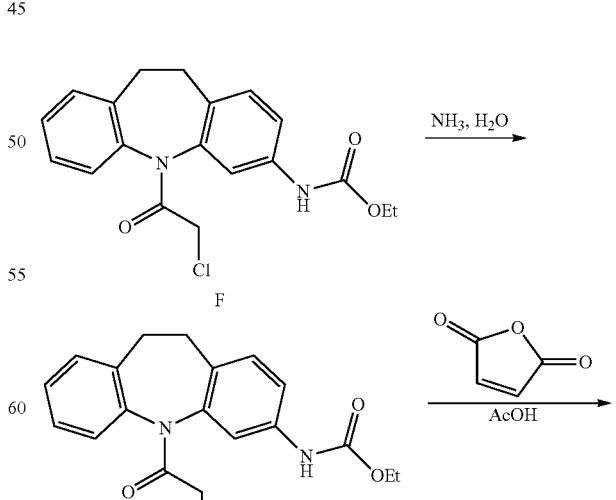

199

-continued

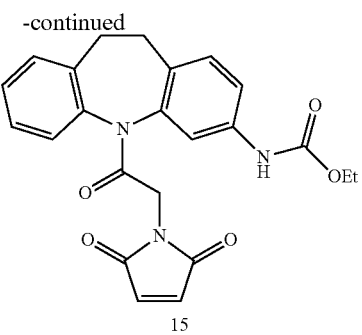

(i) Preparation of ethyl (5-glycyl-10,11-dihydro-5H-dibenzo[b,f]azepin-3-yl)carbamate (Compound K)

Compound F (200.00 mg, 557.38 µmol) in MeOH (3 mL) was added NH$_3$.H$_2$O (10 mL) in one portion at 25° C. The mixture was stirred at 120° C. in a sealed tube for 12 hours. TLC showed the reaction was completed. The mixture was concentrated under vacuum to afford Compound K (185.00 mg, 545.10 µmol, 97.80%) as a yellow solid.

(ii) Preparation of ethyl (5-(2-(2,5-dioxo-2,5-dihydro-1H-pyrrol-1-yl)acetyl)-10,11-dihydro-5H-dibenzo[b,f]azepin-3-yl)carbamate (15)

Compound K (180.00 mg, 530.36 µmol) in AcOH (5 mL) was added furan-2,5-dione (260.04 mg, 2.65 mmol) in one portion at 25° C. The mixture was stirred at 100° C. for 12 hours. TLC showed the reaction was completed. The mixture was cooled to 25° C. and concentrated under reduced pressure. The residue was poured into saturated NaHCO$_3$ solution (5 mL) and stirred for 3 min. The aqueous phase was extracted with ethyl acetate (3 mL×3). The combined organic phase was washed with saturated brine (3 mL), dried with anhydrous Na$_2$SO$_4$, filtered and concentrated under vacuum. The residue was purified by silica gel chromatography (Petroleum ether/ethyl acetate=3/1 to 1/1) to afford 15 (14.00 mg, 33.38 µmol, 6.29%) as an off-white solid. LCMS: MS+1=420.2. $^1$H NMR (400 MHz, CDCl$_3$) δ (ppm) 1.23-1.42 (m, 3 H), 2.79-2.93 (m, 2 H), 3.29-3.43 (m, 1 H), 3.48-3.61 (m, 1 H), 3.82-3.99 (m, 1 H), 4.17-4.31 (m, 2 H), 4.35-4.57 (m, 1 H), 6.50-6.69 (m, 1 H), 6.76 (s, 2 H), 7.07-7.23 (m, 2 H), 7.25-7.39 (m, 7 H), 7.43 (d, J=7.53 Hz, 1 H), 7.58 (s, 1 H).

k. Synthesis of ethyl (5-(2-(tert-butoxy)acetyl)-10,11-dihydro-5H-dibenzo[b,f]azepin-3-yl)carbamate (19)

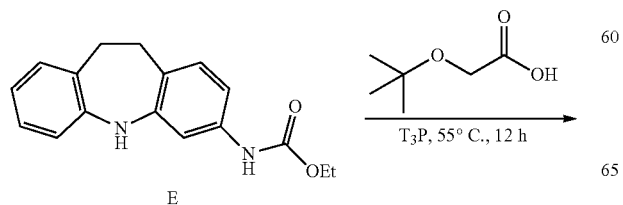

200

-continued

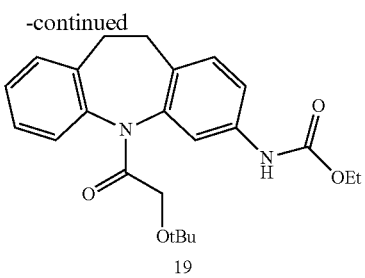

A mixture of compound E (150 mg, 530 µmol) and 2-tert-butoxyacetic acid (105.32 mg, 796.91 µmol) in propylphosphonic acid (T$_3$P) (5 mL) was stirred at 55° C. for 12 hr. LCMS showed DP. The mixture was washed with NaHCO$_3$ aqueous solution (20 mL×3). The organic layer was dried with anhydrous Na$_2$SO$_4$ and concentrated under vacuum to give a residue. The residue was purified by preparative HPLC to give 19 (50.00 mg, 126.11 mol, 23.74%) as a white solid. LCMS: MS+1=397.1. $^1$H NMR (400 MHz, DMSO-d$_6$) δ (ppm) 9.63 (br. s., 1 H), 7.03-7.61 (m, 7 H), 4.04-4.22 (m, 2 H), 3.87 (d, J=8.91 Hz, 2 H), 3.10-3.32 (m, 2 H), 2.63-2.87 (m, 2 H), 1.23 (t, J=7.09 Hz, 3 H), 0.92 (br. s., 9 H).

l. Synthesis of Compounds 22 and 23

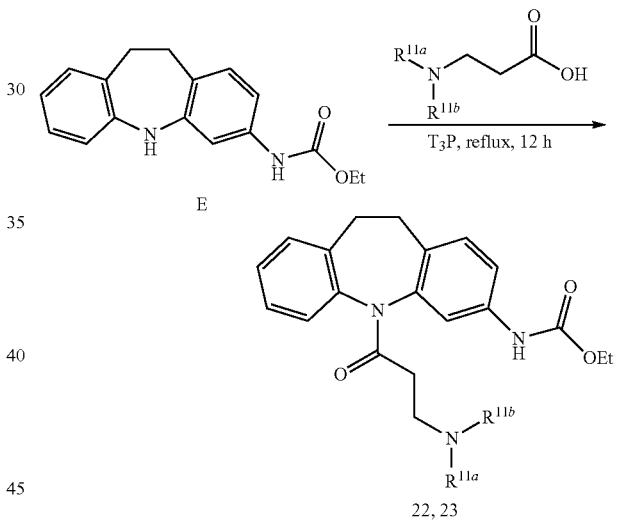

(i) Preparation of ethyl (5-(3-(diethylamino)propanoyl)-10,11-dihydro-5H-dibenzo[b,f]azepin-3-yl)carbamate (22)

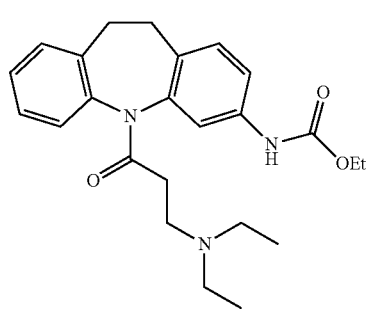 [SMILES: CCOC(=O)Nc1ccc2c(c1)N(C(=O)CCN(CC)CC)c1ccccc1CC2]

A mixture of 3-(diethylamino)propanoic acid (850.04 µmol) and Compound E (200.00 mg, 708.37 µmol) in T₃P (5 mL) was stirred at reflux for 12 h. LCMS showed DP. The mixture was concentrated to give a residue. The residue was purified by preparative HPLC to give 22 (147.3 mg, 360 µmol, 50.8%) as a white solid. LCMS: MS+1=410.2. ¹H NMR (400 MHz, DMSO-d₆) δ (ppm) 9.32 (br. s., 1H), 8.16 (s, 1H), 7.50 (br. s., 1H), 7.19-7.35 (m, 5H), 7.15 (d, J=8.28 Hz, 1H), 4.14 (q, J=7.15 Hz, 2H), 3.19-3.28 (m, 2H), 2.69-2.81 (m, 4H), 2.32-2.43 (m, 6H), 1.26 (t, J=7.09 Hz, 3H), 0.85-0.94 (m, 6H).

(ii) Preparation of ethyl (5-(3-(diethylamino)propanoyl)-10,11-dihydro-5H-dibenzo[b,f]azepin-3-yl)carbamate (23)

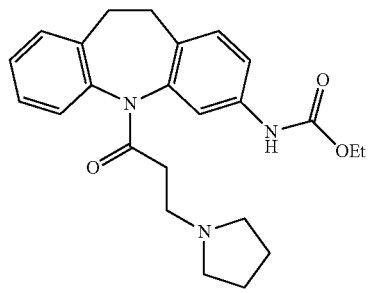 [SMILES: CCOC(=O)Nc1ccc2c(c1)N(C(=O)CCN1CCCC1)c1ccccc1CC2]

A mixture of 1-pyrrolidinepropanoic acid (850.04 µmol) and Compound E (200.00 mg, 708.37 µmol) in T₃P (5 mL) was stirred at reflux for 12 h. LCMS showed DP. The mixture was concentrated to give a residue. The residue was purified by preparative HPLC to give 23 (197.4 mg, 485 µmol, 68.5%) as a white solid. LCMS: MS+1=408.1. ¹H NMR (400 MHz, DMSO-d₆) δ (ppm) 9.25 (br. s., 1H), 8.14 (s, 1H), 7.47 (s, 1H), 7.10-7.30 (m, 5H), 4.13 (q, J=6.97 Hz, 2H), 3.03-3.15 (m, 2H), 2.70 (t, J=6.97 Hz, 4H), 2.20-2.44 (m, 6H), 1.65 (td, J=3.30, 6.59 Hz, 4H), 1.25 (t, J=7.06 Hz, 3H).

m. Synthesis of Compound 25

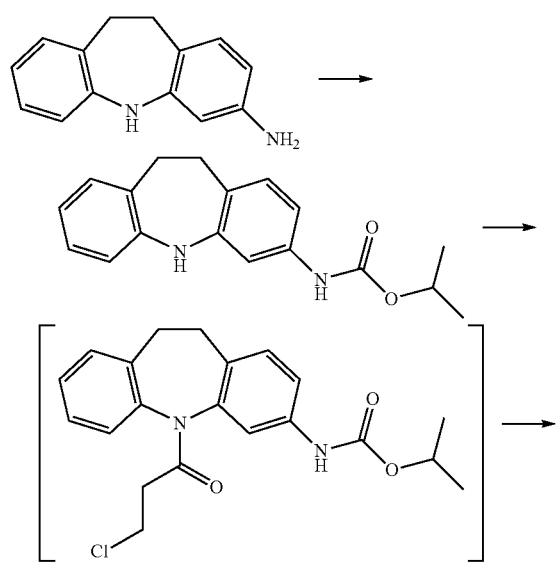

-continued

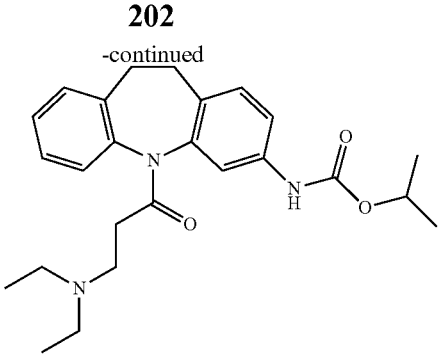

(i) Preparation of isopropyl (10,11-dihydro-5H-dibenzo[b,f]azepin-3-yl)carbamate

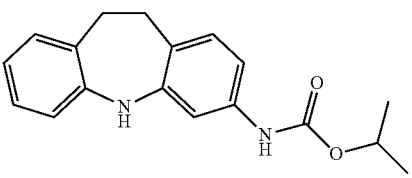 [SMILES: CC(C)OC(=O)Nc1ccc2c(c1)Nc1ccccc1CC2]

Isopropyl carbonochloridate (4.20 g, 34.24 mmol) was added dropwise to a solution of 10,11-dihydro-5H-dibenzo[b,f]azepin-3-amine (3.60 g, 17.12 mmol) in ethanol (36 mL) at 0° C. for approximately 20 min. A solution of sodium carbonate (1.81 g, 17.12 mmol) in water (36 mL) was then added dropwise while the temperature was maintained below 15° C. The reaction was stirred at 25° C. for 1 hour. TLC showed that starting material was depleted. The reaction solution was poured into water and filtered yielding pure isopropyl (10,11-dihydro-5H-dibenzo[b,f]azepin-3-yl)carbamate (5.20 g, crude) as a green solid. LC-MS: MS+1=297.15. ¹H NMR (400 MHz, DMSO-d₆) δ(ppm) 9.35 (s, 1H), 8.28 (s, 1H), 7.24 (s, 1H), 7.01-6.96 (m, 3H), 6.87-6.85 (d, J=8.0 Hz, 1H), 6.66-6.64 (m, 2H), 4.91-4.85 (m, 1H), 2.93-2.84 (m, 4H), 1.26-1.25 (d, J=4.0 Hz, 6H).

(ii) Preparation of isopropyl (5-(3-(diethylamino)propanoyl)-10,11-dihydro-5H-Dibenzo[b,f]azepin-3-yl)carbamate (25)

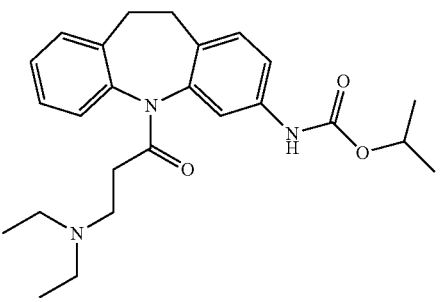 [SMILES: CCN(CC)CCC(=O)N1c2ccccc2CCc2ccc(NC(=O)OC(C)C)cc21]

A mixture of isopropyl (10,11-dihydro-5H-dibenzo[b,f]azepin-3-yl)carbamate (200 mg, 674.85 µmol) and 3-chloropropionyl chloride (128.5 mg, 1.01 mmol) in toluene (2 mL) was stirred at 100° C. for 3 hours. TLC showed that the reaction was complete. The mixture was concentrated to afford isopropyl (5-(3-chloropropanoyl)-10,11-dihydro-5H-dibenzo[b,f]azepin-3-yl)carbamate as gray gum, which was directly used in the next step. A mixture of isopropyl (5-(3-chloropropanoyl)-10,11-dihydro-5H-dibenzo[b,f]azepin-3-yl)carbamate (261 mg, 675 μmol) and diethyl amine (247 mg, 3.38 mmol) in toluene (2 mL) was stirred at 100° C. for 10 hours. TLC showed that the reaction was complete. The solvent was removed, and the residue was first purified by flash column chromatography (petroleum ether/EtOAc=10/1 to 100% EtOAc) and then further purified by preparative HPLC to afford compound 25 (60 mg, 382.48 μmol, 56.66% yield, 96.4% purity) as a colorless oil. $^1$H NMR (400 MHz, DMSO-$d_6$) δ (ppm) 9.50-9.79 (d, J=34 Hz, 1 H) 8.93 (br, 1 H) 7.73-7.07 (m, 7 H) 4.81-4.95 (m, 1 H) 3.15-3.36 (m, 5 H) 3.05-3.15 (m, 4 H) 2.86-2.99 (m, 1 H) 2.71-2.85 (m, 2 H) 2.33-2.45 (m, 1 H) 1.24 (d., J=5.8 Hz, 6 H) 1.09-1.20 (m, 6 H). ESI-TOF HRMS: m/z 424.2604 ($C_{25}H_{33}N_3O_3$+H$^+$ requires 424.2602).

n. Synthesis of Compounds 26-28

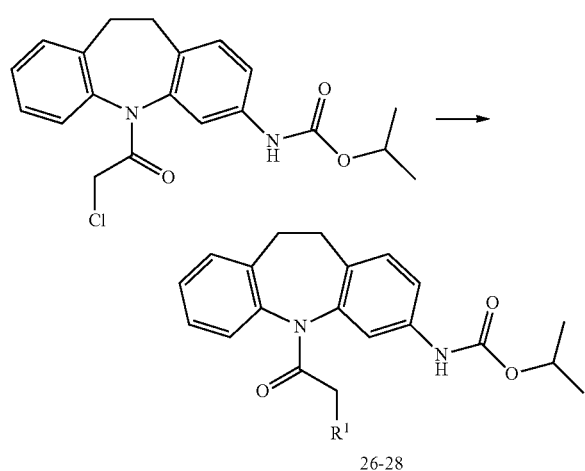

26-28

(i) Preparation of isopropyl (5-(2-chloroacetyl)-10,11-dihydro-5H-dibenzo[b,f]azepin-3-yl)carbamate

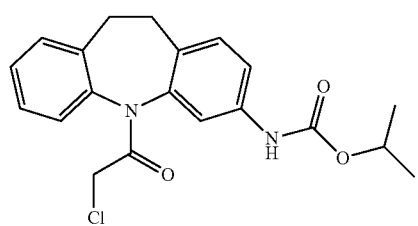 [SMILES: CC(C)OC(=O)Nc1ccc2c(c1)N(C(=O)CCl)c1ccccc1CC2]

A mixture of isopropyl (10,11-dihydro-5H-dibenzo[b,f]azepin-3-yl)carbamate (5.2 g, 17.55 mmol) and 2-chloroacetyl chloride (2.97 g, 26.32 mmol) in toluene (52 mL) was stirred at 100° C. for 3 hours. TLC showed that the reaction was complete. The mixture was concentrated to afford isopropyl (5-(2-chloroacetyl)-10,11-dihydro-5H-dibenzo[b,f]azepin-3-yl)carbamate (5.20 g, 13.95 mmol, 79.47% yield) as a green solid. LC-MS: MS+1=373.12. $^1$H NMR (400 MHz, DMSO-$d_6$) δ (ppm) 9.62-9.59 (d, J=12.0 Hz, 1H), 7.63-7.11 (m, 7H), 4.91-4.85 (m, 1H), 4.34-4.09 (m, 2H), 3.21-3.02 (m, 2H), 2.77-2.68 (m, 2H), 1.25-1.24 (m, 6H).

(ii) Preparation of isopropyl (5-(2-(1H-pyrrol-1-yl)acetyl)-10,11-dihydro-5H-dibenzo[b,f]azepin-3-yl)carbamate (26)

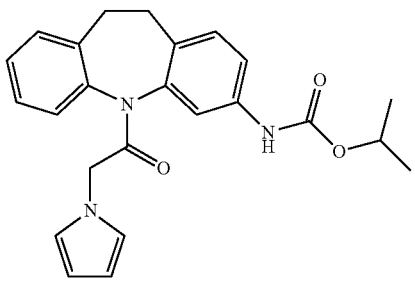 [SMILES: CC(C)OC(=O)Nc1ccc2c(c1)N(C(=O)Cn1cccc1)c1ccccc1CC2]

NaH (12 mg, 500 μmol) was added to a mixture of pyrrole (40 mg, 596 μmol) in DMF (2 mL) at 25° C. The mixture was stirred at 25° C. for 0.5 hour. Isopropyl (5-(2-chloroacetyl)-10,11-dihydro-5H-dibenzo[b,f]azepin-3-yl)carbamate (100 mg, 268 μmol) in DMF (1 mL) was then added dropwise. The mixture was stirred at 25° C. for 2.5 hour, and LC-MS showed that starting material was mostly depleted. The reaction was quenched with aqueous NH$_4$Cl solution. The product was extracted with EtOAc (50 mL×3), and the combined organic layer was washed with brine (20 mL×2), dried by anhydrous Na$_2$SO$_4$, filtered, and concentrated to give a residue. The residue was dissolved in acetonitrile (3 mL), purified by preparative HPLC to give the compound 26 (50 mg, 124 μmol, 46.3% yield, 99.4% purity). $^1$H NMR (400 MHz, Methanol-$d_4$) δ (ppm) 7.67 (s, 1H), 7.50 (s, 1H), 7.36-7.31 (m, 2H), 7.24 (s, 2H), 7.13-7.11 (d, J=8.0 Hz, 1H), 6.52-6.49 (d, J=12.0 Hz, 2H), 6.03 (s, 2H), 4.76-4.59 (m, 3H), 3.24-3.20 (m, 2H), 2.79-2.77 (d, J=8.0 Hz, 2 H), 1.33-1.29 (m, 6H). ESI-TOF HRMS: m/z 404.1978 ($C_{24}H_{25}N_3O_3$+H$^+$ requires 404.1976).

(iii) Preparation of isopropyl (5-(2-(piperidin-1-yl)acetyl)-10,11-dihydro-5H-dibenzo[b,f]azepin-3-yl)carbamate (27)

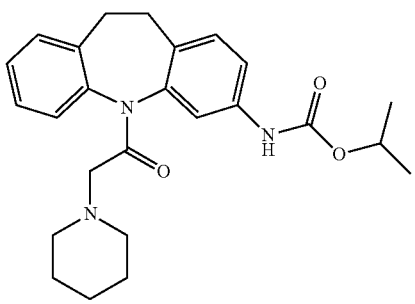 [SMILES: CC(C)OC(=O)Nc1ccc2c(c1)N(C(=O)CN1CCCCC1)c1ccccc1CC2]

NaH (12 mg, 500 μmol) was added to a mixture of piperidine (50 mg, 587 μmol) in DMF (2 mL) at 25° C. The reaction was stirred at 25° C. for 0.5 hour. Isopropyl (5-(2-chloroacetyl)-10,11-dihydro-5H-dibenzo[b,f]azepin-3-yl)carbamate (100 mg, 268 μmol) in DMF (1 mL) was then added dropwise. The mixture was stirred at 25° C. for 2.5 hours, and LC-MS showed that starting material was mostly depleted. The reaction was quenched with aqueous NH₄Cl solution. The product was extracted with EtOAc (50 mL×3), and the combined organic layer was washed with brine (20 mL×2), dried with anhydrous Na₂SO₄, filtered, and concentrated to give a residue. The residue was dissolved in acetonitrile (3 mL) and purified by preparative HPLC to give the compound 27 (83.6 mg, 198 μmol, 73.8% yield, 99.1% purity). $^1$H NMR (400 MHz, DMSO-d₆) δ (ppm) 9.62-9.59 (m, 1H), 7.60-7.10 (m, 7H), 4.89-4.86 (m, 1H), 3.34-3.16 (m, 6H), 2.77-2.74 (m, 4 H), 1.50 (s, 4 H), 1.35 (s, 2 H), 1.26-1.24 (dd, $J_1$=4.0 Hz, $J_2$=4.0 Hz, 6H). ESI-TOF HRMS: m/z 422.2452 ($C_{25}H_{31}N_3O_3+H^+$ requires 422.2445).

(iv) Preparation of isopropyl (5-(dipropylglycyl)-10,11-dihydro-5H-dibenzo[b,f]azepin-3-yl)carbamate (28)

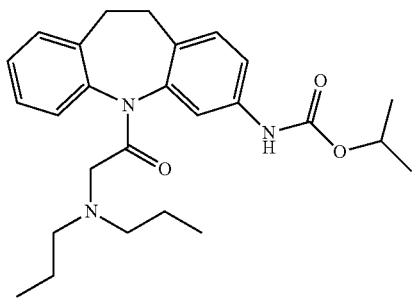 [SMILES: CCCN(CCC)CC(=O)N1c2ccccc2CCc2ccc(NC(=O)OC(C)C)cc21]

NaH (12 mg 500 μmol) was added to a mixture of dipropylamine (60 mg, 592 μmol) in DMF (2 mL) at 25° C. The mixture was stirred at 25° C. for 0.5 hour. Isopropyl (5-(2-chloroacetyl)-10,11-dihydro-5H-dibenzo[b,f]azepin-3-yl)carbamate (100 mg, 268 μmol) in DMF (1 mL) was then added dropwise. The mixture was stirred at 25° C. for 2.5 hours, and LC-MS showed that starting material was mostly depleted. The reaction was quenched with aqueous NH₄Cl solution. The product was extracted with EtOAc (50 mL×3), and the combined organic layer was washed with brine (20 mL×2), dried with anhydrous Na₂SO₄, filtered, and concentrated to give a residue. The residue was dissolved in acetonitrile (3 mL), purified by preparative HPLC to give the compound 28 (52 mg, 119 μmol, 44.4% yield, 98.6% purity). $^1$H NMR (400 MHz, DMSO-d₆) δ (ppm) 9.68 (s, 1H), 7.61-7.32 (m, 7H), 4.97 (s, 1H), 3.54-3.30 (m, 8H), 2.83 (s, 2H), 1.33 (s, 10 H), 0.85 (s, 6H). ESI-TOF HRMS: m/z 438.2759 ($C_{26}H_{35}N_3O_3+H^+$ requires 438.2758).

o. Synthesis of Compounds 29-36

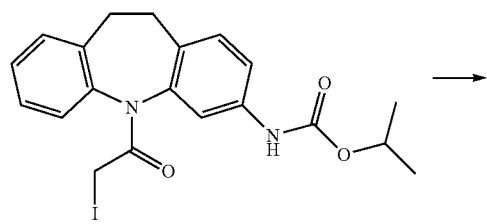

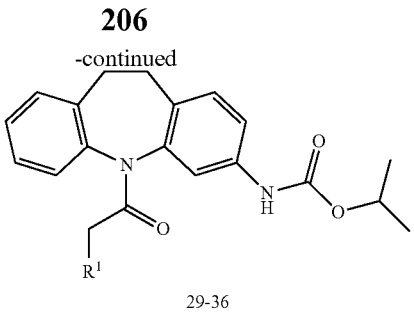

29-36

(i) Preparation of isopropyl (5-(2-iodoacetyl)-10,11-dihydro-5H-dibenzo[b,f]azepin-3-yl)carbamate

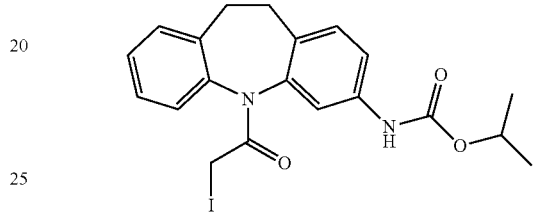

Sodium iodide (1.21 g, 8.05 mmol) was added to a mixture of isopropyl (5-(2-chloroacetyl)-10,11-dihydro-5H-dibenzo[b,f]azepin-3-yl)carbamate (3.00 g, 8.05 mmol) in acetone (30 mL) in one portion at 25° C. The mixture was stirred at 25° C. for 12 hours, and LC-MS showed that starting material was depleted. The mixture was concentrated, and water (80 mL) was added to the residue. The aqueous phase was extracted with ethyl acetate (200 mL×3). The combined organic phase was washed with saturated brine (200 mL×2), dried with anhydrous sodium sulfate, filtered, and vacuum concentrated to afford isopropyl (5-(2-iodoacetyl)-10,11-dihydro-5H-dibenzo[b,f]azepin-3-yl)carbamate (3.00 g, 6.46 mmol, 80.25% yield) as a gray solid. LC-MS: MS+1=465.1.

(ii) Preparation of isopropyl (5-(2-ethoxyacetyl)-10,11-dihydro-5H-dibenzo[b,f]azepin-3-yl)carbamate (29)

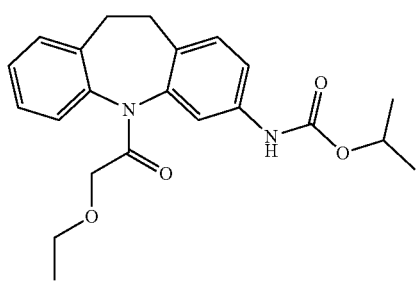 [SMILES: CCOCC(=O)N1c2ccccc2CCc2ccc(NC(=O)OC(C)C)cc21]

Ethanol (90 mg, 1.95 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f]azepin-3-yl)carbamate (300 mg, 646 μmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL) and purified by preparative HPLC to give compound 29 (51 mg, 133 µmol, 20.6% yield, 99.5% purity). $^1$H NMR (400 MHz, chloroform-d) δ (ppm) 7.08-7.54 (m, 7H), 6.71 (s, 1H), 5.01 (br, s, 1H), 4.16-4.30 (m, 1H), 3.76-3.08 (m, 1H), 3.54 (q, J=8.0 Hz, 2H), 3.35 (br, s, 2H), 2.77-2.82 (m, 2H), 1.30 (d, J=8.0 Hz, 6H), 1.20 (t, J=4.0 Hz, 3H). ESI-TOF HRMS: m/z 383.1970 ($C_{22}H_{26}N_2O_4$+H$^+$ requires 383.1973).

(iii) Preparation of isopropyl (5-(2-isopropoxy-acetyl)-10,11-dihydro-5H-dibenzo[b,f]azepin-3-yl) carbamate (30)

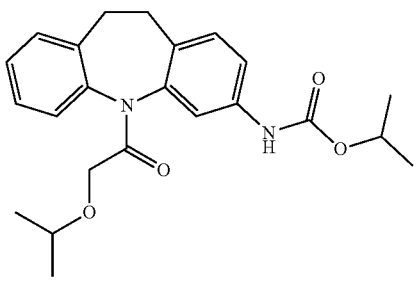 [SMILES: CC(C)OCC(=O)N1c2ccccc2CCc2ccc(NC(=O)OC(C)C)cc21]

Isopropanol (117 mg, 1.94 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3) and washed with brine (20 mL×2). The organic layer was dried with anhydrous sodium sulfate and concentrated to give a residue. The residue was dissolved in acetonitrile (3 mL) and purified by preparative HPLC to give compound 30 (52 mg, 131 µmol, 20.3% yield, 99.1% purity). $^1$H NMR (400 MHz, DMSO-d$_6$) δ (ppm) 9.58 (s, 1H), 7.52-7.11 (m, 7H), 4.91-4.86 (m, 1H), 4.07-3.78 (m, 3H), 3.24 (m, 2H), 2.75 (m, 2H), 1.26-1.24 (d, J=8.0 Hz, 6H), 0.99-0.98 (d, J=4.0 Hz, 6H). ESI-TOF HRMS: m/z 397.2129 ($C_{23}H_{28}N_2O_4$+H$^+$ requires 397.2129).

(iv) Preparation of isopropyl (5-(2-(sec-butoxy) acetyl)-10,11-dihydro-5H-dibenzo[b,f]azepin-3-yl) carbamate (31)

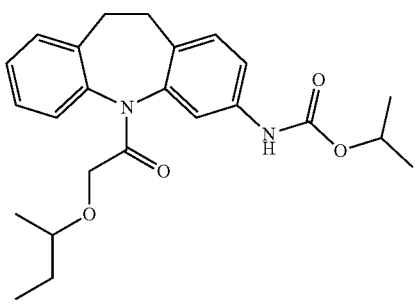 [SMILES: CCC(C)OCC(=O)N1c2ccccc2CCc2ccc(NC(=O)OC(C)C)cc21]

2-Butanol (144 mg, 1.94 mmol) was added to NaHMDS (1 M, 2.07 mL, 2.07 mmol) at 0° C. under nitrogen. The mixture was stirred at 0° C. for 0.5 h. Isopropyl (5-(2-iodoacetyl)-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL) and purified by preparative HPLC to give compound 31 (17 mg, 41.4 µmol, 6.4% yield, 95.0% purity). $^1$H NMR (400 MHz, chloroform-d) δ (ppm) 7.62-6.96 (m, 6H), 6.66 (br. s., 1H), 5.10-4.88 (m, 1H), 4.39-3.65 (m, 2H), 3.54-3.18 (m, 3H), 2.93-2.66 (m, 2H), 1.61-1.48 (m, 1H), 1.46-1.34 (m, 1H), 1.30 (d, J=6.3 Hz, 6H), 1.07 (br. s., 3H), 0.87 (t, J=7.5 Hz, 3H). ESI-TOF HRMS: m/z 411.2287 ($C_{24}H_{30}N_2O_4$+H$^+$ requires 411.2286).

(v) Preparation of isopropyl (5-(2-(neopentyloxy) acetyl)-10,11-dihydro-5H-dibenzo[b,f]azepin-3-yl) carbamate (32)

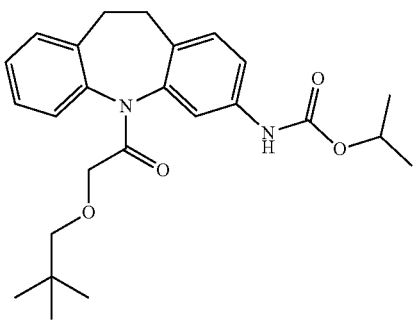 [SMILES: CC(C)OC(=O)Nc1ccc2c(c1)N(C(=O)COCC(C)(C)C)c1ccccc1CC2]

2,2-Dimethyl-1-Propanol (171 mg, 1.94 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f] azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL), purified by preparative HPLC to give compound 32 (102.8 mg, 242 µmol, 37.5% yield, 99.4% purity). $^1$H NMR (400 MHz, DMSO-d$_6$) δ (ppm) 9.59 (s, 1H), 7.53 (s, 1H), 7.45-7.10 (m, 6H), 4.91-4.85 (m, 1H), 4.19-4.16 (d, J=12.0 Hz, 1H), 3.83-3.72 (m, 1H), 3.23 (s, 2H), 2.80-2.75 (m, 2 H), 1.26-1.25 (d, J=4.0 Hz, 6H), 0.82 (s, 9H). ESI-TOF HRMS: m/z 425.2451 ($C_{25}H_{32}N_2O_4$+H$^+$ requires 425.2442).

(vi) Preparation of isopropyl (5-(2-cyclopropoxy-acetyl)-10,11-dihydro-5H-dibenzo[b,f]azepin-3-yl)carbamate (33)

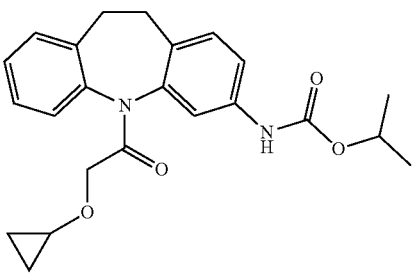 [SMILES: CC(C)OC(=O)Nc1ccc2c(c1)N(C(=O)COC1CC1)c1ccccc1CC2]

Cyclopropanol (113 mg, 1.94 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL) and purified by preparative HPLC to give compound 33 (82 mg, 208 µmol, 32.2% yield, 98.6% purity). $^1$H NMR (400 MHz, chloroform-d) δ (ppm) 7.38-7.86 (m, 7H), 5.32 (br, s, 1H), 4.51-4.65 (m, 1H), 4.13-4.24 (m, 1H), 3.68-3.84 (m, 4H), 3.08-3.15 (m, 2H), 1.61 (d, J=4.0 Hz, 6H), 0.88 (br, s, 2H), 0.74-0.75 (m, 2H). ESI-TOF HRMS: m/z 395.1974 ($C_{23}H_{26}N_2O_4+H^+$ requires 395.1973).

(vii) Preparation of isopropyl (5-(2-cyclobutoxy-acetyl)-10,11-dihydro-5H-dibenzo[b,f]azepin-3-yl)carbamate (34)

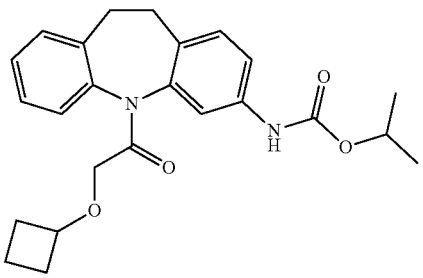 [SMILES: CC(C)OC(=O)Nc1ccc2c(c1)N(C(=O)COC1CCC1)c1ccccc1CC2]

Cyclobutanol (140 mg, 1.94 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3) and washed with brine (20 mL×2). The organic layer was dried with anhydrous sodium sulfate and concentrated to give a residue. The residue was dissolved in acetonitrile (3 mL) and purified by preparative HPLC to give compound 34 (52 mg, 127 µmol, 19.7% yield, 98.5% purity). $^1$H NMR (400 MHz, chloroform-d) δ (ppm) 7.08-7.52 (m, 7H), 6.69 (s, 1H), 5.01 (br, s, 1H), 3.69-4.18 (m, 3H), 2.07 (br, s, 2H), 2.77-2.82 (m, 2H), 2.14-2.23 (m, 2H), 1.90 (t, J=8.0 Hz, 2H), 1.61-1.69 (m, 1H), 1.37-1.49 (m, 1H), 1.30 (d, J=8.0 Hz, 6H). ESI-TOF HRMS: m/z 409.2138 ($C_{24}H_{28}N_2O_4+H^+$ requires 409.2129).

(viii) Preparation of isopropyl (5-(2-(cyclopentyloxy)acetyl)-10,11-dihydro-5H-dibenzo[b,f]azepin-3-yl)carbamate (35)

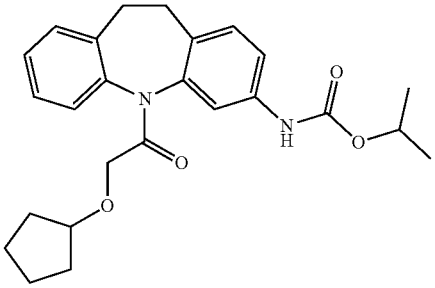 [SMILES: CC(C)OC(=O)Nc1ccc2c(c1)N(C(=O)COC1CCCC1)c1ccccc1CC2]

Cyclopentanol (167 mg, 1.94 mmol) was added to NaHMDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL) and purified by preparative HPLC to give compound 35 (80.5 mg, 190.6 µmol, 29.5% yield, 99.3% purity). $^1$H NMR (400 MHz, DMSO-$d_6$) δ (ppm) 9.59 (s, 1H), 7.52-7.10 (m, 7H), 4.91-4.85 (m, 1H), 3.99 (s, 1H), 3.78 (s, 2H), 3.24-3.18 (m, 2H), 2.75 (m, 2 H), 1.51-1.41 (d, J=40.0 Hz, 8H), 1.26-1.24 (d, J=8.0 Hz, 6H). ESI-TOF HRMS: m/z 423.2288 ($C_{25}H_{30}N_2O_4+H^+$ requires 423.2286).

(ix) Preparation of isopropyl (5-(2-(cyclohexyloxy)acetyl)-10,11-dihydro-5H-dibenzo[b,f]azepin-3-yl)carbamate (36)

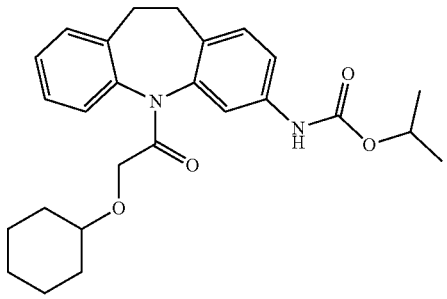 [SMILES: CC(C)OC(=O)Nc1ccc2c(c1)N(C(=O)COC1CCCCC1)c1ccccc1CC2]

Cyclohexanol (194 mg, 1.94 mmol) was added to NaH-MDS (1 M, 2.07 mL, 2.07 mmol) at 0° C. under nitrogen. The mixture was stirred at 0° C. for 0.5 hour. Isopropyl (5-(2-iodoacetyl)-10,11-dihydro-5H-dibenzo[b,f]azepin-3-yl)carbamate (300 mg, 646 µmol) in THF (3 mL) was then added dropwise. The mixture was stirred at 25° C. for 1 hour. TLC showed that starting material was depleted. The reaction was quenched with aqueous saturated ammonium chloride solution, extracted with ethyl acetate (20 mL×3), and washed with brine (20 mL×2). The organic layer was dried with anhydrous sodium sulfate and concentrated to give a residue. The residue was dissolved in acetonitrile (3 mL) and purified by preparative HPLC to give compound 36 (28 mg, 64.2 µmol, 9.9% yield, 99.3% purity). $^1$H NMR (400 MHz, chloroform-$d_6$) δ (ppm) 7.09-7.52 (m, 7H), 6.60 (s, 1H), 5.01 (d, J=4.0 Hz, 1H), 3.84-4.25 (m, 2H), 3.28-3.30 (m, 3H), 2.79-2.82 (m, 2H), 1.86-1.88 (m, 3H), 1.68 (br, s, 2H), 1.51 (br, s, 1H), 1.17-1.31 (m, 10H). ESI-TOF HRMS: m/z 437.2445 ($C_{26}H_{32}N_2O_4$+H$^+$ requires 437.2442).

p. Synthesis of Compounds 37 and 38

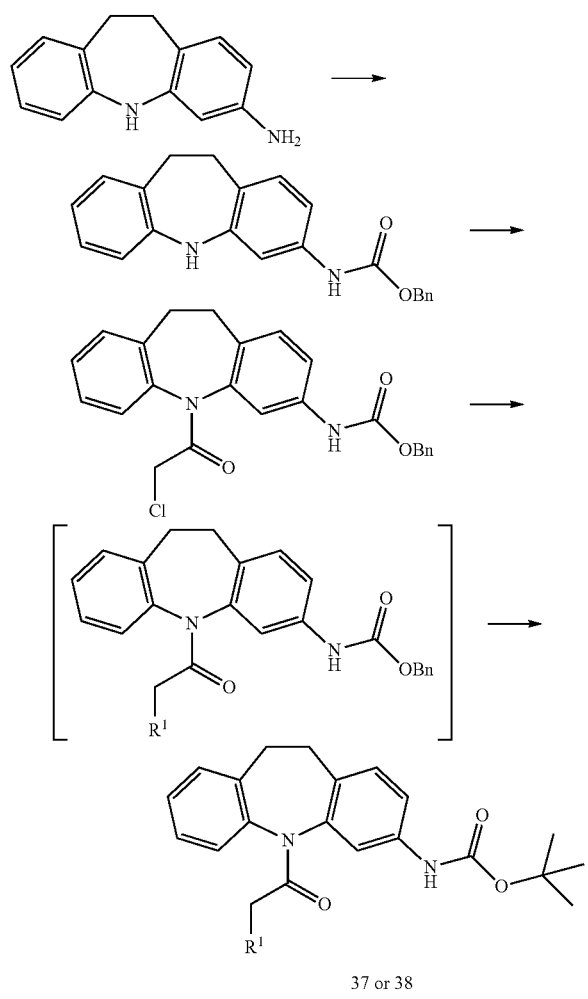

37 or 38

(i) Preparation of benzyl (10,11-dihydro-5H-dibenzo[b,f]azepin-3-yl)carbamate

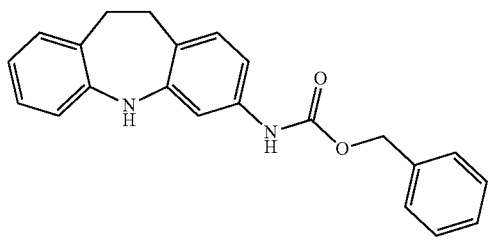 [SMILES: O=C(Nc1ccc2c(c1)Nc1ccccc1CC2)OCc1ccccc1]

Benzyl chloroformate (16.23 g, 95.12 mmol) was added dropwise to a solution of 10,11-dihydro-5H-dibenzo[b,f]azepin-3-amine (10 g, 47.56 mmol) in EtOH (100 mL) at 0° C. over a period of 1 hour. A solution of $Na_2CO_3$ (5.04 g, 47.56 mmol) in $H_2O$ (50 mL) was then added dropwise while the reaction temperature was maintained below 15° C. The reaction was stirred for another hour until TLC demonstrated that starting material was depleted. The reaction solution was poured into water (500 mL) and filtered to give the crude product. The crude product was triturated with petroleum ether/ethyl acetate=100/1, filtered, and concentrated to give benzyl (10,11-dihydro-5H-dibenzo[b,f]azepin-3-yl)carbamate (15.00 g, crude) as a white solid. $^1$H NMR (400 MHz, DMSO-$d_6$) δ (ppm) 2.91 (d, J=5.77 Hz, 4 H), 5.15 (s, 2 H), 6.61-6.71 (m, 2 H), 6.87 (d, J=8.03 Hz, 1 H), 6.95-7.03 (m, 2 H), 7.25 (br. s., 1 H), 7.31-7.49 (m, 6 H), 8.30 (s, 1 H), 9.57 (s, 1 H).

(ii) Preparation of benzyl (5-(2-chloroacetyl)-10,11-dihydro-5H-dibenzo[b,f]azepin-3-yl)carbamate

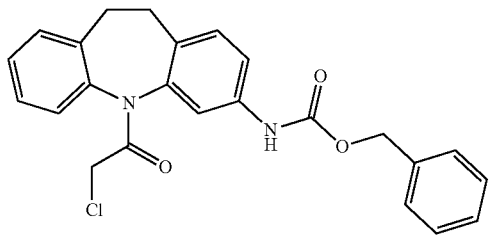 [SMILES: O=C(Nc1ccc2c(c1)N(C(=O)CCl)c1ccccc1CC2)OCc1ccccc1]

A mixture of benzyl (10,11-dihydro-5H-dibenzo[b,f]azepin-3-yl)carbamate (15 g, 43.55 mmol) and 2-chloroacetyl chloride (7.38 g, 65.33 mmol) in toluene (150 mL) was stirred at 110° C. for 3 hours, and LCMS showed that compound 77 was depleted. The mixture was concentrated, and the residue was purified by re-crystallization with petroleum ether and EtOAc (500 mL, 10/1), filtered, and concentrated to give benzyl (5-(2-chloroacetyl)-10,11-dihydro-5H-dibenzo[b,f]azepin-3-yl)carbamate (14.00 g, crude) as a white solid. LCMS: MS+1=420.12.

(iii) Preparation of tert-butyl (5-(dipropylglycyl)-10,11-dihydro-5H-dibenzo[b,f]azepin-3-yl)carbamate (37)

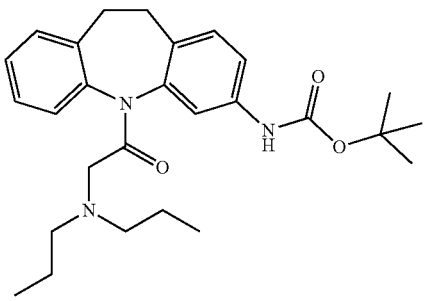 [SMILES: CCCN(CCC)CC(=O)N1c2ccccc2CCc2ccc(NC(=O)OC(C)(C)C)cc21]

A mixture of benzyl (5-(2-chloroacetyl)-10,11-dihydro-5H-dibenzo[b,f]azepin-3-yl)carbamate (500 mg, 1.19 mmol) and dipropylamine (120 mg, 1.19 mmol) in toluene (1.8 mL) was stirred at 110° C. for 6 hours, and LCMS showed that starting material was depleted. The mixture was concentrated and purified by pre-HPLC (FA) to give benzyl (5-(diisopropylglycyl)-10,11-dihydro-5H-dibenzo[b,f]azepin-3-yl)carbamate. Then, 10% Pd/C (65.00 mg) was added to the solution of compound 79 that was just prepared in MeOH (5 mL), and the mixture was stirred at room temperature under $H_2$ (15psi) for 12 hours. TLC showed that benzyl (5-(diisopropylglycyl)-10,11-dihydro-5H-dibenzo[b,f]azepin-3-yl)carbamate was depleted. $(Boc)_2O$ (260 mg, 1.19 mmol) was then added at 25° C., and the mixture was stirred at 25° C. for 3 hours; LCMS showed that the reaction was complete. The mixture was filtered and concentrated to give crude product that was further purified by preparative HPLC to give compound 37 (116 mg, 257 μmol, 21.6% yield, 99.5% purity). $^1$H NMR (400 MHz, chloroform-$d_6$) δ (ppm) 0.826 (t, J=7.2 Hz, 6 H), 1.36 (s, 4 H), 1.51 (s, 9 H), 2.53-2.55 (m, 3 H), 2.74-2.80 (m, 2 H), 3.11-3.45 (m, 4 H), 6.47 (s, 1 H), 7.06-7.49 (m, 7 H). ESI-TOF HRMS: m/z 452.2914 ($C_{27}H_{37}N_3O_3$+H$^+$ requires 452.2915).

(iv) Preparation of tert-butyl (5-(2-(piperidin-1-yl)acetyl)-10,11-dihydro-5H-dibenzo[b,f]azepin-3-yl)carbamate (38)

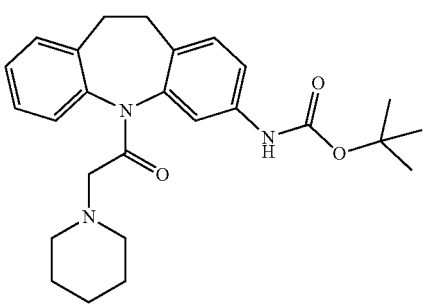 [SMILES: CC(C)(C)OC(=O)Nc1ccc2c(c1)N(C(=O)CN1CCCCC1)c1ccccc1CC2]

A mixture of compound 77 (500 mg, 1.19 mmol) and piperidine (101 mg, 1.19 mmol) in toluene (1.8 mL) was stirred at 110° C. for 6 hours, and LCMS showed that starting material compound 77 was depleted. The mixture was concentrated and purified by pre-HPLC (FA) to give benzyl (5-(2-(piperidin-1-yl)acetyl)-10,11-dihydro-5H-dibenzo[b,f]azepin-3-yl)carbamate. Then, 10% Pd/C (65.00 mg) was added to the solution of benzyl (5-(2-(piperidin-1-yl)acetyl)-10,11-dihydro-5H-dibenzo[b,f]azepin-3-yl)carbamate that was just prepared in MeOH (5 mL), and the mixture was stirred at room temperature under $H_2$ (15psi) for 12 hours. TLC showed that benzyl (5-(2-(piperidin-1-yl)acetyl)-10,11-dihydro-5H-dibenzo[b,f]azepin-3-yl)carbamate was depleted. $(Boc)_2O$ (260 mg, 1.19 mmol) was then added at 25° C., and the mixture was stirred at 25° C. for 3 hours; LCMS showed that the reaction was complete. The mixture was filtered and concentrated to give crude product that was further purified by preparative HPLC to give compound 38 (100 mg, 229.7 μmol, 19.3% yield, 99.6% purity). $^1$H NMR (400 MHz, chloroform-$d_6$) δ (ppm) 1.30-1.91 (m, 15 H), 2.11-2.90 (m, 5 H), 2.96-3.73 (m, 4 H), 6.28-6.58 (m, 1 H), 6.95-7.69 (m, 7 H). ESI-TOF HRMS: m/z 436.2604 ($C_{26}H_{33}N_3O_3$+H$^+$ requires).

q. Synthesis of Compound 39

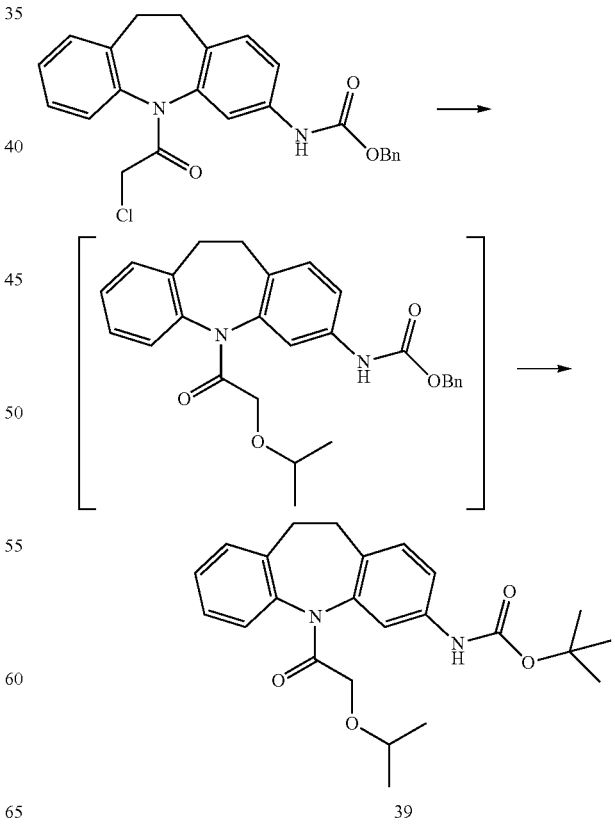

215

(i) Preparation of tert-butyl (5-(2-isopropoxyacetyl)-10,11-dihydro-5H-dibenzo[b,f]azepin-3-yl)carbamate (39)

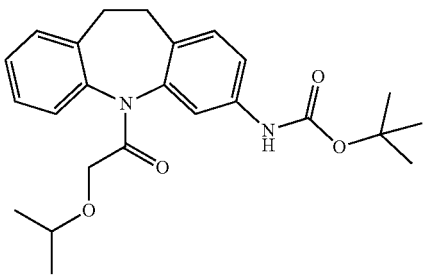 [SMILES: CC(C)OCC(=O)N1c2ccccc2CCc2ccc(NC(=O)OC(C)(C)C)cc21]

Na (0.5 g, 21.7 mmol) was added to 2-propanol (20 mL), and the reaction mixture was heated at 90° C. until Na was completely consumed. The reaction mixture (6 mL) was then added to a solution of benzyl (5-(2-chloroacetyl)-10,11-dihydro-5H-dibenzo[b,f]azepin-3-yl)carbamate (2.0 g, 4.75 mmol) in 2-propanol (20 mL) at 60° C. After 30 min, TLC showed that the starting material was depleted, and the desired compound was detected by LCMS. Water (20 mL) was added, and the reaction mixture was extracted with EtOAc (20 mL×3). The combined organic phase was washed with brine, dried with anhydrous $Na_2SO_4$, and concentrated to give a brown oil that was purified by prep-HPLC (TFA) to give benzyl (5-(2-isopropoxyacetyl)-10,11-dihydro-5H-dibenzo[b,f]azepin-3-yl)carbamate (400 mg, 18.9% yield) as a white solid. A mixture of benzyl (5-(2-isopropoxyacetyl)-10,11-dihydro-5H-dibenzo[b,f]azepin-3-yl)carbamate (400 mg, 0.90 mmol), $Boc_2O$ (237 mg, 1.09 mmol), and 10% Pd/C (40 mg) in MeOH (10 mL) was stirred under $H_2$ atmosphere (15 psi) at 25° C. for 2 hours. TLC showed that benzyl (5-(2-isopropoxyacetyl)-10,11-dihydro-5H-dibenzo[b,f]azepin-3-yl)carbamate was depleted, and the desired compound 39 was detected by LCMS. The reaction mixture was filtered through a Celite pad, and the filtrate was concentrated to give a crude product that was purified by silica gel chromatography (Petroleum ether/Ethyl acetate=10/1 to 3/1) to afford compound 39 (103 mg, 27.9% yield, 95.6% purity) as an off-white solid. $^1$H NMR (400 MHz, DMSO-$d_6$) δ (ppm) 9.39 (br. s., 1 H), 7.02-7.67 (m, 6 H), 3.97-4.21 (m, 1 H), 3.70-3.89 (m, 1 H), 3.38-3.52 (m, 1 H), 3.21 (d, J=11.80 Hz, 2 H), 2.75 (br. s., 2 H), 1.47 (s, 9 H), 0.99 (d, J=5.52 Hz, 6 H). ESI-TOF HRMS: m/z 411.2289 ($C_{24}H_{30}N_2O_4$+H$^+$ requires 411.2286).

r. Synthesis of Compounds 40-44

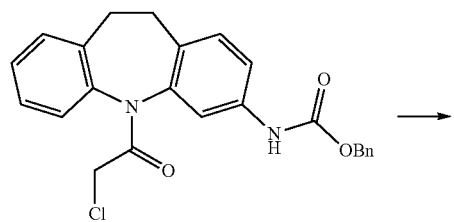

216

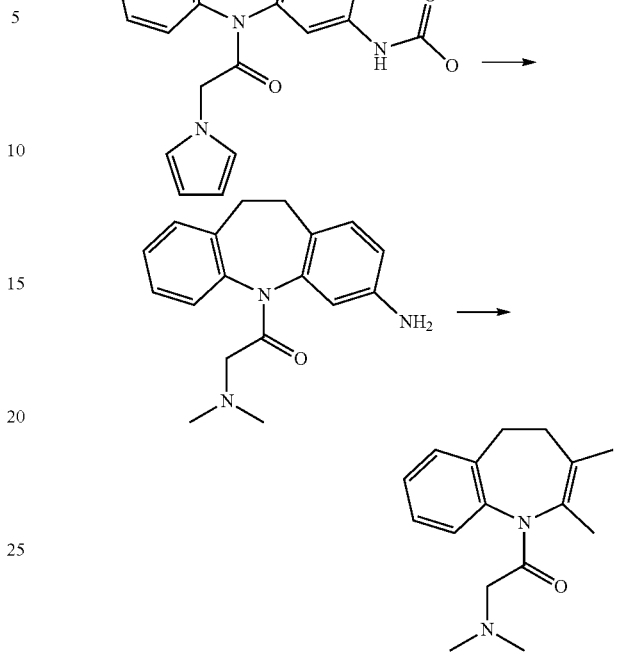

(i) Preparation of benzyl (5-(2-(1H-pyrrol-1-yl)acetyl)-10,11-dihydro-5H-dibenzo[b,f]azepin-3-yl)carbamate

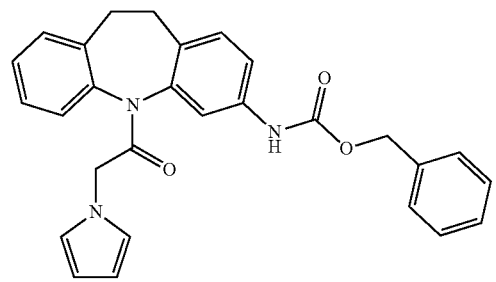 [SMILES: O=C(Nc1ccc2c(c1)N(C(=O)Cn1cccc1)c1ccccc1CC2)OCc1ccccc1]

NaH (836.4 mg, 20.91 mmol) was added to a mixture of pyrrole (1.4 g, 20.91 mmol) in DMF (30 mL) in portions at 0° C. under $N_2$. The mixture was stirred at 0° C. for 1 hour, then a solution of benzyl (5-(2-chloroacetyl)-10,11-dihydro-5H-dibenzo[b,f]azepin-3-yl)carbamate (8.0 g, 19.01 mmol) in DMF (70 mL) was added dropwise at 0° C. The mixture was allowed to warm to room temperature (25° C.) and stirred for 12 hours. LCMS showed that the reaction was complete. The mixture was diluted with water and extracted with EtOAc (50 mL×3). The combined organic layers were washed twice with water, dried with anhydrous $Na_2SO_4$, and concentrated to afford crude product that was purified by silica gel chromatography (Petroleum ether/Ethyl acetate=4/1 to 3/2) to afford benzyl (5-(2-(1H-pyrrol-1-yl)acetyl)-10,11-dihydro-5H-dibenzo[b,f]azepin-3-yl)carbamate (2.30 g, 5.1 mmol, 26.8% yield) as a yellow solid. LCMS: MS+1=452.1. $^1$H NMR (400 MHz, chloroform-$d_6$) δ (ppm) 7.63-7.01 (m, 11H), 6.81 (d, J=17.7 Hz, 1H), 6.47

(d, J=8.9 Hz, 2H), 6.12 (t, J=2.0 Hz, 2H), 5.21 (d, J=16.9 Hz, 2H), 4.74-4.41 (m, 2H), 3.26-3.07 (m, 2H), 2.86-2.65 (m, 2H).

(ii) Preparation of 1-(3-amino-10,11-dihydro-5H-dibenzo[b,f]azepin-5-yl)-2-(1H-pyrrol-1-yl)ethan-1-one

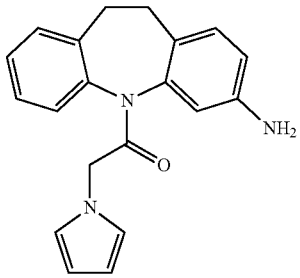 [SMILES: Nc1ccc2c(c1)N(C(=O)Cn1cccc1)c1ccccc1CC2]

First, 10% Pd/C (200.00 mg) was added to a solution of benzyl (5-(2-(1H-pyrrol-1-yl)acetyl)-10,11-dihydro-5H-dibenzo[b,f]azepin-3-yl)carbamate (2.30 g, 5.1 mmol) in EtOAc (50 mL) at 25° C. The mixture was degassed under vacuum and purged with $H_2$. The mixture was then stirred under $H_2$ (15 psi) for 4 hours. TLC (Petroleum ether/Ethyl acetate=2/1) showed that the reaction was complete. After the solution was filtered over celite pad, the filtrate was concentrated to afford 1-(3-amino-10,11-dihydro-5H-dibenzo[b,f]azepin-5-yl)-2-(1H-pyrrol-1-yl)ethan-1-one (1.20 g, crude) as a yellow solid. LCMS: MS+1=318.1.

(iii) Preparation of tert-butyl (5-(2-(1H-pyrrol-1-yl)acetyl)-10,11-dihydro-5H-dibenzo[b,f]azepin-3-yl)carbamate (40)

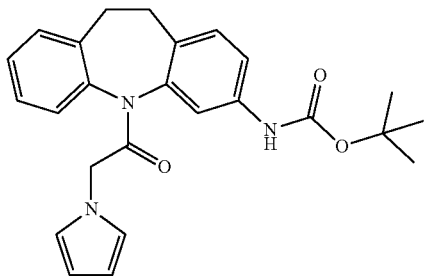 [SMILES: CC(C)(C)OC(=O)Nc1ccc2c(c1)N(C(=O)Cn1cccc1)c1ccccc1CC2]

A solution of tert-butoxycarbonyl chloride (65 mg, 475 µmol) in THF (0.5 mL) was added dropwise to a solution of 1-(3-amino-10,11-dihydro-5H-dibenzo[b,f]azepin-5-yl)-2-(1H-pyrrol-1-yl)ethan-1-one (150 mg, 475 µmol) in THF (0.5 mL) at 0° C. A solution of $Et_3N$ (48 mg, 475 µmol) in THF (1 mL) was then added dropwise at 0° C. The mixture was allowed to warm to room temperature (25° C.) and stirred for 2 hours. The mixture was filtered, and the filtrate was concentrated. The residue was purified by preparative TLC (petroleum ether/ethyl acetate=2/1) to give compound 40 (103 mg, 247 µmol, 52.0% yield, 99.4% purity) as a white solid. $^1$H NMR (400 MHz, chloroform-$d_6$) (ppm) 7.64-6.98 (m, 6H), 6.62-6.37 (m, 3H), 6.12 (s, 2H), 4.75-4.51 (m, 2H), 3.24-3.08 (m, 2H), 2.82-2.67 (m, 2H), 1.53 (d, J=12.4 Hz, 9H). ESI-TOF HRMS: m/z 440.1960 ($C_{25}H_{27}N_3O_3$+Na$^+$ requires 440.1952).

(iv) Preparation of cyclopropyl (5-(2-(1H-pyrrol-1-yl)acetyl)-10,11-dihydro-5H-dibenzo[b,f]azepin-3-yl)carbamate (41)

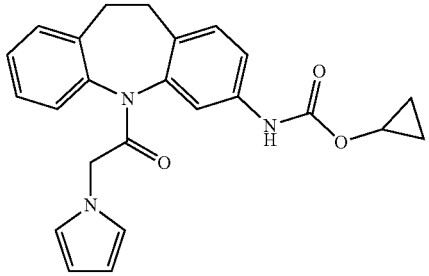 [SMILES: O=C(Nc1ccc2c(c1)N(C(=O)Cn1cccc1)c1ccccc1CC2)OC1CC1]

A solution of cyclopropyl chloroformate (58 mg, 475 µmol) in THF (0.5 mL) was added dropwise to a solution of 1-(3-amino-10,11-dihydro-5H-dibenzo[b,f]azepin-5-yl)-2-(1H-pyrrol-1-yl)ethan-1-one (150 mg, 475 µmol) in THF (0.5 mL) at 0° C. A solution of $Et_3N$ (48 mg, 475 µmol) in THF (1 mL) was then added dropwise at 0° C. The mixture was allowed to warm to room temperature (25° C.) and stirred for 2 hours. The mixture was filtered, and the filtrate was concentrated. The residue was purified by preparative TLC (petroleum ether/ethyl acetate=2/1) to give compound 41 (58 mg, 144.5 µmol, 30.4% yield, 95.1% purity) as a white solid. $^1$H NMR (400 MHz, chloroform-$d_6$) δ (ppm) 7.69-6.98 (m, 6H), 6.62 (br. s., 1H), 6.48 (d, J=7.5 Hz, 2H), 6.12 (s, 2H), 4.71-4.51 (m, 2H), 4.21-4.06 (m, 1H), 3.23-3.09 (m, 2H), 2.81-2.66 (m, 2H), 0.76 (d, J=12.4 Hz, 4H). ESI-TOF HRMS: m/z 402.1821 ($C_{24}H_{23}N_3O_3$+H$^+$ requires 402.1819).

(v) Preparation of cyclobutyl (5-(2-(1H-pyrrol-1-yl)acetyl)-10,11-dihydro-5H-dibenzo[b,f]azepin-3-yl)carbamate (42)

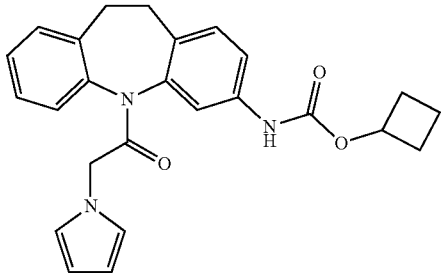 [SMILES: O=C(Nc1ccc2c(c1)N(C(=O)Cn1cccc1)c1ccccc1CC2)OC1CCC1]

A solution of cyclobutyl chloroformate (64 mg, 475 µmol) in THF (0.5 mL) was added dropwise to a solution of 1-(3-amino-10,11-dihydro-5H-dibenzo[b,f]azepin-5-yl)-2-(1H-pyrrol-1-yl)ethan-1-one (150 mg, 475 µmol) in THF (0.5 mL) at 0° C. A solution of $Et_3N$ (48 mg, 475 µmol) in THF (1 mL) was then added dropwise at 0° C. The mixture was allowed to warm to room temperature (25° C.) and stirred for 2 hours. The mixture was filtered, and the filtrate was concentrated. The residue was purified by preparative TLC (petroleum ether/ethyl acetate=2/1) to give compound 42 (65 mg, 156.5 µmol, 32.9% yield, 96.1% purity) as a white solid. $^1$H NMR (400 MHz, chloroform-$d_6$) δ (ppm) 7.62-6.95 (m, 6H), 6.68-6.40 (m, 3H), 6.19-6.04 (m, 2H), 5.16-4.94 (m, 1H), 4.78-4.47 (m, 2H), 3.24-3.07 (m, 2H), 2.84-2.65 (m, 2H), 2.40 (br. s., 2H), 2.22-2.05 (m, 2H), 1.92-1.76 (m, 1H), 1.73-1.63 (m, 1H). ESI-TOF HRMS: m/z 416.1978 ($C_{25}H_{25}N_3O_3$+H$^+$ requires 416.1976).

(vi) Preparation of cyclopentyl (5-(2-(1H-pyrrol-1-yl)acetyl)-10,11-dihydro-5H-dibenzo[b,f]azepin-3-yl)carbamate (43)

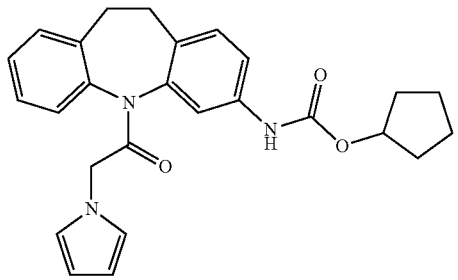 [SMILES: O=C(Nc1ccc2c(c1)N(C(=O)Cn1cccc1)c1ccccc1CC2)OC1CCCC1]

A solution of cyclopentyl chloroformate (71 mg, 475 μmol) in THF (0.5 mL) was added dropwise to a solution of 1-(3-amino-10,11-dihydro-5H-dibenzo[b,f]azepin-5-yl)-2-(1H-pyrrol-1-yl)ethan-1-one (150 mg, 475 μmol) in THF (0.5 mL) at 0° C. A solution of Et$_3$N (48 mg, 475 μmol) in THF (1 mL) was then added dropwise at 0° C. The mixture was allowed to warm to room temperature (25° C.) and stirred for 2 hours. The mixture was filtered, and the filtrate was concentrated. The residue was purified by preparative TLC (petroleum ether/ethyl acetate=2/1) to give compound 43 (87 mg, 202.7 μmol, 42.7% yield, 97.8% purity) as a white solid. $^1$H NMR (400 MHz, chloroform-d$_6$) δ (ppm) 7.72-6.97 (m, 6H), 6.69-6.40 (m, 3H), 6.12 (s, 2H), 5.21 (d, J=15.8 Hz, 1H), 4.79-4.47 (m, 2H), 3.27-3.07 (m, 2H), 2.82-2.64 (m, 2H), 2.04-1.64 (m, 8H). ESI-TOF HRMS: m/z 430.2137 ($C_{26}H_{27}N_3O_3$+H$^+$ requires 430.2132).

(vii) Preparation of cyclohexyl (5-(2-(1H-pyrrol-1-yl)acetyl)-10,11-dihydro-5H-dibenzo[b,f]azepin-3-yl)carbamate (44)

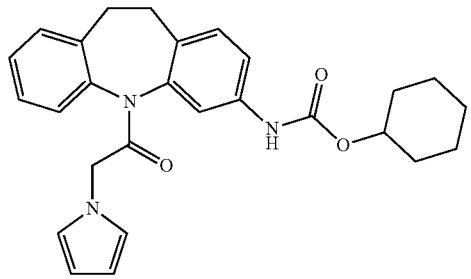 [SMILES: O=C(Nc1ccc2c(c1)N(C(=O)Cn1cccc1)c1ccccc1CC2)OC1CCCCC1]

A solution of cyclohexyl chloroformate (77 mg, 475 μmol) in THF (0.5 mL) was added dropwise to a solution of 1-(3-amino-10,11-dihydro-5H-dibenzo[b,f]azepin-5-yl)-2-(1H-pyrrol-1-yl)ethan-1-one (150 mg, 475 μmol) in THF (0.5 mL) at 0° C. A solution of Et$_3$N (48 mg, 475 μmol) in THF (1 mL) was then added dropwise at 0° C. The mixture was allowed to warm to room temperature (25° C.) and stirred for 2 hours. The mixture was filtered, and the filtrate was concentrated. The residue was purified by preparative TLC (petroleum ether/ethyl acetate=2/1) to give compound 44 (134 mg, 302.3 μmol, 63.6% yield, 98.0% purity) as a white solid. $^1$H NMR (400 MHz, chloroform-d$_6$) δ (ppm) 7.67-6.95 (m, 6H), 6.67-6.39 (m, 3H), 6.12 (s, 2H), 4.82-4.49 (m, 3H), 3.27-3.03 (m, 2H), 2.85-2.63 (m, 2H), 2.01-1.86 (m, 2H), 1.83-1.71 (m, 2H), 1.55-1.28 (m, 6H). ESI-TOF HRMS: m/z 444.2290 ($C_{27}H_{29}N_3O_3$+H$^+$ requires 444.2289).

3. Characterization of Exemplary Compounds

The compounds below in Table 3 were either synthesized with methods identical or analogous to those described herein. The requisite starting materials were commercially available, described in the literature, or readily synthesized by one skilled in the art of organic synthesis.

TABLE 3

| No. | SJ No. | Structure | LC-MS [M + 1]$^+$ |
|---|---|---|---|
| 1 | CINPA1 | 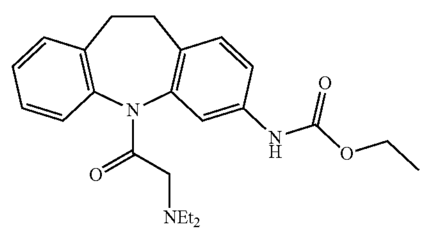 | 396.2 |
| 2 | LTC-101 | 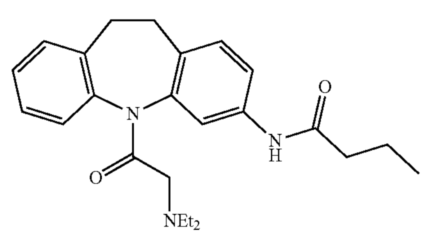 | 394.2 |

TABLE 3-continued

| No. | SJ No. | Structure | LC-MS [M + 1]⁺ |
|---|---|---|---|
| 3 | LTC-102 | 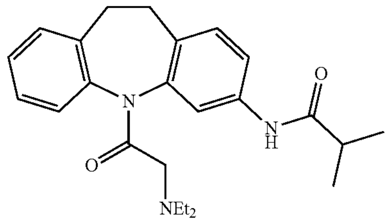 | 410.1 |
| 4 | LTC-103 | 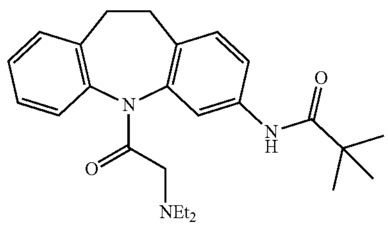 | 424.2 |
| 5 | LTC-104 | 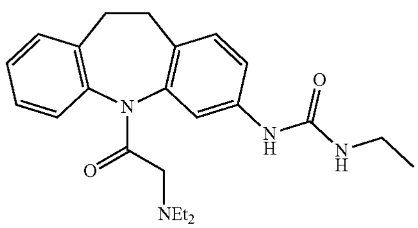 | 395.1 |
| 6 | LTC-105 | 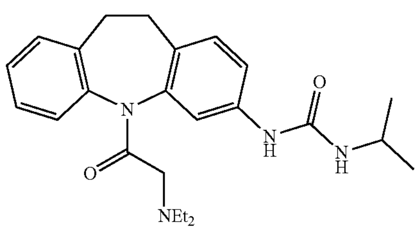 | 409.1 |
| 7 | LTC-106 | 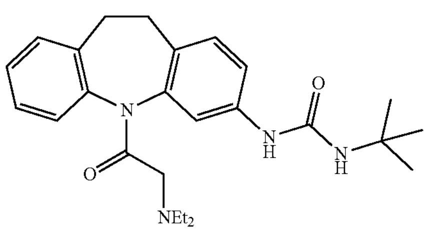 | 423.2 |
| 8 | LTC-107 | 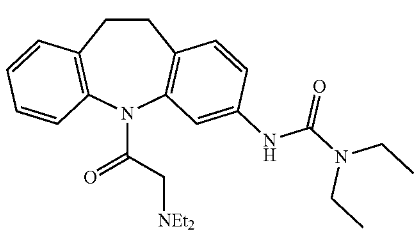 | 423.2 |

TABLE 3-continued
| No. | SJ No. | Structure | LC-MS [M + 1]+ |
|---|---|---|---|
| 9 | LTC-108 | 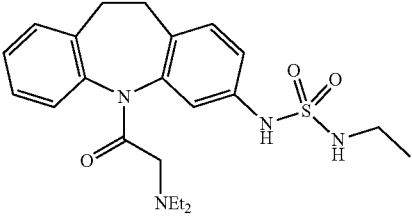 | 431.1 |
| 10 | LTC-109 | 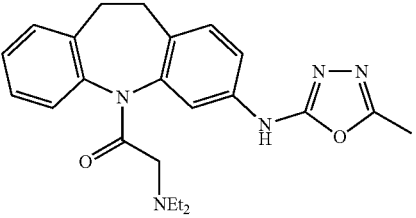 | 406.3 |
| 11 | LTC-121 | 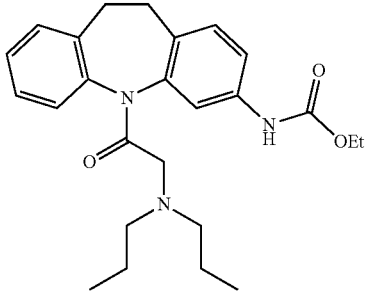 [SMILES: CCCN(CCC)CC(=O)N1c2ccccc2CCc2ccc(NC(=O)OCC)cc21] | 424.2 |
| 12 | LTC-122 | 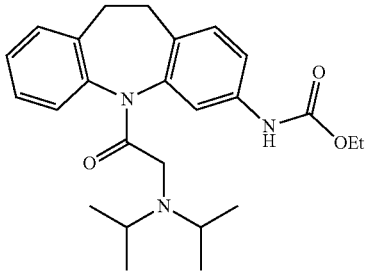 [SMILES: CCOC(=O)Nc1ccc2c(c1)N(C(=O)CN(C(C)C)C(C)C)c1ccccc1CC2] | 424.2 |
| 13 | LTC-124 | 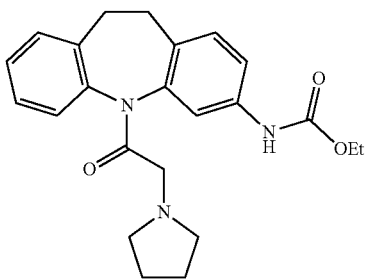 [SMILES: CCOC(=O)Nc1ccc2c(c1)N(C(=O)CN1CCCC1)c1ccccc1CC2] | 394.2 |

TABLE 3-continued
| No. | SJ No. | Structure | LC-MS [M + 1]+ |
|---|---|---|---|
| 14 | LTC-125 | 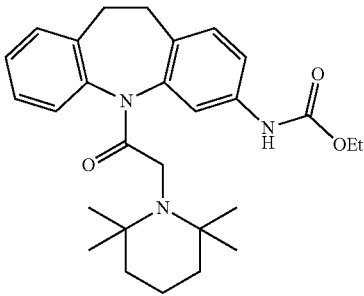 [SMILES: CCOC(=O)Nc1ccc2c(c1)N(C(=O)CN1C(C)(C)CCCC1(C)C)c1ccccc1CC2] | 464.2 |
| 15 | LTC-126 | 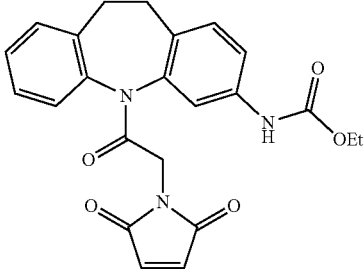 [SMILES: CCOC(=O)Nc1ccc2c(c1)N(C(=O)CN1C(=O)C=CC1=O)c1ccccc1CC2] | 420.2 |
| 16 | LTC-127 | 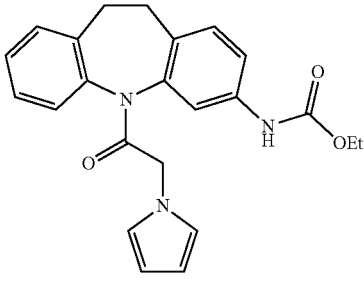 [SMILES: CCOC(=O)Nc1ccc2c(c1)N(C(=O)Cn1cccc1)c1ccccc1CC2] | 390.2 |
| 17 | LTC-128 | 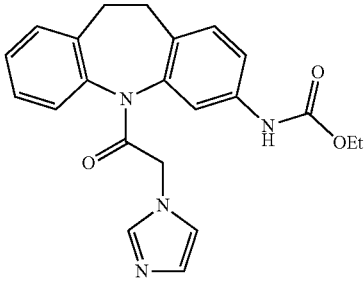 [SMILES: CCOC(=O)Nc1ccc2c(c1)N(C(=O)Cn1ccnc1)c1ccccc1CC2] | 391.2 |
| 18 | LTC-129 | 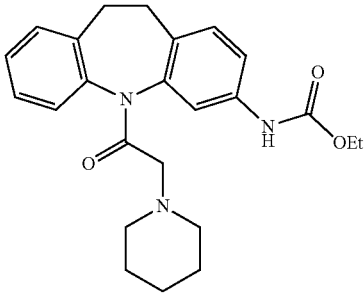 [SMILES: CCOC(=O)Nc1ccc2c(c1)N(C(=O)CN1CCCCC1)c1ccccc1CC2] | 408.1 |

TABLE 3-continued

| No. | SJ No. | Structure | LC-MS [M + 1]⁺ |
|---|---|---|---|
| 19 | LTC-130 | 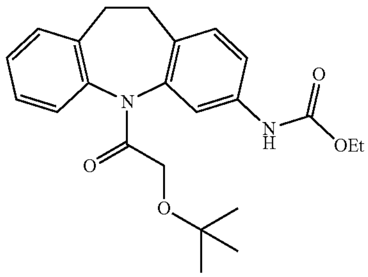 [SMILES: CCOC(=O)Nc1ccc2c(c1)N(C(=O)COC(C)(C)C)c1ccccc1CC2] | 397.1 |
| 20 | LTC-132 | 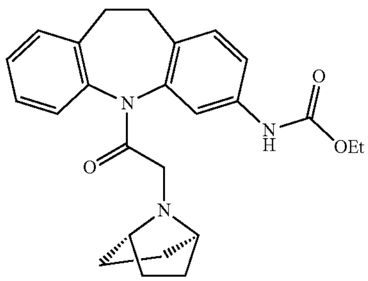 [SMILES: CCOC(=O)Nc1ccc2c(c1)N(C(=O)CN1[C@H]3CC[C@@H]1CC3)c1ccccc1CC2] | 420.1 |
| 21 | LTC-133 | 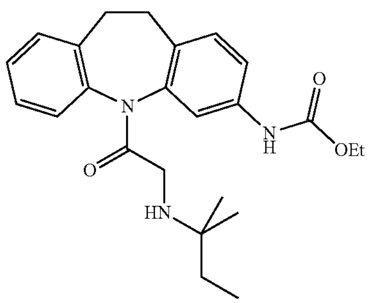 [SMILES: CCOC(=O)Nc1ccc2c(c1)N(C(=O)CNC(C)(C)CC)c1ccccc1CC2] | 410.1 |
| 22 | LTC-141 | 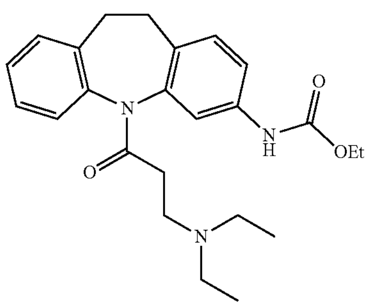 [SMILES: CCOC(=O)Nc1ccc2c(c1)N(C(=O)CCN(CC)CC)c1ccccc1CC2] | 410.2 |
| 23 | LTC-142 | 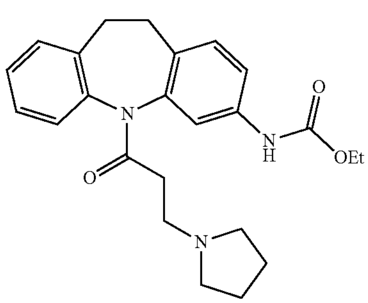 [SMILES: CCOC(=O)Nc1ccc2c(c1)N(C(=O)CCN1CCCC1)c1ccccc1CC2] | 408.1 |

TABLE 3-continued

| No. | SJ No. | Structure | LC-MS [M + 1]+ |
|---|---|---|---|
| 24 | LTC-151 | 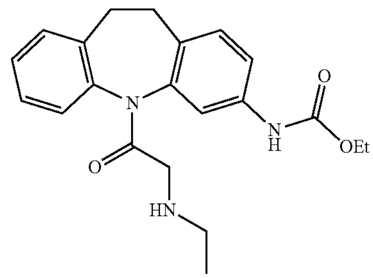 [SMILES: CCNCC(=O)N1c2ccccc2CCc2ccc(NC(=O)OCC)cc21] | 368.1 |
| 25 | LTC-222 | 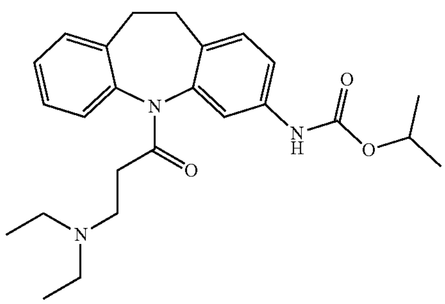 [SMILES: CCN(CC)CCC(=O)N1c2ccccc2CCc2ccc(NC(=O)OC(C)C)cc21] | 424.3 |
| 26 | LTC-211 | 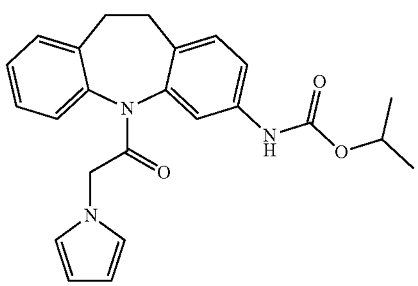 [SMILES: CC(C)OC(=O)Nc1ccc2c(c1)N(C(=O)Cn1cccc1)c1ccccc1CC2] | 404.2 |
| 27 | LTC-214 | 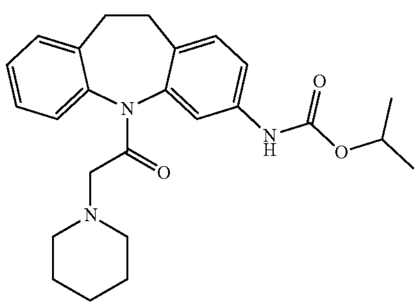 [SMILES: CC(C)OC(=O)Nc1ccc2c(c1)N(C(=O)CN1CCCCC1)c1ccccc1CC2] | 422.2 |
| 28 | LTC-213 | 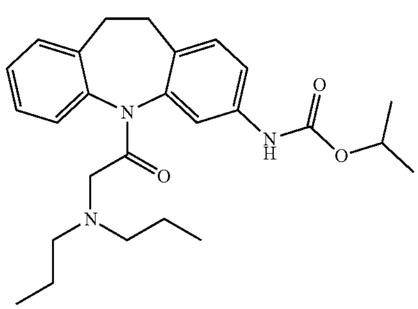 [SMILES: CCCN(CCC)CC(=O)N1c2ccccc2CCc2ccc(NC(=O)OC(C)C)cc21] | 438.3 |

TABLE 3-continued

| No. | SJ No. | Structure | LC-MS [M + 1]+ |
|---|---|---|---|
| 29 | LTC-217 | 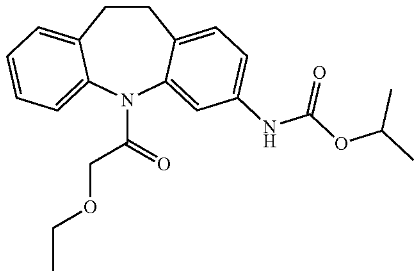 [SMILES: CCOCC(=O)N1c2ccccc2CCc2ccc(NC(=O)OC(C)C)cc21] | 383.2 |
| 30 | LTC-215 | 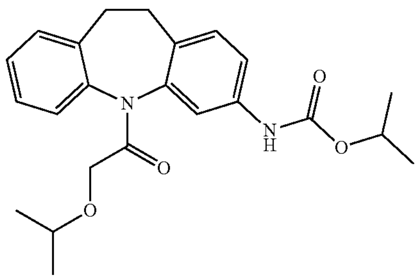 [SMILES: CC(C)OCC(=O)N1c2ccccc2CCc2ccc(NC(=O)OC(C)C)cc21] | 397.2 |
| 31 | LTC-216 | 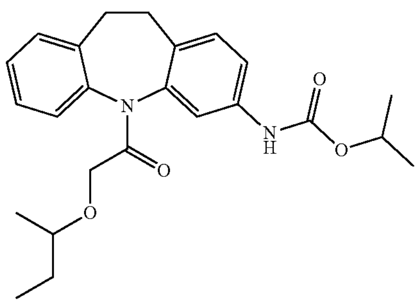 [SMILES: CCC(C)OCC(=O)N1c2ccccc2CCc2ccc(NC(=O)OC(C)C)cc21] | 411.2 |
| 32 | LTC-212 | 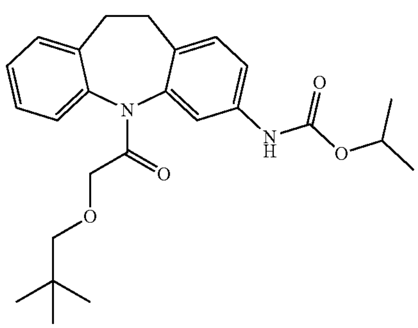 [SMILES: CC(C)OC(=O)Nc1ccc2c(c1)N(C(=O)COCC(C)(C)C)c1ccccc1CC2] | 425.2 |
| 33 | LTC-218 | 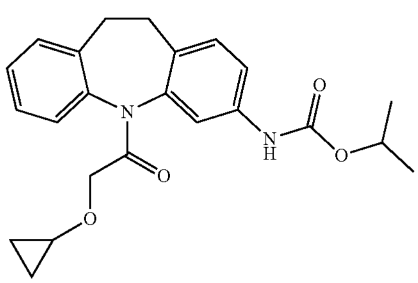 [SMILES: CC(C)OC(=O)Nc1ccc2c(c1)N(C(=O)COC1CC1)c1ccccc1CC2] | 395.2 |

TABLE 3-continued

| No. | SJ No. | Structure | LC-MS [M + 1]+ |
|---|---|---|---|
| 34 | LTC-219 | 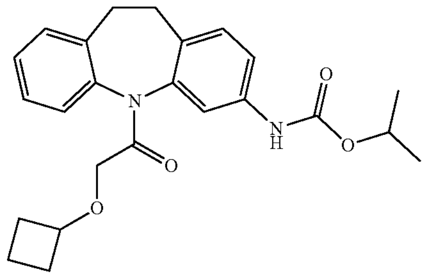 [SMILES: CC(C)OC(=O)Nc1ccc2c(c1)N(C(=O)COC1CCC1)c1ccccc1CC2] | 409.2 |
| 35 | LTC-220 | 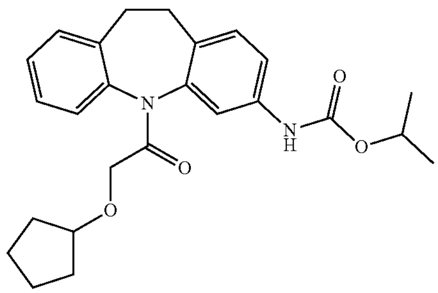 [SMILES: CC(C)OC(=O)Nc1ccc2c(c1)N(C(=O)COC1CCCC1)c1ccccc1CC2] | 423.2 |
| 36 | LTC-221 | 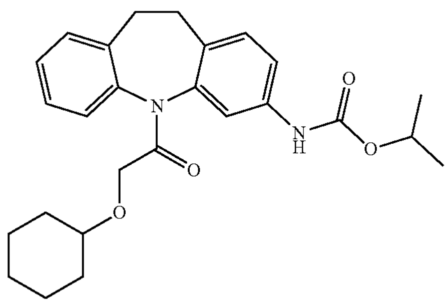 [SMILES: CC(C)OC(=O)Nc1ccc2c(c1)N(C(=O)COC1CCCCC1)c1ccccc1CC2] | 437.2 |
| 37 | LTC-203 | 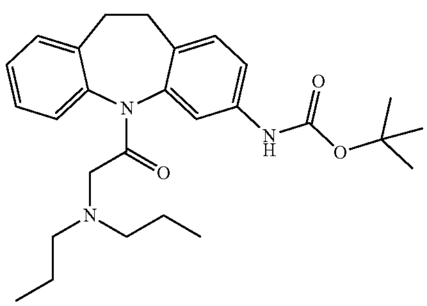 [SMILES: CCCN(CCC)CC(=O)N1c2ccccc2CCc2ccc(NC(=O)OC(C)(C)C)cc21] | 452.3 |
| 38 | LTC-204 | 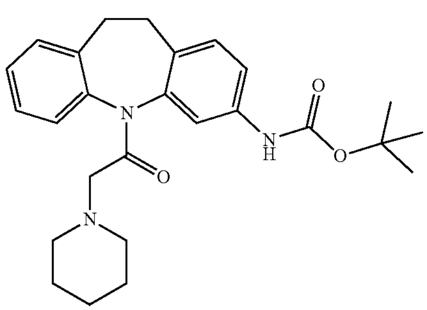 [SMILES: CC(C)(C)OC(=O)Nc1ccc2c(c1)N(C(=O)CN1CCCCC1)c1ccccc1CC2] | 436.3 |

TABLE 3-continued
| No. | SJ No. | Structure | LC-MS [M + 1]+ |
|---|---|---|---|
| 39 | LTC-223 | 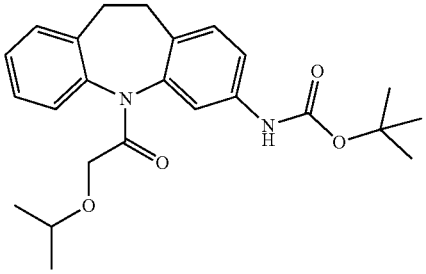 [SMILES: CC(C)OCC(=O)N1c2ccccc2CCc2ccc(NC(=O)OC(C)(C)C)cc21] | 411.2 |
| 40 | LTC-201 | 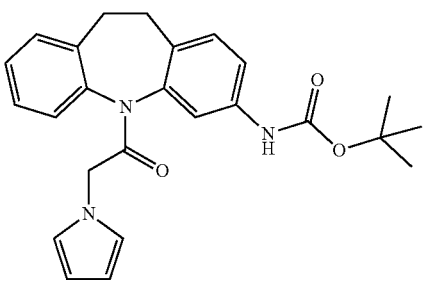 [SMILES: CC(C)(C)OC(=O)Nc1ccc2c(c1)N(C(=O)Cn1cccc1)c1ccccc1CC2] | 440.2 |
| 41 | LTC-231 | 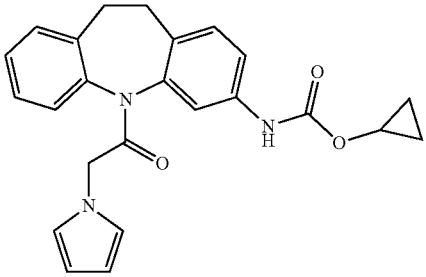 [SMILES: O=C(Nc1ccc2c(c1)N(C(=O)Cn1cccc1)c1ccccc1CC2)OC1CC1] | 402.2 |
| 42 | LTC-232 | 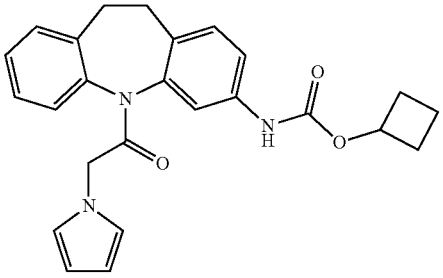 [SMILES: O=C(Nc1ccc2c(c1)N(C(=O)Cn1cccc1)c1ccccc1CC2)OC1CCC1] | 416.2 |
| 43 | LTC-233 | 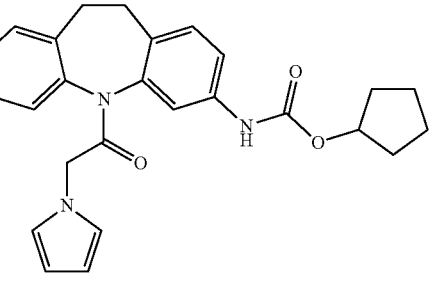 | 430.2 |

TABLE 3-continued

| No. | SJ No. | Structure | LC-MS [M + 1]+ |
|---|---|---|---|
| 44 | LTC-234 | 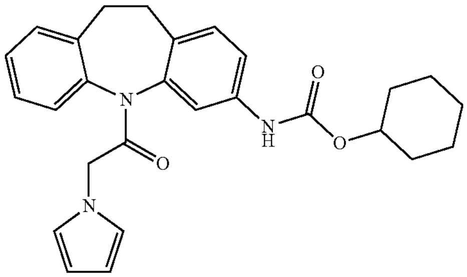 [SMILES: O=C(Nc1ccc2c(c1)N(C(=O)Cn1cccc1)c1ccccc1CC2)OC1CCCCC1] | 444.2 |
| 45 | LTC-301 | 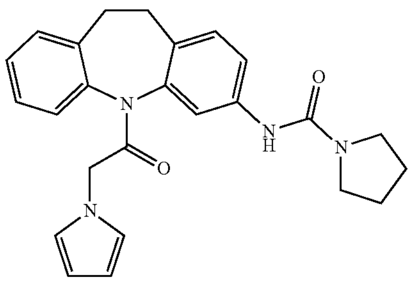 [SMILES: O=C(Nc1ccc2c(c1)N(C(=O)Cn1cccc1)c1ccccc1CC2)N1CCCC1] | 415.3 |
| 46 | LTC-302 | 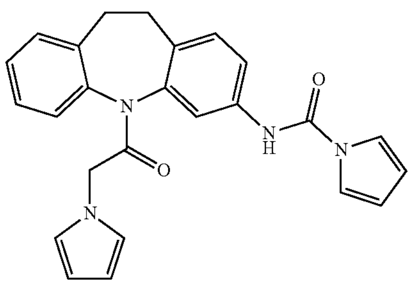 [SMILES: O=C(Cn1cccc1)N1c2ccccc2CCc2ccc(NC(=O)n3cccc3)cc21] | 411.2 |
| 47 | LTC-303 | 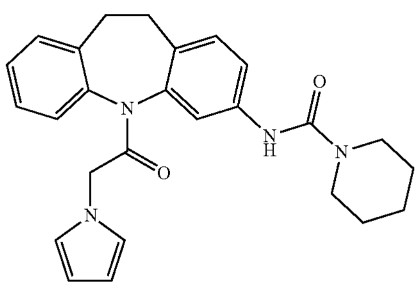 | 429.3 |
| 48 | LTC-304 | 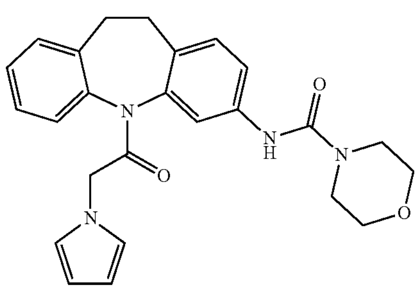 [SMILES: O=C(Nc1ccc2c(c1)N(C(=O)Cn1cccc1)c1ccccc1CC2)N1CCCCC1] | 431.2 |

TABLE 3-continued
| No. | SJ No. | Structure | LC-MS [M + 1]+ |
|---|---|---|---|
| 49 | LTC-311 | 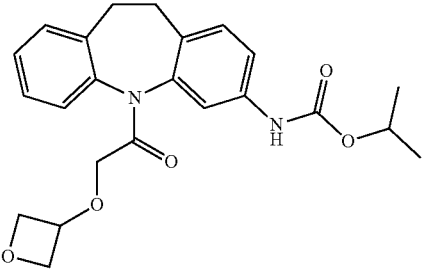 [SMILES: CC(C)OC(=O)Nc1ccc2c(c1)N(C(=O)COC1COC1)c1ccccc1CC2] | 411.3 |
| 50 | LTC-312 | 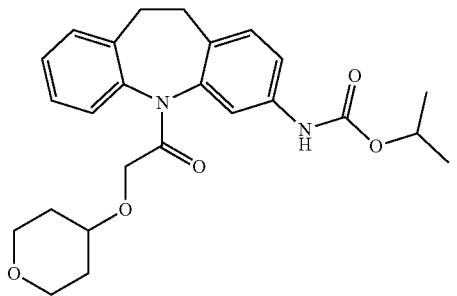 [SMILES: CC(C)OC(=O)Nc1ccc2c(c1)N(C(=O)COC1CCOCC1)c1ccccc1CC2] | 437.2 |
| 51 | LTC-375 | 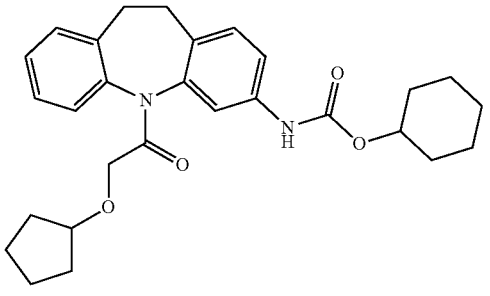 [SMILES: O=C(Nc1ccc2c(c1)N(C(=O)COC1CCCC1)c1ccccc1CC2)OC1CCCCC1] | 463.2 |
| 52 | LTC-333 | 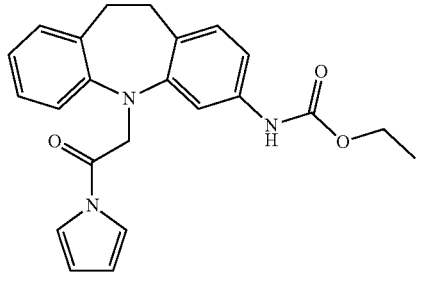 [SMILES: CCOC(=O)Nc1ccc2c(c1)N(CC(=O)n1cccc1)c1ccccc1CC2] | 404.1 |
| 53 | LTC-334 | 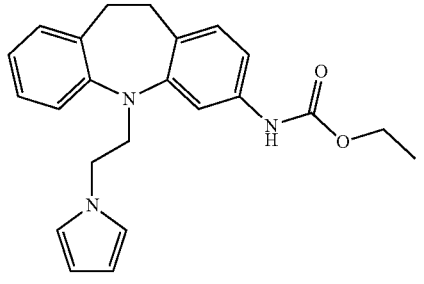 [SMILES: CCOC(=O)Nc1ccc2c(c1)N(CCn1cccc1)c1ccccc1CC2] | 390.3 |

TABLE 3-continued

| No. | SJ No. | Structure | LC-MS [M + 1]+ |
|---|---|---|---|
| 54 | LTC-361 | 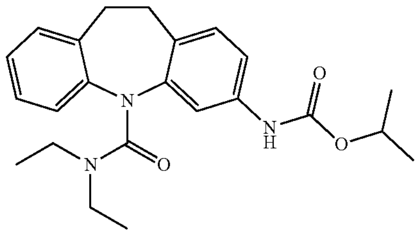 [SMILES: CCN(CC)C(=O)N1c2ccccc2CCc2ccc(NC(=O)OC(C)C)cc21] | 396.3 |
| 55 | LTC-363 | 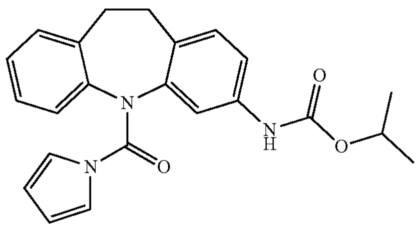 [SMILES: CC(C)OC(=O)Nc1ccc2c(c1)N(C(=O)n1cccc1)c1ccccc1CC2] | 390.1 |
| 56 | LTC-364 | 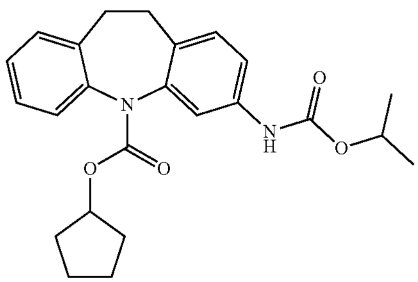 [SMILES: CC(C)OC(=O)Nc1ccc2c(c1)N(C(=O)OC1CCCC1)c1ccccc1CC2] | 409.3 |
| 57 | LTC-365 | 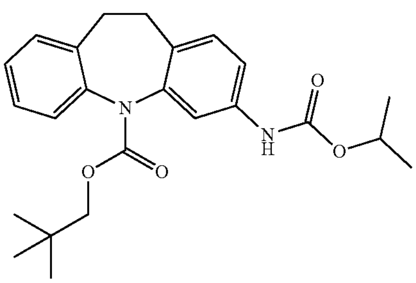 [SMILES: CC(C)OC(=O)Nc1ccc2c(c1)N(C(=O)OCC(C)(C)C)c1ccccc1CC2] | 411.3 |
| 58 | LTC-371 | 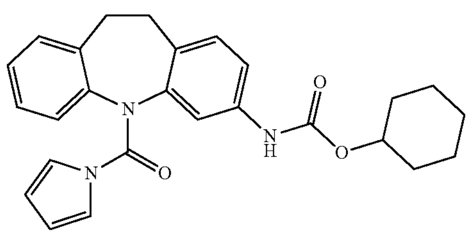 [SMILES: O=C(Nc1ccc2c(c1)N(C(=O)n1cccc1)c1ccccc1CC2)OC1CCCCC1] | 430.2 |
| 59 | LTC-372 | 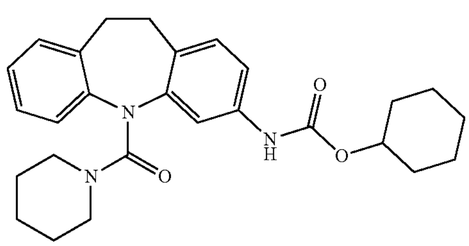 [SMILES: O=C(Nc1ccc2c(c1)N(C(=O)N1CCCCC1)c1ccccc1CC2)OC1CCCCC1] | 448.2 |

TABLE 3-continued

| No. | SJ No. | Structure | LC-MS [M + 1]+ |
|---|---|---|---|
| 60 | LTC-373 | 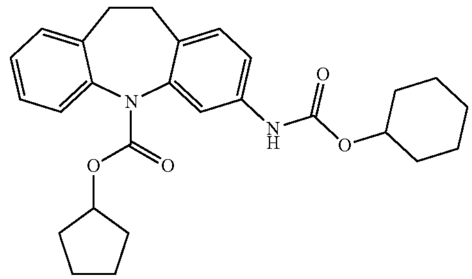 [SMILES: O=C(Nc1ccc2c(c1)N(C(=O)OC1CCCC1)c1ccccc1CC2)OC1CCCCC1] | 449.2 |
| 61 | LTC-374 | 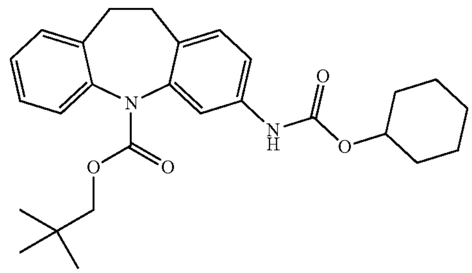 [SMILES: CC(C)(C)COC(=O)N1c2ccccc2CCc2ccc(NC(=O)OC3CCCCC3)cc21] | 451.2 |
| 62 | LTC-401 | 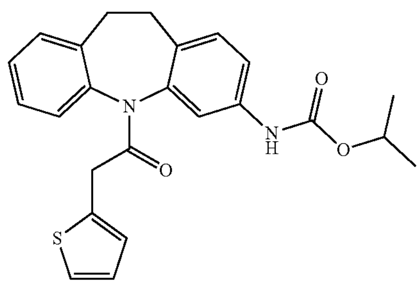 [SMILES: CC(C)OC(=O)Nc1ccc2c(c1)N(C(=O)Cc1cccs1)c1ccccc1CC2] | 421.2 |
| 63 | LTC-402 | 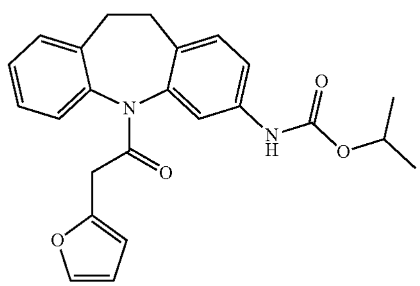 | 405.3 |
| 64 | LTC-405 | 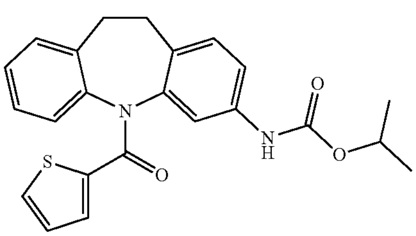 | 407.1 |
| 65 | LTC-406 | 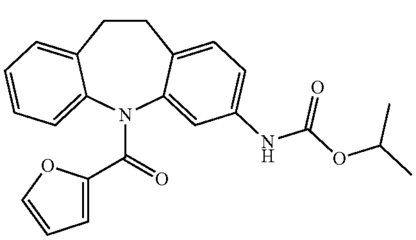 [SMILES: CC(C)OC(=O)Nc1ccc2c(c1)N(C(=O)c1ccco1)c1ccccc1CC2] | 391.1 |

TABLE 3-continued

| No. | SJ No. | Structure | LC-MS [M + 1]+ |
|---|---|---|---|
| 66 | LTC-403 | 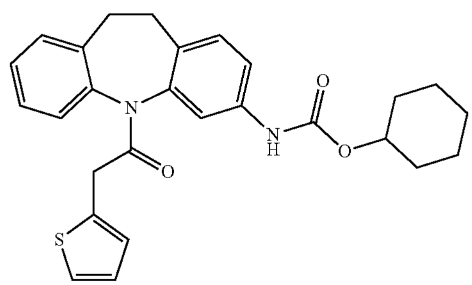 [SMILES: O=C(Nc1ccc2c(c1)N(C(=O)Cc1cccs1)c1ccccc1CC2)OC1CCCCC1] | 461.2 |
| 67 | LTC-404 | 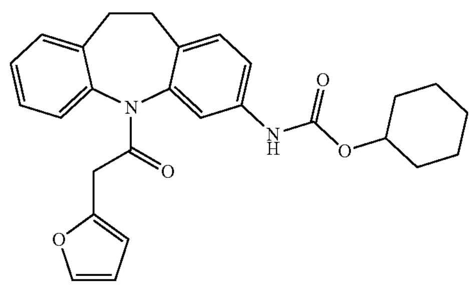 [SMILES: O=C(Nc1ccc2c(c1)N(C(=O)Cc1ccco1)c1ccccc1CC2)OC1CCCCC1] | 445.2 |
| 68 | LTC-407 | 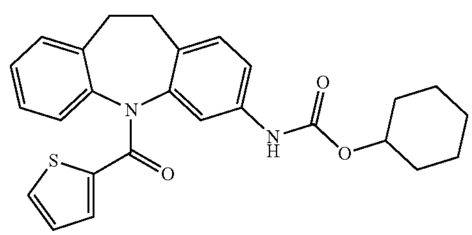 [SMILES: O=C(Nc1ccc2c(c1)N(C(=O)c1cccs1)c1ccccc1CC2)OC1CCCCC1] | 447.1 |
| 69 | LTC-408 | 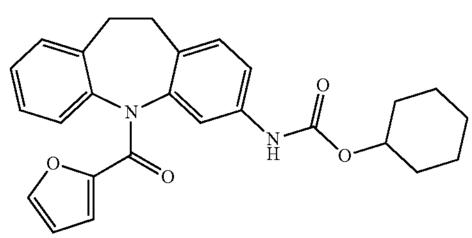 | 431.2 |
| 70 | LTC-27 | 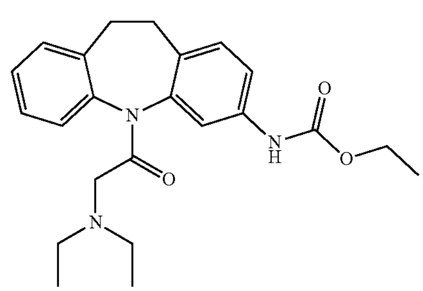 [SMILES: CCOC(=O)Nc1ccc2c(c1)N(C(=O)CN(CC)CC)c1ccccc1CC2] | 396.2 |

TABLE 3-continued

| No. | SJ No. | Structure | LC-MS [M + 1]+ |
|---|---|---|---|
| 71 | | 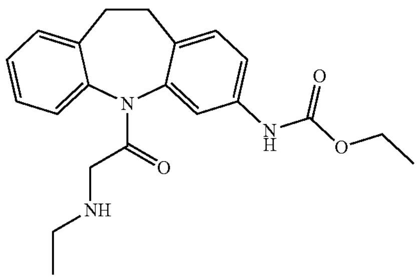 [SMILES: CCNCC(=O)N1c2ccccc2CCc2ccc(NC(=O)OCC)cc21] | Not determined |
| 72 | | 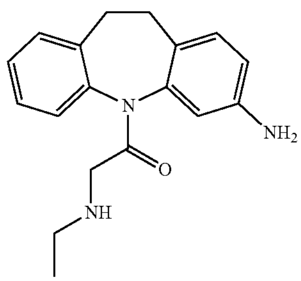 [SMILES: CCNCC(=O)N1c2ccccc2CCc2ccc(N)cc21] | 296.1 |
| 73 | | 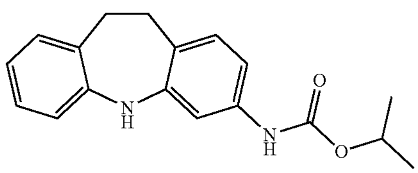 [SMILES: CC(C)OC(=O)Nc1ccc2c(c1)Nc1ccccc1CC2] | 297.2 |
| 74 | | 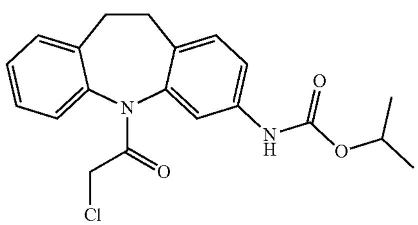 [SMILES: CC(C)OC(=O)Nc1ccc2c(c1)N(C(=O)CCl)c1ccccc1CC2] | 373.1 |
| 75 | | 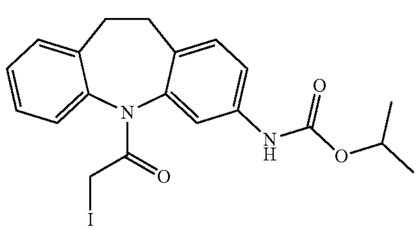 [SMILES: CC(C)OC(=O)Nc1ccc2c(c1)N(C(=O)CI)c1ccccc1CC2] | 465.1 |
| 76 | | 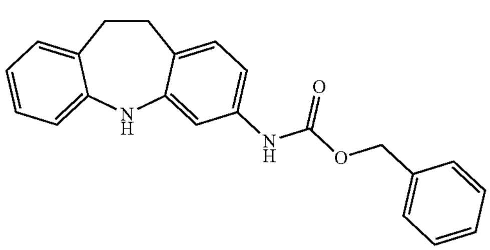 [SMILES: O=C(Nc1ccc2c(c1)Nc1ccccc1CC2)OCc1ccccc1] | |

TABLE 3-continued

| No. | SJ No. | Structure | LC-MS [M + 1]+ |
|---|---|---|---|
| 77 | | 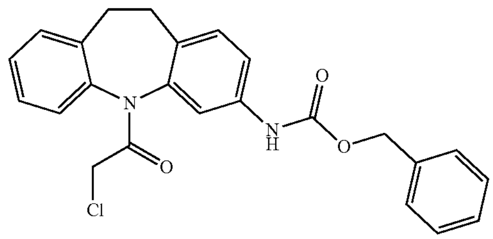 [SMILES: O=C(Nc1ccc2c(c1)N(C(=O)CCl)c1ccccc1CC2)OCc1ccccc1] | 420.1 |
| 78 | | 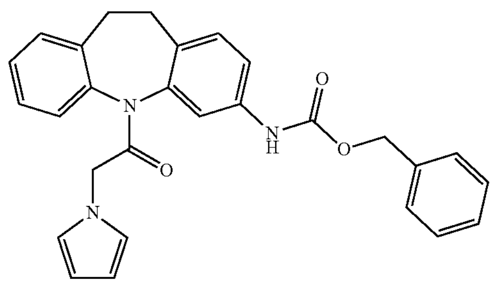 [SMILES: O=C(Nc1ccc2c(c1)N(C(=O)Cn1cccc1)c1ccccc1CC2)OCc1ccccc1] | 452.1 |
| 79 | | 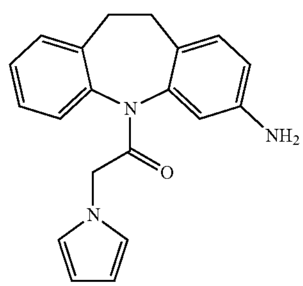 [SMILES: Nc1ccc2c(c1)N(C(=O)Cn1cccc1)c1ccccc1CC2] | 318.1 |

4. Activity of Substituted 1-(3-amino)-10,11-dihydro-5H-dibenzo[b,f]azepin-5-yl)alkan-1-ones in the CoAct Binding Inverse Agonist Assay Substituted 1-(3-amino)-10,11-dihydro-5H-dibenzo[b,f]azepin-5-yl)alkan-1-one analogs were synthesized as described above. Activity was determined in the CoAct binding inverse agonist assay as described above, and the data are shown in Table 4. The compound number corresponds to the compound numbers used in Table 3 and the experimental examples described above.

TABLE 4

| No. | % Inhibition (70 μM) | IC$_{50}$ (μM) |
|---|---|---|
| 1 | 116.2 | 0.69 |
| 2 | 105.9 | 2.32 |
| 3 | 113.8 | 0.68 |
| 4 | 112.8 | 1.03 |
| 5 | 94.9 | 14.42 |
| 6 | 106.8 | 4.93 |
| 7 | 101.4 | 12.97 |
| 8 | 93.8 | 13.99 |
| 9 | 92.0 | 19.09 |
| 10 | 93.8 | 18.79 |
| 11 | 112.8 | 0.21 |
| 12 | 110.5 | 3.05 |
| 13 | 115.3 | 1.58 |
| 14 | 90.5 | 4.08 |
| 15 | 76.0 | 39.81 |
| 16 | 121.2 | 0.037 |
| 17 | 101.2 | 6.89 |
| 18 | 118.8 | 0.62 |
| 19 | 119.7 | 0.071 |
| 20 | 118.2 | 1.41 |
| 21 | 116.2 | 2.06 |
| 22 | 118.6 | 2.43 |
| 23 | 117.7 | 3.18 |
| 24 | 88.4 | 24.49 |
| 25 | — | 6.40 |
| 26 | — | 0.021 |
| 27 | — | 0.25 |
| 28 | — | 0.12 |
| 29 | — | 11.35 |
| 30 | — | 0.060 |
| 31 | — | 0.035 |
| 32 | — | 0.021 |
| 33 | — | 0.082 |
| 34 | — | 0.038 |
| 35 | — | 0.020 |
| 36 | — | 0.024 |
| 37 | — | 0.153 |
| 38 | — | 0.22 |
| 39 | — | 0.12 |
| 40 | — | 0.032 |
| 41 | — | 0.022 |
| 42 | — | 0.020 |
| 43 | — | 0.014 |
| 44 | — | 0.012 |
| 45 | — | 0.28 |
| 46 | — | 0.081 |

TABLE 4-continued

| No. | % Inhibition (70 μM) | IC$_{50}$ (μM) |
|---|---|---|
| 47 | — | 0.099 |
| 48 | — | 0.37 |
| 49 | — | 0.66 |
| 50 | — | 0.021 |
| 51 | — | 0.065 |
| 52 | — | 1.17 |
| 53 | — | 0.31 |
| 54 | — | 0.019 |
| 55 | — | 0.018 |
| 56 | — | 0.016 |
| 57 | — | 0.025 |
| 58 | — | 0.014 |
| 59 | — | 0.15 |
| 60 | — | 0.017 |
| 61 | — | 0.041 |
| 62 | — | 0.021 |
| 63 | — | 0.037 |
| 64 | — | 0.012 |
| 65 | — | 0.075 |
| 66 | — | 0.026 |
| 67 | — | 0.031 |
| 68 | — | 0.019 |
| 69 | — | 0.050 |
| 70 | 104.8 | 0.62 |
| 71 | 77.6 | 28.00 |
| 72 | 27.0 | NA |
| Clotrimazole | 100 (42 μM) | 0.12 |

5. Activity of Substituted 1-(3-amino)-10,11-dihydro-5H-dibenzo[b,f]azepin-5-yl)alkan-1-ones in the Cell-Based Inverse Agonist Assay Substituted 1-(3-amino)-10,11-dihydro-5H-dibenzo[b,f]azepin-5-yl)alkan-1-one analogs were synthesized as described above. Activity was determined in the cell-based inverse agonist assay as described above, and the data are shown in Table 5. The compound number corresponds to the compound numbers used in Table 3 and the experimental examples described above.

TABLE 5

| No. | % Inhibition (56 μM) | IC$_{50}$ (μM) |
|---|---|---|
| 1 | 0.07923 | 105.5 |
| 2 | 0.1737 | 104.3 |
| 3 | 0.03612 | 104.4 |
| 4 | 0.1431 | 103.9 |
| 5 | 3.693 | 107.8 |
| 6 | 0.4332 | 105.4 |
| 7 | 0.761 | 103.3 |
| 8 | 2.849 | 109.6 |
| 9 | 4.757 | 105.9 |
| 10 | 6.281 | 111.6 |
| 11 | 0.05814 | 101.8 |
| 12 | 0.2391 | 104.7 |
| 13 | 0.1175 | 106 |
| 14 | 10.17 | 126.3 |
| 15 | 52.13 | 197.4 |
| 16 | 0.001597 | 103.4 |
| 17 | 1.331 | 103.4 |
| 18 | 0.03154 | 104.2 |
| 19 | 0.01306 | 102.1 |
| 20 | 0.2644 | 107.1 |
| 21 | 0.7665 | 112.2 |
| 22 | 0.08167 | 105.3 |
| 23 | 0.3822 | 110.9 |
| 24 | 8.019 | 112.2 |
| Clotrimazole | 25.71 | 140.7 |

6. Identification of CINPA1 as an Inhibitor of CAR-Mediated Transactivation

Figure 1B:
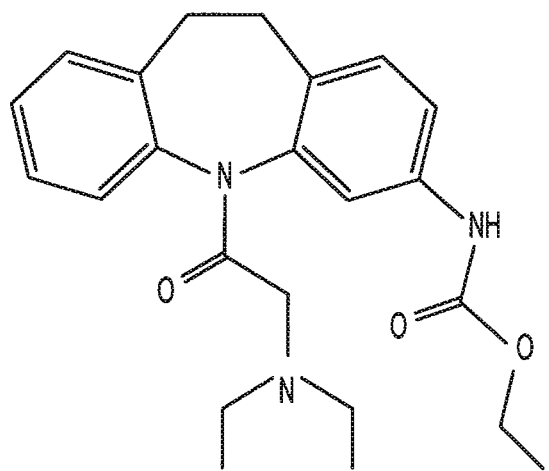
FIG. 1B shows the structure of the compound referred to herein throughout as CINPA1.
Figure 2A:
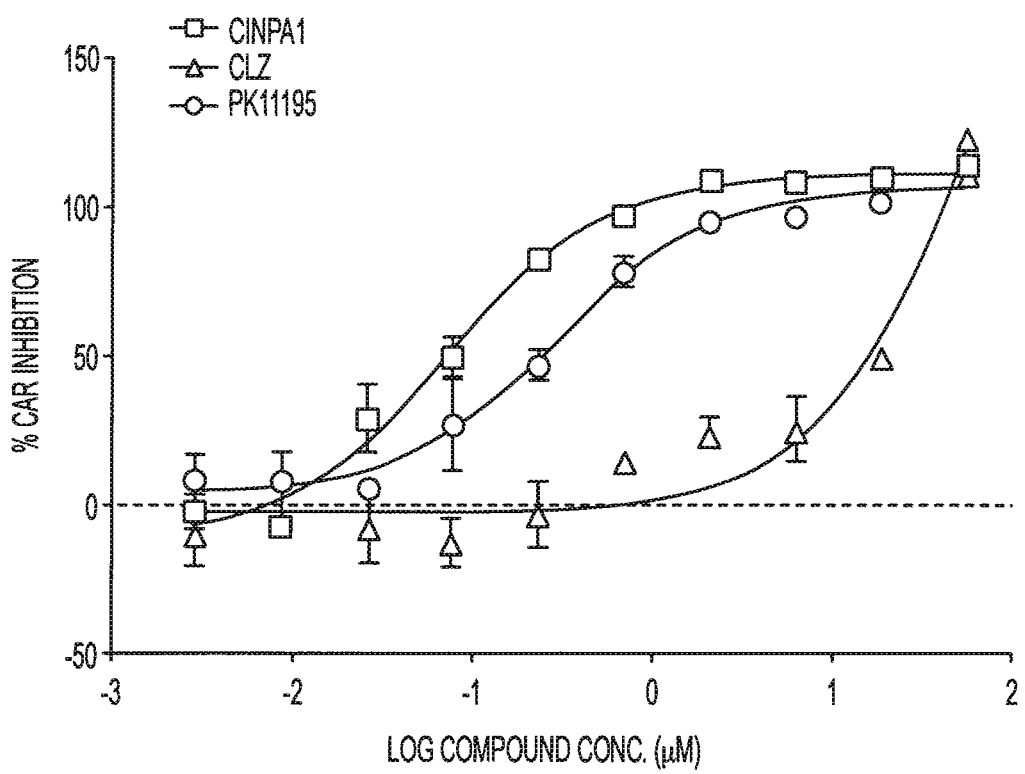
FIG. 2A and FIG. 2B show representative data demonstrating that CINPA1 inhibits CAR-mediated transactivation without activating PXR.
Figure 2B:
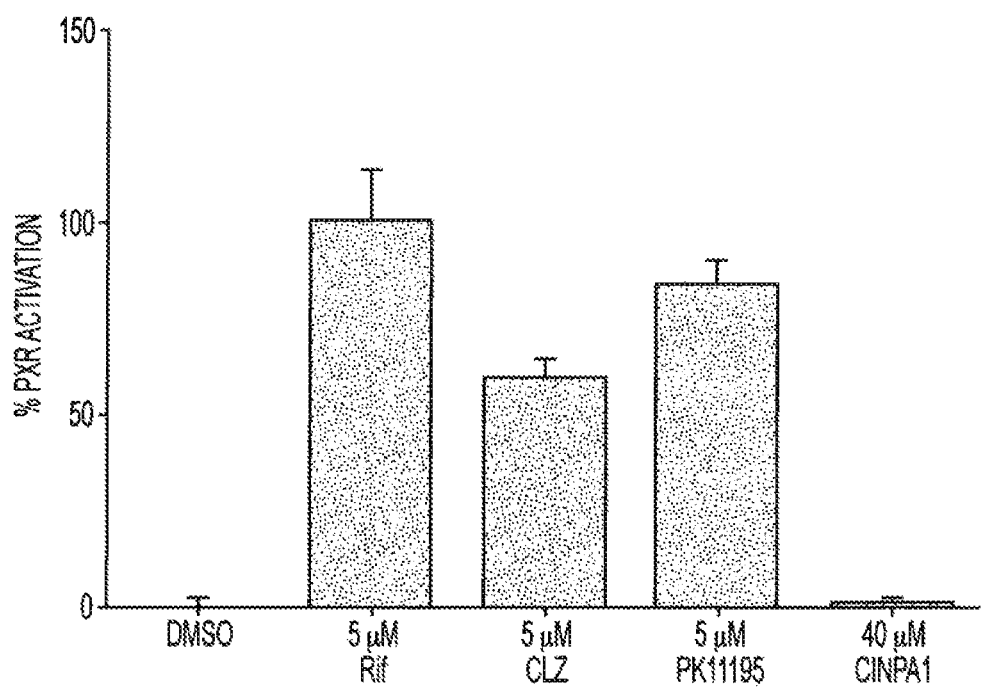
Figure 3A:
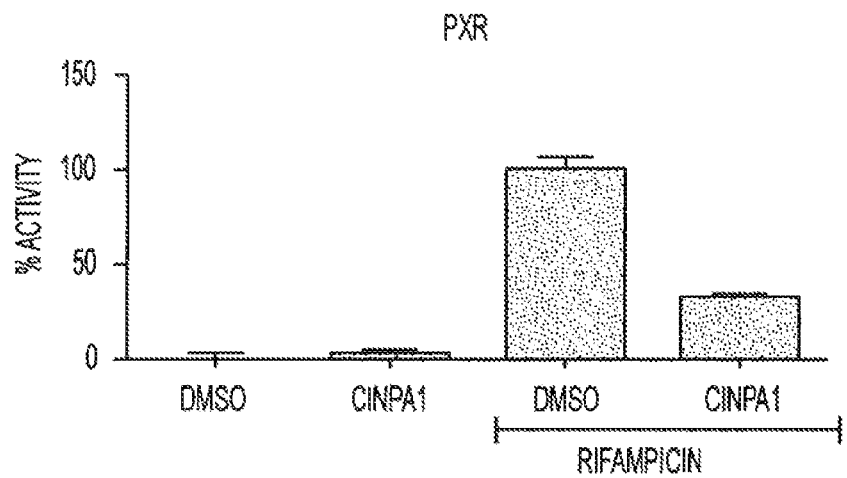
FIG. 3A-FIG. 3I show representative data demonstrating that CINPA a weak antagonist of PXR but does not modulate the activity of other nuclear receptors.
Figure 3B:
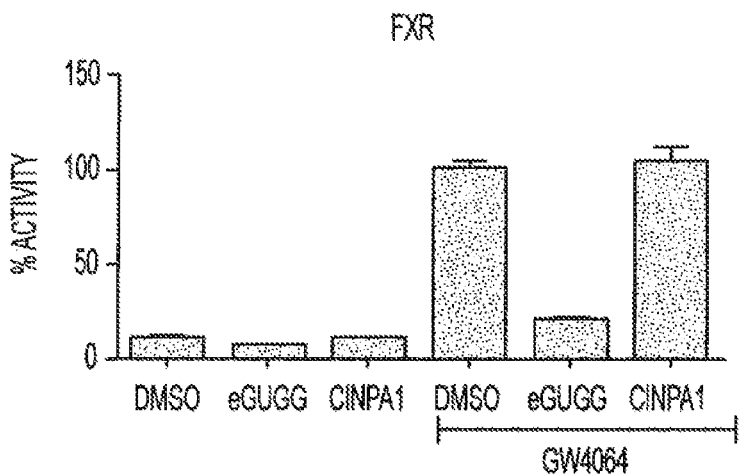
Figure 3C:
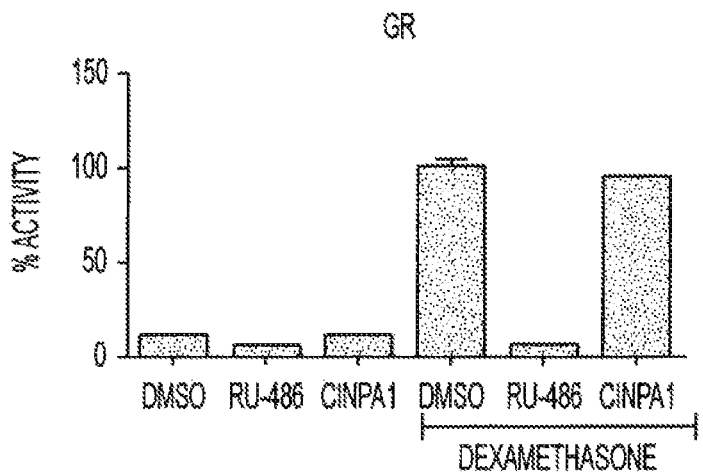
Figure 3D:
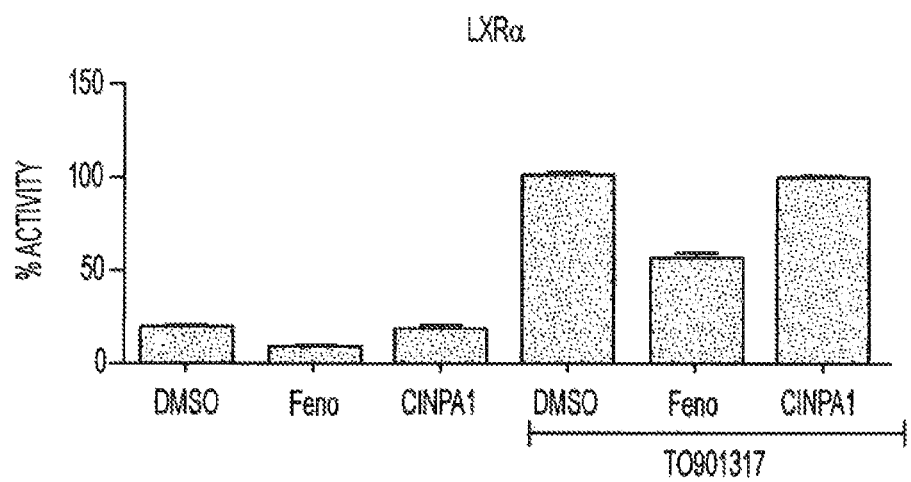
Figure 3E:
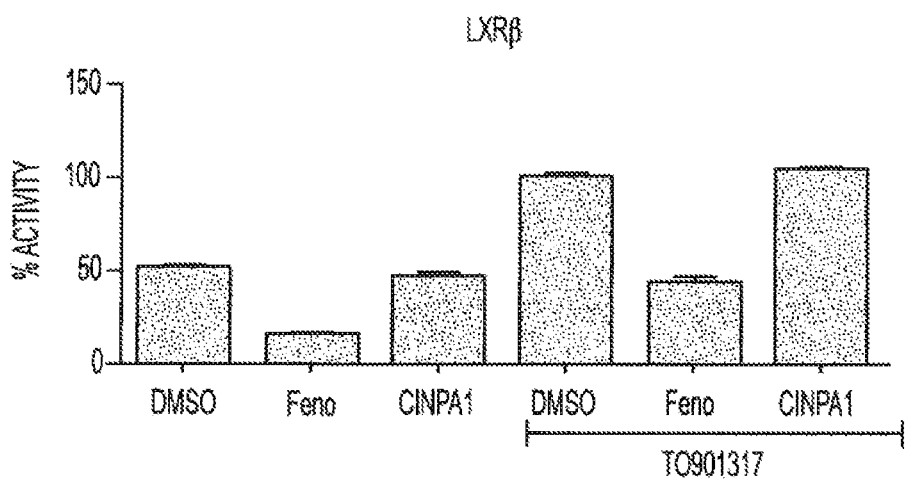
Figure 3F:
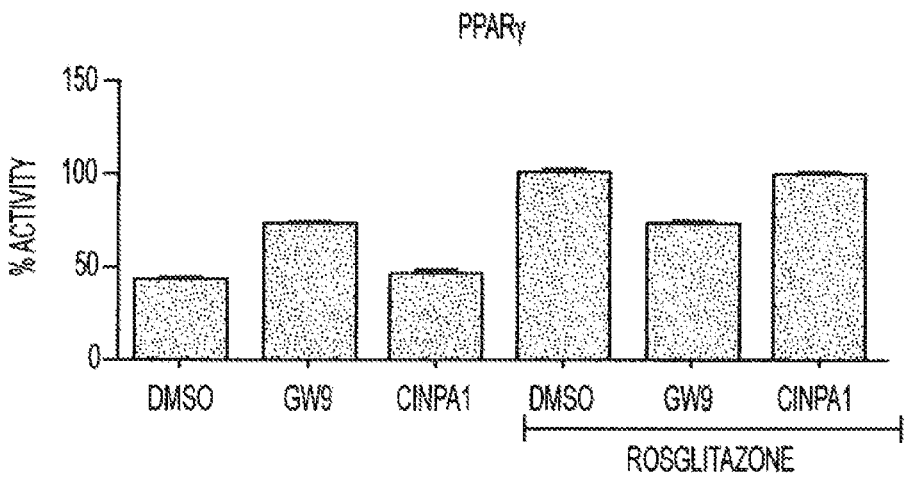
Figure 3G:
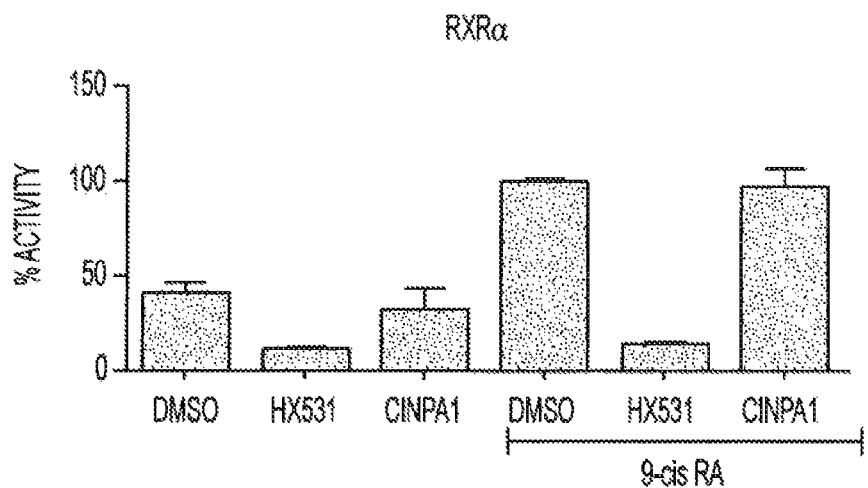
Figure 3H:
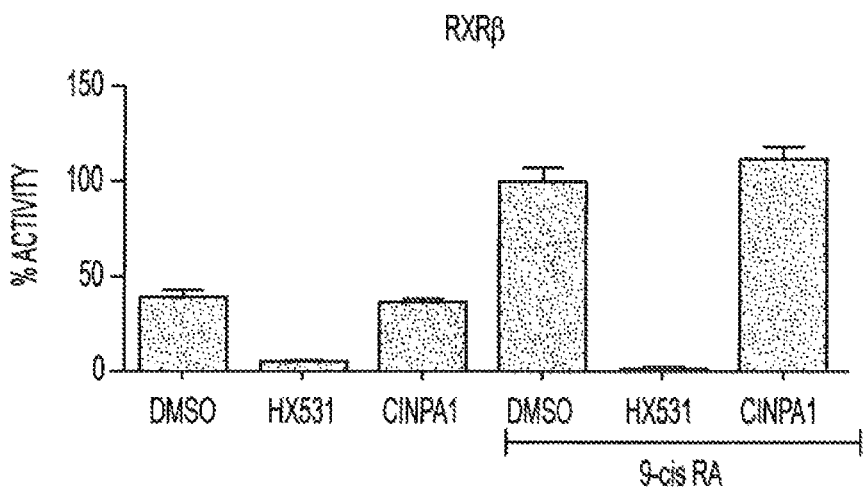
Figure 3I:
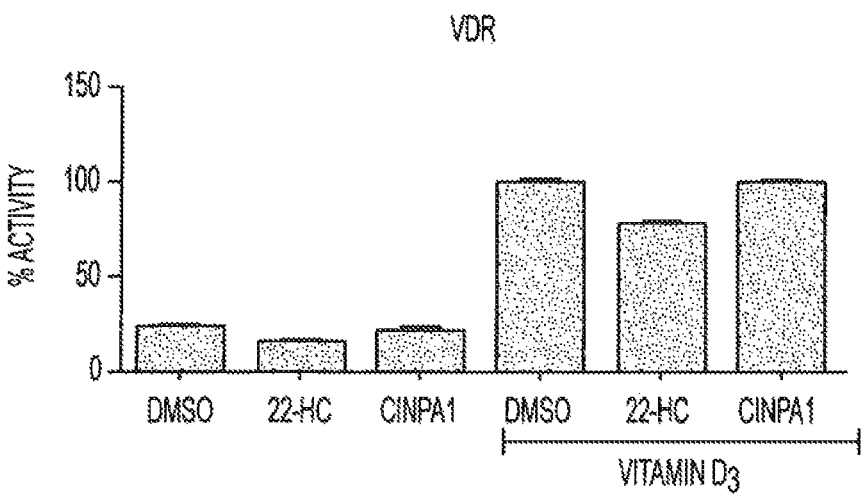
Figure 4A:
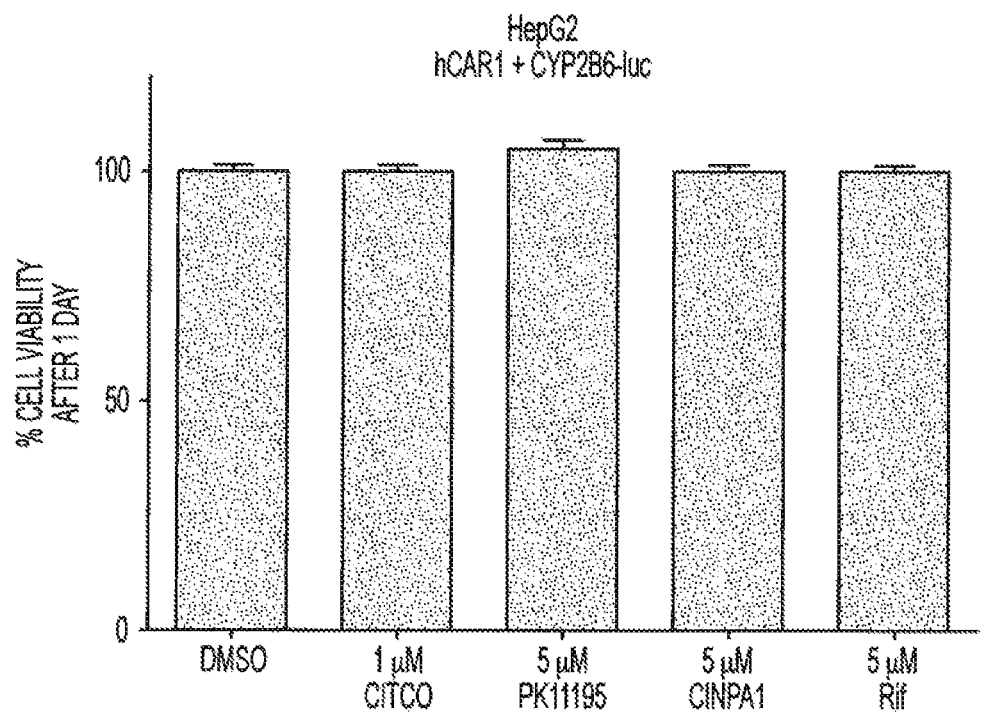
FIG. 4A and FIG. 4B show representative data demonstrating that CINPA1 is not cytotoxic within the concentration range effective for modulating CAR and PXR.
Figure 4B:
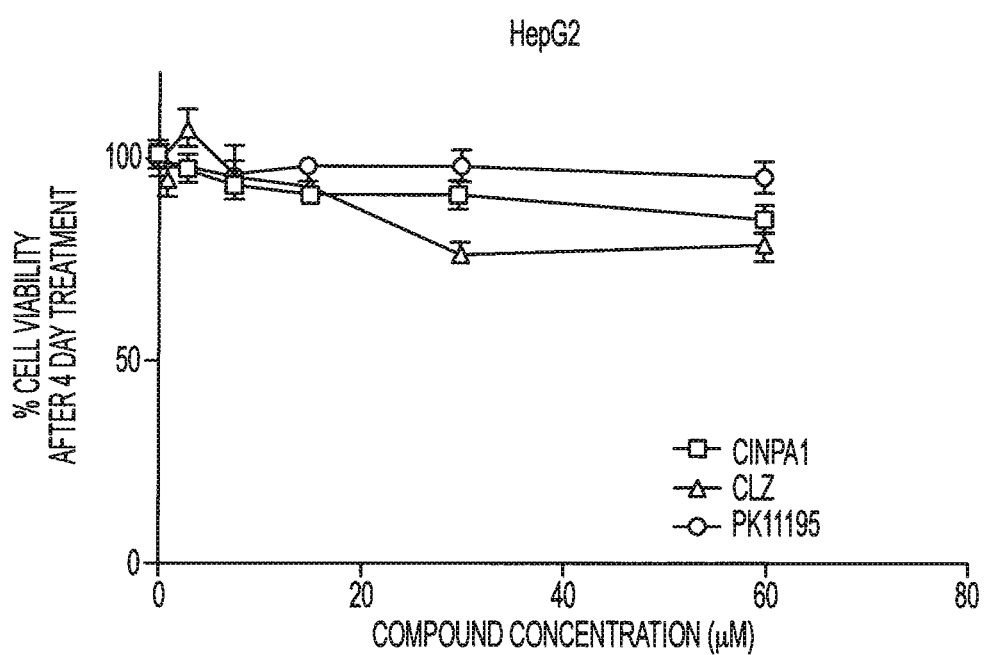
Figure 4C:
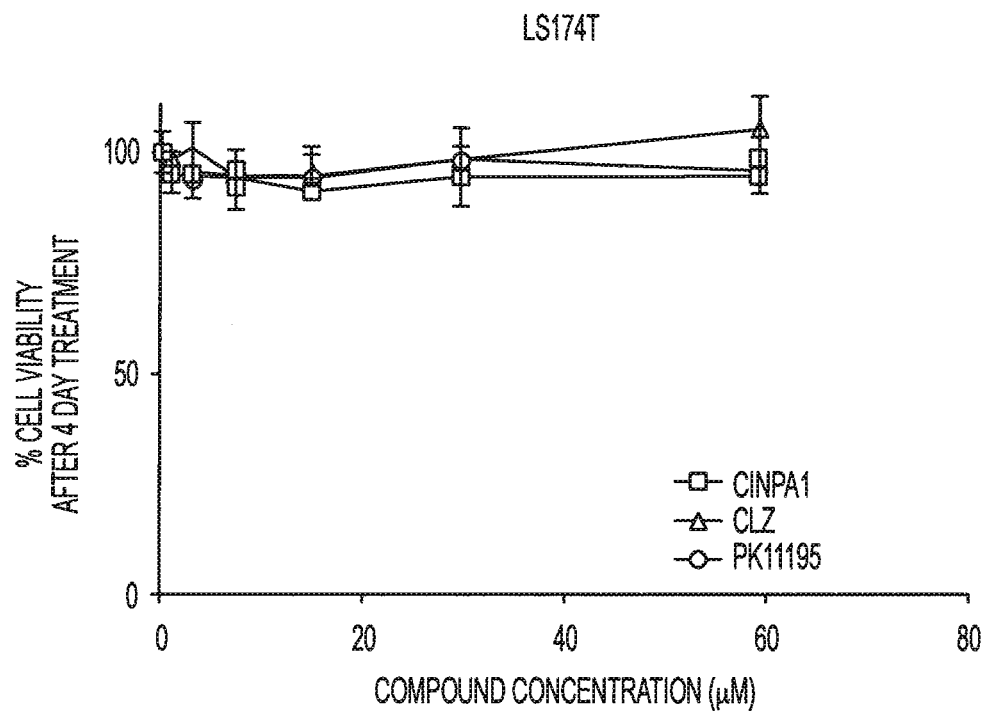
Figure 4D:
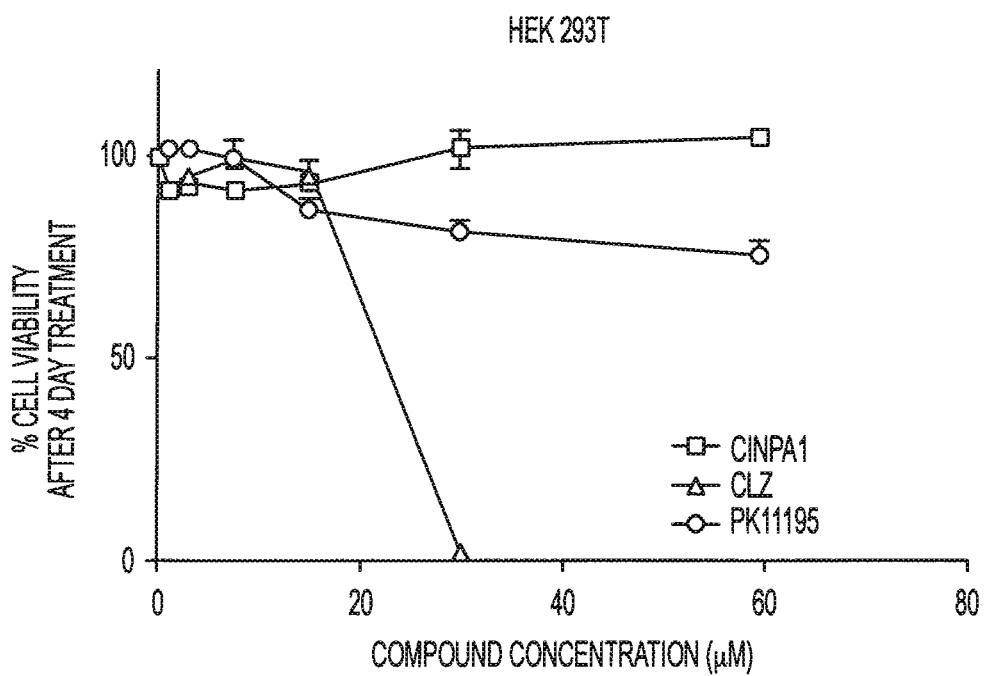
Figure 10A:
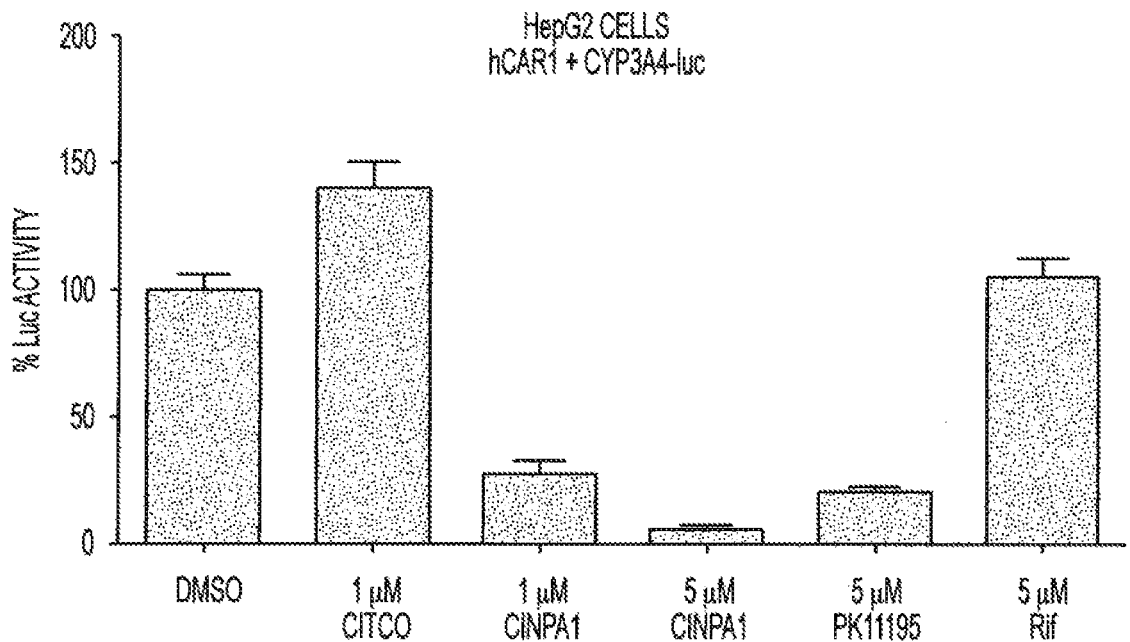
FIG. 10A-FIG. 10C show representative data demonstrating CINPA1 inhibits CAR or PXR-mediated luciferase activity.
Figure 10B:
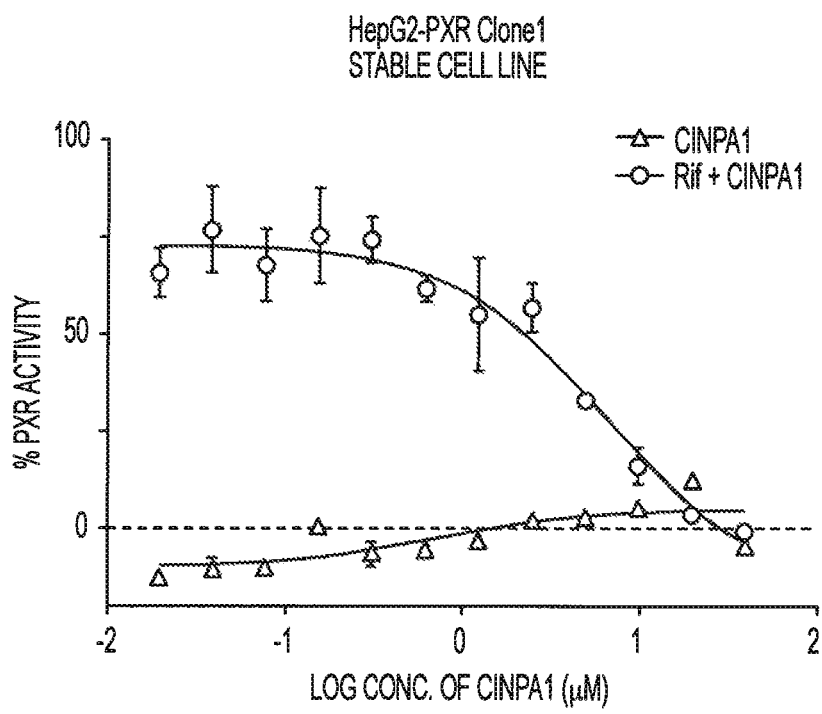

In order to identify CAR inhibitors that are not agonists of PXR, the primary screen was performed using a dose-response library of ~1000 chemicals previously identified as possible antagonists of PXR in a dose-responsive format. A flowchart of our screening strategy is illustrated in FIG. 1A. HepG2 cells were transiently transfected with pcDNA-hCAR1 and CYP2B6-luciferase plasmids and treated with varying concentrations of the test compounds in 384-well plates for 24 h, and CAR-mediated luciferase activity was measured. Twenty-five hits, defined as those displaying dose-responsive inhibitory effect on the constitutively active hCAR1, were selected and tested in various secondary screening assays. CINPA1 (FIG. 1B) was selected based on its potent inhibitory effect on hCAR1 and lack of detectable agonistic activity against PXR. CINPA1 inhibited CAR-mediated CYP2B6-luciferase activity with an IC$_{50}$ of 72 nM, which is slightly more potent than PK11195 (FIG. 2A). CINPA1 inhibition of CAR was not limited to the CYP2B6 gene but was also seen in CAR-mediated CYP3A4-luciferase activity (FIG. 10A). In contrast to other known CAR inhibitors such as PK11195 (PK) and clotrimazole (CLZ), CINPA1, even at 40 μM, did not exhibit any agonistic effect on PXR-regulated gene expression (FIG. 2B and FIG. 10B).

7. CINPA1 a Potent CAR-Specific Inhibitor and a Weak Antagonist of PXR

CAR and PXR have flexible ligand binding pockets (Wu, B., et al. (2013) *Drug Discov. Today* 18, 574-581) that allows binding of many different chemical core structures. CAR inhibitors identified in the past had limitations because of their PXR agonistic effect, which made them less useful for dissecting CAR-specific gene manipulations, especially in the context of genes regulated by many nuclear receptors. We evaluated CINPA in a panel of GeneBlazer cells individually expressing the ligand-binding domains of selected nuclear receptors closely related to PXR or CAR: FXR, GR, LXRα, LXRβ, PPARγ, RXRα, RXRβ or VDR, fused to the GAL4-DNA binding domain (GAL4-DBD).

CINPA1 did not activate any of the nuclear receptors tested (FIGS. 3A-I). CINPA1 is a weak antagonist of PXR with an estimated IC$_{50}$ value of 6.6 μM in a stable HepG2 cell line co-expressing PXR and a CYP3A4-luciferase plasmid (HepG2-PXR Clone 1 as previously described in (Li, G., et al. (2012) *Toxicol. Appl. Pharmacol.* 258, 268-274; and Lin, W., et al. (2998) *J. Biol. Chem.* 283, 30650-30657). The data are shown in FIG. 10B. Whereas CINPA1 weakly inhibited PXR-mediated gene expression (FIG. 3A), it did not attenuate the agonist-induced activation of any of the receptors tested in the GeneBLAzer assays (FIGS. 3B-I).

Within the concentration range effective in inhibiting CAR and PXR, CINPA1 does not exhibit general cytotoxicity in any of the cells lines evaluated in an extended 4-day cell viability assay (FIGS. 4A-D). At higher concentrations (30 μM and 60 μM), all compounds tested, i.e., CINPA1, clotrimazole, and PK11195, were cytotoxic to varying degrees in different cell lines.

Figure 5A:
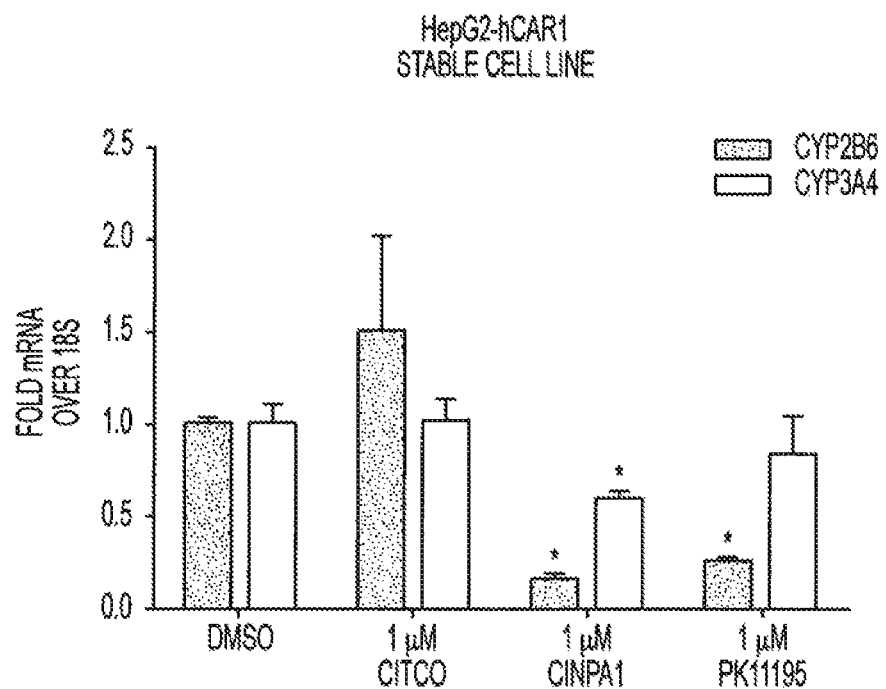
FIG. 5A-FIG. 5E show representative data demonstrating that CINPA1 attenuates CAR-mediated gene expression in CAR-expressing cell lines and human primary hepatocytes.
Figure 11A:
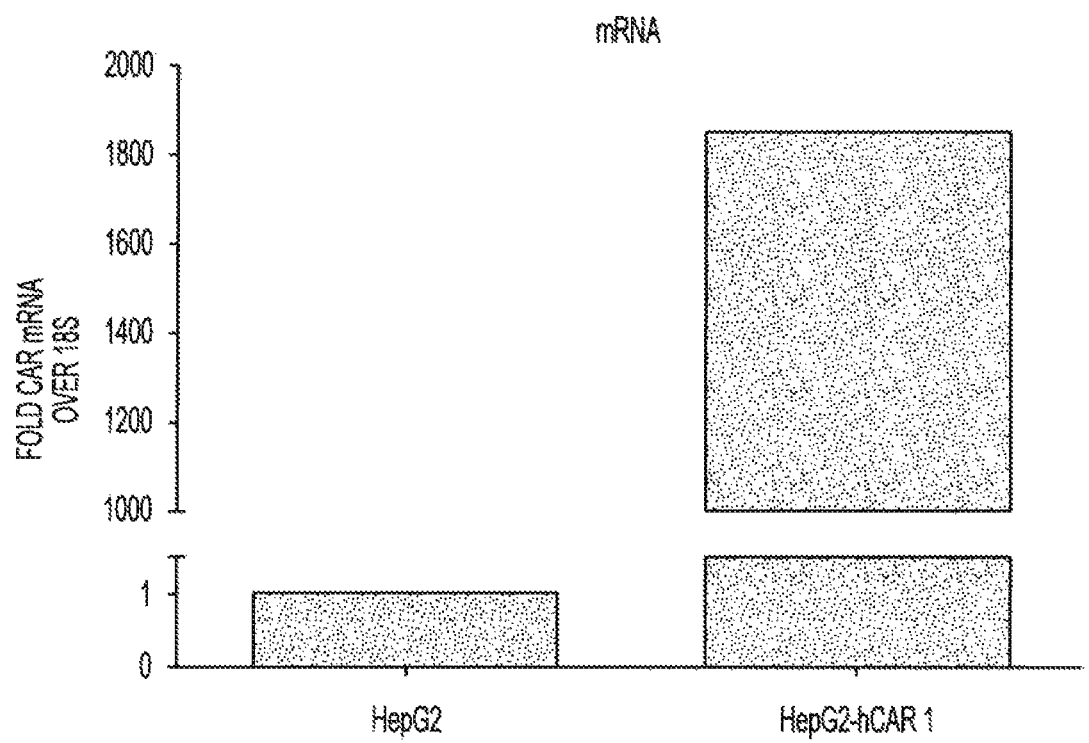
FIG. 11A and FIG. 11B show representative data demonstrating CAR expression levels in a HepG2-hCAR1 stable cell line (Clone 17).
Figure 11B:
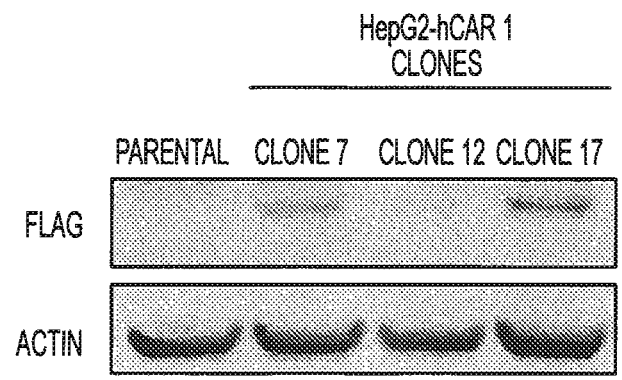
Figure 12A:
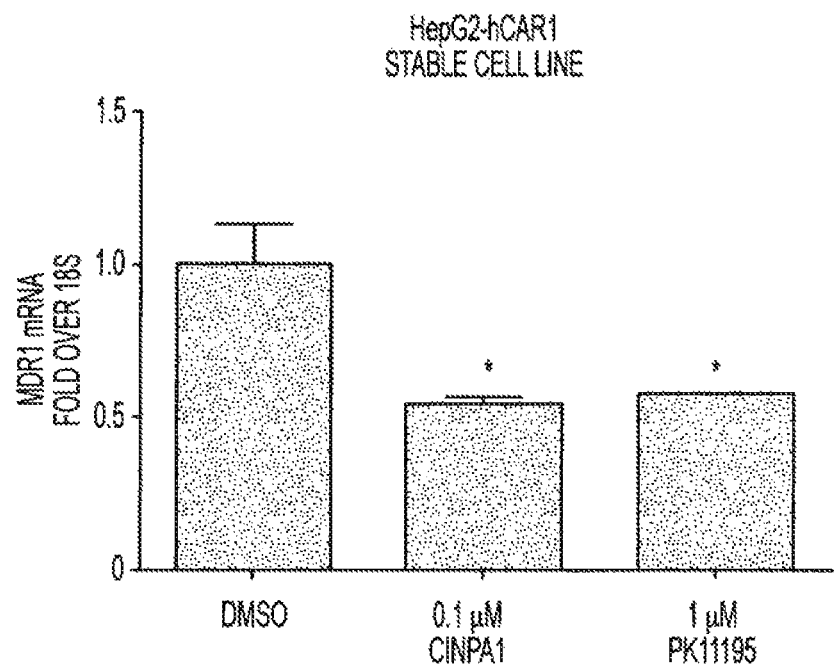
FIG. 12A and FIG. 12B show representative data demonstrating CINPA1 attenuates CAR-mediated MDR1 mRNA expression in CAR expressing cell lines.
Figure 12B:
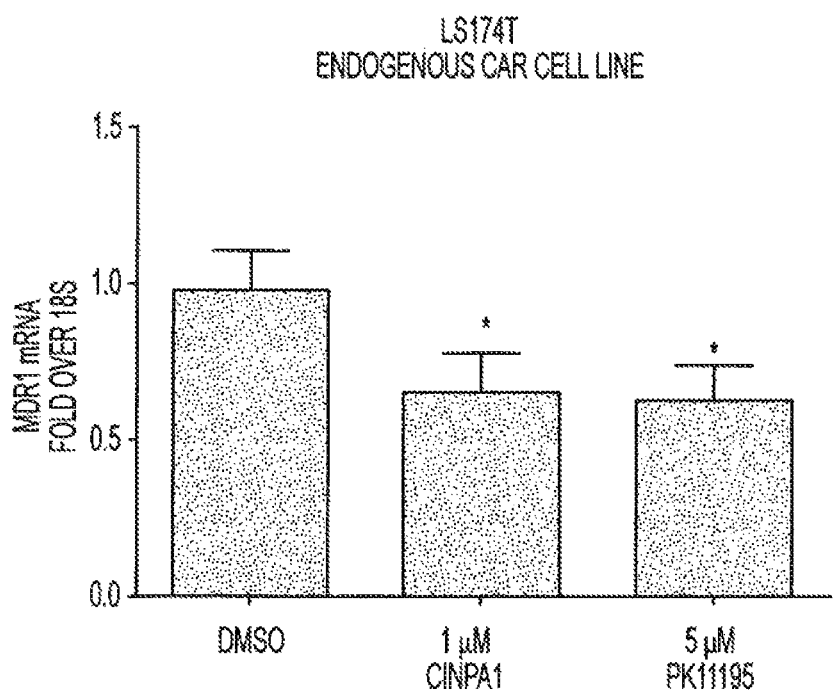

8. CINPA1 Inhibits Expression of CAR-Regulated Genes in Cell Lines and Human Hepatocytes CAR is a transcription factor that regulates the expression of various gene families, including those involved in drug metabolism and lipogenesis, and CYP2B6 is considered to be a principal CAR-regulated gene. A stable clone of HepG2 cells that overexpress hCAR1 was established (HepG2-hCAR1, Clone 17, FIG. 11A and FIG. 11B). Various other cell lines were examined, and LS174T was identified as moderately expressing endogenous CAR and its downstream targets; LS174T has previously been reported to express endogenous PXR with inducible activity (Wang, Y. M., et al. (2013) *Toxicol. Appl. Pharmacol.* 272, 96-107). In HepG2-hCAR1, where CAR but not PXR is overexpressed and known to be constitutively active, CINPA1 substantially and significantly attenuated the levels of both endogenous CYP2B6 and CYP3A4 genes although PK11195 attenuated the level of CYP2B6 without significantly affecting that of CYP3A4 (FIG. 5A). However, in LS174T cells that endogenously express both CAR and PXR, CINPA1 moderately reduced the levels of CYP2B6 without significantly affecting CYP3A4, whereas PK11195 reduced the levels of CYP2B6 but increased that of CYP3A4 (FIG. 5B), most likely working through PXR activation as previously reported (24). Interestingly, both CINPA1 and PK11195 reduced MDR1 levels in both HepG2-hCAR1 and LS174T cells (FIG. 12A and FIG. 12B).

Figure 5B:
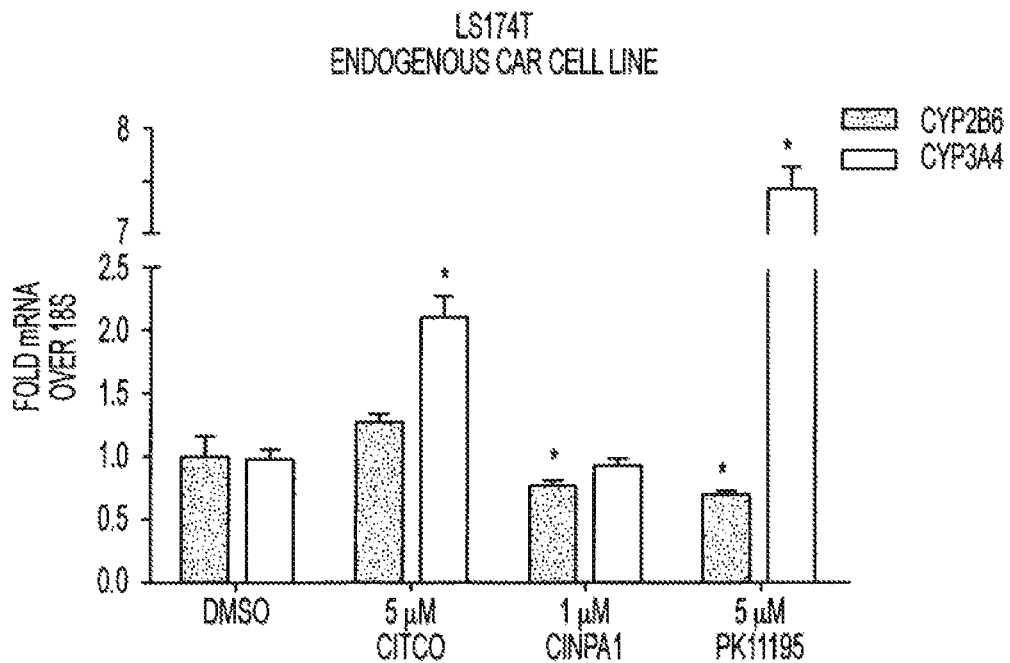
Figure 5C:
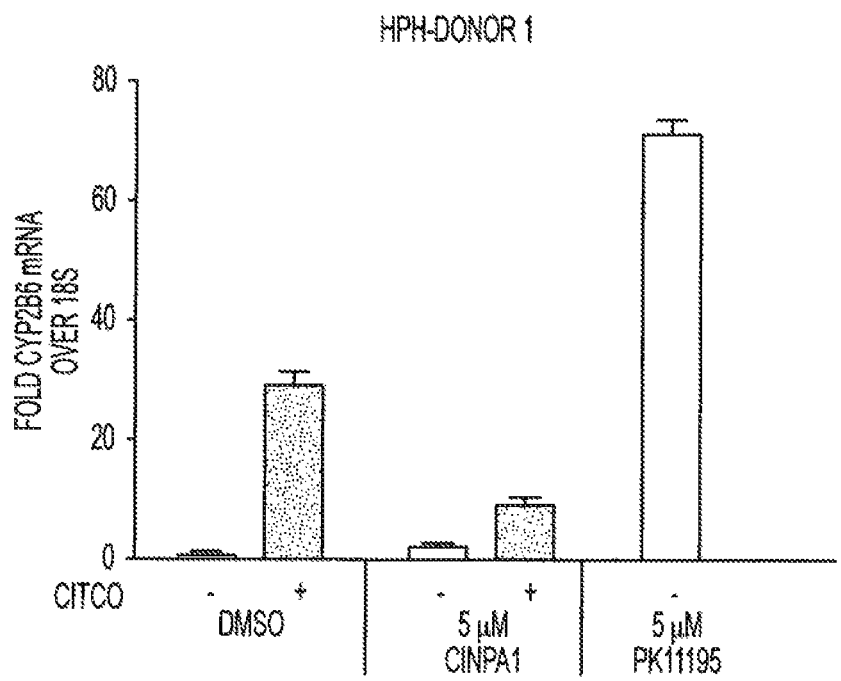
Figure 5D:
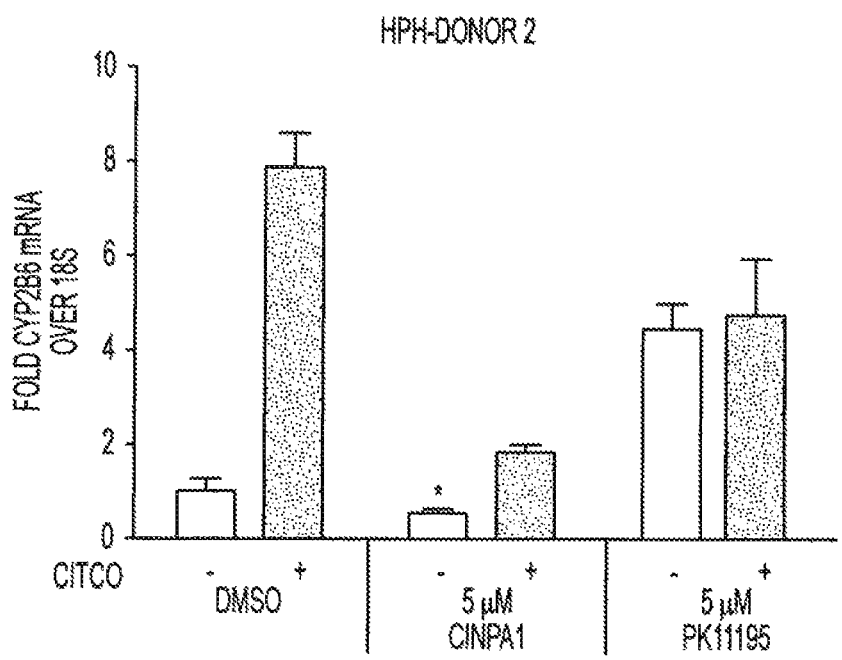
Figure 5E:
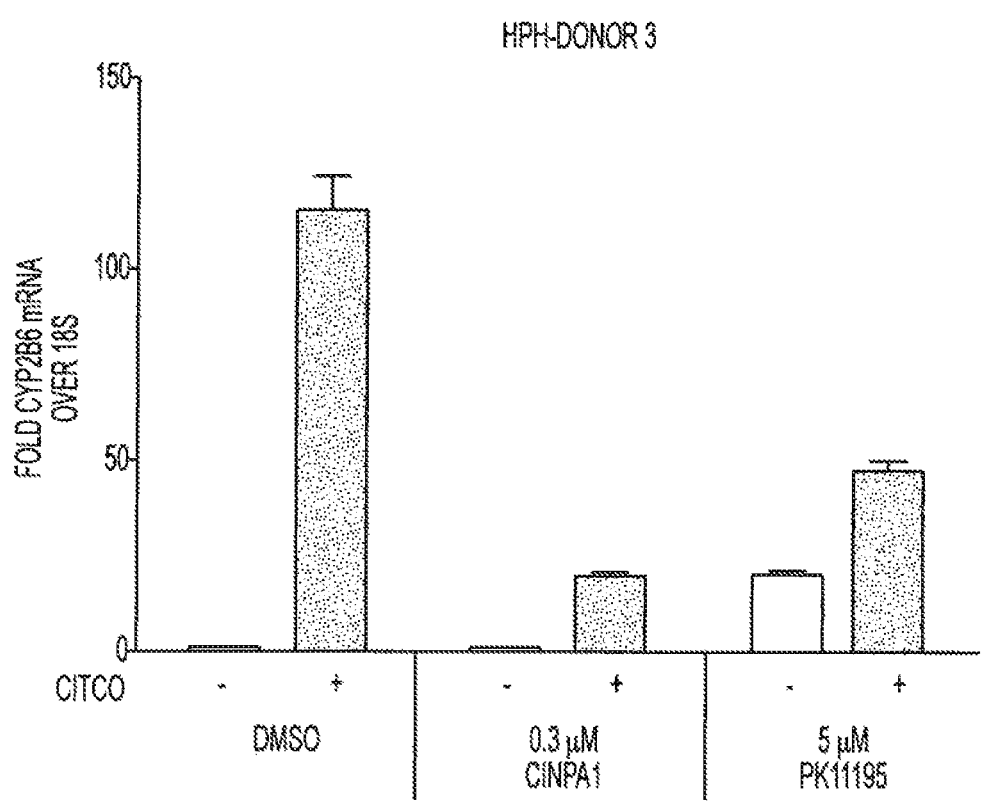
Figure 13:
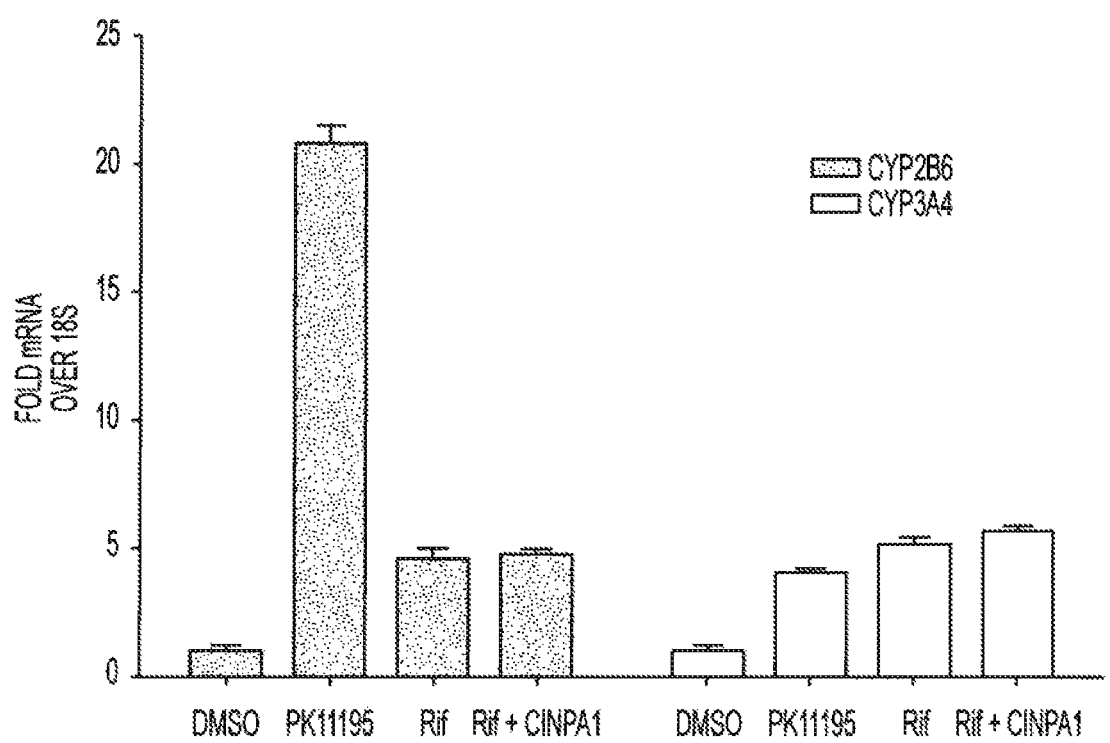
FIG. 13 shows representative data demonstrating CINPA1 does not alter PXR-mediated mRNA expression in human primary hepatocytes. Briefly, human primary hepatocytes (donor 5) were maintained in William's E Media with supplements for 4 days prior to treatment. Cells were treated in the presence of DMSO (control), 5 µM PK11195, 10 µM rifampicin or 10 µM rifampicin+5 µM CINPA1 for 48 hr. RNA extracted was used for cDNA synthesis and measured by quantitative real-time PCR with Taqman probes. CYP2B6 and CYP3A4 mRNA were normalized to the internal control 18S and DMSO-treated samples were set to 1.
Figure 14:
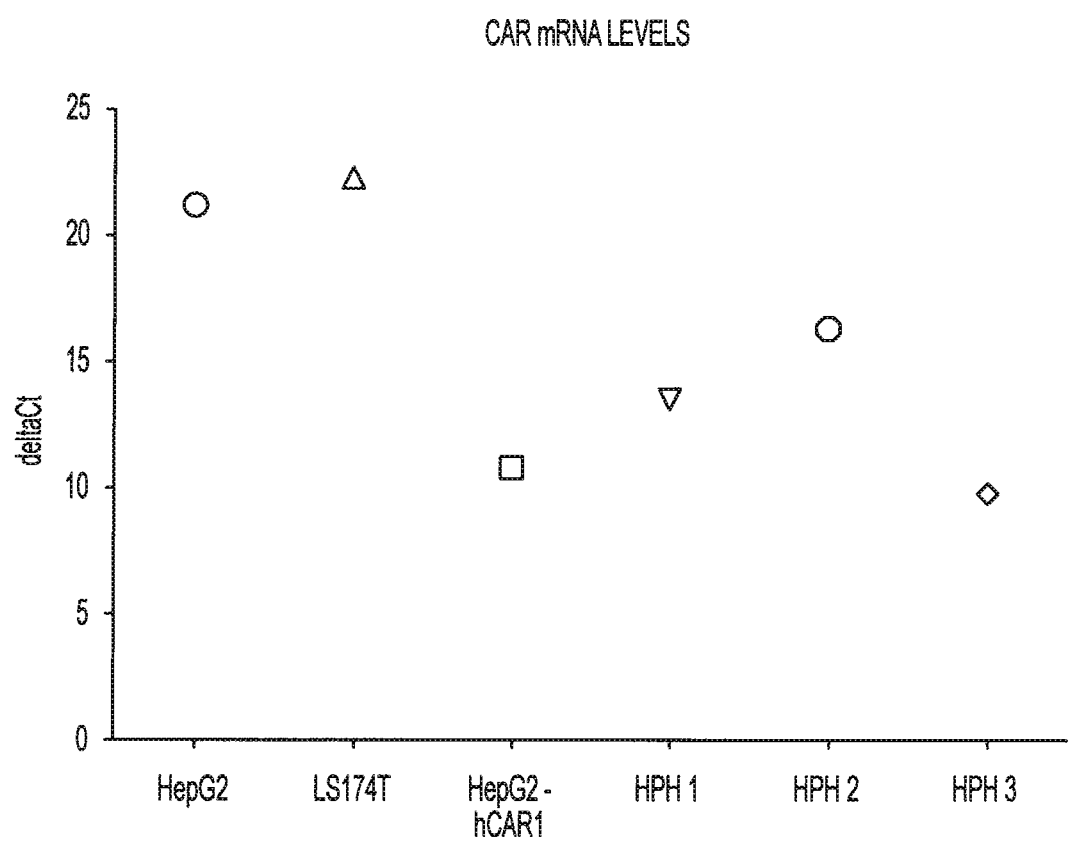
FIG. 14 shows representative data for the CAR mRNA levels in various cell-lines and human primary hepatocyte donor sources. Briefly, the figure shows representative data for the expression levels of CAR mRNA levels in HepG2, LS174T, HepG2-hCAR1, human primary hepatocytes donor 1 ("HPH1"), human primary hepatocytes donor 2 ("HPH2"), and human primary hepatocytes donor 3 ("HPH3") as determined by quantitative real-time PCR. Briefly, RNA extracted from DMSO treated cells (from the experiments detailed in FIG. 5) was used for cDNA synthesis and measured by quantitative real-time PCR with Taqman probes recognizing hCAR. deltaCt (Ct=threshold cycle) values were calculated by normalizing to the internal control 18S. Higher deltaCt values indicate less CAR mRNA detected in the respective cell line/donor.
Figure 15A:
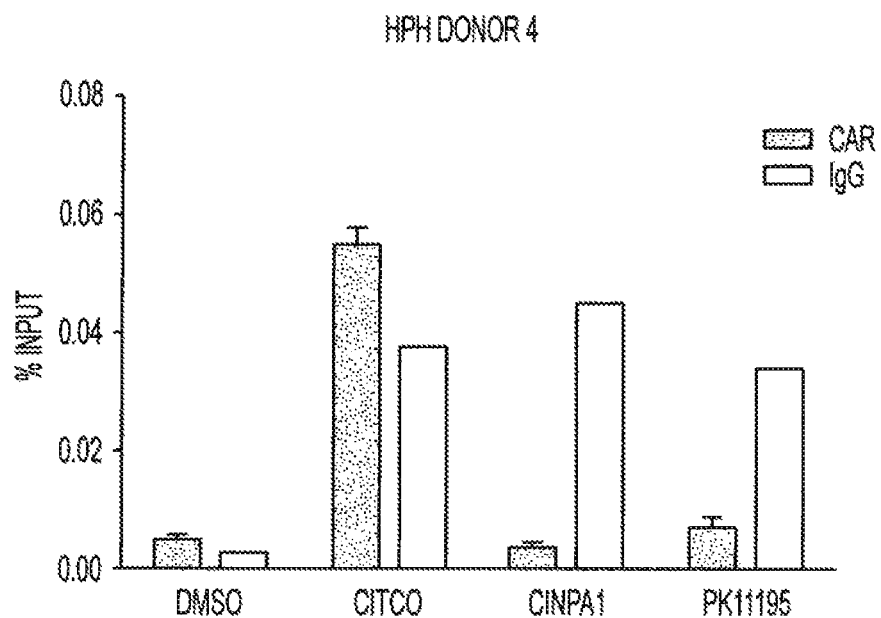
FIG. 15A-FIG. 15F show representative data demonstrating CAR is not detectable at a CAR-free intergenic region. For the data shown in FIG. 15A, FIG. 15B, and FIG. 15C, human primary hepatocytes from three separate donors were treated overnight with DMSO, 1 µM CITCO, 5 µM CINPA1 or 10 µM PK11195 as described in FIG. 8A-FIG. 8C above. Chromatin was immunoprecipitated using anti-CAR antibody ("CAR") or control IgG ("IgG"). CAR occupancy at an intergenic control CAR-free region was determined using quantitative RT-PCR. For the data shown in FIG. 15D and FIG. 15E, human primary hepatocytes from donor 7 were treated for 45 min or HepG2-hCAR1 cells were treated for 4 hr as described in FIG. 9A-FIG. 9C above. Protein complexes were cross-linked and chromatin immunoprecipitated using anti-RNA Polymerase II antibody (RPol), anti-CAR antibody (CAR) or control IgG. RPol or CAR occupancy at an intergenic control CAR-free region about 14 kb downstream of the CYP2B6 promoter region, as shown in FIG. 15F, was determined using quantitative RT-PCR. Percent of Input DNA for each sample was plotted. In comparison, % Input values indicating CAR binding to CAR-specific promoter regions (PBREM and XREM (dNR3), as shown in FIG. 8A) are at least 10-fold higher than CAR binding at this CAR-free intergenic region. Data represent the mean of three PCR experiments±SD and are representative of other experiments.
Figure 15B:
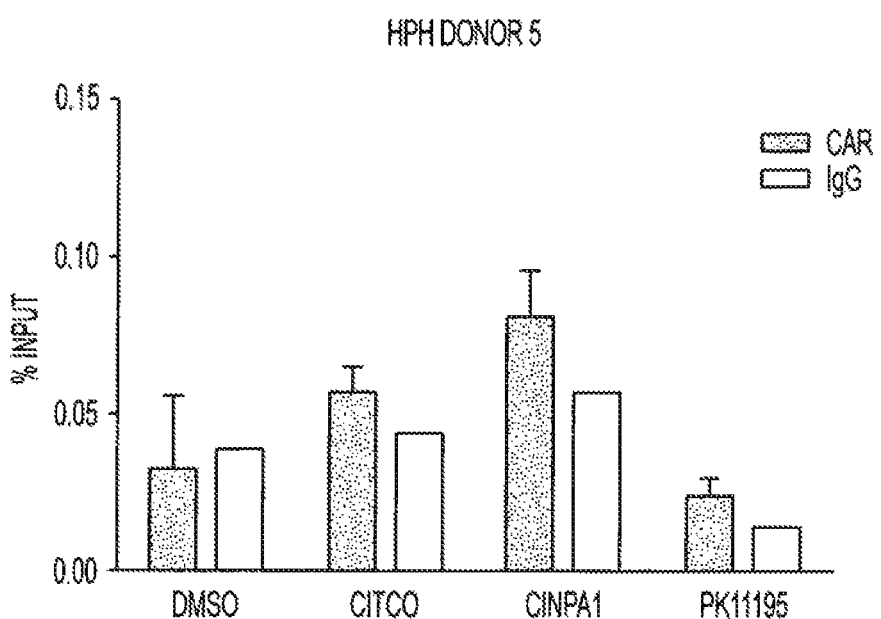
Figure 15C:
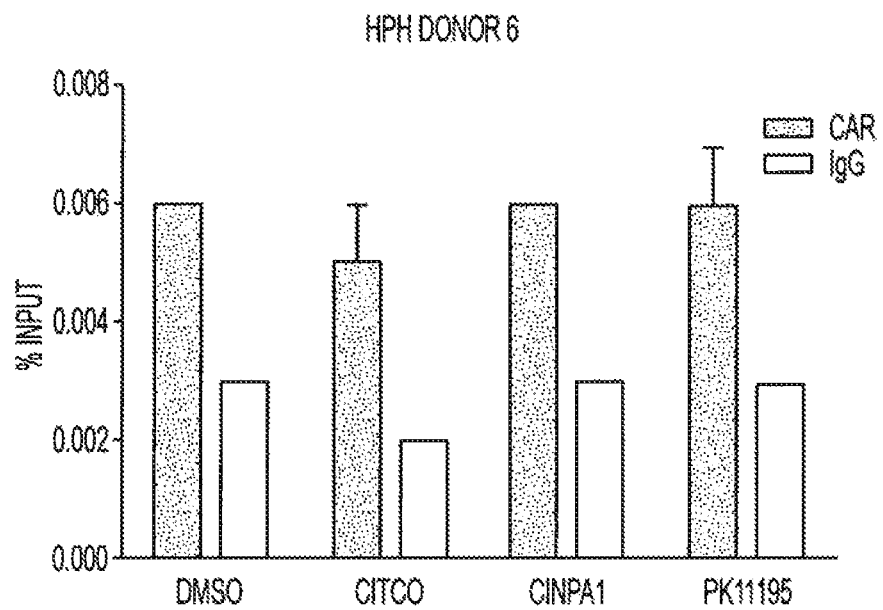
Figure 15D:
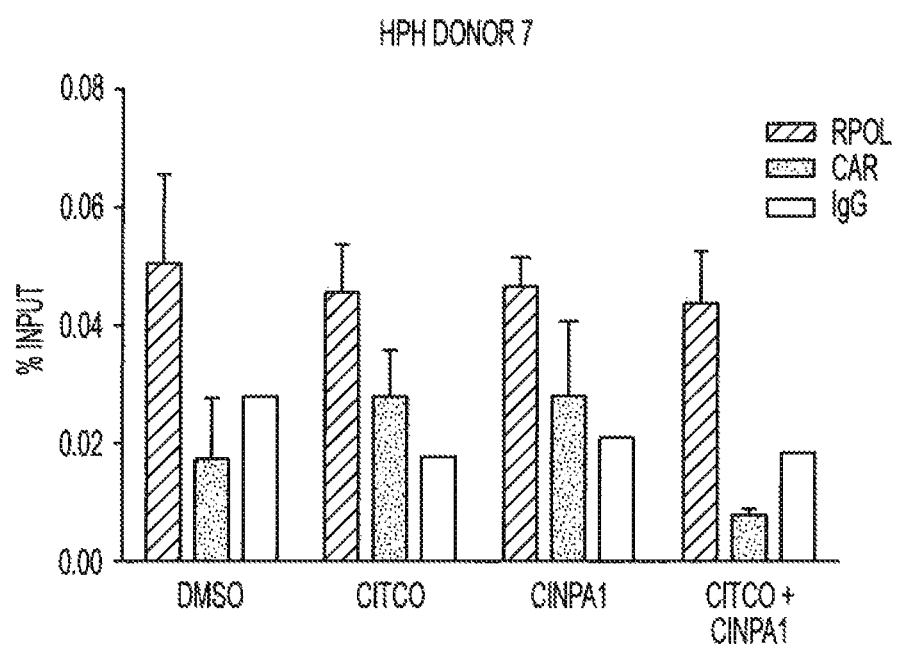
Figure 15E:
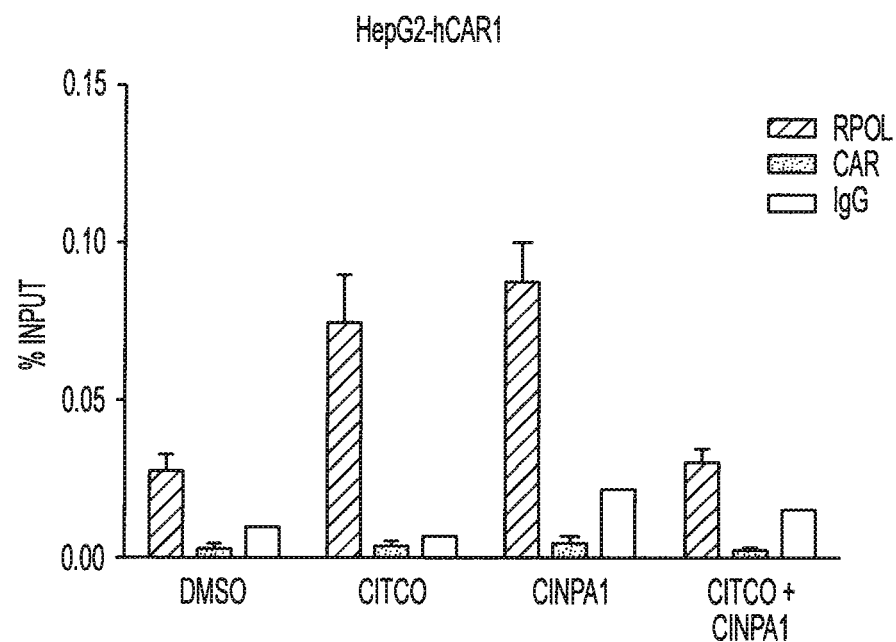
Figure 15F:
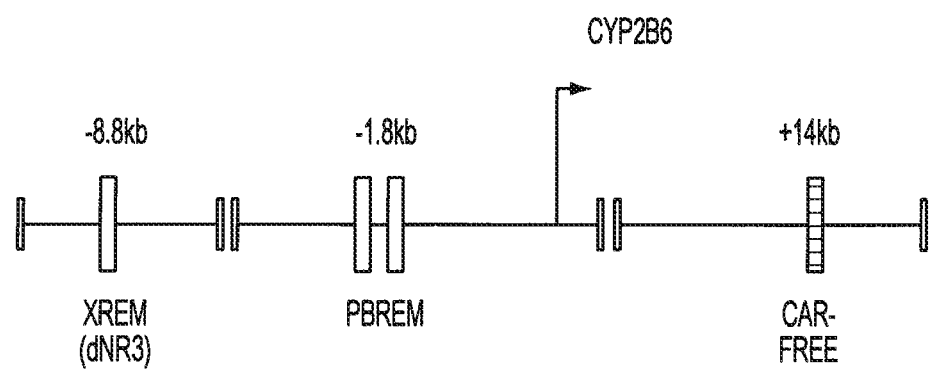

Primary human hepatocytes express varying levels of endogenous PXR and CAR, resulting in varying levels of P450 enzyme. CAR in primary hepatocytes is predominantly cytoplasmic therefore the basal levels of CAR target genes such as CYP2B6 is likely not CAR-mediated (Maglich, J. M., et al. (2003) *J. Biol. Chem.* 278, 17277-17283; and Honkakoski, P., et al. (1998) *Mol. Cell. Biol.* 18, 5652-5658), but can be induced by CAR activators such as CITCO. We tested the effect of CINPA1 on PXR and CAR in primary human hepatocytes from 7 different donors and show the results of a representative set of 3 donors. Fresh or cryopreserved hepatocytes from each donor were obtained and treated with CINPA1 or PK11195 in the presence or absence of CAR activator CITCO. Because hepatocyte sample availability was limited, each donor shown was tested with decreasing concentrations of CINPA1 (5 µM treatment for Donor 1, 1 µM for Donor 2, and 0.3 µM for Donor 3). In all three donors, CITCO induced CYP2B6 levels, indicating that CAR is functional. CINPA1 treatment effectively inhibited CITCO-induced CAR transactivation of the CYP2B6 gene in all three donors (FIGS. 5C-E). We noticed that in donor 2 (FIG. 5D) but not in donors 1 and 3 (FIGS. 5C & 5E), CINPA1 alone significantly reduced basal CAR transactivation, reflecting the donor variations typically observed among primary human hepatocytes. Even as a weak PXR antagonist, 5 µM CINPA1 could not reduce rifampicin-induced PXR-mediated gene expression in primary hepatocytes (FIG. 13). This might be a reflection of the variability commonly observed between hepatocyte donors, which might rise from interaction between various other activated receptors and PXR. In contrast to CINPA1, PK11195 alone increased CYP2B6 transcription in all three donors (FIGS. 5C-E), consistent with a previous report demonstrating that PK11195 induces CYP2B6 through PXR activation (24). Taken together, these data show that unlike PK11195, CINPA1 specifically targets and reduces CAR-mediated gene expression without activating PXR. Supplementary FIG. 5 shows the CAR mRNA levels in the various cell models used to obtain these data. Supplementary FIG. 5B shows CITCO induced CYP2B6 levels in 7 different human primary hepatocyte donors, and CINPA1 successfully inhibits CITCO-induced CAR activity in all donors.

Figure 6A:
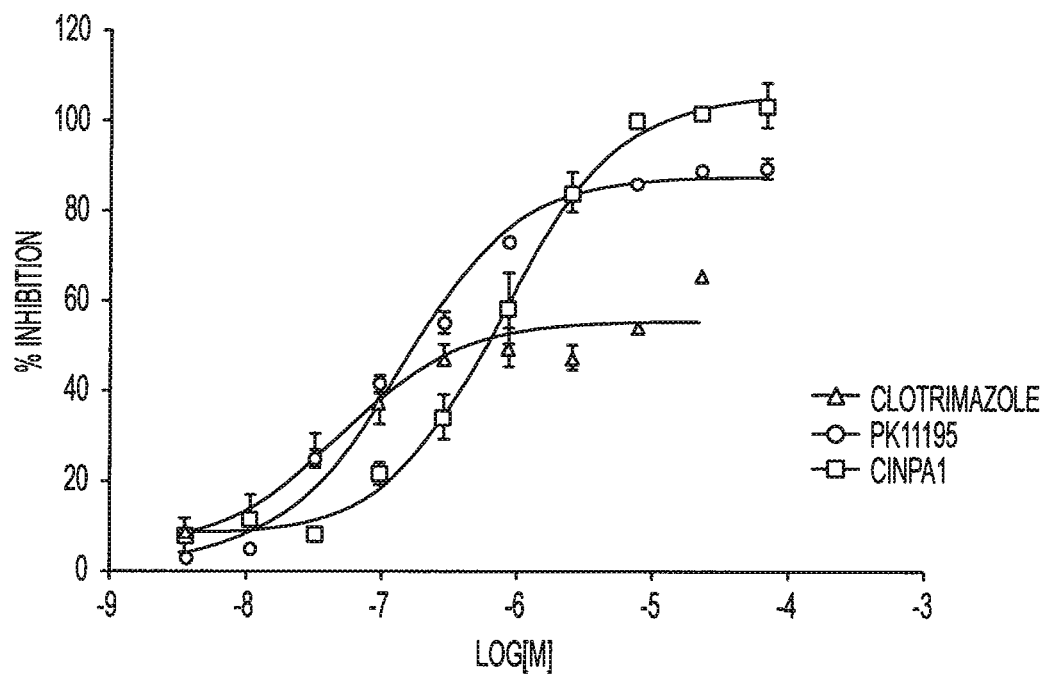
FIG. 6A-FIG. 6C show representative data demonstrating that CINPA1 does not reduce CAR protein levels or alter nuclear translocation.
Figure 6B:
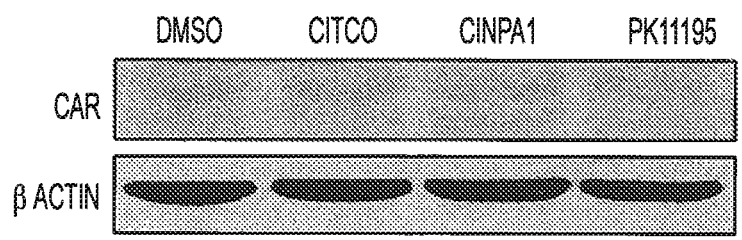
Figure 6C:
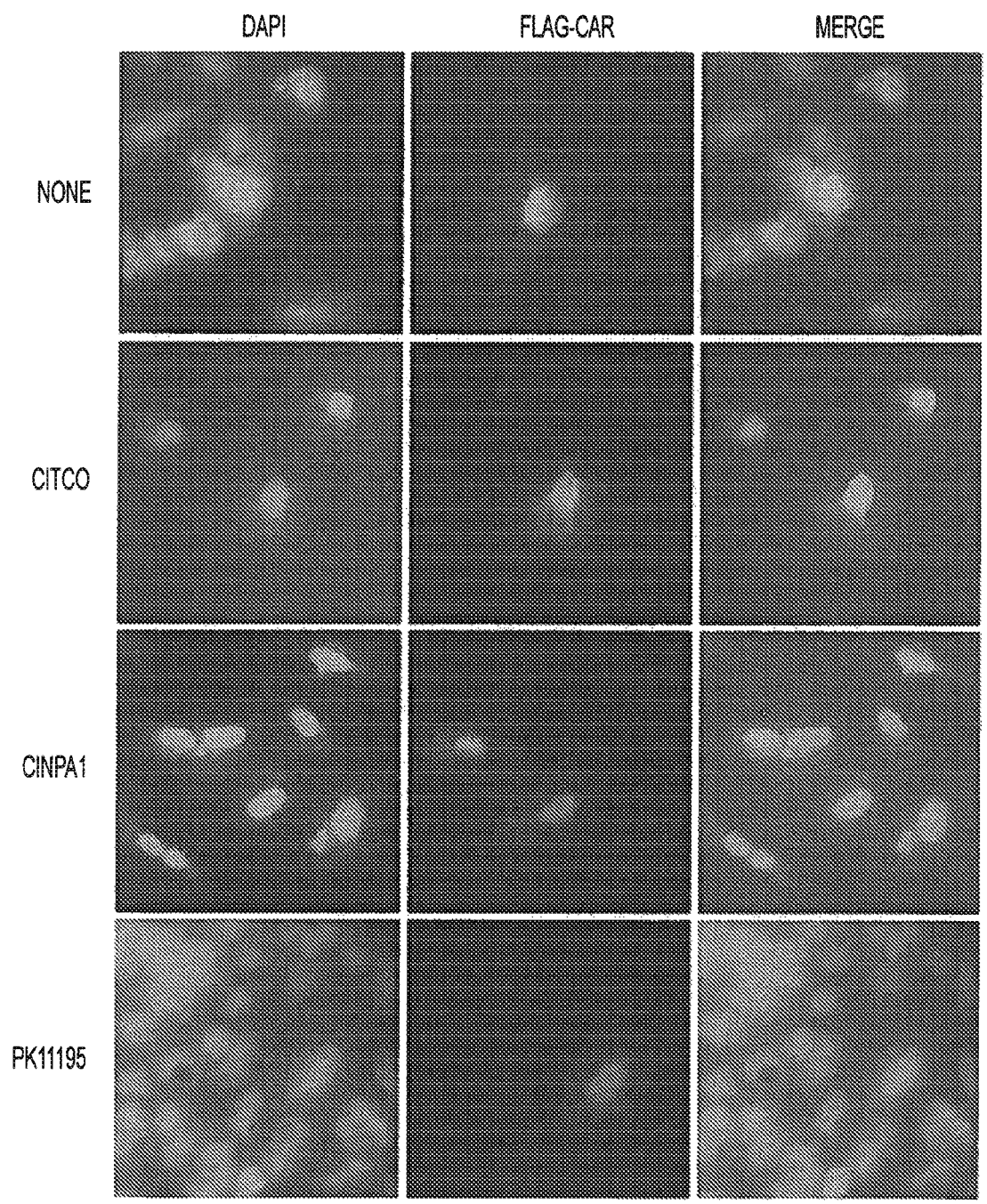
Figure 10C:
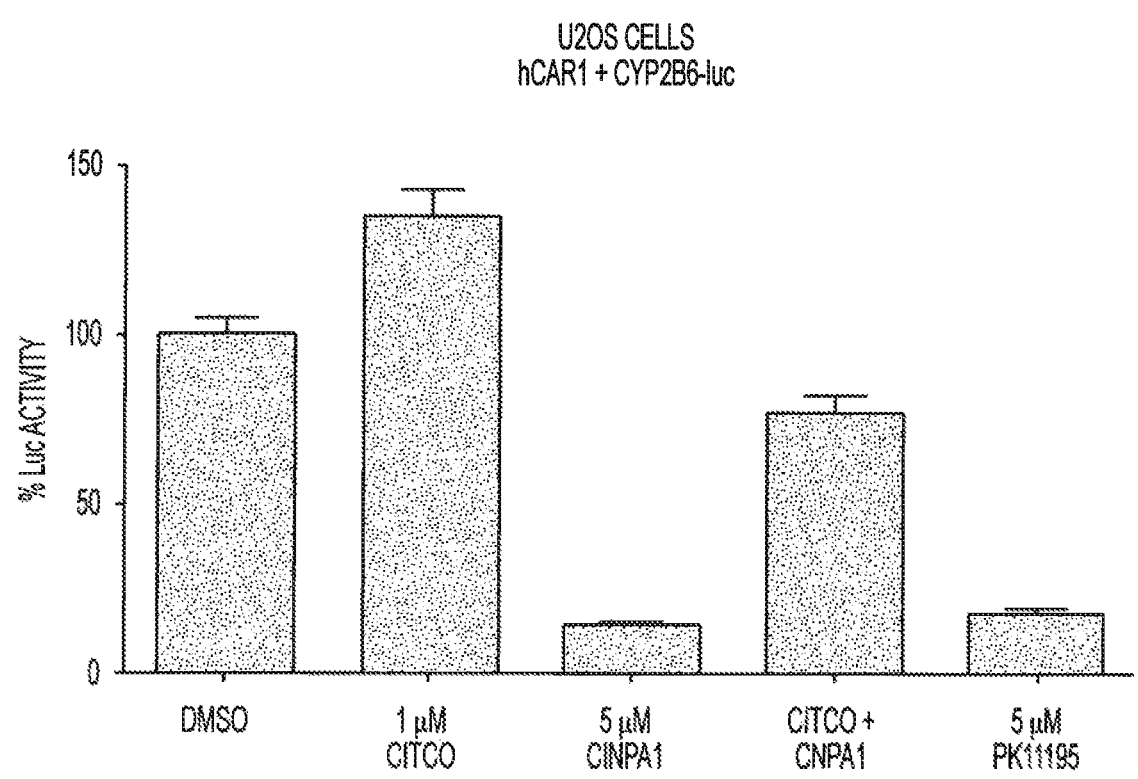

9. CINPA1 Disrupts CAR Interaction with Co-Activators, Enhances Recruitment of Co-Repressors, but does not Reduce CAR Protein Levels or Nuclear Translocation A LanthaScreen™ TR-FRET assay was used initially to determine the effect of CINPA1 on the constitutive interaction between CAR-LBD and a coactivator peptide. In this assay, GST-tagged CAR-LBD constitutively interacts with a fluorescently labeled PGC-1α coactivator peptide and emits a strong FRET signal. CAR inverse agonist-binding to the CAR-LBD results in a reduced FRET signal. We compared CINPA1 to known CAR inverse agonists, clotrimazole and PK11195 in this assay. As shown in FIG. 6A, CINPA1 efficiently inhibits CAR-LBD interaction with the coactivator peptide, indirectly suggesting that CINPA1 is a ligand of CAR. The results of Western blot analysis show that CINPA1 had no effect on the levels of CAR in human hepatocytes (FIG. 6B). In U2OS cells expressing FLAG-hCAR1 and immunostained with FLAG antibody, CAR localized to the nucleus irrespective of treatment conditions (DMSO, CITCO, CINPA1 or PK11195). This indicates that CINPA1 treatment does not alter the nuclear localization of CAR (FIG. 6C). Exogenous CAR is functional in U2OS cells (FIG. 10C) and these cells were chosen for immunofluorescence assays for their flat morphology and large cytoplasmic extensions (Fritz, J., et al. (2009) *Mol. Cell. Biol.* 29, 1487-1497).

Figure 7A:
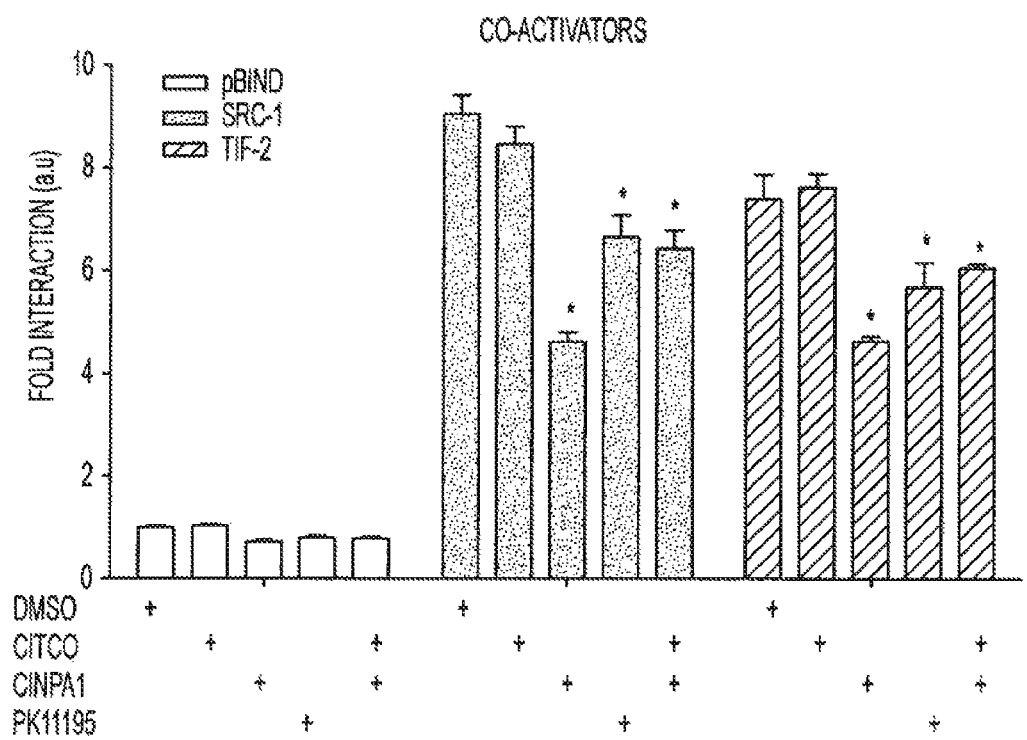
FIG. 7A and FIG. 7B show representative data demonstrating that CINPA1 disrupts interaction of CAR with coactivators and enhances corepressor binding.
Figure 7B:
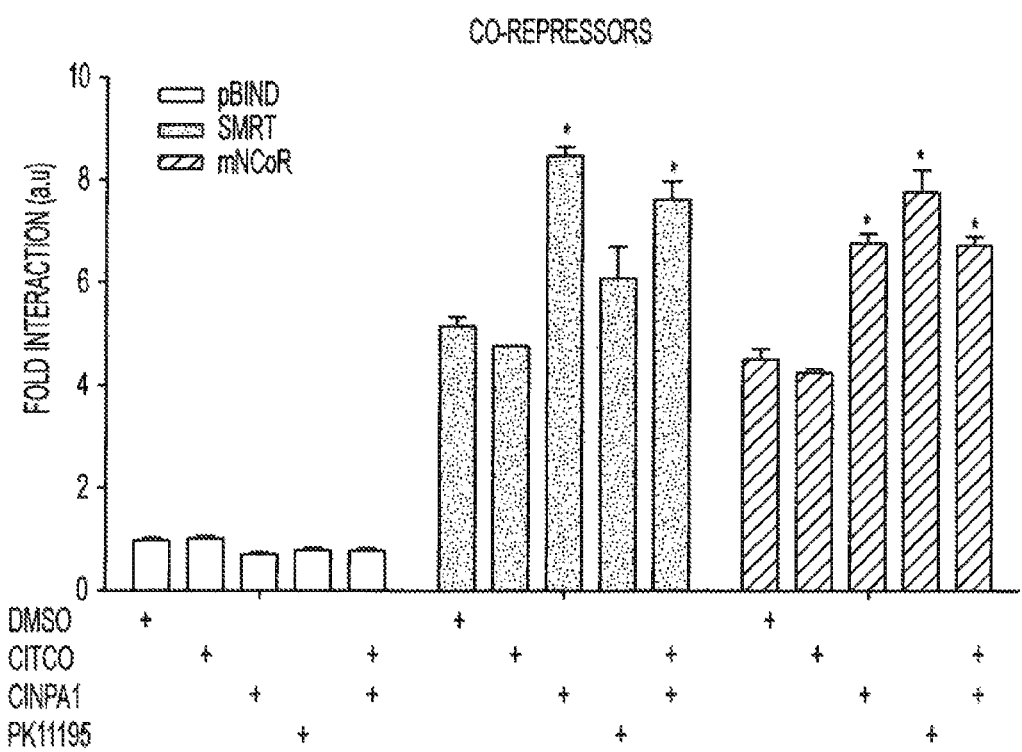

Activated CAR protein binds response elements on DNA and recruits coactivator proteins that are essential for transcriptional activation (Forman, B. M., et al. (1998) *Nature* 395, 612-615; and Min, G., Kemper, J. K., and Kemper, B. (2002) *J. Biol. Chem.* 277, 26356-26363), while inverse agonist bound CAR binds corepressor proteins (Bae, Y., Kemper, J. K., and Kemper, B. (2004) *DNA Cell. Biol.* 23, 81-91; Jyrkkarinne, J., et al. (2003) *J. Med. Chem.* 46, 4687-4695; and Kublbeck, J., et al. (2011) *Mol. Pharmaceut.* 8, 2424-2433). The effect of CINPA on the interaction between CAR-LBD and coregulators was further determined by using mammalian two-hybrid systems. As shown in FIG. 7A, CINPA1 treatment resulted in reduced SRC-1 and TIF-2 coactivator binding to CAR-LBD in the presence or absence of agonist CITCO. This finding is in congruence with that in earlier gene expression assays, in which CINPA1 reduced basal and ligand-initiated CAR activity (FIG. 5) and the TR-FRET assay (FIG. 6A). Conversely, CINPA1 treatment resulted in increased interaction of CAR-LBD with the corepressor proteins SMRTα and mNCoR. Thus, the data show that CINPA1 binding to CAR-LBD results in reduced coactivator recruitment and increased corepressor interaction, which contributes to explaining the inhibitory mechanism of CINPA1.

10. CINPA1 Inhibits CAR Recruitment to the CYP2B6 Gene Promoter

Figure 8A:
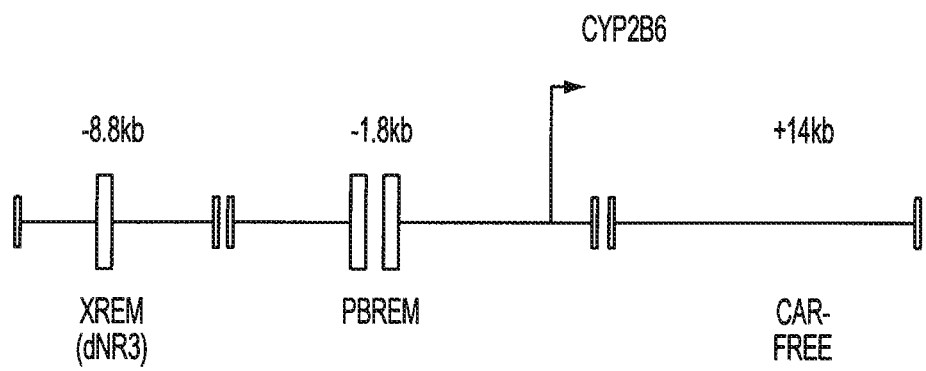
FIG. 8A-FIG. 8C show representative data demonstrating CINPA1 treatment forbids CAR binding to DNA response elements at the CYP2B6 gene promoter in human primary hepatocytes.
Figure 8B:
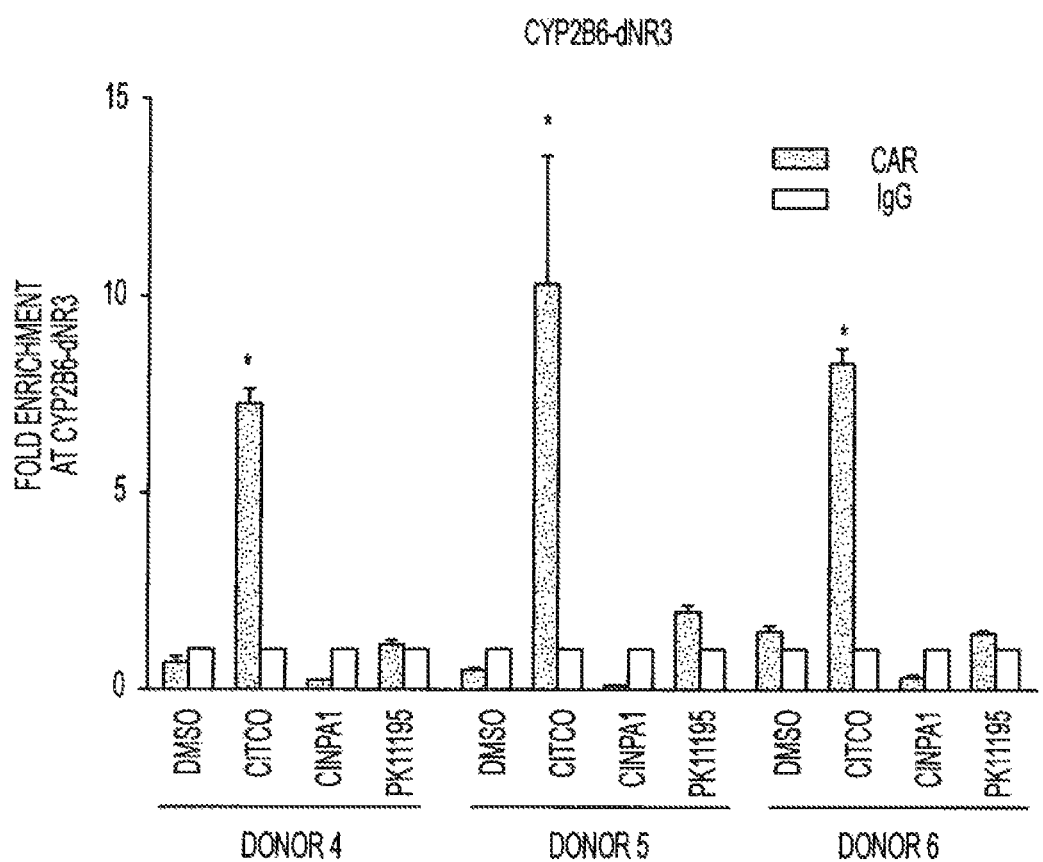
Figure 8C:
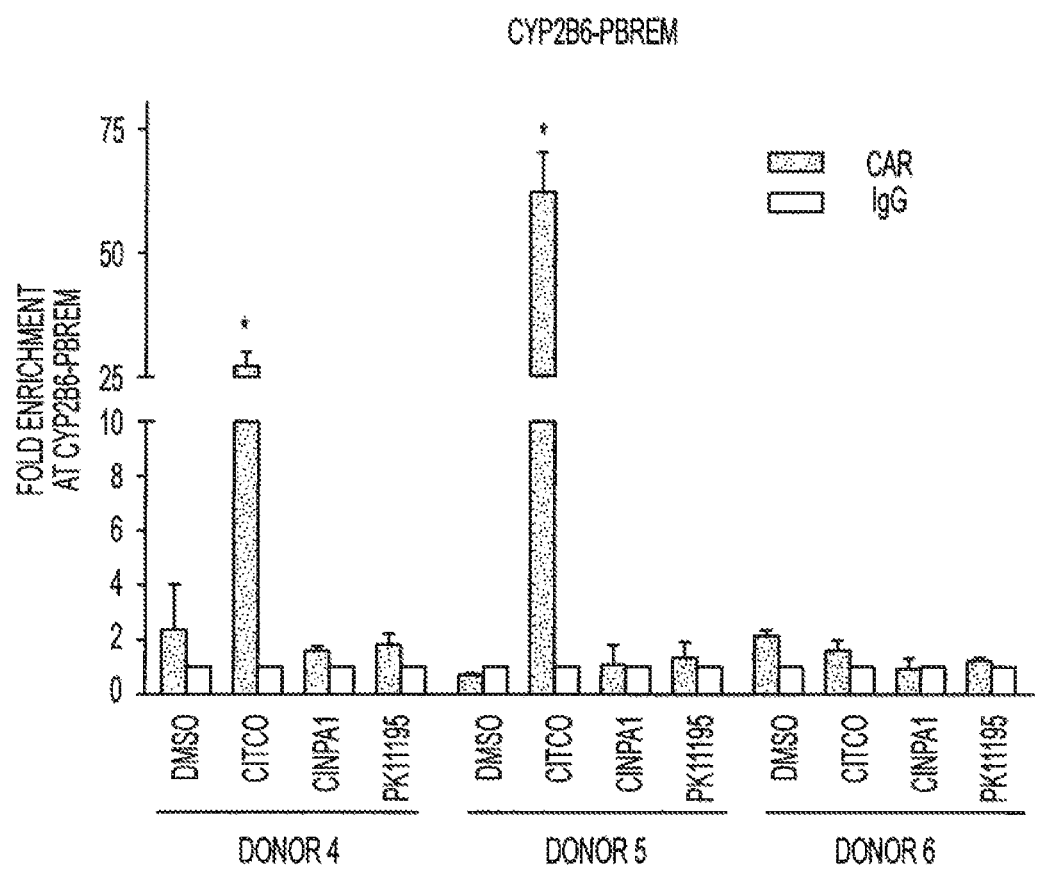

Chromatin immunoprecipitation assays were used to evaluate the effect of CINPA1 on CAR recruitment to promoter regions of CAR-regulated genes in human hepatocytes. CYP2B6 is a well-characterized CAR-regulated gene with a defined PBREM around −1.8 kb upstream, and an XREM (which contains a DR4 motif also called an NR3 binding site) around −8.8 kb upstream of its transcriptional start site, respectively (Wang, H., et al. (2003) *J. Biol. Chem.* 278, 14146-14152). Data are shown in FIG. 8A. Both PXR and CAR are capable of binding to these response elements depending on their differential activation states. As shown in FIGS. 8B and 8C, CITCO treatment enhances recruitment of CAR to the XREM (dNR3) regions of the CYP2B6 gene in all 3 donors (FIG. 8B) and to the PBREM in donors 4 and 5 but not donor 6 (FIG. 8C), consistent with the increased CYP2B6 mRNA levels in response to CITCO shown in FIGS. 5C-E. CINPA1 treatment prevents CAR recruitment to the dNR3 in all 3 donors (FIG. 8 B), but the effect on the PBREM is less consistent among different donors (FIG. 8C). Similar donor variation on the basal level of CYP2B6 in response to CINPA1 was also observed in FIGS. 5C-E. CAR protein was below detection levels (when compared to normal mouse IgG) in ChIP experiments at the CYP2B6 promoter region in 2 other human hepatocyte donors, further demonstrating the donor-to-donor variation in human hepatocytes. Supplementary FIG. 6 illustrates the relative absence of CAR and/or RNA polymerase II (compared to mouse IgG) at a CAR-free intergenic region within the CYP2B6 gene, a negative control for ChIP.

Figure 9A:
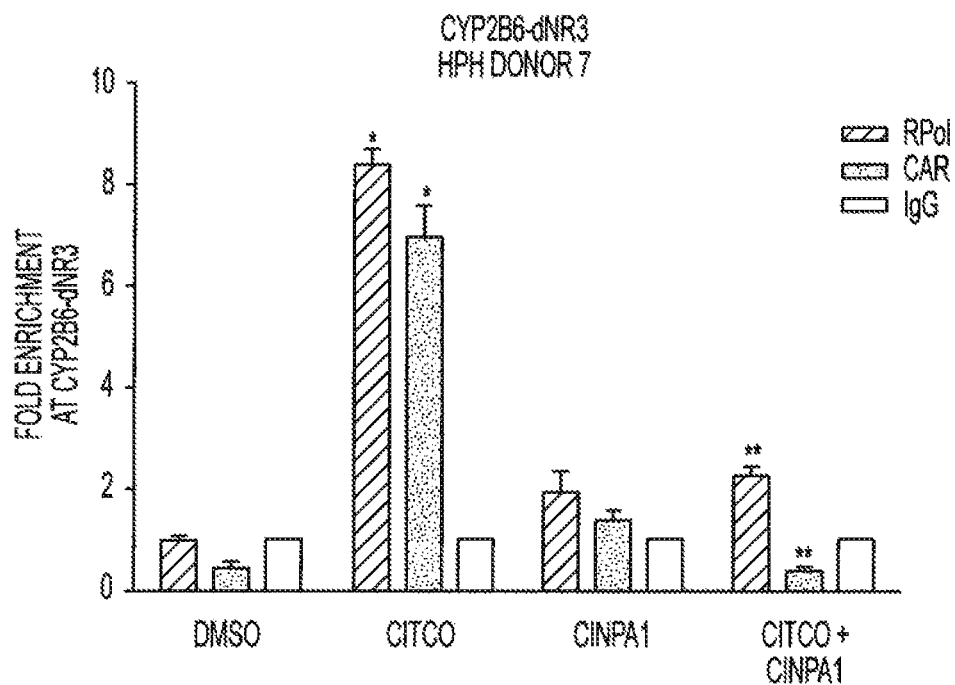
FIG. 9A-FIG. 9C show representative data demonstrating CINPA1 disrupts CITCO-activated CAR binding to DNA response elements at the CYP2B6 gene promoter regions.
Figure 9B:
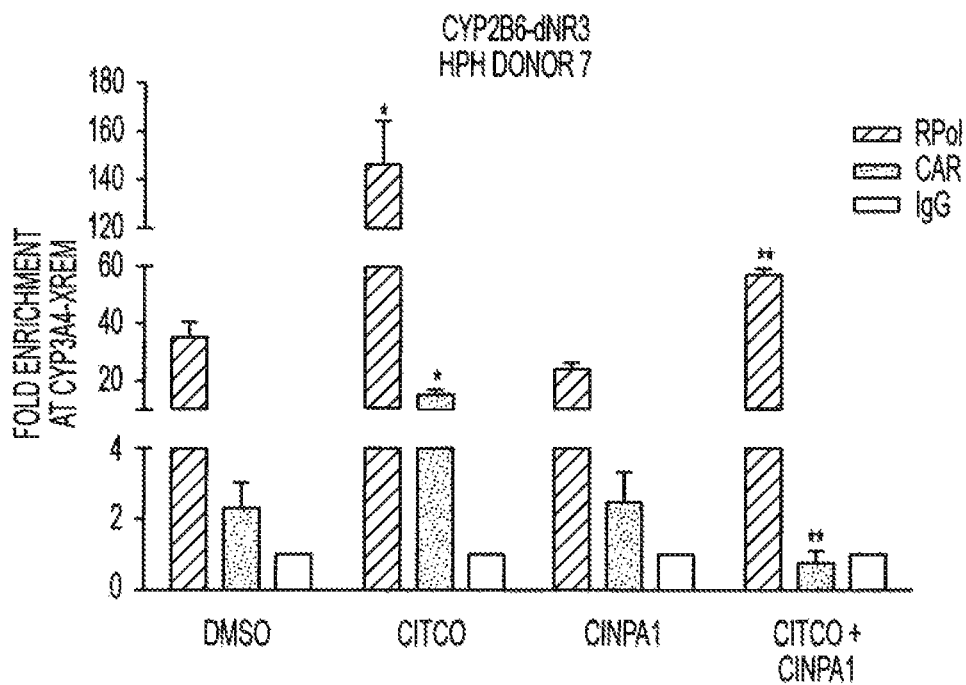
Figure 9C:
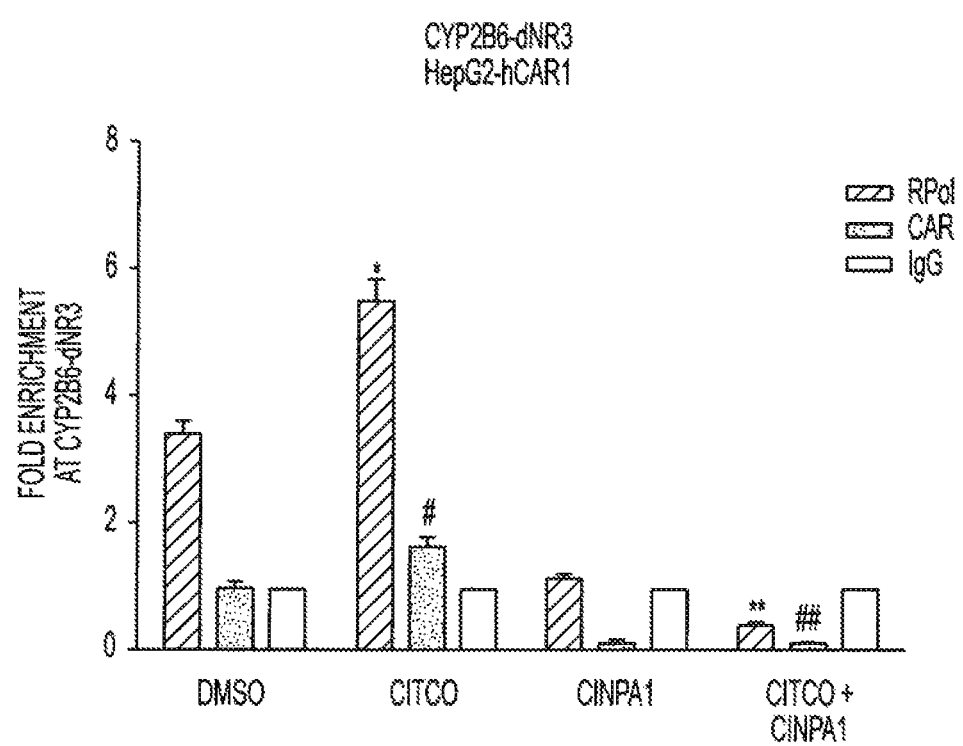

In hepatocytes, CITCO treatment consistently enhanced recruitment of CAR to the XREM (dNR3) region of the CYP2B6 promoter (FIG. 8B) and induced the expression of CYP2B6, which is effectively inhibited by CINPA1 co-treatment (FIGS. 5C-E). Consistent with these observations, CINPA1 effectively reduced the CITCO-mediated recruitment of CAR and RNA polymerase II to the XREM (dNR3) region of the CYP2B6 promoter (FIG. 9A). As expected, CINPA1 also reduced the CITCO-mediated recruitment of CAR and RNA polymerase II to the XREM region of the CYP3A4 promoter (FIG. 9B). Similarly, consistent with the observation that in HepG2-hCAR1 cells where CAR is ectopically overexpressed, constitutively active, and CINPA1 attenuated the levels of endogenous CYP2B6 (FIG. 5A), we found that CINPA effectively blocked the recruitment of CAR and RNA polymerase II to the XREM (dNR3) region of the CYP2B6 promoter in the absence or presence of CITCO (FIG. 9C). The parallel recruitment of CAR and RNA polymerase II to the promoter regions of CYP2B6 observed in the ChIP assays (FIG. 9) is consistent with the corresponding transcriptional activity shown in FIG. 5. Taken together, these data suggest that CINPA1 acts, in part, by reducing the association of CAR with its target promoter.

Figure 16A:
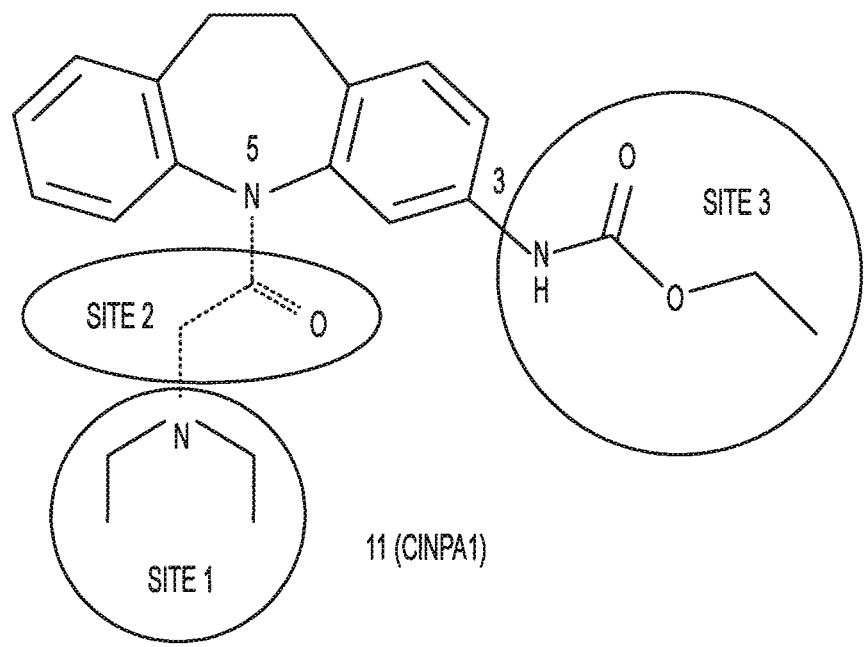
FIG. 16A and FIG. 16B show representative structure-activity relationship summaries based on CINPA1 and commercially available analogs (FIG. 16A) and synthesized analogs (FIG. 16B).

11. CAR Inverse Agonistic Activities of CINPA1 and 10 Commercially Available Analogs On the basis of the chemical scaffold of CINPA1, 3-amino-10,11-dihydro-5H-dibenz[b,f]azepine or saturated 3-amino-dibezapine (FIG. 16A), commercially available close analogs of CINPA were searched for by using Sci-Finder®, (provided by Chemical Abstracts Service) and identified. Based on these results, ten close analogs of CINPA1 were obtained. Their CAR inverse agonistic activities were then evaluated by using a biochemical CAR-mediated fluorescent PGC1α coactivator recruitment/repression assay as previously reported (6, 16), with clotrimazole (positive control) and DMSO (negative control) used as controls. The chemical structures of CINPA1 and the 10 analogs, together with their CAR inverse agonistic activities, are summarized in Table 6. In this assay, clotrimazole had an $IC_{50}$ of 0.13 µM (Table 6), which is consistent with published results (16, 17). CINPA1 (1) had an $IC_{50}$ of 0.69 µM.

TABLE 6

| Cmpd. No. | Structure | $IC_{50}$ (µM) |
|---|---|---|
| 1 (CINPA1) | | 0.69 |
| 80 | 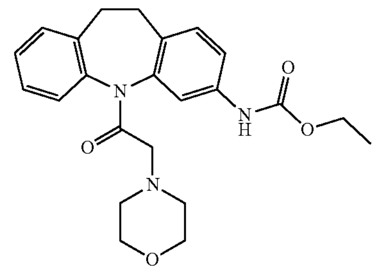 [SMILES: CCOC(=O)Nc1ccc2c(c1)N(C(=O)CN1CCOCC1)c1ccccc1CC2] | 0.24 |
| 81 | 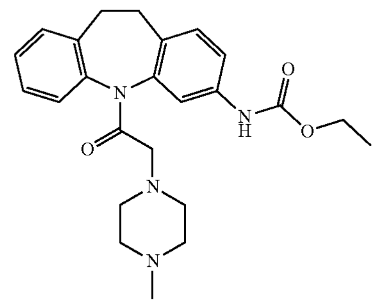 [SMILES: CCOC(=O)Nc1ccc2c(c1)N(C(=O)CN1CCN(C)CC1)c1ccccc1CC2] | 38.76 |
| 82 | 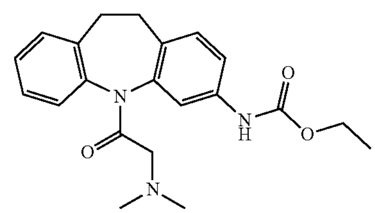 [SMILES: CCOC(=O)Nc1ccc2c(c1)N(C(=O)CN(C)C)c1ccccc1CC2] | 4.08 |
| 83 | 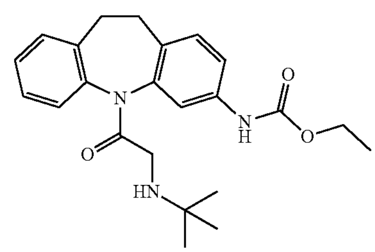 [SMILES: CCOC(=O)Nc1ccc2c(c1)N(C(=O)CNC(C)(C)C)c1ccccc1CC2] | 3.63 |
| 84 | 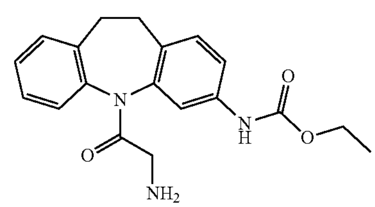 | >70 |
| 85 | 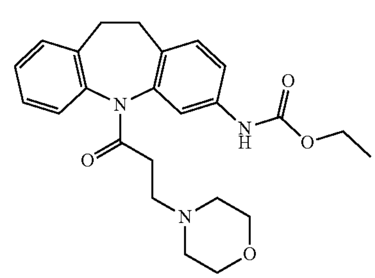 [SMILES: CCOC(=O)Nc1ccc2c(c1)N(C(=O)CCN1CCOCC1)c1ccccc1CC2] | 0.32 |

TABLE 6-continued

| Cmpd. No. | Structure | IC$_{50}$ (µM) |
|---|---|---|
| 86 | 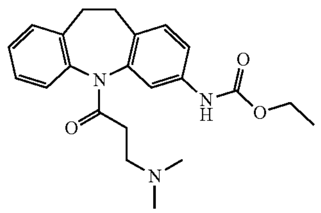 [SMILES: CCOC(=O)Nc1ccc2c(c1)N(C(=O)CCN(C)C)c1ccccc1CC2] | 5.01 |
| 87 | 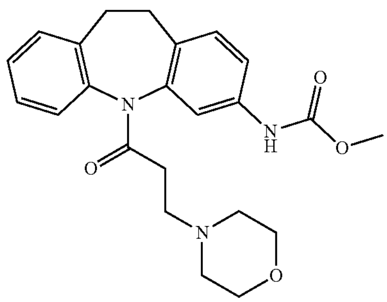 [SMILES: COC(=O)Nc1ccc2c(c1)N(C(=O)CCN1CCOCC1)c1ccccc1CC2] | 0.29 |
| 88 | 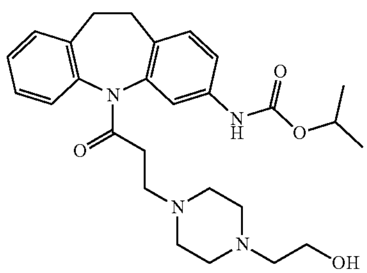 [SMILES: CC(C)OC(=O)Nc1ccc2c(c1)N(C(=O)CCN1CCN(CCO)CC1)c1ccccc1CC2] | >70 |
| 89 | 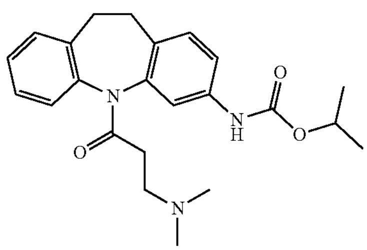 [SMILES: CC(C)OC(=O)Nc1ccc2c(c1)N(C(=O)CCN(C)C)c1ccccc1CC2] | 1.79 |
| Clotrimazole | 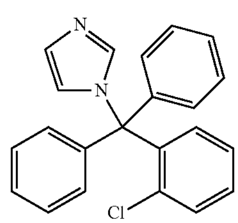 [SMILES: Clc1ccccc1C(c1ccccc1)(c1ccccc1)n1ccnc1] | 0.13 |

CINPA1 has a chemical scaffold of 3-amino-10,11-dihydro-5H-dibenz[b,f]azepine or saturated 3-amino-dibezapine (FIG. 16A) with a diethylamino substitute to the 5-nitrogen on the saturated dibezapine ring through a methylene carbonyl linker and an ethyl carbamate modification at the 3-amino group of the scaffold. These structure features provide CINPA1 with 3 major sites for chemical modifications (if the core scaffold remains unchanged): 1) substitutes (specified as site 1) attached to the 5-nitrogen on the saturated dibezapine ring by the methylene carbonyl linker; 2) the methylene carbonyl linker (specified as site 2); and 3) modifications on the 3-amino group site (specified as site 3) at the scaffold.

CINPA1 and the 10 commercially available analogs (Table 6) have varied modifications at all 3 major modifiable sites. CINPA1 (1) and chemicals 80 to 86 all have an ethyl carbamate group at the 3-amino position (site 3), but have different modifications at site 1 and site 2. However, chemical 87 has a methyl carbamate group at site 3, and chemicals 88 and 89 both have an isopropyl carbamate group at site 3. Although both CINPA1 (1) and chemical 80 have an ethyl carbamate modification at the 3-amino position, chemical 80 has a morpholino structure feature at site 1 instead of the diethylamino group presented in chemical 1 (CINPA1). This modification enhances the CAR inverse agonistic activity of chemical 80 (IC$_{50}$ of 0.24 µM) by about 3-fold over that of lead chemical 1 (IC$_{50}$ of 0.69 µM). The morpholino group is similar in size to the diethylamino group but has reduced rotation flexibility because the diethylamino group in chemical 1 is locked in the form of a 6-member morpholino ring in chemical 80. However, locking the diethylamino group conformation of chemical 1 in the form of an N-methyl-piperazino group resulted in a significantly weaker chemical 81 with a 56-fold higher IC$_{50}$ value (IC$_{50}$ of 38.76 µM) than that of chemical 1. Compared to the morpholino group, the N-methyl-piperazino group is bigger; without wishing to be bound by theory, an additional aliphatic tertiary amino group may allow chemical 81 to be protonated at a greater degree under assay conditions (pH 7.5), which may adversely affect ligand receptor interaction.

Chemicals 82 (IC$_{50}$ of 4.08 µM) and 84 (IC$_{50}$>70 µM) are much weaker CAR inverse agonists. Both have smaller substitutes at the position of the diethylamino group in chemical 1 (IC$_{50}$ of 0.69 µM), with a dimethyl amino group in chemical 82 and an amino group in chemical 84. Therefore, substitutions with a smaller group at the position of the diethylamino group in chemical 1 contributed negatively to the CAR inverse agonistic activities.

Chemical 83 (IC$_{50}$ of 3.63 µM) has a secondary amino group (tert-butylamino) at the position of diethylamino group in chemical 1 (IC$_{50}$ of 0.69 µM), which reduced its CAR inverse agonistic activity (IC$_{50}$ increases by 5-fold). A secondary amino group such as tert-butylamino in chemical 86 at the position of diethylamino group in chemical 1 has a free proton on the nitrogen, which may contribute as a hydrogen bond donor. A hydrogen bond donor at this position may affect the CAR inverse agonistic activity negatively.

In comparison to chemical 80 (IC$_{50}$ of 0.235 µM) and chemical 82 (IC$_{50}$ of 4.08 µM), chemical 85 (IC$_{50}$ of 0.320 µM) and chemical 86 (IC$_{50}$ of 5.01 µM), which have an ethylene carbonyl linker, had slightly decreased CAR inverse agonistic activities, suggesting that a longer linker at site 2 may negatively affect the CAR inverse agonistic activity of the analogs. The only difference between chemical 85 (IC$_{50}$ of 0.320 µM) and chemical 87 (IC$_{50}$ of 0.29 µM) is at site 3, with an ethyl carbamate at 3-amino group in chemical 85 and a methyl carbamate in chemical 87. Here a slightly increased CAR inverse agonistic activity was observed with a methyl carbamate rather than an ethyl carbamate at the 3-amino group. However, a methyl carbamate at the 3-amino group position was not taken into consideration in further development because the activity increase was marginal, and the configuration is less enzymatically and metabolically stable than an ethyl carbamate. More importantly, site 3 with a larger group such as an isopropyl carbamate in chemical 89, endowed the analog with increased CAR inverse agonistic activity.

Chemical 86 (IC$_{50}$ of 5.01 µM) and chemical 89 (IC$_{50}$ of 1.79 µM) have a difference only at site 3, with an ethyl carbamate in chemical 86 and an isopropyl carbamate in chemical 89. The isopropyl carbamate at site 3 increased the potency of chemical 89 by about 3-fold compared to chemical 86. Chemical 88 ($IC_{50}$>70 µM) has an even larger, protonable, and maybe more hydrophilic substitute (2-hydroxyethylpiperazino group) at site 1 and an ethylene carbonyl linker at site 2 which rendered it inactive as a CAR inverse agonist even though its isopropyl carbamate feature at site 3 could increase its CAR inverse agonistic activity.

12. Preliminary Structure-Activity Relationship Summary

Based on the CAR inverse agonistic activities gained from CINPA and the ten commercially available analogs, a preliminary SAR for the CINPA1 analogs was summarized (schematic CINPA1 structural features in FIG. 16A): Scaffold: 3-amino-10,11-dihydro-5H-dibenz[b,f]azepine (saturated 3-amino-dibezapine); Site 1: Medium constrained substitutes to the 5-nitrogen position through the methylene carbonyl linker are favorable, less charged or less protonated favorable, H-bond donor unfavorable; Site 2: A methylene carbonyl linker between 5-nitrogen position of the saturated 3-amino-dibezapine and additional substitutes is preferred over an ethylene carbonyl linker; Site 3: Proper modification at the 3-amino group on the saturated dibezapine ring: isopropyl carbamate>ethyl carbamate≥methyl carbamate.

13. Design, Synthesis, and Activity of Synthesized First Round CINPA1 Analogs a. Design of First Round CINPA1 Analogs By using preliminary SAR gained from CINPA1 and the ten commercially available analogs as CAR inverse agonists, novel analogs were designed in a stepwise approach. Modifications were focused on site 1 (the substitutes to 5-nitrogen position through the methylene carbonyl linker), site 2 (the methylene carbonyl linker), and site 3 (the modifications at the 3-amino group at the saturated dibezapine ring), with the saturated 3-amino-dibezapine scaffold unchanged.

In the first-round chemistry effort, twenty-three analogs were designed, with CINPA1 as the lead compound; their structures are summarized in Table 3 above. Chemicals 11 to 18 and 20 have a variety of di-substituted amino group modifications at site 1: open rings, closed rings, aliphatic rings, or aromatic rings. Chemicals 21 and 24 have an ethylene carbonyl linker at site 2 to further explore and confirm the effect of the additional methylene insert within site 2. Chemicals 22 and 23 have a secondary amino group feature that was designed to further explore and confirm the hydrogen donor property at the site 1 position. Chemical 19 has a tert-butoxy group at the site 1 position instead of a regular tertiary amino group. A tert-butoxy group could eliminate the protonation possibility at site 1 under physiological conditions. Chemicals 2 to 10 have modifications on site 3 with various structure features of amide, carbamates, ureas, sulfamide, and carbamate heterocyclic isostere.

b. CAR Inverse Agonistic Activities of First Round CINPA1 Analogs

After the twenty-three CINPA1 analogs were synthesized, their CAR inverse agonistic activities were determined by using the biochemical CAR-mediated fluorescent PGC1α coactivator recruitment/repression assay. The chemical structures and CAR inverse agonistic activities of the 23 analogs are summarized in Table 4 above along with those of the lead chemical 1 (CINPA1).

Among the twenty-three analogs prepared in the first-round chemistry effort, chemicals 11 to 18, 20, 21, and 24 have modifications only at the site 1 position of the lead chemical CINPA1 (1)'s structure. Chemical 11 ($IC_{50}$ of 0.21 µM) has a dipropylamino group at the site 1 position of CINPA1. The introduction of this dipropylamino group increased the CAR inverse agonistic activity of chemical 11 to 3-fold more than that of lead chemical 1, which has a diethylamino group at this position. However, a branching, disubstituted amino group is not favorable for CAR inverse agonistic activity, as chemical 12 ($IC_{50}$ of 3.05 µnM), which has a diisopropyl amino group at site 1, is much weaker, with an $IC_{50}$ value more than 4-fold higher than that of lead chemical 1.

The preliminary SAR data from the 10 commercially available analogs suggested that reduced side chain flexibility at site 1 might improve the CAR inverse agonistic activity, as seen in chemical 80. To further explore the effect of reducing side chain flexibility, chemicals 13 to 18 and 20 were designed to have ring structure features, which could reduce side chain rotation flexibility at site 1. Chemical 13 ($IC_{50}$ of 1.58 µM) and chemical 18 ($IC_{50}$ of 0.62 µM) were designed and prepared by directly constraining the diethylamino group in chemical 1 ($IC_{50}$ of 0.69 µM) in the form of a pyrrolidinyl group or piperidinyl group, respectively. Compared to the CAR inverse agonistic potency of lead chemical 1, that of chemical 13 decreased ($IC_{50}$ increased by more than 2-fold) whereas that of chemical 18 was marginally increased. Therefore, constraint at site 1 may not always increase CAR inverse agonistic activities of the analogs. However, reasonable size at site 1 might be important as the piperidinyl group in chemical 18 is larger than the pyrrolidinyl group in chemical 13, and chemical 18 exhibited higher CAR inverse agonistic potency than did chemical 13.

Without wishing to be bound by theory, an additional hydrogen-bond acceptor at the farthest end of the site 1 position may also give analogs improved CAR inverse agonistic activities. For example, chemical 80 ($IC_{50}$ of 0.24 µM) has an additional oxygen atom as a hydrogen-bond acceptor at the very end of site 1 within its morpholino group, whereas chemical 18 ($IC_{50}$ of 0.62 µM) has a similar 6-member ring structure to chemical 80 ($IC_{50}$ of 0.24 µM) at site 1 but without a hydrogen-bond acceptor built in, and it is less active as a CAR inverse agonist. Chemical 14 ($IC_{50}$ of 4.08 µM) has a 2,2,6,6-tetramethylpiperidinyl group at site 1: this group is branched at positions next to the nitrogen and is bulkier than the similar 6-member ring feature at this site in chemical 18 ($IC_{50}$ of 0.62 µM). This difference in site 1 rendered chemical 14 significantly less active than chemical 18 (the $IC_{50}$ of chemical 14 is over 6-fold more than that of chemical 18).

Chemical 20 ($IC_{50}$ of 1.41 µM) has a (1s,4s)-7-azabicyclo[2.2.1]heptanyl group at the site 1 position: this group branches at positions next to the nitrogen, with constraint in the form of an additional 5-member ring, and is slightly bulkier than the single 5-member ring in chemical 13 ($IC_{50}$ of 1,580 nM). Chemical 20 is slightly more active than chemical 13, suggesting that chemical groups at site 1 with appropriate bulkiness are desirable for improving the CAR inverse agonistic activities of analogs. Chemical 15 ($IC_{50}$ of 39.81 µM) has a 2,5-dioxo-2,5-dihydro-1H-pyrrolyl substitute at site 1, making it branched at α-positions of the nitrogen atom but with a hydrogen-bond acceptor property. This structural feature rendered chemical 15 less active than chemical 13 as a CAR inverse agonist (the $IC_{50}$ of chemical 15 is 25-fold lower than that of chemical 13) even though a similar 5-member ring structure was maintained at site 1 in both chemical 13 and 15. Without wishing to be bound by theory, this may indicate hydrogen-bond acceptor property at α-positions of the nitrogen atom is not desirable for CAR inverse agonistic activities. Chemicals 16 ($IC_{50}$ of 0.037 µM) and 17 ($IC_{50}$ of 6.89 µM) have a similar 5-member aromatic ring structure feature at site 1 of the lead compound CINPA1, with a pyrrolyl group in chemical 16 and an imidazolyl group in chemical 17. Chemical 16 is the aromatic version of chemical 13 at the site 1 position but is 43- and 19-fold more potent than chemicals 13 and 1 (CINPA1), respectively. The aromatic feature at site 1 has the most significant positive impact for analogs as a CAR inverse agonist. However, when an additional heteroatom in the form of nitrogen was added to the 5-member aromatic ring in chemical 16 to make chemical 17 (which now has an imidazolyl group), a dramatic loss of CAR inverse agonistic activity was observed (the $IC_{50}$ of chemical 17 is 186-fold less than that of chemical 16). Without wishing to be bound by theory, this may indicate that protonable groups at the site 1 position are undesirable for CAR inverse agonistic activity because an imidazolyl group can be easily protonated under assay conditions (pH 7.5).

Chemical 24 ($IC_{50}$ of 24.49 µM) has a mono-substituted amino group (ethylamino group) at site 1, with a proton attached to the nitrogen that can function as a hydrogen-bond donor. The extremely weak activity of chemical 24 further confirms that a hydrogen-bond donor feature at site 1 is undesirable (chemical 24 has an $IC_{50}$ that is over 35-fold less than that of the lead chemical 11) even though a smaller size at site 1 in chemical 24 may also partially contribute to the activity loss. However, chemical 21 ($IC_{50}$ of 2.06 µM), which has a similar mono-substituted amino group (tert-pentylamino group) and reasonable bulkiness, only slightly lost its CAR inverse agonistic activity ($IC_{50}$ is 3-fold less than that of the lead chemical 1). In this example, having a hydrogen-bond donor feature at site 1 is still undesirable, but the suitable group size maintained at site 1 might have compensated for the negative effect of the hydrogen-bond donor and helped retain reasonable CAR inverse agonistic activity for chemical 21. Chemical 22 ($IC_{50}$ of 2.43 µM) has an ethylene carbonyl linker at site 2 to replace the methylene carbonyl linker at the same site in lead chemical 1 ($IC_{50}$ of 0.69 µM). This modification decreased the activity of chemical 22 (a 3.5-fold increase in the $IC_{50}$ value over that of lead chemical 1). Chemical 23 ($IC_{50}$ of 3.18 µM) has a further modification at site 1, with a constrained pyrrolidinyl group to replace the diethylamino group in lead chemical 1 in addition to the ethylene carbonyl linker modification at site 2 as in chemical 22. This constrained modification without enough bulkiness at site 1 caused a slight decrease in CAR inverse agonistic activity ($IC_{50}$ of 2.43 µM for chemical 22 vs. $IC_{50}$ of 3.18 µM for chemical 23), which is consistent with the observed difference between chemical 1 ($IC_{50}$ of 0.69 µM) and chemical 13 ($IC_{50}$ of 1.58 µM). Chemical 19 ($IC_{50}$ of 0.071 µM) has a tert-butoxy group at the site 1 position of lead chemical 1 ($IC_{50}$ of 0.69 µM). This modification in chemical 19 increased its CAR inverse agonistic activity by 9.7-fold over that of lead chemical 1, demonstrating that a non-protonable group with reasonable size at site 1 could improve CAR inverse agonistic activity. However the tert-butoxy group is not protonable under assay conditions (pH 7.5) but has reasonable size, and the diethylamino group in lead chemical 1 is protonable under similar conditions. The success of chemical 19 as a substantially more potent CAR inverse agonist than lead chemical 1 led us to focus on site 1 modifications with the tert-butoxy and diethylamino functional groups, as reflected in 9 of 20 novel chemicals in the second-round chemistry effort.

Chemicals 2 to 10 have modifications on site 3 of lead chemical 1, with structural features of amide in chemical 2, carbamates in chemicals 3 and 4, ureas in chemicals 5 to 8, sulfamide in chemical 9, and carbamate heterocyclic isostere in chemical 10. Chemical 2 ($IC_{50}$ of 2,320 nM) has a butyramide at site 3 instead of the ethyl carbamate of lead chemical 1 ($IC_{50}$ of 687 nM) at the same position. Butyramide and ethyl carbamate are similar in size and shape; the only difference between them is that the ethoxy oxygen (non-carbonyl oxygen) in lead chemical 1 was replaced by a methylene group in chemical 10. The change of the ethoxy oxygen in chemical 1 to a methylene group in chemical 10 decreased the CAR inverse agonistic activity ($IC_{50}$ increased by about 3.4-fold). Therefore, it appears that the ethoxy oxygen in chemical 1 is beneficial for its CAR inverse agonistic activity, possibly because oxygen may serve as a hydrogen bond acceptor. Chemicals 3 and 4 have an isopropyl carbamate and a tert-butyl carbamate, respectively, at site 3 of lead chemical 1 ($IC_{50}$ of 0.69 µM), which has an ethyl carbamate at this site. The isopropyl carbamate modification maintains the CAR inverse agonistic activity for chemical 3 ($IC_{50}$ of 0.68 µM), which is consistent with the observed behavior of chemical 89.

Therefore, an isopropyl carbamate at site 3 was further confirmed as being a more favorable structural feature than ethyl carbamate at the same site. An isopropyl group is slightly larger than an ethyl group, suggesting that a slightly larger chemical group at site 3 may be favored for CAR inverse agonistic activity. In addition, isopropyl carbamate should provide analogs with higher enzymatic and metabolic stability than ethyl carbamate does. Further increase in size at site 3 to a tert-butyl carbamate group in chemical 4 actually slightly decreased its activity ($IC_{50}$ of 1.03 µM) from that of lead chemical 1 ($IC_{50}$ of 0.69 M). Compared to lead chemical 1 ($IC_{50}$ of 0.69 µM), urea, sulfamide, and carbamate heterocyclic isostere modifications at site 3 yielded chemicals 5 ($IC_{50}$ of 14.42 µM), 6 ($IC_{50}$ of 4.93 µM), 7 ($IC_{50}$ of 12.97 µM), 8 ($IC_{50}$ of 13.99 µM), 9 ($IC_{50}$ of 19.09 µM), and 10 ($IC_{50}$ of 18.79 µM), all with dramatically reduced CAR inverse agonistic activity. Therefore, these modifications at site 3 are unfavorable for CAR inverse agonistic activity, confirming that an alkoxy oxygen is optimal at site 3 to maintain the CAR inverse agonistic activity.

Figure 16B:
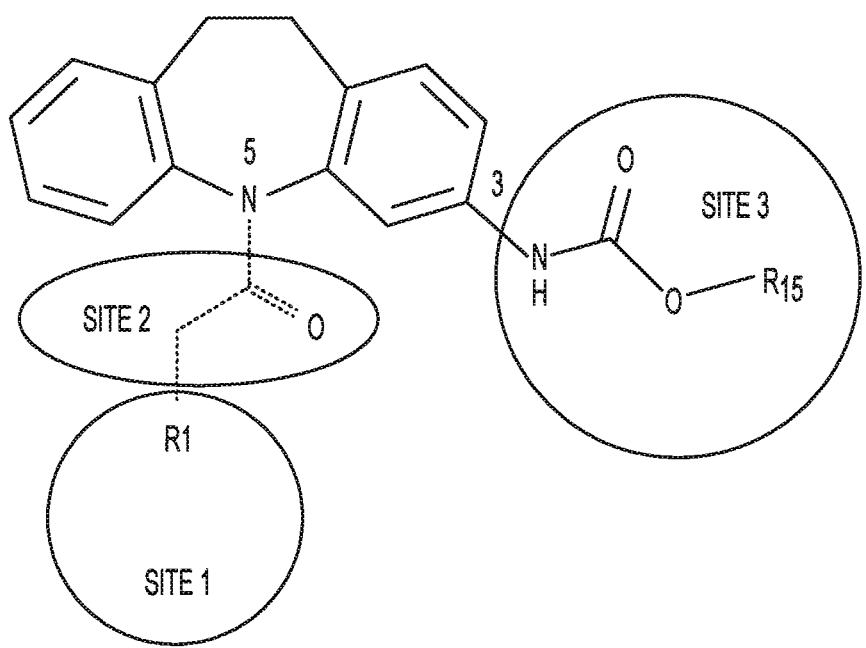

In addition, ureas in chemicals 5, 6, and 7 and sulfamide in chemical 9 both have a proton attached to the nitrogen atom, which could serve as a hydrogen-bond donor. The observation that a hydrogen-bond donor at site 3 may be unfavorable for CAR inverse agonistic activity is again seen in the chemical pair of 5 ($IC_{50}$ of 14.42 µM, with proton on nitrogen) and 8 ($IC_{50}$ of 13.99 µM, without a proton on nitrogen) in which chemical 8 is marginally more active than chemical 5. However, a diethyl substitution in chemical 8 instead of a mono-ethyl substitution in chemical 5 might also contribute to the marginal difference. Chemical 10, which has the non-carbonyl oxygen but the carbonyl oxygen is replaced with nitrogen, had dramatically lower activity ($IC_{50}$ of 18.79 µM) than did lead chemical 1 ($IC_{50}$ of 0.69 µM), indicating that a carbamate structure with both carbonyl oxygen and non-carbonyl oxygen (alkoxy oxygen) is required for optimal CAR inverse agonistic activity.

c. Summary of Structure-Activity Relationship from CINPA1, Commercially Available Analogs, and Synthesized First Round Analogs Based on the overall CAR inverse agonistic activities from the first round CINPA1 analogs, a brief SAR report of analogs with CAR inverse agonistic activities at least comparable to CINPA1 was summarized (structural features shown in FIG. 16A and FIG. 16B).

Scaffold of 3-amino-10,11-dihydro-5H-dibenz[b,f]azepine (saturated 3-amino-dibezapine).

Site 1: Without wishing to be bound by theory, an unbranched disubstituted amino group may be favorable; protonability is undesirable; a suitably bulky group may be desirable; an oxygen-contained group in the form of an alkoxy group may be better than a nitrogen-containing group in the form of an aliphatic tertiary amino group because an aliphatic amino group is susceptible to protonation under assay conditions (pH 7.5), which may be unfavorable for CAR inverse agonistic activity; a mono-nitrogen-containing aromatic ring may be favorable because it is not as susceptible to protonation under assay conditions (pH 7.5) as an aliphatic tertiary amino group is.

Site 2: Without wishing to be bound by theory, a methylene carbonyl linker may be better than an ethylene carbonyl linker.

Site 3: Without wishing to be bound by theory, a carbamate structure may be favorable; a hydrogen-bond donor may be unfavorable; medium-sized substitutes, such as isopropyl carbamate, may be favorable.

14. Design, Synthesis, and Activity of Synthesized Second Round CINPA1 Analogs a. Design of Second Round CINPA1 Analogs The SAR obtained from CINPA1, the 23 CINPA1 analogs of the first-round of chemistry, and the 10 analogs from commercial sources demonstrated that isopropyl carbamate at site 3 may be desirable for CAR inverse agonistic activity. Therefore, 12 analogs with isopropyl carbamate at site 3 were designed. In addition, 4 analogs with tert-butyl carbamate at site 3 were designed for comparison. Among these 16 analogs, 9 were given various alkoxy groups at site 1 because SAR from the 23 analogs in round 1 suggested that an alkoxy group at this site could improve CAR inverse agonistic activity. The other 7 analogs were given several site 1 and site 2 groups that are similar to those explored in the first-round chemistry effort in combination with either isopropyl carbamate or tert-butyl carbamate at site 3 to gain additional insight about the functional preference at site 3. To identify optimal groups at site 3, 4 additional chemicals having novel carbamates at site 3 and the optimal pyrrolyl group at site 1 were designed. In total, 20 CINPA1 analogs were designed in the second-round chemistry effort.

b. CAR Inverse Agonistic Activities of Second Round CINPA1 Analogs

The CAR inverse agonistic activities of these 20 CINPA1 analogs was evaluated using the biochemical CAR-mediated fluorescent PGC1α coactivator recruitment/repression assay. Their structures and CAR inverse agonistic activities are summarized in Tables 3 and 4 above along with those of lead chemical 1 (CINPA1).

Among the 20 CINPA1 analogs from the round 2 chemistry, chemical 25 is the only one with an ethylene carbonyl group modification and an isopropyl carbamate at site 3. Chemical 25 ($IC_{50}$ of 6.40 µM) is substantially less active than is lead chemical 1 ($IC_{50}$ of 0.69 µM) even though the isopropyl carbamate group at site 3 is expected to increase the CAR inverse agonistic activity as observed in other analogs with the isopropyl carbamate structural feature at site 3. The ethylene carbonyl linker at site 2 is again proven to be a less desirable group than the methylene carbonyl linker group.

Chemicals 11 ($IC_{50}$ of 0.21 µM), 28 ($IC_{50}$ of 0.12 µM), and 37 ($IC_{50}$ of 0.15 µM) are only different at site 3, with a corresponding ethyl, isopropyl, or tert-butyl carbamate group. Among this group of 3 chemicals, chemical 28, which has an isopropyl carbamate at site 3, has the highest CAR inverse agonistic activity. This slight positive effect of a site 3 isopropyl carbamate on the CAR inverse agonistic activity was also observed among chemicals 16 ($IC_{50}$ of 0.037 µM), 26 ($IC_{50}$ of 0.021 µM), and 40 ($IC_{50}$ of 0.032 µM), with the only difference being their respective ethyl, isopropyl, or tert-butyl carbamate groups at site 3. In another group of chemicals –18 ($IC_{50}$ of 0.062 µM), 27 ($IC_{50}$ of 0.25 µM), and 38 ($IC_{50}$ of 0.22 µM)—that had a corresponding ethyl, isopropyl, or tert-butyl carbamate group at site 3, 38 (with a tert-butyl carbamate) was only slightly more active than 27 (with an isopropyl carbamate), but both were substantially more active than 18, which has an ethyl carbamate. Overall, an isopropyl carbamate is similar to a tert-butyl carbamate, but both are better than an ethyl carbamate at site 3 for the CAR inverse agonistic activity. Having an $IC_{50}$ of 0.022 µM, chemical 26 was the most active CAR inverse agonist and is 32.8-fold more potent than lead chemical 1 ($IC_{50}$ 0.69 µM).

Chemicals 29 to 36 and 39 have alkoxy groups at site 1 and an isopropyl or tert-butyl carbamate at site 3. These structural features improve the CAR inverse agonistic activities of the analogs compared to that of lead chemical 1, with the exception of chemical 29 ($IC_{50}$ value 11.35 µM), which has an ethoxy group at site 1 that might be too small to maintain a high CAR inverse agonistic activity. Chemicals 30 ($IC_{50}$ 0.060 µM) and 39 ($IC_{50}$ 0.12 µM) both have an isopropoxy group at site 1 and an isopropyl or a tert-butyl carbamate, respectively, at site 3. Both 30 and 39 are substantially more active than lead chemical 1 ($IC_{50}$ of 0.69 µM). Here, the isopropyl carbamate at site 3 in chemical 30 again endowed the analog with higher CAR inverse agonistic activity than did the tert-butyl carbamate at the same site in chemical 39. Increasing the size of the alkoxy group at site 1 from an ethoxy group in chemical 29 ($IC_{50}$ of 11.35 µM) and an isopropoxy group in chemical 30 ($IC_{50}$ of 0.060 µM) to a sec-butoxy group in chemical 31 ($IC_{50}$ of 0.035 µM) and a neopentyloxy group in chemical 32 ($IC_{50}$ of 0.021 µM) increases CAR inverse agonistic activity. Similar observations were made in the cyclic alkoxy group series at site 1: from chemical 33 ($IC_{50}$ of 0.082 µM) with a cyclopropoxy group to chemical 34 ($IC_{50}$ of 0.038 µM) with a cyclobutoxy group, and to chemical 35 ($IC_{50}$ of 0.020 µM) with a cyclopentyloxy group. However, a slight activity decrease was observed when the size of site 1 was further increased by incorporating a cyclohexyloxy group, as in chemical 36 ($IC_{50}$ of 0.024 µM). The highest CAR inverse agonistic activities were observed when a branched 5-carbon alkoxy group was at site 1, as in chemicals 32 and 35.

Chemicals 41 to 44 were designed to further explore the effect of cyclic carbamates at site 3 on CAR inverse agonistic activities. Chemicals 41 ($IC_{50}$ of 0.022 µM), 42 ($IC_{50}$ of 0.020 µM), 43 ($IC_{50}$ of 0.014 µM), and 44 ($IC_{50}$ of 0.012 µM), which respectively have cyclopropyl, cyclobutyl, cyclopentyl, and cyclohexyl carbamates at site 3 and the optimal pyrrolyl functional group at site 1, had substantially higher CAR inverse agonistic activities than did lead chemical 1 ($IC_{50}$ of 0.69 µM). These results demonstrate the significant contribution of cyclohexyl carbamates at site 3 to high CAR inverse agonistic activity. Chemical 44 is the most active CAR inverse agonist among chemicals 41 to 44: having an $IC_{50}$ value of 0.012 µM, it is approximately 59-fold more potent than the lead compound 1 (CINPA1) and is the most active analog among all 54 analogs evaluated in this study.

c. Summary of Structure-Activity Relationship of Second Round CINPA1 Analogs

Based on the overall CAR inverse agonistic activities of the 54 CINPA1 analogs, this brief summary of the SAR of modifications that affect CAR inverse agonistic activities (structural features in FIG. 16B) is provided:

Scaffold: 3-amino-10,11-dihydro-5H-dibenz[b,f]azepine (saturated 3-amino-dibezapine).

Site 1: Without wishing to be bound by theory, medium size alkoxy groups or tertiary amino groups in aromatic rings with no additional substitute at α-position to the nitrogen; hydrogen-bond donor may be highly unfavorable; protonability is undesirable at this site.

Site 2: Without wishing to be bound by theory, a methylene carbonyl linker may be better than an ethylene carbonyl linker.

Site 3: Without wishing to be bound by theory, a carbamate may be better than an amide, urea, sulfamide, or carbamate heterocyclic isostere structure; a medium-sized aliphatic cyclic carbamate structure may be favorable; a hydrogen-bond donor may be unfavorable.

15. Prophetic Pharmaceutical Composition Examples

"Active ingredient" as used throughout these examples relates to one or more disclosed compounds or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

(1) Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

(2) Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

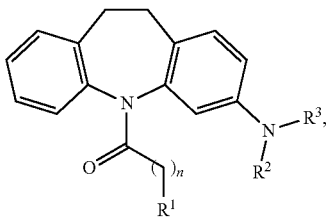

wherein n is an integer selected from 1, 2, and 3;
wherein $R^1$ is —$NR^{11a}R^{11b}$;
wherein $R^{11a}$ is hydrogen and $R^{11b}$ is —$C(CH_3)_2$(C2-C8 alkyl);

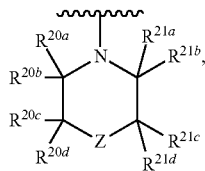

wherein $R^2$ is selected from hydrogen and C1-C4 alkyl;
wherein $R^3$ is selected from —$SO_2R^{12}$, —(C=O)$R^{13}$, —(C=O)$NR^{14a}R^{14b}$, —(C=O)$OR^{15}$, and $Ar^2$;
wherein $R^{12}$, when present, is selected from C1-C3 alkyl, C1-C3 monohaloalkyl, C1-C3 polyhaloalkyl, cyclopropyl, and —$NR^{22a}R^{22b}$;
wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle;
wherein $R^{13}$, when present, is selected from C1-C3 alkyl, C1-C3 monohaloalkyl, C1-C3 polyhaloalkyl, and cyclopropyl;
wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle;
wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl;
wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group;

or a pharmaceutically acceptable salt thereof.

2. The compound of claim 1, wherein $R^{11a}$ is hydrogen and $R^{11b}$ is —$C(CH_3)_2CH_2CH_3$.

3. The compound of claim 1, wherein $R^2$ is hydrogen or C1-C4 alkyl.

4. The compound of claim 1, wherein $R^3$ is selected from —$SO_2R^{12}$, —(C=O)$R^{13}$, —(C=O)$NR^{14a}R^{14b}$, and —(C=O)$OR^{15}$.

5. The compound of claim 1, wherein $R^3$ is $Ar^2$.

6. A pharmaceutical composition comprising an effective amount of a compound of claim 1, and a pharmaceutically acceptable carrier.

7. A compound having a structure represented by a formula:

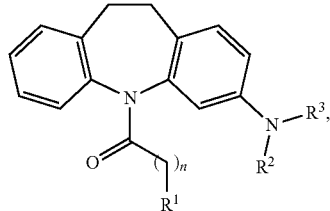

wherein n is an integer selected from 1, 2, and 3;
wherein $R^1$ is selected from —$OR^{10}$, —$NR^{11a}R^{11b}$, and $Ar^1$;
wherein $R^{10}$, when present, is selected from hydrogen, C1-C8 alkyl, and $Cy^1$;
wherein $Cy^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl;
wherein each of $R^{11a}$ and $R^{11b}$, when present, is independently selected from C1-C8 alkyl; or
wherein $R^{11a}$, when present, is hydrogen and $R^{11b}$, when present, is —$C(CH_3)_2$(C2-C8 alkyl); or
wherein each of $R^{11a}$ and $R^{11b}$, when present, are optionally covalently bonded and, together with the nitrogen atom to which they are attached, comprise a 3- to 5-membered heterocycle; or
wherein each of $R^{11a}$ and $R^{11b}$, when present, are optionally covalently bonded and, together with the nitrogen atom to which they are attached, comprise a 6-membered heterocycle having a structure represented by a formula:

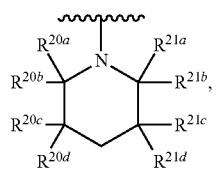

wherein Z, when present, is selected from C, NH, and NCH$_3$;

wherein each of R$^{20a}$, R$^{20b}$, R$^{20c}$, and R$^{20d}$, when present, is independently selected from hydrogen and C1-C4 alkyl, provided that R$^{20a}$ and R$^{20b}$ are not simultaneously hydrogen; or wherein each of R$^{20a}$ and R$^{20c}$, when present, are hydrogen and R$^{20b}$ and R$^{20d}$, when present, are optionally covalently bonded and, together with the nitrogen atom to which they are attached, comprise a 5- to 6-membered heterocycle;

wherein each of R$^{21a}$, R$^{21b}$, R$^{21c}$, and R$^{21d}$, when present, is independently selected from hydrogen and C1-C4 alkyl, provided that R$^{21a}$ and R$^{21b}$ are not simultaneously hydrogen; or wherein each of R$^{21a}$ and R$^{21c}$, when present, are hydrogen and R$^{21b}$ and R$^{21d}$, when present, are optionally covalently bonded and, together with the nitrogen atom to which they are attached, comprise a 5- to 6-membered heterocycle;

wherein Ar$^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group;

wherein R$^2$ is selected from hydrogen and C1-C4 alkyl;

wherein R$^3$ is Ar$^2$;

wherein Ar$^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group;

or a pharmaceutically acceptable salt thereof.

8. The compound of claim 7, wherein R$^2$ is hydrogen or C1-C4 alkyl.

9. The compound of claim 7, wherein Ar$^2$ is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, and C1-C4 polyhaloalkyl.

10. The compound of claim 7, wherein Ar$^2$ is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, and C1-C4 polyhaloalkyl, and wherein two of the substituents are covalently bonded, and together with the intermediate atoms, comprise an optionally substituted 5- to 6-membered fused ring group.

11. The compound of claim 7, wherein Ar$^2$ is selected from furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyrimidinyl, thiophenyl, benzo [d] oxazolyl, benzo [d] thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tert-butyl, sec-butyl, isobutyl, tent-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

12. The compound of claim 7, wherein Ar$^2$ is selected imidazolyl, pyrimidinyl, tetrazolyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, indolyl, indazolyl, benzimidazolyl, imidazopyridinyl, pyrazolopyridinyl, pyrazolopyrimidinyl, pyridinyl, pyrimidinyl, benzo [d] oxazolyl, benzo [d] thiazolyl, quinazolinyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl and substituted with 0, 1, 2, or 3 substituents independently selected from —F, —Cl, methyl, ethyl, propyl, isopropyl, tent-butyl, sec-butyl, isobutyl, tent-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

13. A pharmaceutical composition comprising an effective amount of a compound of claim 7 and a pharmaceutically acceptable carrier.

14. A compound having a structure represented by a formula:

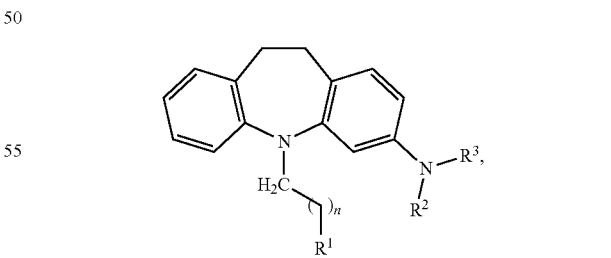

wherein n is an integer selected from 1, 2, and 3;

wherein R$^1$ is selected from —OR$^{10}$, —NR$^{11a}$R$^{11b}$, and Ar$^1$;

wherein R$^{10}$, when present, is selected from hydrogen, C1-C8 alkyl, and Cy$^1$;

wherein Cy$^1$, when present, is C3-C6 cycloalkyl or C2-C5 heterocycloalkyl and substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl;

wherein $R^{11a}$ and $R^{11b}$, when present, are covalently bonded and, together with the nitrogen atom to which they are attached, comprise a 3- to 5-membered heterocycle; or wherein $R^{11a}$ and $R^{11b}$, when present, are covalently bonded and, together with the nitrogen atom to which they are attached, comprise a 6-membered heterocycle having a structure represented by a formula:

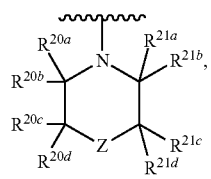

wherein Z, when present, is selected from C, NH, and $NCH_3$;

wherein each of $R^{20a}$, $R^{20b}$, $R^{20c}$, and $R^{20d}$, when present, is independently selected from hydrogen and C1-C4 alkyl, provided that $R^{20a}$ and $R^{20b}$ are not simultaneously hydrogen; or wherein each of $R^{20a}$ and $R^{20c}$, when present, are hydrogen and $R^{20b}$ and $R^{20d}$, when present, are optionally covalently bonded and, together with the nitrogen atom to which they are attached, comprise a 5- to 6-membered heterocycle;

wherein each of $R^{21a}$, $R^{21b}$, $R^{21c}$, and $R^{21d}$, when present, is independently selected from hydrogen and C1-C4 alkyl, provided that $R^{21a}$ and $R^{21b}$ are not simultaneously hydrogen; or wherein each of $R^{21a}$ and $R^{21c}$, when present, are hydrogen and $R^{21b}$ and $R^{21d}$, when present, are optionally covalently bonded and, together with the nitrogen atom to which they are attached, comprise a 5- to 6-membered heterocycle;

wherein $Ar^1$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group;

wherein $R^2$ is selected from hydrogen and C1-C4 alkyl;

wherein $R^3$ is selected from $-SO_2R^{12}$, $-(C=O)R^{13}$, $-(C=O)NR^{14a}R^{14b}$, $-(C=O)OR^{15}$, and $Ar^2$;

wherein $R^{12}$, when present, is selected from C1-C3 alkyl, C1-C3 monohaloalkyl, C1-C3 polyhaloalkyl, cyclopropyl, and $-NR^{22a}R^{22b}$;

wherein each of $R^{22a}$ and $R^{22b}$, when present, is independently selected from hydrogen, C1-C3 alkyl, C1-C3 monohaloalkyl, C1-C3 polyhaloalkyl, and cyclopropyl; or wherein $R^{22a}$ and $R^{22b}$, when present, are optionally covalently bonded and, together with the nitrogen atom to which they are attached, comprise a 3- to 6-membered heterocycle;

wherein $R^{13}$, when present, is selected from C1-C3 alkyl, C1-C3 monohaloalkyl, C1-C3 polyhaloalkyl, and cyclopropyl;

wherein each of $R^{14a}$ and $R^{14b}$, when present, is independently selected from hydrogen, C1-C3 alkyl, C1-C3 monohaloalkyl, C1-C3 polyhaloalkyl, and cyclopropyl; or wherein $R^{14a}$ and $R^{14b}$, when present, are optionally covalently bonded and, together with the nitrogen atom to which they are attached, comprise a 3- to 6-membered heterocycle;

wherein $R^{15}$, when present, is selected from hydrogen, C1-C4 alkyl, C1-C4 monohaloalkyl, C1-C4 polyhaloalkyl, and $Cy^2$, provided that $R^{15}$ is i-propyl only when n is 1, and provided that when n is 1 or 2 and each of $R^{11a}$ and $R^{11b}$ is ethyl then $R^{15}$ is not ethyl;

wherein $Cy^2$, when present, is C3-C6 cycloalkyl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl; and wherein $Ar^2$, when present, is C2-C6 heteroaryl substituted with 0, 1, 2, or 3 groups independently selected from halogen, C1-C4 alkyl, C1-C4 alkoxyalkyl, C1-C4 hydroxyalkyl, C1-C4 monohaloalkyl, C1-C4 polyhaloalkyl, and wherein two of the substituents are optionally covalently bonded, and together with the intermediate atoms, comprise an optionally substituted 5- to 6-membered fused ring group;

or a pharmaceutically acceptable salt thereof.

15. The compound of claim 14, wherein $R^1$ is selected from $-OR^{10}$ and $Ar^1$.

16. The compound of claim 14, wherein $R^2$ is hydrogen or C1-C4 alkyl.

17. The compound of claim 14, wherein $R^3$ is selected from $-SO_2R^{12}$, $-(C=O)R^{13}$, $-(C=O)NR^{14a}R^{14b}$, and $-(C=O)OR^{15}$.

18. The compound of claim 14, wherein $R^1$ is $-OR^{10}$, wherein the compound has a structure selected from:

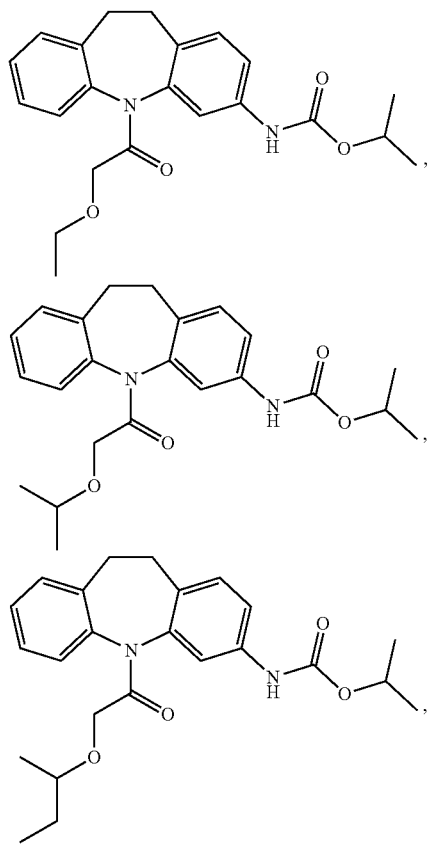

277
-continued
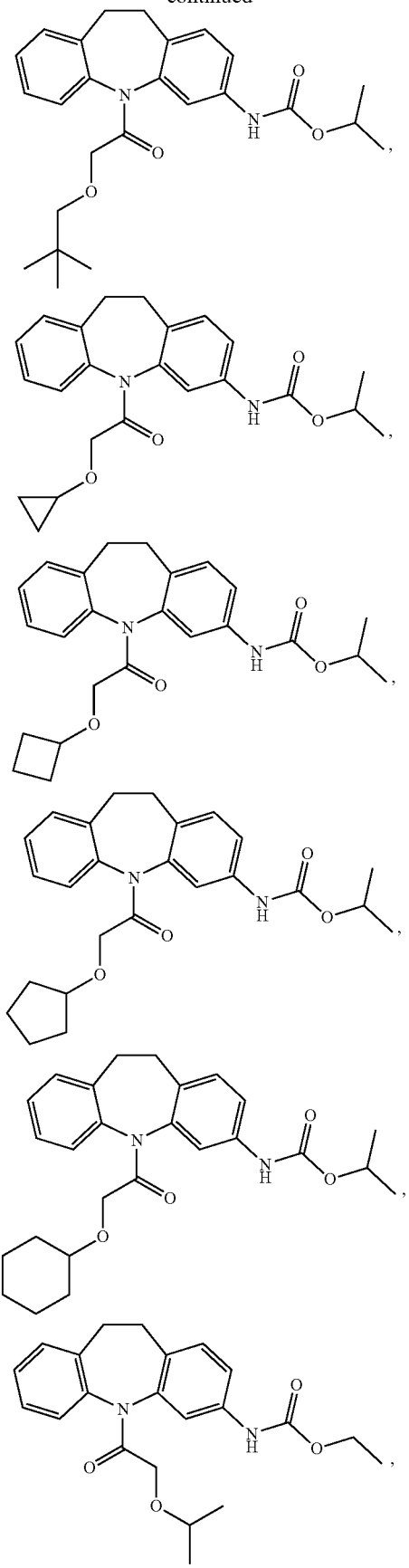
278
-continued
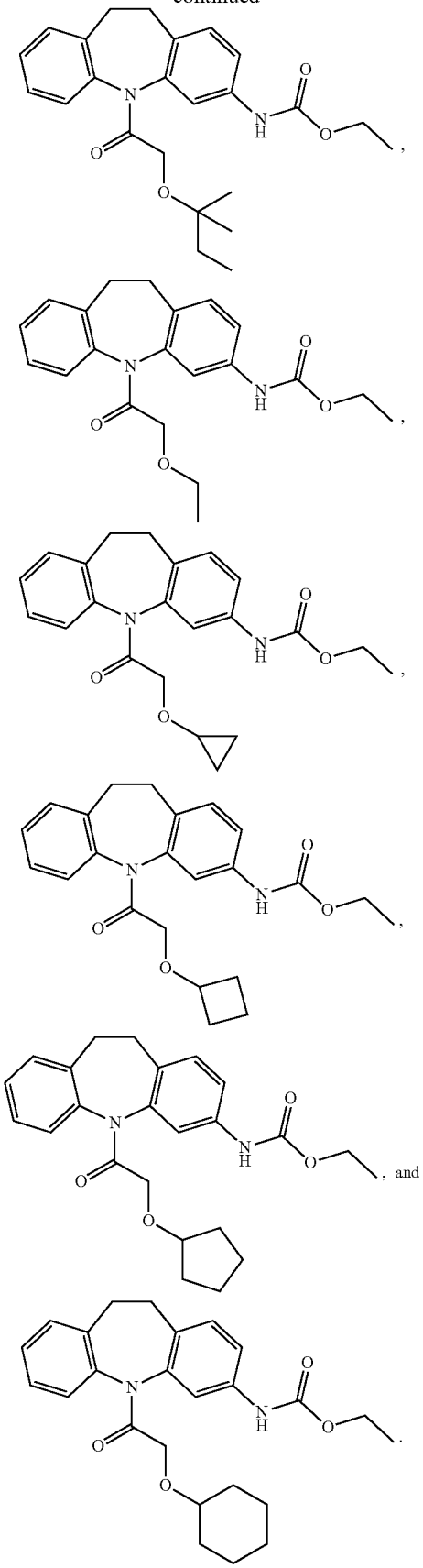

19. The compound of claim 14, wherein R¹ is Ar¹, wherein the compound has a structure selected from:
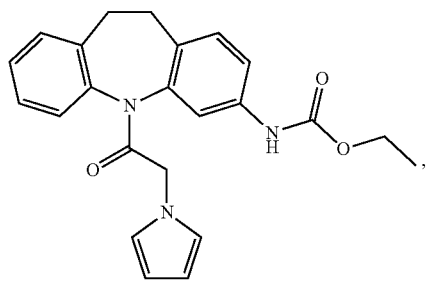
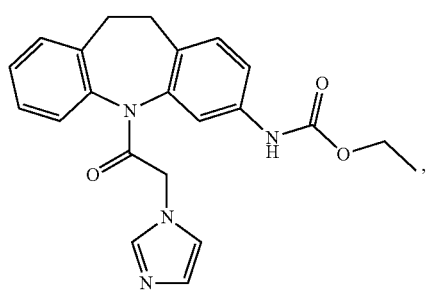
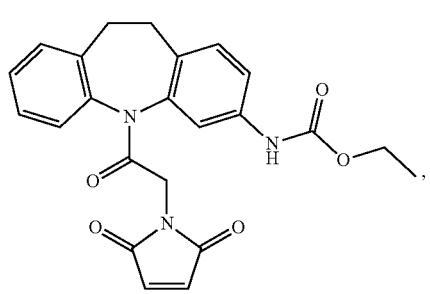
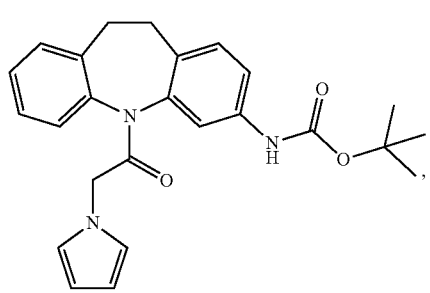
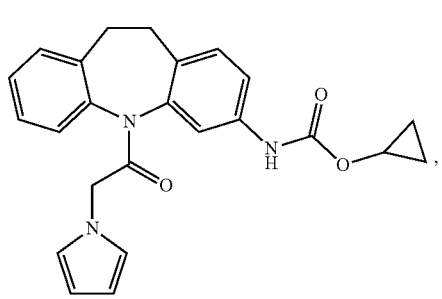
-continued
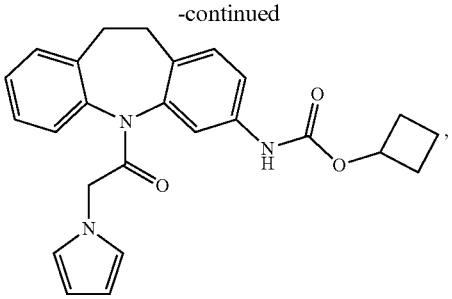
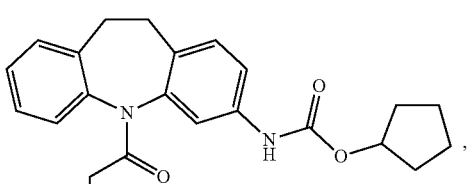
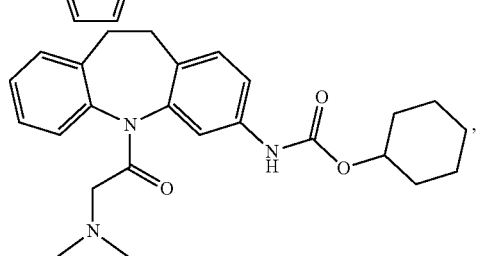
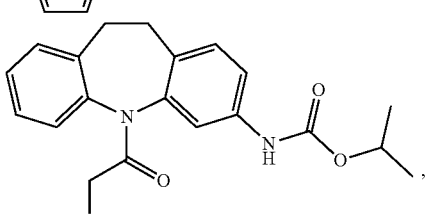
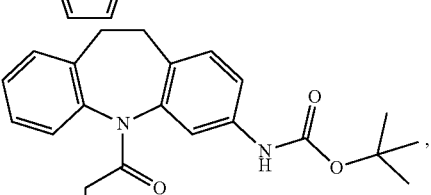
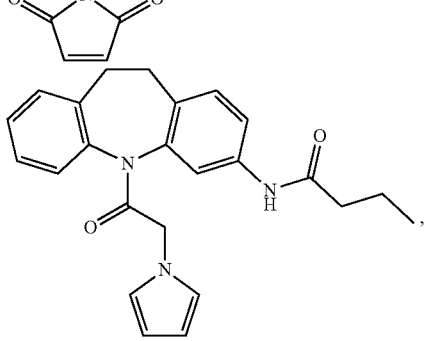

281
-continued
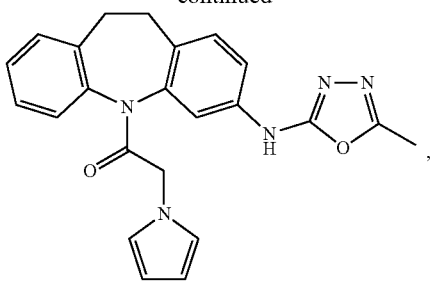
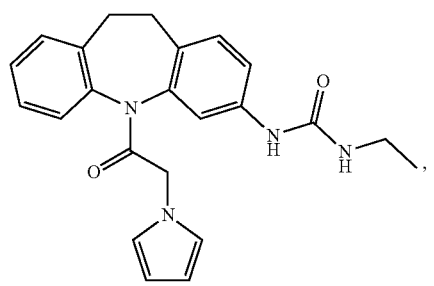
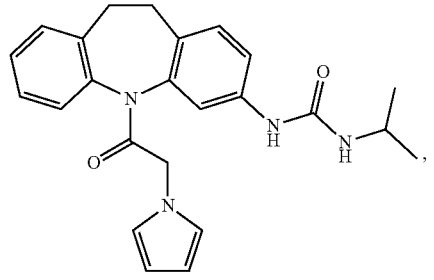
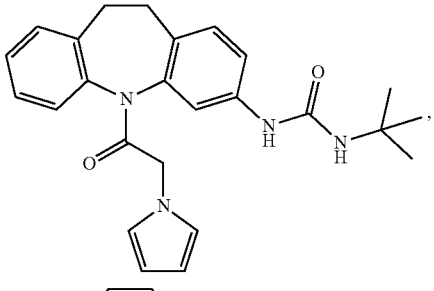
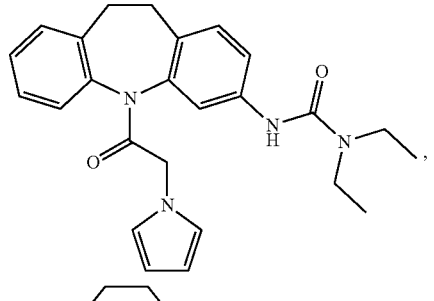
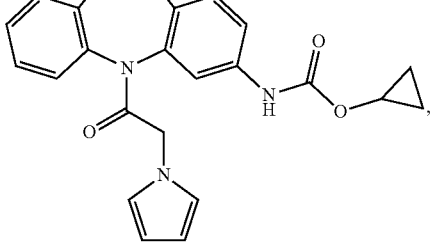
282
-continued
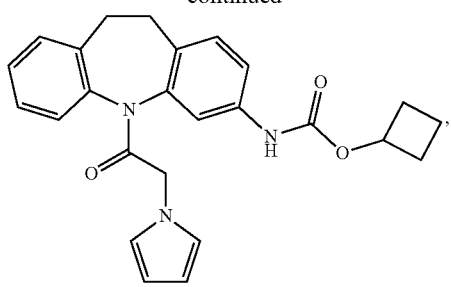
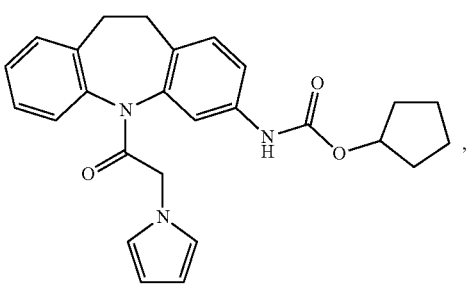
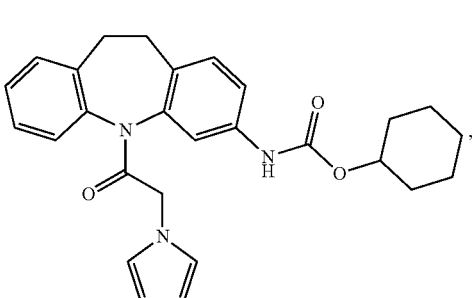
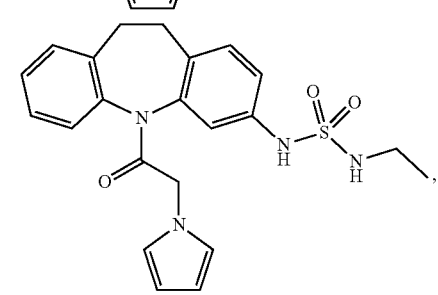
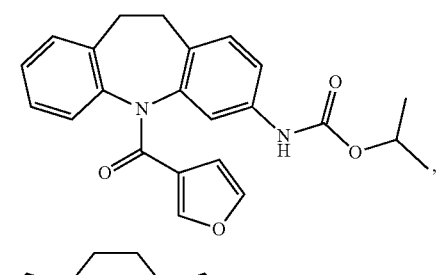
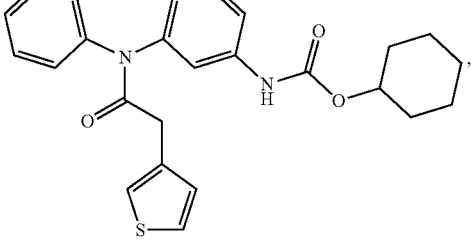

283
-continued
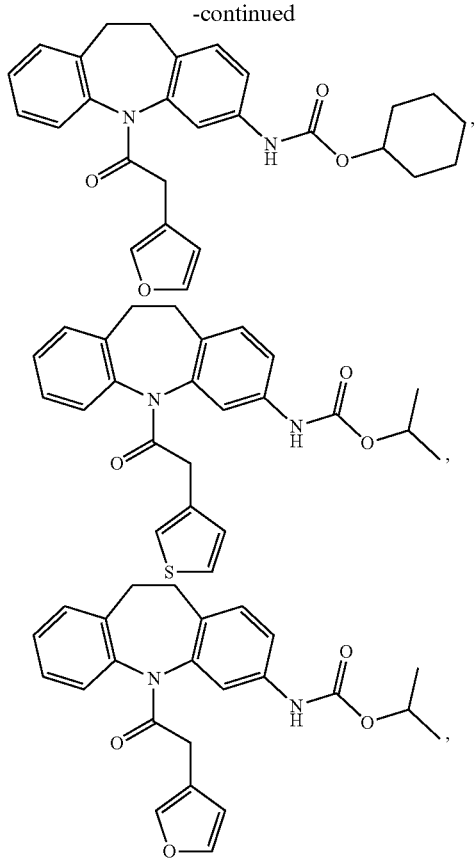
284
-continued
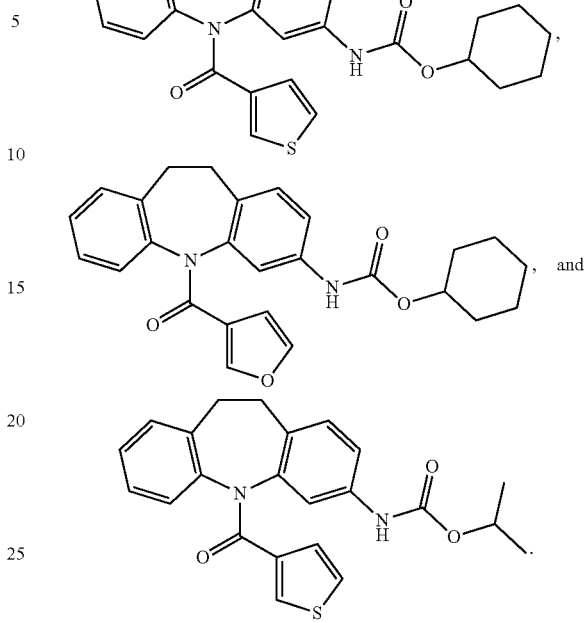
20. A pharmaceutical composition comprising an effective amount of a compound of claim 14 and a pharmaceutically acceptable carrier.
* * * * *